(12) United States Patent
Behnke et al.

(10) Patent No.: US 8,957,049 B2
(45) Date of Patent: Feb. 17, 2015

(54) INHIBITORS OF FATTY ACID AMIDE HYDROLASE

(75) Inventors: Mark L. Behnke, Somerville, MA (US); Alfredo C. Castro, Winchester, MA (US); Catherine A. Evans, Somerville, MA (US); Louis Grenier, Newton, MA (US); Michael J. Grogan, Winchester, MA (US); Tao Liu, Ashland, MA (US); Daniel A. Snyder, Somerville, MA (US); Thomas T. Tibbitts, Westford, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 81 days.

(21) Appl. No.: 12/901,421

(22) Filed: Oct. 8, 2010

(65) Prior Publication Data

US 2011/0172186 A1    Jul. 14, 2011

Related U.S. Application Data

(63) Continuation of application No. PCT/US2009/039872, filed on Apr. 8, 2009.

(60) Provisional application No. 61/043,686, filed on Apr. 9, 2008.

(51) Int. Cl.
*C07F 5/02*    (2006.01)
*A61K 31/69*    (2006.01)

(52) U.S. Cl.
CPC . *A61K 31/69* (2013.01); *C07F 5/02* (2013.01); *C07F 5/025* (2013.01)
USPC .............................................. 514/64; 548/110

(58) Field of Classification Search
None
See application file for complete search history.

(56) References Cited

U.S. PATENT DOCUMENTS

| 4,270,537 A | 6/1981 | Romaine |
| 4,596,556 A | 6/1986 | Morrow et al. |

(Continued)

FOREIGN PATENT DOCUMENTS

| DE | 40 14 488 A1 | 11/1991 |
| DE | 4220065 | 12/1993 |

(Continued)

OTHER PUBLICATIONS

"Guidance for Industry: Q3C—Tables and List." US DHHS, FDA, CDER, CBER, Nov. 2003, Revision 1.*

(Continued)

*Primary Examiner* — Alicia L Otton
(74) *Attorney, Agent, or Firm* — Jones Day

(57) ABSTRACT

The present invention provides compounds, and pharmaceutically acceptable compositions thereof, encompassed by any of formulae (I), (II), (III), (IV), (V), or (VI), or subgenera thereof. The present invention also provides methods for treating an FAAH mediated disease, disorder or condition by administering a therapeutically effective amount of a compound or composition comprising a compound of any of formulae (I), (II), (III), (IV), (V), or (VI), or subgenera thereof, to a patient in need thereof. Additionally, the present invention provides methods for inhibiting FAAH by administering a therapeutically effective amount of a compound or composition comprising a compound of any of formulae (I), (II), (III), (IV), (V), or (VI), or subgenera thereof, to a patient in need thereof.

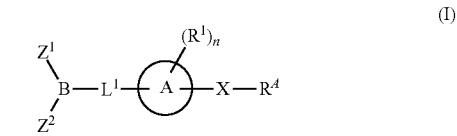

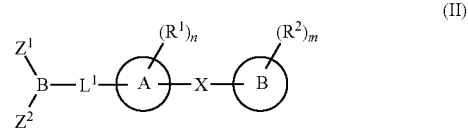

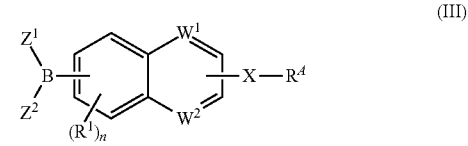

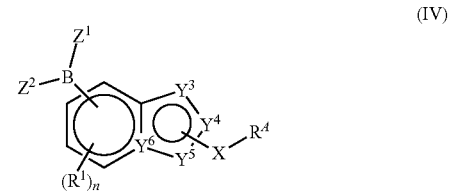

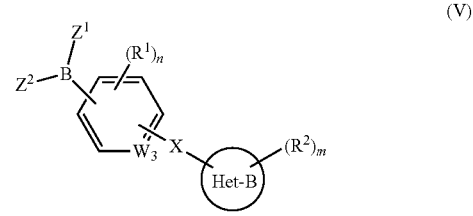

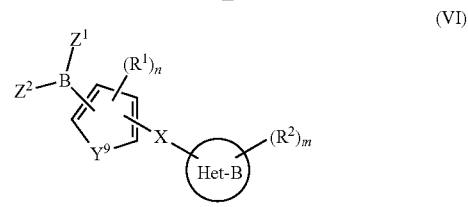

21 Claims, No Drawings

(56) References Cited

U.S. PATENT DOCUMENTS

| | | |
|---|---|---|
| 4,790,824 A | 12/1988 | Morrow et al. |
| 4,853,150 A | 8/1989 | Bezborodov et al. |
| 4,886,499 A | 12/1989 | Cirelli et al. |
| 4,940,640 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,089,499 A | 2/1992 | Baker et al. |
| 5,141,496 A | 8/1992 | Dalto et al. |
| 5,190,521 A | 3/1993 | Hubbard et al. |
| 5,198,149 A | 3/1993 | Gray et al. |
| 5,273,680 A | 12/1993 | Gray et al. |
| 5,312,335 A | 5/1994 | McKinnon et al. |
| 5,328,483 A | 7/1994 | Jacoby |
| 5,328,637 A | 7/1994 | Buchechker et al. |
| 5,334,144 A | 8/1994 | Alchas et al. |
| 5,339,163 A | 8/1994 | Homma et al. |
| 5,340,898 A | 8/1994 | Cavezzan et al. |
| 5,383,851 A | 1/1995 | McKinnon et al. |
| 5,417,662 A | 5/1995 | Hjertman et al. |
| 5,417,885 A | 5/1995 | Suzuki et al. |
| 5,466,220 A | 11/1995 | Brenneman |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,541,061 A | 7/1996 | Fodor et al. |
| 5,543,075 A | 8/1996 | Parri et al. |
| 5,550,236 A | 8/1996 | Schlosser et al. |
| 5,569,189 A | 10/1996 | Parsons |
| 5,576,220 A | 11/1996 | Hudson et al. |
| 5,599,302 A | 2/1997 | Lilley et al. |
| 5,616,582 A | 4/1997 | Barker |
| 5,643,893 A | 7/1997 | Benson et al. |
| 5,649,912 A | 7/1997 | Peterson |
| 5,683,623 A | 11/1997 | Chan et al. |
| 5,693,688 A | 12/1997 | Priou |
| 5,704,911 A | 1/1998 | Parsons |
| 5,800,733 A | 9/1998 | Kelly |
| 5,847,149 A | 12/1998 | Fuss et al. |
| 5,849,958 A | 12/1998 | Barnes et al. |
| 5,892,131 A | 4/1999 | Barnes et al. |
| 5,893,397 A | 4/1999 | Peterson et al. |
| 5,993,412 A | 11/1999 | Deily et al. |
| 5,998,673 A | 12/1999 | Barnes et al. |
| 6,075,014 A | 6/2000 | Weston et al. |
| 6,096,784 A | 8/2000 | Lerner et al. |
| 6,174,458 B1 | 1/2001 | Koga et al. |
| 6,177,440 B1 | 1/2001 | Bach et al. |
| 6,218,445 B1 | 4/2001 | Priou et al. |
| 6,262,319 B1 | 7/2001 | Barnes et al. |
| 6,271,015 B1 | 8/2001 | Gilula et al. |
| 6,309,406 B1 | 10/2001 | Jones et al. |
| 6,326,156 B1 | 12/2001 | Civelli et al. |
| 6,344,474 B1 | 2/2002 | Maruani et al. |
| 6,423,378 B1 | 7/2002 | Cotting et al. |
| 6,600,066 B1 | 7/2003 | Schottek et al. |
| 6,617,125 B2 | 9/2003 | Adler, Jr. |
| 6,753,046 B2 | 6/2004 | Manabe et al. |
| 6,818,260 B2 | 11/2004 | Farrand et al. |
| 6,911,235 B2 | 6/2005 | Frances et al. |
| 6,924,269 B2 | 8/2005 | Miljkovic et al. |
| 6,927,216 B2 | 8/2005 | Cherney et al. |
| 7,037,905 B2 | 5/2006 | Ebdrup et al. |
| 7,037,938 B2 | 5/2006 | Hattori et al. |
| 7,049,304 B2 | 5/2006 | Holmes-Farley et al. |
| 7,074,836 B1 | 7/2006 | Kawada et al. |
| 7,101,915 B1 | 9/2006 | Kawada et al. |
| 7,148,219 B2 | 12/2006 | Lou et al. |
| 7,183,447 B2 | 2/2007 | Pauluth et al. |
| 7,220,783 B2 | 5/2007 | Kawada et al. |
| 7,320,972 B2 | 1/2008 | Martinez et al. |
| 7,351,452 B2 | 4/2008 | Goodby et al. |
| 7,351,728 B2 | 4/2008 | Brooks et al. |
| 7,411,100 B2 | 8/2008 | Pauluth et al. |
| 7,425,281 B2 | 9/2008 | Wand et al. |
| 7,432,375 B2 | 10/2008 | Graczyk et al. |
| 7,521,455 B2 | 4/2009 | Nagase et al. |
| 7,553,496 B2 | 6/2009 | Ambati |
| 7,582,681 B2 | 9/2009 | Baker et al. |
| 7,626,020 B2 | 12/2009 | Butlin et al. |
| 7,645,776 B2 | 1/2010 | Ackermann et al. |
| 7,767,277 B2 | 8/2010 | Lietzau et al. |
| 7,776,922 B2 | 8/2010 | Bruggemeier et al. |
| 7,999,137 B2 | 8/2011 | Kunz et al. |
| 2002/0164769 A1 | 11/2002 | Curtis et al. |
| 2003/0096854 A1 | 5/2003 | Lin et al. |
| 2004/0053889 A1 | 3/2004 | Ebdrup et al. |
| 2004/0115475 A1 | 6/2004 | Hashimoto |
| 2004/0204473 A1 | 10/2004 | Lin et al. |
| 2005/0090383 A1 | 4/2005 | Thiele et al. |
| 2005/0182045 A1 | 8/2005 | Nagase et al. |
| 2005/0250825 A1 | 11/2005 | Brooks et al. |
| 2006/0058527 A1 | 3/2006 | Kirsch et al. |
| 2006/0135423 A1 | 6/2006 | Ambati |
| 2006/0211698 A1 | 9/2006 | Botyanszki et al. |
| 2006/0234981 A1 | 10/2006 | Baker et al. |
| 2006/0293502 A1 | 12/2006 | Dreyer et al. |
| 2007/0010559 A1 | 1/2007 | Christiansen et al. |
| 2007/0015003 A1 | 1/2007 | Hwang et al. |
| 2007/0082877 A1 | 4/2007 | Dunkel et al. |
| 2007/0125712 A1 | 6/2007 | Little et al. |
| 2007/0129544 A1 | 6/2007 | Ackermann et al. |
| 2008/0132716 A1 | 6/2008 | Lietzau et al. |
| 2008/0171786 A1 | 7/2008 | Bruggemeier et al. |
| 2008/0188371 A1 | 8/2008 | Fischer et al. |
| 2008/0242708 A1 | 10/2008 | Dunkel et al. |
| 2008/0280992 A1 | 11/2008 | Kunz et al. |
| 2008/0311075 A1* | 12/2008 | Bachand et al. ............ 424/85.2 |
| 2009/0005321 A1 | 1/2009 | Zimmer et al. |
| 2009/0075995 A1* | 3/2009 | Weinstein et al. ......... 514/232.8 |
| 2010/0063041 A1* | 3/2010 | Moon et al. ................ 514/230.5 |

FOREIGN PATENT DOCUMENTS

| | | |
|---|---|---|
| DE | 4445224 | 6/1996 |
| DE | 19710614 A1 | 9/1998 |
| DE | 19909761 | 10/1999 |
| DE | 19858594 A1 | 6/2000 |
| DE | 10009714 | 9/2001 |
| DE | 102005037925 | 2/2007 |
| DE | 102007009944 | 9/2007 |
| EP | 0440082 A2 | 8/1991 |
| EP | 145441 B1 | 3/1992 |
| EP | 562897 A1 | 9/1993 |
| EP | 614958 A1 | 9/1994 |
| EP | 792883 B1 | 12/1997 |
| EP | 811593 A1 | 12/1997 |
| EP | 811596 A1 | 12/1997 |
| EP | 0987238 | 3/2000 |
| EP | 1160233 | 12/2001 |
| EP | 1236726 | 9/2002 |
| EP | 1388538 | 2/2004 |
| EP | 952149 | 6/2004 |
| EP | 1444981 | 8/2004 |
| FR | 2727416 A1 | 5/1996 |
| FR | 2758329 A1 | 7/1998 |
| GB | 2258232 | 2/1993 |
| GB | 2280181 | 1/1995 |
| GB | 2344817 A | 6/2000 |
| GB | 2410745 | 8/2005 |
| GB | 2424881 | 10/2006 |
| JP | 07145174 | 6/1995 |
| JP | 07165717 A | 6/1995 |
| JP | 07206715 | 8/1995 |
| JP | 08092137 | 4/1996 |
| JP | 9278676 A | 10/1997 |
| JP | 10025261 | 1/1998 |
| JP | 10059882 A | 3/1998 |
| JP | 2000-001463 | 1/2000 |
| JP | 2000035596 A | 2/2000 |
| JP | 2000336045 B | 12/2000 |
| JP | 2002284768 A | 10/2002 |
| JP | 3555325 A | 8/2004 |

(56) References Cited

FOREIGN PATENT DOCUMENTS

| | | | |
|---|---|---|---|
| JP | 2004-292766 | * | 10/2004 |
| JP | 2005-162660 | | 6/2005 |
| JP | 05331107 | A | 12/2005 |
| JP | 2006-290786 | | 10/2006 |
| JP | 2007-308483 | | 11/2007 |
| JP | 08040953 | A | 2/2008 |
| JP | 09030996 | A | 2/2009 |
| PL | 167141 | | 7/1995 |
| WO | WO-92/19707 A1 | | 11/1992 |
| WO | WO 94/15920 | | 7/1994 |
| WO | WO-95/12655 A1 | | 5/1995 |
| WO | WO-95/35300 | | 12/1995 |
| WO | WO-96/20689 A2 | | 7/1996 |
| WO | WO 97/06124 | | 2/1997 |
| WO | WO 97/13537 | | 4/1997 |
| WO | WO 97/33705 | | 10/1997 |
| WO | WO 98/24396 | | 6/1998 |
| WO | WO-98/28663 A1 | | 7/1998 |
| WO | WO-98/31688 A1 | | 7/1998 |
| WO | WO-98/35924 A1 | | 8/1998 |
| WO | WO 99/34850 | | 7/1999 |
| WO | WO-00/04111 A2 | | 1/2000 |
| WO | WO 00/20466 | | 4/2000 |
| WO | WO-00/42213 | | 7/2000 |
| WO | WO 01/21606 | | 3/2001 |
| WO | WO 02/14381 | | 2/2002 |
| WO | WO-02/57273 | | 7/2002 |
| WO | WO-02/059155 | | 8/2002 |
| WO | WO-02/085916 | | 10/2002 |
| WO | WO-03/045228 | | 6/2003 |
| WO | WO 03/059903 | | 7/2003 |
| WO | WO 03/064484 | | 8/2003 |
| WO | WO-03/105860 | | 12/2003 |
| WO | WO 2004/044169 A2 | | 5/2004 |
| WO | WO 2004/080989 | | 9/2004 |
| WO | WO-2004/081008 | | 9/2004 |
| WO | WO-2005/004799 A2 | | 1/2005 |
| WO | WO-2005/013892 | | 2/2005 |
| WO | WO-2005/037227 A2 | | 4/2005 |
| WO | WO 2005/041904 | | 5/2005 |
| WO | WO-2005/080403 A2 | | 9/2005 |
| WO | WO-2006/007384 | | 1/2006 |
| WO | WO 2006/024389 | | 3/2006 |
| WO | WO 2006/038100 | * | 4/2006 |
| WO | WO-2006/050053 | | 5/2006 |
| WO | WO-2006/050054 | | 5/2006 |
| WO | WO-2006/050236 | | 5/2006 |
| WO | WO-2006/053250 | | 5/2006 |
| WO | WO-2006/089067 | | 8/2006 |
| WO | WO 2006/091799 | | 8/2006 |
| WO | WO-2006/099261 | | 9/2006 |
| WO | WO 2006/122186 | | 11/2006 |
| WO | WO 2006/124713 | | 11/2006 |
| WO | WO-2006/133559 A1 | | 12/2006 |
| WO | WO-2007/028104 | | 3/2007 |
| WO | WO-2007/031512 A2 | | 3/2007 |
| WO | WO-2007/064809 A2 | | 6/2007 |
| WO | WO-2007/076875 | | 7/2007 |
| WO | WO-2007/078340 | | 7/2007 |
| WO | WO-2007/088148 A1 | | 8/2007 |
| WO | WO-2007/095638 | | 8/2007 |
| WO | WO 2007/104783 | | 9/2007 |
| WO | WO 2007/118318 | | 10/2007 |
| WO | WO-2007/146965 | | 12/2007 |
| WO | WO-2008/002674 | | 1/2008 |
| WO | WO 2008/014497 | | 1/2008 |
| WO | WO 2008/019743 | | 2/2008 |
| WO | WO-2008/020920 | | 2/2008 |
| WO | WO 2008/039829 | | 4/2008 |
| WO | WO-2008/047229 | | 4/2008 |
| WO | WO 2008/063300 A2 | | 5/2008 |
| WO | WO 2008/090780 | | 7/2008 |
| WO | WO 2008/105286 | | 9/2008 |
| WO | WO-2008/107480 | | 9/2008 |
| WO | WO 2009/011904 A1 | | 1/2009 |
| WO | WO-2009/126691 A1 | | 10/2009 |
| WO | WO-2009/136646 A1 | | 11/2009 |
| WO | WO-2009/138176 A1 | | 11/2009 |

OTHER PUBLICATIONS

CAPlus entry for US 20090075995. Accession No. 2009:336377, Document Number: 150:306630. Accessed via STN on Jan. 4, 2013.*

Machine translation of JP 2004-292766. Accessed Apr. 23, 2013. Obtained from <http://dossier.ipdl.inpit.go.jp/text_trans.html>.*

Adamo et al., "Mechanism of the Palladium-Catalyzed Homocoupling of Arylboronic Acids: Key Involvement of a Palladium Peroxo Complex," *JACS* 128:6829-6836 (2006).

Bellina et al., "Palladium Catalysts for the Suzuki Cross-Coupling Reaction: An Overview of Recent Advances," *Syn.* 2419-2440 (2004).

Berge et al., "Pharmaceutical Salts," *J. Pharm. Sci.* 66(1):1-19 (1977).

Bickerdike et al., "The Influence of 5-Hydroxytryptamine Re-uptake Blockade on CCK Receptor Antagonist Effects in the Rat Elevated Zero-Maze," *Eur. J. Pharm.* 271:403-411 (1994).

Bracey et al., "Structural Adaptations in Membrane Enzyme That Terminates Endocannabinoid Signaling," *Science* 298:1793-1796 (2002).

Cravatt et al., "Supersensitivity to Anandamide and Enhanced Endogenous Cannabinoid Signaling in Mice Lacking Fatty Acid Amide Hydrolase," *Proc. Natl. Acad. Sci. U.S.A.* 98:9371-9376 (2001).

Cravatt et al., "Functional disassociation of the central and peripheral fatty acid amide signaling systems," *Proc. Natl. Acad. Sci. U.S.A.* 101(29):10821-10826 (2004).

Helble, Joseph. "Determination of Boronic Acids Derivatized with Azomethine and HPLC Separation with Visible Wavelength Detection." Mar. 6, 2009. Pittcon Analytical Chemistry Conference, Chicago, IL, Mar. 10, 2009.

Helble, Joseph. "Determination of Boronic Acids Derivatized with Azomethine and HPLC Separation with Visible Wavelength Detection." American Association of Pharmaceutical Scientists National Convention, Los Angeles, Nov. 9, 2009.

Insel et al., "Rat Pup Ultrasonic Calls: Possible Mediation by the Benzodiazepine Receptor Complex," *Pharmacol. Biochem. Behav.* 24:1263-1267 (1986).

Jiang et al., "Use of in Situ Isopropoxide Protection in the Metal-Halogen Exchange of Arylboronates," *J. Org. Chem.* 72:6618-6620 (2007).

Jun et al., "Determination of Boron with Chromotropic Acid by High-performance Liquid Chromatography," *Analyst* 113:1631-1634 (1988).

Kedia et al., "Reaction Progress Analysis: Powerful Tool for Understanding Suzuki-Miyura Reaction and Control of Polychlorobiphenyl Impurity," *Org. Proc. Res. Dev.* 13:420-428 (2009).

Koehler et al., "2-Phenylethaneboronic Acid, a Possible Transition-State Analog for Chymotrypsin," *Biochemistry* 10:2477 (1971).

Lambert and Fowler, "The endocannabinoid system: Drug targets, lead compounds, and potential therapeutic applications," *J. Med. Chem.* 48. Med. Chem. 48(16):5059-5087 (2005).

Li et al., "An Improved Protocol for the Preparation of 3-Pyridyl- and Some Arylboronic Acids," *J. Org. Chem.* 67:5394-5397 (2002).

Lynch et al., "Effects of Neuropeptide Y on Ingestion of Flavored Solutions in Nondeprived Rats," *Physiol. Behav.* 54:877-880 (1993).

Miczek, et al., "Aggression, Anxiety and Vocalizations in Animals: GABAa and 5-HT Anxiolytics," *Psychopharmacology* 121:38-56 (1995).

Miller et al., "Suppression of a Palladium-Mediated Homocoupling in a Suzuki Cross-Coupling Reaction. Development of an Impurity Control Strategy Supporting Synthesis of LY451395," *Org. Proc. Res. Dev.* 11:359-364 (2007).

Miyaura et al., "Palladium-Catalyzed Cross—Coupling Reactions of Organoboron Compounds," *Chem. Rev.* 95:2457-2483 (1995).

(56) References Cited

OTHER PUBLICATIONS

Negishi et al., "Formation of Carbon-Carbon and Carbon-Heteroatom Bonds via Organoboranes and Organoborates," *Organic Reactions* 33:1-78 (1985).
Pacher et al., "The endocannabinoid system as an emerging target of pharmacotherapy," *Pharmacol. Rev.* 58(3):389-462 (2006).
Pillarisetti et al., "Pain and beyond: fatty acide amides and fatty acide amide hydrolase inhibitors in cardiovascular and metabolic diseases," *Drug Discov.* 1-14 (2009).
Piomelli et al., "Pharmacological Profile of the Selective FAAH Inhibitor KDS-4103 (URB597)," *CNS Drug Rev.* 12(1):21-38 (2006).
Porsolt et al., "Depression: A New Animal Model Sensitive to Antidepressant Treatments," *Nature* 266:730-732 (1977).
Quistad et al., "Fatty Acid Amide Hydrolase Inhibition by Neurotoxic Organophosphous Pesticides," *Toxicol. Appl. Pharmacol.* 173(1):48-55 (2001).
Ramarao et al., "A Fluorescence-Based Assay for Fatty Acid Amide Hydrolase Compatible with High-Throughput Screening," *Anal. Biochem.* 343:143-151 (2005).
RN 874288-40-1 (Entered STN: Feb. 15, 2006).
RN 874289-19-7 (Entered STN: Feb. 15, 2006).
RN 874290-59-2 (Entered STN: Feb. 15, 2006).
Rock et al., "An Anti-Fungal Agent Inhibits an Aminoacyl-tRNA Synthetase by Trapping tRNA in the Editing Site," *Science* 316:1759-1761(2007).
Santucci et al., "Some Bromine-containing and Sulfur-containing Aromatic Boronic Acids," *JACS* 80:193-196 (1958).
Schlosburg et al., "Targeting Fatty Acide Amide Hydrolase (FAAH) to Treat Pain and Inflammation," *The AAOS J.* 11(1):39-44 (2009).
Shepherd et al., "Behavioural and Pharmacological Characterisation of the Elevated "Zero-Maze" as an Animal Model of Anxiety," *Psychopharmacology* 116:56-64 (1994).
Snyder et al., "Aryl Boronic Acids. II. Aryl Boronic Anhydrides and Their Amine Complexes," *JACS* 80:3611 (1958).
Soloway, A.H., "Correlation of drug penetration of brain and chemical structure," *Science* 128(3338):1572-1574 (1958).
Steru et al., "The Tail Suspension Test: A New Method for Screening Antidepressants in Mice," *Psychopharmacology* 85:367-370 (1985).
Uehara et al., "Determination of Trace Amounts of Boron in Steel by Reversed-Phase High-Performance Liquid Chromatography with Azomethine-H as a Precolumn Derivatization Agent," *Anal. Sci.* 17:1421-1424 (2001).
Wang et al., "High-Throughput Screening for the Discovery of Inhibitors of Fatty Acid Amide Hydrolase Using a Microsome-Based Fluorescent Assay," *J. Biomol. Screen.* 11:519-527(2006).
Wang et al., "Preparation of Unsymmetrical Biaryls by Pd(II)-Catalyzed Cross-Coupling of Aryl Iodides," *Org. Lett.* 11:1079-1082 (2009).
Wilen et al., "Strategies in Optical Resolution," *Tetrahedron* 33:2725-2736 (1977).
Willner, "Validity, Reliability and Utility of the Chronic Mild Stress Model of Depression: a 10-year Review and Evaluation," *Psychopharmacology* 134:319-329 (1997).
Winslow et al., "Infant Rat Separation is a Sensitive Test for Novel Anxiolyitics," *Prog. Neuro-Psychopharmacol. & Biol. Psychiat.* 15:745-757 (1991).
Patricelli et al., "Comparative characterization of a wild type and transmembrane domain-deleted fatty acid amide hydrolase: identification of the transmembrane domain as a site for oligomerization," *Biochemistry* 37(43):15177-15187 (1998).
Maurelli et al, "Two novel classes of neuroactive fatty acid amides are substrates for mouse neuroblastoma 'anandamide amidohydrolase'," *FEBS Lett.* 377(1):82-86 (1995).
Hillard et al., "Characterization of the kinetics and distribution of N-arachidonylethanolamine (anandamide) hydrolysis by rat brain," *Biochim. Biophys. Acta.* 1257-(3):249-256 (1995).
Giang and Cravatt, "Molecular characterization of human and mouse fatty acid amide hydrolases," *Proc. Natl. Acad. Sci. U.S.A.* 94(6):2238-2242 (1997).

Zhong et al., "Suzuki coupling of aryl organics on diamond," *Chem. Mater.* 20(9):3137-3144 (2008).
Vashchenko et al., "Palladium-catalyzed Suzuki Cross-coupling Reactions in a Microemulsion," *Tetrahedron Lett.* 49(9):1445-1449 (2008).
Prasad et al., "Synthesis of Novel 3-Aryl-N-Methyl-1,2,5,6-Tetrahydropyridine Derivatives by Suzuki coupling: As Acetyl Cholinesterase Inhibitors," *Open Med. Chem. J.* 1:4-10 (2007).
Glendenning et al., "The synthesis and mesomorphic properties of 4,4"-dialkyl-2,2',3- and 2,2',3'-trifluoro-1,1':4',1"-terphenyls for high dielectric biaxiality ferroelectric liquid crystal mixtures," *J. Chem. Soc. Perkin Trans. 2* 27-34 (2000).
Glendenning et al., "The synthesis and mesomorphic properties of 2,2',3-tri- and 2,2',3,3'-tetra-fluoro-1,1':4',1-terphenyls for high dielectric biaxiality ferroelectric liquid crystal mixtures," *J. Chem. Soc. Perkin Trans. 2* (3):481-492 (1999)
Dong et al., "The synthesis and transition temperatures of some fluorinated terphenyls with chiral and alkenyl terminal chains," *Ferroelectrics* (180):245-257 (1996).
Hird et al., "Cyclohexenyl triflates and arylboronic acids in palladium-catalysed cross-couplings. Synthesis and transition temperatures of some fluro-substituted biphenylylcyclohexenes," *J. Mater. Chem.* (5):2239-2245 (1995).
Hird et al., "The relationship between molecular structure and mesomorphic properties of 2,2'- and 3,2'-difluoroterphenyls synthesized by palladium-catalysed cross-couplings," *Liquid Crystals* 18(1):1-11 (1995).
Gray et al., "The synthesis and transition-temperatures of some 4,4"-dialkyl-1,1'- 4',1"-terphenyl and 4,4"-alkoxyalkyl-1,1'- 4',1"-terphenyl with 2,3-difluoro or 2',3'-difluoro substituents and of their biphenyl analogs," *J. Chem. Soc.-Perkin Trans. 2* 2041-2053 (1989).
Wermuth, C.G. (ed.), "Chapter 13: Molecular Variations Based on Isosteric Replacements", The Practice of Medicinal Chemistry, pp. 204-237, Academic Press Ltd., Copyright (1996).
Wei et al., "A second fatty acid amide hydrolase with variable distribution among placental mammals," *J. Biol. Chem.* 281(48):36569-36578 (2006).
Drake et al., "Characterizing high-affinity antigen/antibody complexes by kinetic- and equilibrium-based methods," *Anal. Biochem.* 328(1):35-43 (2004).
Deutsch, "Design of On-Target FAAH Inhibitors," *Chem. Biol.* 12(11):1157-1158 (2005).
Huang et al., "identification of a new class of molecules, the arachidonyl amino acids, and characterization of one member that inhibits pain," *J. Biol. Chem.* 276(46):42639-42644 (2001).
Karbarz, et al., "Biochemical and Biological Properties of 4-(3-phenyl-[1,2,4]thiadiazol-5-y1)-piperazine-1-carboxylic acid phenylamide, a Mechanism-Based Inhibitor of Fatty Acid Amide Hydrolase," *Anesthesia & Analgesia* 108, 316-329 (2009).
Kathuria et al., "Modulation of anxiety through blockade of anandamide hydrolysis," *Nat. Med.* 9(1):76-81 (2003).
McPartland et al,. "A shifted repertoire of endocannabinoid genes in the zebrafish (Danio rerio)," *Mol. Genet. Genomics* 277:555-570 (2007).
Mendelson and Basile, "The Hypnotic Actions of the Fatty Acid Amide, Oleamide," Neuropsychopharmacology 25(5 Suppl):S36-S39 (2001).
Saghetelian et al., "A FAAH-regulated class of N-acyl taurines that activates TRP ion channels," *Biochemistry* 45(30):9007-9015 (2006).
Walker et al., "Pain modulation by release of the endogenous cannabinoid anandamide," *Proc. Natl. Acad. Sci. U. S. A.* 96(21):12198-203 (1999).
Zhang et al., "Studies on antitumor drugs. II. Synthesis of diarylborinic .alpha.-amino acid anhydrides and diarylborinic aminoethyl esters," XP002663674, Retrieved from STN Database Accession No. 1983:17023.
Asano et al., Design, Synthesis, and Biological Evaluation of Aminoboronic Acids as Growth-Factor Receptor Inhibitors of EGFR and VEGFR-1 Tyrosine Kinases, ChemBioChem, (2004), 5, pp. 483-490.

(56) References Cited

OTHER PUBLICATIONS

Buzzoni et al., Aza-boronic Acids as Non- β-Lactam Inhibitors of AmpC- β-Lactamase, Bioorganic & Medicinal Chemistry Letters, (2004), pp. 3979-3983, 14.
Carter et al., The Inhibition of Rat Liver Chromatin Potease by Congeners of the Phenyboronic Acids, Biochimica et Biophysica Acta, 484, (1977), pp. 103-108.
CAS File Registry for [4-[2-(2,6-difluoro-4-propylphenyl)ethyl)]-2,6-difluorophenyl]-boronic acid, published Mar. 3, 2003 in Japanese patent application No. JP10059882.
CAS File Registry, Registry No. 874288-40-1, published Feb. 15, 2006.
CAS File Registry, Registry No. 874289-19-7, published Feb. 15, 2006.
CAS File Registry, Registry No. 874290-59-2, published Feb. 15, 2006.
Caujolle et al., Arylboronic Acid Metabolism in the Rat, Sciences Naturelles, (1970), 270(11), pp. 1529-31, including English language abstract.
Caujolle et al., Etude comparee du pouvoir renforcateur des organoboriques a l'egard des hypnotiques//potentiation of hypnotics by organoboron derivatives. Agressologie, 1969, 51-54, 10(1).
Caujolle et al., The effect of organoboron derivatives on cardiovascular and ventilatory manifestations of electroshock. Agressologie: Revue Internationale De Physio-Biologie et de Pharmacologie Appliquees aux Effets de l'Agression, 1967, 425-432, 8(5).
Ebdrup et al., Structure-Activity Relationship for Aryl and Heteroaryl Boronic Acid Inhibitors of Hormone-Sensitive Lipase, Bioorganic & Medicinal Chemistry, (2005), vol. 13, Issue 6, pp. 2305-2312.
European Office Action for EP 07870774.2 dated Sep. 11, 2009.
Frings et al., Salt Excretion by Nasal Gland of Laysan and Black-Footed Albatrosses, Science, (1958), pp. 1572-1574, vol. 128.
Gavezzotti, Are Crystal Structures Predictable? Accounts of Chemical Research, 1994 27, 309-314.
Innocenti et al., Carbonic Anhydrase Inhibitors. Inhibition of Fungal β-Carbonic Anhydrases from Candida Albicans and Cryptococcus Neoformans with Boronic Acids, Bioorganic & Medicinal Chemistry Letters, (2009), pp. 1-4.
International Search Report for International Application No. PCT/US07/021626 published as WO2008/063300 on May 29, 2008.
International Search Report for International Application No. PCT/US2009/039872 published as WO2009/126691 on Oct. 15, 2009.
International Search Report for International Patent Application PCT/US2010/030276 mailed from the International Searching Authority on Jul. 7, 2010.
Jauhiainen et al., Aromatic Boronic Acids as Probes of the Catalytic Site of Human Plasma Lecithin-Cholesterol Acyltransferase, Biochimica et Biophysica Acta 918, (1987), pp. 175-188.
Kong et al., Structure-Based Discovery of a Boronic Acid Bioisostere of Combretastatin A-4, Chemistry & Biology, (2005), vol. 12, 1007-1014.
Labar et al., Fatty Acid Amide Hydrolase: From Characterization to Therapeutics, Chemistry & Biodiversity, (2007), 4, pp. 1882-1902.
Lienhard et al., 2 Phenylethaneboronic Acid, A Possible Transition-State Analog for Chymotrypsin, Biochemistry, (1971), 10(13), 2477-2483.
Martin et al., Inhibition of the RTEM-1 β-Lactamase by Boronic Acids, Bioorganic & Medicinal Chemistry Letters, (1994), pp. 1229-1234, vol. 4.
McKinney, et al., "Structure and Function of Fatty Acid Amide Hydrolase," Ann. Rev. Biochem. 2005, vol. 74, p. 411-432.
Miller et al., "The hypolipidemic and anti-inflammatory activity of boronated aromatic amino acids in CF1 male mice" Metal-Based Drugs, 1999, 337-344, 6(6), ISSN: 0793-0291.
Minkkila et al., "Discovery of Boronic Acids as Novel and Potent Inhibitors of Fatty Acid Amide Hydrolase," J. Med. Chem. 2008, 51, 7057-7060.
Morandi et al., Nanomolar Inhibitors of AmpC β-Lactamase, J. Am. Chem. Soc., (2003), pp. 685-695, 125.
Nakamura et al., Synthesis and Biological Evaluation of Boronic Acid Containing cis-Stilbenes as Apoptotic Tubulin Polymerization Inhibitors, ChemMedChem, (2006), pp. 729-740, 1.
Philipp et al., Inhibition of Serine Proteases by Arylboronic Acids, Proceedings of the National Academy of Sciences, (1971), pp. 478-480, vol. 68, No. 2.
Seufer-Wasserthal et al., Probing the Specificity of the S1 Binding Site of Subtilisin Carlsberg with Boronic Acids, Bioorganic & Medicinal Chemistry, (1994), pp. 35-48, vol. 2, No. 1.
Simpelkamp et al., Borinic Acid Inhibitors as Probes of the Factors Involved in Binding at the Active Sites of Subtilisin Carlsberg and α-Chymotrypsin, Bioorganic & Medicinal Chemistry Letters, (1994) pp. 1391-1394, vol. 2, No. 11.
Smoum et al., A Study of the Effect on Nucleophilic Hydrolytic Activity of Pancreatic Elastase, Trypsin, Chymotrypsin, and Leucine Aminopeptidase by Boronic Acids in the Presence of Arabinogalactan: A Subsequent Study on the Hydrolytic Activity of Chymotrypsin by Boronic Acids in the Presence of Mono-, Di-, and Trisaccharides, Bioorganic Chemistry, (2003), pp. 464-474, 31.
Smoum et al., Noncovalent Inhibition of the Serine Proteases, α-chymotrypsin and Trypsin by Trifluoro(organo)borates, Org. Biomol. Chem., (2005), pp. 941-944, 3.
Suzuki et al., Design, Synthesis, and Biological Activity of Boronic Acid-Based Histone Deacetylase Inhibitors, J. Med. Chem., (2009). 52(9), 2909-2922.
Tanaka et al., "Suppression of arthritis by the inhibitors of dipeptidyl peptidase IV" International Journal of Immunopharmacology, 1997, 15-24, ISSN: 0192-0561.
Tondi et al., Structure-based design and in-parallel synthesis of inhibitors of AmpC β-lactamase, Chemistry & Biology (2001) pp. 593-610, Aug. 2006.
Vandervoorde, "Overview of the Chemical Families of Fatty Acid Amide Hydrolase and Monoacylglycerol Lipase Inhibitors," Current Topics in Medicinal Chemistry 2008, 8, 247-267.
Vippagunta et al, Crystalline Solids. Advanced Drug Delivery Review 2001, 48, 3-26.
Weston et al., Structure-Based Enhancement of Boronic Acid-Based Inhibitors of AmpC β-Lactamase, J.Med.Chem, (1998), pp. 4577-4586, 41.
Winum et al., "Carbonic anhydrase inhibitors. Synthesis and inhibition of cytosolic/tumor-associated carbonic anhydrase isozymes I, II, and IX with boron-containing sulfonamides, sulfamides, and sulfamates: Toward agents for boron neutron capture therapy of hypoxic tumors" Bioorganic & Medicinal Chemistry Letters 2005, 15(13), 3302-3306.
Written Opinion for International Application No. PCT/US07/021626 published as WO2008/063300 on May 29, 2008.
Written Opinion for International Patent Application PCT/US2010/030276 mailed from the International Searching Authority on Jul. 7, 2010.
Yang et al., Boronic Acid Compounds as Potential Pharmaceutical Agents, Medicinal.
Research Reviews, (2003), pp. 346-368, vol. 23, No. 3.

\* cited by examiner

SEQUENCE LISTING

```
<160> NUMBER OF SEQ ID NOS: 1

<210> SEQ ID NO 1
<211> LENGTH: 579
<212> TYPE: PRT
<213> ORGANISM: Homo sapiens

<400> SEQUENCE: 1

Met Val Gln Tyr Glu Leu Trp Ala Ala Leu Pro Gly Ala Ser Gly Val
1               5                   10                  15

Ala Leu Ala Cys Cys Phe Val Ala Ala Val Ala Leu Arg Trp Ser
            20                  25                  30

Gly Arg Arg Thr Ala Arg Gly Ala Val Val Arg Ala Arg Gln Arg Gln
        35                  40                  45

Arg Ala Gly Leu Glu Asn Met Asp Arg Ala Ala Gln Arg Phe Arg Leu
    50                  55                  60
```

```
Gln Asn Pro Asp Leu Asp Ser Glu Ala Leu Leu Ala Leu Pro Leu Pro
 65                  70                  75                  80

Gln Leu Val Gln Lys Leu His Ser Arg Glu Leu Ala Pro Glu Ala Val
             85                  90                  95

Leu Phe Thr Tyr Val Gly Lys Ala Trp Glu Val Asn Lys Gly Thr Asn
            100                 105                 110

Cys Val Thr Ser Tyr Leu Ala Asp Cys Glu Thr Gln Leu Ser Gln Ala
            115                 120                 125

Pro Arg Gln Gly Leu Leu Tyr Gly Val Pro Val Ser Leu Lys Glu Cys
            130                 135                 140

Phe Thr Tyr Lys Gly Gln Asp Ser Thr Leu Gly Leu Ser Leu Asn Glu
145                 150                 155                 160

Gly Val Pro Ala Glu Cys Asp Ser Val Val His Val Leu Lys Leu
                165                 170                 175

Gln Gly Ala Val Pro Phe Val His Thr Asn Val Pro Gln Ser Met Phe
            180                 185                 190

Ser Tyr Asp Cys Ser Asn Pro Leu Phe Gly Gln Thr Val Asn Pro Trp
        195                 200                 205

Lys Ser Ser Lys Ser Pro Gly Gly Ser Gly Gly Glu Gly Ala Leu
210                 215                 220

Ile Gly Ser Gly Gly Ser Pro Leu Gly Leu Gly Thr Asp Ile Gly Gly
225                 230                 235                 240

Ser Ile Arg Phe Pro Ser Ser Phe Cys Gly Ile Cys Gly Leu Lys Pro
                245                 250                 255

Thr Gly Asn Arg Leu Ser Lys Ser Gly Leu Lys Gly Cys Val Tyr Gly
            260                 265                 270

Gln Glu Ala Val Arg Leu Ser Val Gly Pro Met Ala Arg Asp Val Glu
            275                 280                 285

Ser Leu Ala Leu Cys Leu Arg Ala Leu Leu Cys Glu Asp Met Phe Arg
290                 295                 300

Leu Asp Pro Thr Val Pro Pro Leu Pro Phe Arg Glu Glu Val Tyr Thr
305                 310                 315                 320

Ser Ser Gln Pro Leu Arg Val Gly Tyr Tyr Glu Thr Asp Asn Tyr Thr
            325                 330                 335

Met Pro Ser Pro Ala Met Arg Arg Ala Val Leu Glu Thr Lys Gln Ser
            340                 345                 350

Leu Glu Ala Ala Gly His Thr Leu Val Pro Phe Leu Pro Ser Asn Ile
            355                 360                 365

Pro His Ala Leu Glu Thr Leu Ser Thr Gly Gly Leu Phe Ser Asp Gly
            370                 375                 380

Gly His Thr Phe Leu Gln Asn Phe Lys Gly Asp Phe Val Asp Pro Cys
385                 390                 395                 400

Leu Gly Asp Leu Val Ser Ile Leu Lys Leu Pro Gln Trp Leu Lys Gly
                405                 410                 415

Leu Leu Ala Phe Leu Val Lys Pro Leu Pro Arg Leu Ser Ala Phe
            420                 425                 430

Leu Ser Asn Met Lys Ser Arg Ser Ala Gly Lys Leu Trp Glu Leu Gln
            435                 440                 445

His Glu Ile Glu Val Tyr Arg Lys Thr Val Ile Ala Gln Trp Arg Ala
        450                 455                 460

Leu Asp Leu Asp Val Val Leu Thr Pro Met Leu Ala Pro Ala Leu Asp
465                 470                 475                 480
```

```
Leu Asn Ala Pro Gly Arg Ala Thr Gly Ala Val Ser Tyr Thr Met Leu
            485                 490                 495
Tyr Asn Cys Leu Asp Phe Pro Ala Gly Val Val Pro Val Thr Thr Val
            500                 505                 510
Thr Ala Glu Asp Glu Ala Gln Met Glu His Tyr Arg Gly Tyr Phe Gly
            515                 520                 525
Asp Ile Trp Asp Lys Met Leu Gln Lys Gly Met Lys Lys Ser Val Gly
        530                 535                 540
Leu Pro Val Ala Val Gln Cys Val Ala Leu Pro Trp Gln Glu Glu Leu
545                 550                 555                 560
Cys Leu Arg Phe Met Arg Glu Val Glu Arg Leu Met Thr Pro Glu Lys
                565                 570                 575
Gln Ser Ser
```

INHIBITORS OF FATTY ACID AMIDE HYDROLASE

PRIORITY INFORMATION

This application is a Continuation of International Application No. PCT/US2009/039872 filed Apr. 8, 2009, which claims priority to U.S. provisional patent application Ser. No. 61/043,686, filed Apr. 9, 2008, the entirety of each of which is hereby incorporated herein by reference.

The present specification is being filed with a computer readable form (CRF) copy of the Sequence Listing. The CRF entitled 12928-002-999_SeqListing.txt, which was created on Feb. 24, 2011 and is 5,349 bytes in size, is identical to the paper copy of the Sequence Listing and is incorporated herein by reference in its entirety.

BACKGROUND

Fatty acid amide hydrolase (FAAH), also referred to as oleamide hydrolase and anandamide amidohydrolase, is an integral membrane protein that degrades fatty acid primary amides and ethanolamides, including oleamide and anandamide. FAAH degrades neuromodulating fatty acid amides at their sites of action and is intimately involved in their regulation.

FAAH has been demonstrated to be involved in a number of biological processes and its inhibition has been shown to be effective in treating a variety of conditions. For example, inhibiting FAAH has been shown to be useful in treating chronic pain, acute pain, neuropathic pain, anxiety, depression, feeding behaviors, movement disorders, glaucoma, neuroprotection and cardiovascular disease. However, current inhibitors of FAAH lack the target selectivity, biological activity and/or bioavailability needed for in vivo studies and therapeutic use. Thus, to date, the therapeutic potential of FAAH inhibitors remains essentially unexplored.

SUMMARY

Compounds described herein, and pharmaceutically acceptable compositions thereof, are effective inhibitors of fatty acid amide hydrolase (FAAH). Such compounds are encompassed by formula (I):

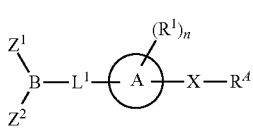
(I)

or pharmaceutically acceptable salts or prodrugs thereof, wherein $Z^1$, $Z^2$, $L^1$, X, Ring A, $R^1$, $R^A$ and n are as defined herein.

In certain embodiments, Ring A is a $C_{3-10}$ carbocyclyl or $C_{6-10}$ aryl group. In some embodiments, Ring A is phenyl. In other embodiments, Ring A is a 3-10 membered heterocyclyl group or a 5-10 membered heteroaryl group. In some embodiments, Ring A is monocyclic, while in other embodiments Ring A is bicyclic.

In certain embodiments, $R^A$ is Ring B, i.e., providing compounds which are encompassed by formula (II):

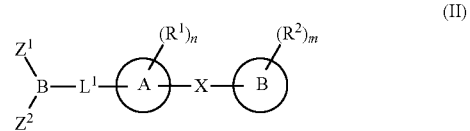
(II)

or pharmaceutically acceptable salts or prodrugs thereof, wherein $Z^1$, $Z^2$, $L^1$, X, Ring A, Ring B, $R^1$, $R^2$, n and m are as defined herein. In certain embodiments, Ring B is a 3-10 membered heterocyclyl group or a 5-10 membered heteroaryl group. In some embodiments, Ring B is monocyclic, while in other embodiments Ring B is bicyclic.

Also provided are methods for treating conditions associated with excessive FAAH activity by administering a therapeutically effective amount of a compound provided herein, or a pharmaceutical composition thereof, to a patient in need thereof.

Also provided are methods for inhibiting FAAH in a patient by administering a therapeutically effective amount of a compound provided herein, or a pharmaceutically acceptable composition thereof, to a patient in need thereof.

Sequence Identification Numbers

SEQ ID NO. 1: *Homo Sapiens* FAAH Amino Acid Sequence:

```
MVQYELWAALPGASGVALACCFVAAAVALRWSGRRTARGAVVRARQRQR
AGLENMDRAAQRFRLQNPDLDSEALLALPLPQLVQKLHSRELAPEAVLF
TYVGKAWEVNKGTNCVTSYLADCETQLSQAPRQGLLYGVPVSLKECFTY
VKGQDSTLGLSLNEGVPAECDSVVVHLKLQGAVPFVHTNVPQSMFSYDC
SNPLFGQTVNPWKSSKSPGGSSGGEGALIGSGGSPLGLGTDIGGSIRFP
SSFCGICGLKPTGNRLSKSGLKGCVYGQEAVRLSVGPMARDVESLALCL
RALLCEDMFRLDPTVPPLPFREEVYTSSQPLRVGYYETDNYTMPSPAMR
RAVLETKQSLEAAGHTLVPFLPSNIPHALETLSTGGLFSDGGHTFLQNF
KGDFVDPCLGDLVSILKLPQWLKGLLAFLVKPLLPRLSAFLSNMKSRSA
GKLWELQHEIEVYRKTVIAQWRALDLDVVLTPMLAPALDLNAPGRATGA
VSYTMLYNCLDFPAGVVPVTTVTAEDEAQMEHYRGYFGDIWDKMLQKGM
KKSVGLPVAVQCVALPWQEELCLRFMREVERLMTPEKQSS
```

DETAILED DESCRIPTION

1. General Description of Compounds

Provided are inhibitors of FAAH that contain at least one Lewis acidic boron head group, such as, for example, a boronic acid, boronic ester, borinic acid or borinic ester head group. Such compounds include compounds of formula (I):

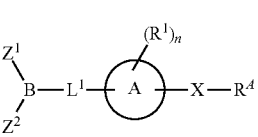
(I)

or a pharmaceutically acceptable salt or prodrug thereof;

wherein:

(i) $Z^1$ is —OH or —OR$^3$; and $Z^2$ is —OH, —OR$^4$, an optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl group;

(ii) $Z^1$ and $Z^2$ taken together with the boron atom to which they are bound, form a 5- to 8-membered ring having at least one O, S, N or NR$^5$ atom directly bonded to the boron atom;

(iii) $Z^1$ is —OH or —OR$^3$; and $Z^2$ and Ring A taken together form an optionally substituted 5- to 7-membered ring;

$L^1$ is a covalent bond, an optionally substituted straight or branched $C_{1-6}$ alkylene, or an optionally substituted straight or branched $C_{2-6}$ alkenylene moiety;

Ring A is optionally substituted $C_{3-10}$ carbocyclyl, optionally substituted 3-10 membered heterocyclyl, optionally substituted $C_{6-10}$ aryl, or optionally substituted 5-10 membered heteroaryl;

X is a covalent bond, —O—, —N=N—, —C=N—, —NR$^6$—, —C(NR$^6$)—, —S—, —C(O)—, —S(O)—, —S(O)$_2$—, or optionally substituted $C_{1-6}$ alkylene, wherein one, two or three methylene units of the $C_{1-6}$ alkylene are optionally and independently replaced with one or more groups selected from —O—, —N=N—, —C=N—, —NR$^6$—, —C(NR$^6$)—, —S—, —C(O)—, —S(O)—, and —S(O)$_2$—;

$R^A$ is hydrogen, halogen, —OR$^7$, —CF$_3$, —CN, —NO$_2$, —SO$_2$R$^7$, —SOR$^7$, —C(O)R$^7$, —CO$_2$R$^7$, —C(O)N(R$^7$)$_2$, —N$_3$, —N$_2$R$^7$, —N(R$^7$)$_2$, or Ring B having formula:

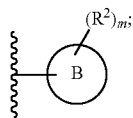

wherein Ring B is optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of $R^1$ is, independently, halogen, —OR$^8$, —CF$_3$, —CN, —NO$_2$, —SO$_2$R$^8$, —SOR$^8$, —C(O)R$^8$, —CO$_2$R$^8$, —C(O)N(R$^8$)$_2$, —N$_3$, —N$_2$R$^8$, —N(R$^8$)$_2$, —B(OH$_2$), optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of $R^2$ is, independently, halogen, —OR$^9$, —CF$_3$, —CN, —NO$_2$, —SO$_2$R$^9$, —SOR$^9$, —C(O)R$^9$, —CO$_2$R$^9$, —C(O)N(R$^9$)$_2$, —N$_3$, —N$_2$R$^9$, —N(R$^9$)$_2$, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of $R^3$ and $R^4$ is, independently, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of $R^5$, $R^6$, $R^7$, $R^8$, $R^9$, and $R^{10}$ is, independently, hydrogen, —SO$_2$R$^{11}$, —SOR$^{11}$, —C(O)R$^{11}$, —CO$_2$R$^{11}$, —C(O)N(R$^{11}$)$_2$, —C(O)NH(R$^{11}$), —C(O)NH$_2$, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of $R^{11}$ is, independently, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

n is 0, 1, 2 or 3; and m is 0, 1, 2, 3, 4 or 5.

In certain embodiments, $R^A$ is Ring B, i.e., compounds encompassed by formula (II):

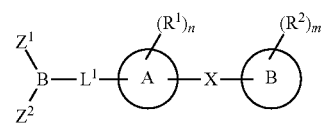

(II)

or a pharmaceutically acceptable salt or prodrug thereof, wherein $Z^1$, $Z^2$, $L^1$, X, Ring A, Ring B, $R^1$, $R^2$, n and m are as defined herein.

In certain embodiments, Ring A is a $C_{3-10}$ carbocyclyl or $C_{6-10}$ aryl group. In some embodiments, Ring A is phenyl. In other embodiments, Ring A is a 3-10 membered heterocyclyl group or a 5-10 membered heteroaryl group. In some embodiments, Ring A is monocyclic, while in other embodiments Ring A is bicyclic.

In certain embodiments, Ring B is a 3-10 membered heterocyclyl group or a 5-10 membered heteroaryl group. In some embodiments, Ring B is monocyclic, while in other embodiments Ring B is bicyclic. For example, in certain embodiments, Ring B is a 5-6 membered monocyclic heteroaryl group, while in other embodiments, Ring B is a 9-10 membered bicyclic heteroaryl group.

2. Compounds and Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Certain compounds of the present invention can comprise one or more asymmetric centers, and thus can exist in various isomeric forms, e.g., stereoisomers and/or diastereomers. Thus, provided compounds, and pharmaceutically acceptable compositions thereof, may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and, alternatively, as mixtures of various isomers, e.g., racemic mixtures of stereoisomers.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972).

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, $C_{5-6}$ alkyl.

As used herein a "direct bond" or "covalent bond" refers to a single bond.

As used herein, the term "boronic acid" refers to any chemical compound comprising a —B(OH)$_2$ moiety. Arylboronic acid compounds readily form oligomeric anhydrides by dehydration of the boronic acid moiety (see, for example, Snyder et al., *J. Am. Chem. Soc.* (1958) 80: 3611). Thus, unless otherwise apparent from context, the term "boronic acid" is expressly intended to encompass free boronic acids, oligomeric anhydrides, including, but not limited to, dimers, trimers, and tetramers, and mixtures thereof.

The terms "boronic ester", "borinic acid" and "borinic ester" are art understood terms referring to a —B(OR)$_2$ moiety, a —B(R)OH moiety and a —B(R)OR moiety, respectively, wherein R is a group other than hydrogen (e.g., for example, an optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocycyl, optionally substituted 3-10 membered heterocycyl, optionally substituted $C_{6-10}$ aryl, or optionally substituted 5-10 membered heteroaryl group, or two R groups are joined to form a 5- to 8-membered ring optionally containing 1 to 4 heteroatoms selected from optionally substituted nitrogen, oxygen or sulfur).

As used herein, alone or as part of another group, "halo" and "halogen" refer to fluorine (fluoro, —F), chlorine (chloro, —Cl), bromine (bromo, —Br), or iodine (iodo, —I).

As used herein, alone or as part of another group, "alkyl" refers to a monoradical of a straight-chain or branched saturated hydrocarbon group having from 1 to 8 carbon atoms ("$C_{1-8}$ alkyl"). In some embodiments, an alkyl group can have from 1 to 6 carbon atoms ("$C_{1-6}$ alkyl"). In some embodiments, an alkyl group can have from 1 to 4 carbon atoms ("$C_{1-4}$ alkyl"). Examples of $C_{1-4}$ alkyl groups include methyl, ethyl, propyl, isopropyl, butyl, isobutyl, sec-butyl and tert-butyl. Examples of $C_{1-6}$ alkyl groups include the aforementioned $C_{1-4}$ alkyl groups as well as pentyl, isopentyl, neopentyl, hexyl and the like. Additional examples of alkyl groups include heptyl, octyl and the like. Unless otherwise specified, each instance of an "optionally substituted" alkyl group is independently unsubstituted or substituted with 1-5 groups as described below.

As used herein, alone or as part of another group, "alkenyl" refers to a monoradical of a straight-chain or branched hydrocarbon group having from 2 to 8 carbon atoms and one or more carbon-carbon double bonds ("$C_{2-8}$ alkenyl"). In some embodiments, an alkenyl group can have from 2 to 6 carbon atoms ("$C_{2-6}$ alkenyl"). In some embodiments, an alkenyl group can have from 2 to 4 carbon atoms ("$C_{2-4}$ alkenyl"). The one or more carbon-carbon double bonds can be internal (such as in 2-butenyl) or terminal (such as in 1-butenyl). Examples of $C_{2-4}$ alkenyl groups include ethenyl, 1-propenyl, 2-propenyl, 1-butenyl, 2-butenyl, butadienyl and the like. Examples of $C_{2-6}$ alkenyl groups include the aforementioned $C_{2-4}$ alkenyl groups as well as pentenyl, pentadienyl, hexenyl and the like. Additional examples of alkenyl include heptenyl, octenyl, octatrienyl and the like. Unless otherwise specified, each instance of an "optionally substituted" alkenyl group is independently unsubstituted or substituted with 1-5 groups as described below.

As used herein, alone or as part of another group, "alkynyl" refers to a monoradical of a straight-chain or branched hydrocarbon group having from 2 to 8 carbon atoms and one or more carbon-carbon triple bonds ("$C_{2-8}$ alkynyl"). In some embodiments, an alkynyl group can have from 2 to 6 carbon atoms ("$C_{2-6}$ alkynyl"). In some embodiments, an alkynyl group can have from 2 to 4 carbon atoms ("$C_{2-4}$ alkynyl"). The one or more carbon-carbon triple bonds can be internal (such as in 2-butynyl) or terminal (such as in 1-butynyl). Examples of $C_{2-4}$ alkynyl groups include ethynyl, 1-propynyl, 2-propynyl, 1-butynyl, 2-butynyl and the like. Examples of $C_{2-6}$ alkenyl groups include the aforementioned $C_{2-4}$ alkynyl groups as well as pentynyl, hexynyl and the like. Additional examples of alkynyl include heptynyl, octynyl and the like. Unless otherwise specified, each instance of an "optionally substituted" alkynyl group is independently unsubstituted or substituted with 1-5 groups as described below.

As used herein, alone or as part of another group, "heteroalkyl" refers to an alkyl group, as defined herein, wherein one or more carbon atoms are replaced with one or more heteroatoms selected from optionally substituted nitrogen, oxygen and sulfur. For example, "heteroalkyl" refers to a monoradical of a straight-chain or branched hydrocarbon group having from 1 to 8 carbon atoms and one or more heteroatoms ("$C_{1-8}$ heteroalkynyl"). Unless otherwise specified, each instance of an "optionally substituted" heteroalkyl group is independently unsubstituted or substituted with 1-5 groups as described below.

As used herein, alone or as part of another group, "heteroalkenyl" refers to an alkenyl group, as defined herein, wherein one or more carbon atoms are replaced with one or more heteroatoms selected from optionally substituted nitrogen, oxygen and sulfur. For example, "heteroalkenyl" refers to a monoradical of a straight-chain or branched hydrocarbon group having from 2 to 8 carbon atoms, one or more carbon-carbon double bonds, and one or more heteroatoms ("$C_{2-8}$ heteroalkenyl"). Unless otherwise specified, each instance of an "optionally substituted" heteroalkenyl group is independently unsubstituted or substituted with 1-5 groups as described below.

As used herein, alone or as part of another group, "heteroalkynyl" refers to an alkynyl group, as defined herein, wherein one or more carbon atoms are replaced with one or more heteroatoms selected from optionally substituted nitrogen, oxygen and sulfur. For example, "heteroalkynyl" refers to a monoradical of a straight-chain or branched hydrocarbon group having from 2 to 8 carbon atoms, one or more carbon-carbon triple bonds, and one or more heteroatoms ("$C_{2-8}$ heteroalkynyl"). Unless otherwise specified, each instance of an "optionally substituted" heteroalkynyl group is independently unsubstituted or substituted with 1-5 groups as described below.

As used herein, alone or as part of another group, "alkylene" refers to a diradical of a straight-chain or branched saturated hydrocarbon group having from 1 to 6 carbon atoms ("$C_{1-6}$ alkylene"). In some embodiments, an alkylene group can have from 1 to 4 carbon atoms ("$C_{1-4}$ alkylene"). In some embodiments, an alkylene group can have from 1 to 2 carbon atoms ("$C_{1-2}$ alkylene"). Examples of $C_{1-2}$ alkylene groups include methylene and ethylene. Examples of $C_{1-4}$ alkylene groups include the aforementioned $C_{1-2}$ alkylene groups as well as trimethylene (1,3-propanediyl), propylene (1,2-propanediyl), tetramethylene (1,4-butanediyl), butylene (1,2-butanediyl), 1,3-butanediyl, 2-methyl-1,3-propanediyl and the like. Examples of $C_{1-6}$ alkylene groups include the aforementioned $C_{1-4}$ alkylene groups as well as pentamethylene (1,5-pentanediyl), pentylene (1,2-pentanediyl), hexamethylene (1,6-hexanediyl), hexylene (1,2-hexanediyl), 2,3-dimethyl-1,4-butanediyl and the like. In some embodiments, an alkylene group is an α,ω-diradical. Examples of α,ω-diradical alkylene groups include methylene, ethylene, trimethylene, tetramethylene, pentamethylene and hexamethylene.

As used herein, alone or as part of another group, "alkenylene" refers to a diradical of a straight-chain or branched hydrocarbon group having from 2 to 6 carbon atoms and one or more carbon-carbon double bonds ("$C_{2-6}$ alkenylene"). In some embodiments, an alkenylene group can have from 2 to 4 carbon atoms ("$C_{2-4}$ alkenylene"). In some embodiments, an alkenylene group can have 2 carbon atoms, i.e., ethenediyl. The one or more carbon-carbon double bonds can be internal (such as in 1,4-but-2-enediyl) or terminal (such as in 1,4-but-1-enediyl). Examples of $C_{2-4}$ alkenylene groups include ethenediyl, 1,2-propenediyl, 1,3-propenediyl, 1,4-but-1-enediyl, 1,4-but-2-enediyl and the like. Examples of $C_{2-6}$ alkenylene groups include the aforementioned $C_{2-4}$ alkenylene groups as well as 1,5-pent-1-enediyl, 1,4-pent-2-enediyl, 1,6-hex-2-enediyl, 2,5-hex-3-enediyl, 2-methyl-1,4-pent-2-enediyl and the like. In some embodiments, an alkenylene group is an α,ω-diradical. Examples of α,ω-diradical alkenylene groups include ethenediyl, 1,3-propenediyl, 1,4-but-2-enediyl, 1,5-pent-1-enediyl, 1,6-hex-3-enediyl and the like.

As used herein, alone or as part of another group, "alkynylene" refers to a diradical of a straight-chain or branched hydrocarbon group having from 2 to 6 carbon atoms and one or more carbon-carbon triple bonds ("$C_{2-6}$ alkynylene"). In some embodiments, an alkynylene group can have from 2 to 4 carbon atoms ("$C_{2-4}$ alkynylene"). In some embodiments, an alkynylene group can have 2 carbon atoms, i.e., ethynediyl. The one or more carbon-carbon triple bonds can be internal (such as in 1,4-but-2-ynediyl) or terminal (such as in 1,4-but-1-ynediyl). Examples of $C_{2-4}$ alkynylene groups include ethynediyl, propynediyl, 1,4-but-1-ynediyl, 1,4-but-2-ynediyl and the like. Examples of $C_{2-6}$ alkynylene groups include the aforementioned $C_{2-4}$ alkynylene groups as well as 1,5-pent-1-ynediyl, 1,4-pent-2-ynediyl, 1,6-hex-2-ynediyl, 2,5-hex-3-ynediyl, 3-methyl-1,5-hex-1-ynediyl and the like. In some embodiments, an alkynylene group is an α,ω-diradical. Examples of α,ω-diradical alkynylene groups include ethynediyl, propynediyl, 1,4-but-2-ynediyl, 1,5-pent-1-ynediyl, 1,6-hex-3-ynediyl and the like.

As used herein, alone or as part of another group, "perhaloalkyl" refers to an alkyl group having from 1 to 3 carbon atoms, wherein all of the hydrogen atoms are each independently replaced with fluoro or chloro. In some embodiments, all of the hydrogen atoms are each replaced with fluoro. In some embodiments, all of the hydrogen atoms are each replaced with chloro. Examples of perhaloalkyl groups include —$CF_3$, —$CF_2CF_3$, —$CF_2CF_2CF_3$, —$CCl_3$, —$CFCl_2$, —$CF_2Cl$ and the like.

As used herein, alone or as part of another group, "alkoxy" or "alkyloxy" refers to an —O-alkyl group having from 1 to 8 carbon atoms ("$C_{1-8}$ alkoxy"). In some embodiments, an alkoxy group can have from 1 to 6 carbon atoms ("$C_{1-6}$ alkoxy"). In some embodiments, an alkoxy group can have from 1 to 4 carbon atoms ("$C_{1-4}$ alkoxy"). Examples of $C_{1-4}$ alkoxy groups include methoxy, ethoxy, propoxy, isopropoxy, butoxy, tert-butoxy and the like. Examples of $C_{1-6}$ alkoxy groups include the aforementioned $C_{1-4}$ alkoxy groups as well as pentyloxy, isopentyloxy, neopentyloxy, hexyloxy and the like. Additional examples of alkoxy groups include heptyloxy, octyloxy and the like. Unless otherwise specified, each instance of an "optionally substituted" alkoxy group is independently unsubstituted or substituted with 1-5 groups as described below.

As used herein, alone or as part of another group, "perhaloalkoxy" refers to an alkoxy group having from 1 to 3 carbon atoms, wherein all of the hydrogen atoms are each independently replaced with fluoro or chloro. In some embodiments, all of the hydrogen atoms are each replaced with fluoro. In some embodiments, all of the hydrogen atoms are each replaced with chloro. Examples of perhaloalkoxy groups include —$OCF_3$, —$OCF_2CF_3$, —$OCF_2CF_2CF_3$, —$OCCl_3$, —$OCFCl_2$, —$OCF_2Cl$ and the like.

As used herein, alone or as part of another group, "alkylthio" refers to an —S-alkyl group having from 1 to 8 carbon atoms. In some embodiments, an alkylthio group can have from 1 to 6 carbon atoms. In some embodiments, an alkylthio group can have from 1 to 4 carbon atoms. Examples of $C_{1-4}$ alkylthio groups include methylthio, ethylthio, propylthio, isopropylthio, butylthio, isobutylthio and the like. Examples of $C_{1-6}$ alkylthio groups include the aforementioned $C_{1-4}$ alkylthio groups as well as pentylthio, isopentylthio, hexylthio and the like. Additional examples of alkylthio groups include heptylthio, octylthio and the like. Unless otherwise specified, each instance of an "optionally substituted" alkylthio group is independently unsubstituted or substituted with 1-5 groups as described below.

As used herein, alone or as part of another group, "carbocyclyl" or "carbocycle" refers to a radical of a non-aromatic cyclic hydrocarbon group having from 3 to 10 ring carbon atoms ("$C_{3-10}$ carbocyclyl"). In some embodiments, a carbocyclyl group can have from 3 to 8 ring carbon atoms ("$C_{3-8}$ carbocyclyl"). In some embodiments, a carbocyclyl group can have from 3 to 6 ring carbon atoms ("$C_{3-6}$ carbocyclyl"). Examples of $C_{3-6}$ carbocyclyl groups include cyclopropyl, cyclobutyl, cyclopentyl, cyclopentenyl, cyclohexyl, cyclohexenyl, cyclohexadienyl and the like. Examples of $C_{3-8}$ carbocyclyl groups include the aforementioned $C_{3-6}$ carbocyclyl groups as well as cycloheptyl, cycloheptadienyl, cycloheptatrienyl, cyclooctyl, bicyclo[2.2.1]heptanyl, bicyclo[2.2.2]octanyl and the like. Examples of $C_{3-10}$ carbocyclyl groups include the aforementioned $C_{3-8}$ carbocyclyl groups as well as octahydro-1H-indenyl, decahydronaphthalenyl, spiro[4.5]decanyl and the like. As the foregoing examples illustrate, in some embodiments a carbocyclyl group can be monocyclic ("monocyclic carbocyclyl") or bicyclic (e.g., containing a fused, bridged or spiro ring system), and can be saturated or can contain one or more carbon-carbon double or triple bonds. "Carbocyclyl" also refers to a phenyl group (as defined below) fused to a monocyclic carbocyclyl group. Examples of such carbocyclyl groups include 1,2,3,4-tetrahydronaphthalene (e.g., 1,2,3,4-tetrahydronaphthalen-1-yl, 1,2,3,4-tetrahydronaphthalen-5-yl, and the like), 2,3-dihydro-1H-indene (e.g., 2,3-dihydro-1H-inden-1-yl, 2,3-dihydro-1H-inden-4-yl, and the like), indene (e.g., 1H-inden-1-yl, 1H-inden-7-yl, and the like), 5,6,7,8-tetrahydroquinoline (e.g., 5,6,7,8-tetrahydroquinolin-5-yl, 5,6,7,8-tetrahydroquinolin-2-yl, and the like), 4,5,6,7-tetrahydro-1H-indole (e.g., 4,5,6,7-tetrahydro-1H-indol-4-yl, 4,5,6,7-tetrahydro-1H-indol-3-yl, and the like), 4,5,6,7-tetrahydrobenzofuran (e.g., 4,5,6,7-tetrahydrobenzofuran-7-yl, 4,5,6,7-tetrahydrobenzofuran-2-yl, and the like) and the like. Unless otherwise specified, each instance of an "optionally substituted" carbocyclyl or carbocycle group is independently unsubstituted or substituted with 1-5 groups as described below.

In some embodiments, "carbocyclyl" or "carbocycle" can refer to a monocyclic, saturated carbocyclyl group ("cycloalkyl") having from 3 to 8 ring carbon atoms ("$C_{3-8}$ cycloalkyl"). In some embodiments, a cycloalkyl group can have from 3 to 6 ring carbon atoms ("$C_{3-6}$ cycloalkyl"). In some embodiments, a cycloalkyl group can have from 5 to 6 ring carbon atoms ("$C_{5-6}$ cycloalkyl"). Examples of $C_{5-6}$ cycloalkyl groups include cyclopentyl and cyclohexyl. Examples of $C_{3-6}$ cycloalkyl groups include the aforementioned $C_{5-6}$ cycloalkyl groups as well as cyclopropyl and cyclobutyl. Examples of $C_{3-8}$ cycloalkyl groups include the aforementioned $C_{3-6}$ cycloalkyl groups as well as cycloheptyl and cyclooctyl. Unless otherwise specified, each instance of an "optionally substituted" cycloalkyl group is independently unsubstituted or substituted with 1-5 groups as described below.

As used herein, alone or as part of another group, "heterocyclyl" or "heterocycle" refers to a radical of a 3- to 10-membered non-aromatic ring system having ring carbon atoms and 1 to 4 ring heteroatoms, each heteroatom independently selected from optionally substituted nitrogen, oxygen and sulfur. In some embodiments, a heterocyclyl group can have from 3 to 7 ring atoms selected from carbon atoms and 1 to 3 heteroatoms, each heteroatom independently selected from optionally substituted nitrogen, oxygen and sulfur. In some embodiments, a heterocyclyl group can have from 5 to 7 ring atoms selected from carbon atoms and 1 or 2 heteroatoms, each heteroatom independently selected from nitrogen, oxygen and sulfur. In some embodiments, a heterocyclyl group can have from 5 to 6 ring atoms selected from carbon atoms and 1 to 3 heteroatoms, each heteroatom independently selected from optionally substituted nitrogen, oxygen and sulfur.

In heterocyclyl groups that contain one or more optionally substituted nitrogen atoms, the point of attachment can be a carbon or the optionally substituted nitrogen atom, as valency permits. Examples of heterocyclyl groups with 1-2 ring heteroatoms include oxiranyl, aziridinyl, oxetanyl, azetidinyl, pyrrolidinyl, dihydropyrrolyl, tetrahydrofuranyl, dihydrofuranyl, dioxolanyl, tetrahydrothiophenyl, dihydrothiophenyl, pyrazolidinyl, imidazolidinyl, oxazolidinyl, isoxazolidinyl, thiazolidinyl, piperidinyl, tetrahydropyridinyl, dihydropyridinyl, piperazinyl, tetrahydropyranyl, dioxanyl, morpholinyl, azepanyl, diazepanyl, diazepinyl, oxepanyl, dioxepanyl, oxazepanyl, oxazepinyl and the like. Examples of heterocyclyl groups with 1-3 heteroatoms include the aforementioned heterocyclyl groups as well as triazolidinyl, oxadiazolidinyl, triazinanyl and the like. Heterocycyl groups can be monocyclic (as in the aforementioned examples), bicyclic, or tricyclic. Bicyclic heterocyclyl groups can include one or more heteroatoms in one or both rings. Examples of such heterocyclyl groups include tetrahydroindolyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole and the like.

"Heterocyclyl" or "heterocycle" also refers to a radical of a 5- to 10-membered fused ring system having ring carbon atoms and 1 to 4 ring heteroatoms, each heteroatom independently selected from nitrogen, oxygen and sulfur, wherein one ring is aromatic and the other is non-aromatic. In some embodiments, at least one heteroatom is present in either the aromatic or non-aromatic ring, while in other embodiments, at least one heteroatom is present in both rings. In heterocyclyl groups that contain one or more optionally substituted nitrogen atoms, the point of attachment can be a carbon or nitrogen atom, as valency permits. Examples of such heterocyclyl groups include indolinyl (e.g., indolin-1-yl, indolin-4-yl, and the like), isoindolinyl (e.g., isoindolin-1-yl, isoindolin-4-yl, and the like), 4,5,6,7-tetrahydro-1H-indolyl (e.g., tetrahydro-1H-indol-2-yl, 4,5,6,7-tetrahydro-1H-indol-4-yl, and the like), dihydrobenzofuranyl (e.g., dihydrobenzofuran-3-yl, dihydrobenzofuran-5-yl, and the like), 4,5,6,7-tetrahydrobenzofuranyl (e.g., 4,5,6,7-tetrahydrobenzofuran-2-yl, 4,5,6,7-tetrahydrobenzofuran-5-yl, and the like), dihydrobenzothienyl (e.g., dihydrobenzothien-2-yl, dihydrobenzothien-4-yl, and the like), 4,5,6,7-tetrahydrobenzothiophenyl (e.g., 4,5,6,7-tetrahydrobenzothiophen-2-yl, 4,5,6,7-tetrahydrobenzothiophen-7-yl, and the like), 1,2,3,4-tetrahydroquinolinyl (e.g., 1,2,3,4-tetrahydroquinolin-1-yl, 1,2,3,4-tetrahydroquinolin-7-yl, and the like), chromanyl (e.g., chroman-2-yl, chroman-5-yl, and the like), chromenyl (chromen-4-yl, chromen-8-yl, and the like), thiochromanyl (e.g., thiochroman-3-yl, isochroman-7-yl, and the like), 1H-benzo[e][1,4]diazepinyl (e.g., 1H-benzo[e][1,4]diazepin-2-yl, 1H-benzo[e][1,4]diazepin-6-yl, and the like), 2,3-dihydro-1H-pyrrolo[2,3-b]pyridinyl (e.g., 2,3-dihydro-1H-pyrrolo[2,3-b]pyridin-1-yl, 2,3-dihydro-1H-pyrrolo[2,3-b]pyridin-4-yl, and the like), 4,5,6,7-tetrahydro-1H-pyrrolo[2,3-b]pyridinyl (e.g., 4,5,6,7-tetrahydro-1H-pyrrolo-[2,3-b]pyridin-2-yl, 4,5,6,7-tetrahydro-1H-pyrrolo[2,3-b]pyridin-4-yl, and the like), 1,4,5,7-tetrahydropyrano[3,4-b]pyrrolyl (e.g., 1,4,5,7-tetrahydropyrano[3,4-b]pyrrol-2-yl, 1,4,5,7-tetrahydropyrano[3,4-b]pyrrol-4-yl, and the like), 2,3-dihydrofuro[2,3-b]pyridinyl (e.g., 2,3-dihydrofuro[2,3-b]pyridin-3-yl, 2,3-dihydrofuro[2,3-b]pyridin-5-yl, and the like), 4,5,6,7-tetrahydrofuro[3,2-c]pyridinyl (e.g., 4,5,6,7-tetrahydrofuro[3,2-c]pyridin-2-yl, 4,5,6,7-tetrahydrofuro[3,2-c]pyridin-5-yl, and the like), 4,5,6,7-tetrahydrothieno[3,2-b]pyridinyl (e.g., 4,5,6,7-tetrahydrothieno[3,2-b]pyridin-2-yl, 4,5,6,7-tetrahydrothieno[3,2-b]pyridin-7-yl, and the like), 5,6-dihydro-4H-furo[3,2-b]pyrrolyl (e.g., 5,6-dihydro-4H-furo[3,2-b]pyrrol-6-yl, 5,6-dihydro-4H-furo[3,2-b]pyrrol-2-yl, and the like), 6,7-dihydro-5H-furo[3,2-b]pyranyl (e.g., 6,7-dihydro-5H-furo[3,2-b]pyran-2-yl, 6,7-dihydro-5H-furo[3,2-b]pyran-6-yl, and the like), 5,7-dihydro-4H-thieno[2,3-c]pyranyl (e.g., 5,7-dihydro-4H-thieno[2,3-c]pyran-2-yl, 5,7-dihydro-4H-thieno[2,3-c]pyran-4-yl, and the like), 1,2,3,4-tetrahydro-1,6-naphthyridinyl (e.g., 1,2,3,4-tetrahydro-1,6-naphthyridin-3-yl, 1,2,3,4-tetrahydro-1,6-naphthyridin-8-yl, and the like), and the like.

Unless otherwise specified, each instance of an "optionally substituted" heterocyclyl group is independently unsubstituted or substituted with 1-5 groups as described below.

As used herein, alone or as part of another group, "aryl" refers to a radical of an aromatic monocyclic or bicyclic ring system having 6 or 10 ring carbon atoms. Examples of such aryl groups include phenyl, 1-naphthyl and 2-naphthyl. Unless otherwise specified, each instance of an "optionally substituted" aryl group is independently unsubstituted or substituted with 1-5 groups as described below.

The term "aralkyl" refers to an alkyl group substituted by an aryl group, wherein the alkyl and aryl portions independently are optionally substituted as described below.

As used herein, alone or as part of another group, "heteroaryl" refers to a radical of a 5- to 10-membered aromatic ring system having ring carbon atoms and 1 to 4 ring heteroatoms, each heteroatom independently selected from optionally substituted nitrogen, oxygen and sulfur. Examples of such heteroaryl groups include pyrrolyl, furanyl (furyl), thiophenyl (thienyl), pyrazolyl, imidazolyl, oxazolyl, isoxazolyl, thiazolyl, triazolyl, oxadiazolyl, thiadiazolyl, tetrazolyl, pyridinyl (pyridyl), pyridazinyl, pyrimidinyl, pyrazinyl, triazinyl, indolyl, benzofuranyl, benzothiophenyl (benzothienyl), indazolyl, benzimidazolyl, benzoxazolyl, benzisoxazolyl, benzothiazolyl, quinolinyl, isoquinolinyl, cinnolinyl, quinazolinyl, quinoxalinyl, phthalazinyl, naphthyridinyl and the like. As the foregoing examples illustrate, in some embodiments a heteroaryl group can be monocyclic ("monocyclic heteroaryl"), and in some embodiments a heteroaryl group can be bicyclic ("bicyclic heteroaryl"). For bicyclic heteroaryl groups wherein one ring does not contain a heteroatom (e.g., indolyl, quinolinyl, and the like) the point of attachment may be on either ring, i.e., either the ring bearing a heteroatom (e.g., 2-indolyl) or the ring that does not contain a heteroatom (e.g., 5-indolyl). Unless otherwise specified, each instance of an "optionally substituted" heteroaryl group is independently unsubstituted or substituted with 1-5 groups as described below.

The term "heteroaralkyl" refers to an alkyl group substituted by a heteroaryl group, wherein the alkyl and heteroaryl portions independently are optionally substituted as described below.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a carbon atom of an "optionally substituted" group are independently halogen; —$(CH_2)_{0-4}R^\circ$; —$(CH_2)_{0-4}OR^\circ$; —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with one or more $R^\circ$; —$(CH_2)_{0-4}O(CH_2)_{0-1}Ph$ which may be substituted with $R^\circ$; —CH=CHPh, which may be substituted with one or more $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ alkylene)O—$N(R^\circ)_2$; or —$(C_{1-4}$ alkylene)$C(O)O$—$N(R^\circ)_2$, wherein each $R^\circ$ may be substituted as defined below and is independently hydrogen, $C_{1-8}$ alkyl, $C_{2-8}$ alkenyl, $C_{2-8}$ alkynyl, $C_{1-8}$ heteroalkyl, $C_{2-8}$ heteroalkenyl, $C_{2-8}$ heteroalkynyl, —$CH_2Ph$, —$O(CH_2)_{0-1}Ph$, or a 5- or 6-membered saturated, partially unsaturated, or aromatic ring having 0-4 heteroatoms independently selected from nitrogen, oxygen, or sulfur; or, notwithstanding the definition above, two independent occurrences of $R^\circ$, taken together with the atom(s) to which they are bound, form a 3- to 12-membered saturated, partially unsaturated, or aromatic mono- or bicyclic ring having 0-4 heteroatoms independently selected from nitrogen, oxygen, or sulfur, which may be substituted as defined below.

Suitable monovalent substituents on $R^\circ$ (or the ring formed by two independent occurrences of $R^\circ$ together with the atoms to which they are bound), are independently halogen, —$(CH_2)_{0-2}R^\bullet$, —$(CH_2)_{0-2}OH$, —$(CH_2)_{0-2}OR^\bullet$, —$(CH_2)_{0-2}CH(OR^\bullet)_2$, —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ alkylene)$C(O)OR^\bullet$, or —$SSR^\bullet$ wherein each $R^\bullet$ is unsubstituted or substituted with one or more halogens, and is independently selected from $C_{1-4}$ alkyl, $C_{2-4}$ alkenyl, $C_{2-4}$ alkynyl, —$CH_2Ph$, —$O(CH_2)_{0-1}Ph$, or a 5- or 6-membered saturated, partially unsaturated, or aromatic ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen; C$_{1-6}$ alkyl, C$_{2-6}$ alkenyl, C$_{2-6}$ alkynyl, each of which may be substituted as defined below; or an unsubstituted 5- or 6-membered saturated, partially unsaturated, or aromatic ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen; C$_{1-6}$ alkyl, C$_{2-6}$ alkenyl, C$_{2-6}$ alkynyl, each of which may be substituted as defined below; or an unsubstituted 5- or 6-membered saturated, partially unsaturated, or aromatic ring having 0-4 heteroatoms independently selected from nitrogen, oxygen, or sulfur.

Suitable substituents on a C$_{1-6}$ alkyl, C$_{2-6}$ alkenyl, or C$_{2-6}$ alkynyl R* group include halogen, —R$^\bullet$, -(haloR$^\bullet$), —OH, —OR$^\bullet$, —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or substituted with one or more halogens, and is independently C$_{1-4}$ alkyl, C$_{2-4}$ alkenyl, C$_{2-4}$ alkynyl, —CH$_2$Ph, —O(CH$_2$)$_{0-1}$Ph, or a 5- or 6-membered saturated, partially unsaturated, or aromatic ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen; C$_{1-6}$ alkyl, C$_{2-6}$ alkenyl, C$_{2-6}$ alkynyl, each of which may be substituted as defined below; unsubstituted —OPh; or an unsubstituted 5- or 6-membered saturated, partially unsaturated, or aromatic ring having 0-4 heteroatoms independently selected from nitrogen, oxygen, or sulfur; or, notwithstanding the definition above, two independent occurrences of R$^\dagger$, taken together with the atom(s) to which they are bound form an unsubstituted 3- to 12-membered saturated, partially unsaturated, or aromatic mono- or bicyclic ring having 0-4 heteroatoms independently selected from nitrogen, oxygen, or sulfur.

Suitable substituents on a C$_{1-6}$ alkyl, C$_{2-6}$ alkenyl, or C$_{2-6}$ alkynyl R$^\dagger$ group are independently halogen, —R$^\bullet$, —OH, —OR$^\bullet$, —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or substituted with one or more halogens, and is independently C$_{1-4}$ alkyl, C$_{2-4}$ alkenyl, C$_{2-4}$ alkynyl, —CH$_2$Ph, —O(CH$_2$)$_{0-1}$Ph, or a 5- or 6-membered saturated, partially unsaturated, or aromatic ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "prodrug" refers to a derivative of a parent compound that requires transformation within the body in order to release the parent compound. In certain cases, a prodrug has improved physical and/or delivery properties over the parent compound. Prodrugs are typically designed to enhance pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may enhance drug stability for long-term storage. The compounds of the invention readily undergo dehydration to form oligomeric anhydrides by dehydration of the boronic acid moiety to form dimers, trimers, and tetramers, and mixtures thereof. These oligomeric species hydrolyze under physiological conditions to reform the boronic acid. As such, the oligomeric anhydrides are contemplated as a "prodrug" of the compounds described herein, and may be used in the treatment of disorder and/or conditions a wherein the inhibition of FAAH provides a therapeutic effect.

Exemplary prodrugs of the compounds described herein include, but are not limited to, compounds wherein Z$^1$ and Z$^2$ taken together form a 5- to 8-membered ring having at least one heteroatom atom selected from optionally substituted nitrogen, oxygen and sulfur directly attached to boron (B), wherein the ring is comprised of carbon atoms and optionally one or more additional heteroatoms independently selected from optionally substituted nitrogen, oxygen and sulfur.

Other examples of prodrugs of the compounds described herein are trifluoroborate prodrugs which hydrolyze to the boronic acid (i.e., —BF$_3$ hydrolyzing to —B(OH)$_2$) at acidic pH. Salt forms of the boronic acid (e.g., Na$^+$, Li$^+$, Mg$^{2+}$, Ca$^{2+}$, and the like) are also considered prodrugs. Amino acids can be used to form prodrugs, such as, for example, serine and cysteine protected boronic acids. 1,2 and 1,3 hydroxy sugars can be used to form prodrugs, such as, for example, glycerol, erythritol, threitol, ribitol, arabinitol, xylitol, allitol, altritol, galactitol, sorbitol, mannitol, and iditol protected boronic acids. Other sugars which are useful in the formation of prodrugs include, but are not limited to, maltitol, lactitol, and isomalt; other monosaccharides which include hexoses (e.g., allose, altrose, glucose, mannose, gulose, idose, galactose, talose) and pentoses (e.g., ribose, arabinaose, xylose, lyxose); pentaerythritols and structural derivatives thereof, such as methylated, ethylated, acetate, ethoxylate, and propoxylate derivatives; and phenolic polyols such as 1,2,4 benzenetriol, 5-methyl benzene1,2,3-triol, 2,3,4-trihydroxybenzaldehyde, and 3,4,5-trihydroxybenzamide. Prodrugs also include NMIDA-derivatives.

As used herein, the term "tautomer" includes two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol; amide-to-imide; lactam-to-lactim; enamine-to-imine; and enamine-to-(a different) enamine tautomerizations.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

3. Description of Exemplary Compounds (i) $Z^1$ and $Z^2$

As defined generally above, in certain embodiments, $Z^1$ is —OH or —OR$^3$ and $Z^2$ is —OH, —OR$^4$, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl group.

In certain embodiments, $Z^1$ is —OH and $Z^2$ is —OH.
In certain embodiments, $Z^1$ is —OH and $Z^2$ is —OR$^4$.
In certain embodiments, $Z^1$ is —OR$^3$ and $Z^2$ is —OR$^4$.
In certain embodiments, $Z^1$ is —OH or —OR$^3$, and $Z^2$ is optionally substituted $C_{1-8}$ alkyl, optionally substituted $C_{2-8}$ alkenyl, optionally substituted $C_{2-8}$ alkynyl or an optionally substituted $C_{3-10}$ carbocyclyl.

In other embodiments, $Z^1$ is —OH or —OR$^3$, and $Z^2$ is optionally substituted $C_{1-8}$ heteroalkyl, optionally substituted $C_{2-8}$ heteroalkenyl, optionally substituted $C_{2-8}$ heteroalkynyl, or an optionally substituted 3-10 membered heterocyclyl.

In yet other embodiments, $Z^1$ is —OH or —OR$^3$, and $Z^2$ is an optionally substituted $C_{6-10}$ aryl.

In yet other embodiments, $Z^1$ is —OH or —OR$^3$, and $Z^2$ is an optionally substituted 5-10 membered heteroaryl.

Alternatively, in certain embodiments, $Z^1$ and $Z^2$ taken together with the boron atom to which they are bound, form a 5- to 8-membered ring having at least one O, S, N or NR$^5$ atom directly attached to the boron atom, wherein R$^5$ is hydrogen, —SO$_2$R$^{11}$, —SOR$^{11}$, —C(O)R$^{11}$, —CO$_2$R$^{11}$, —C(O)N(R$^{11}$)$_2$, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl, and each instance of R$^{11}$ is, independently, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl.

In certain embodiments, $Z^1$ and $Z^2$ taken together with the boron atom to which they are bound, form a 5- to 8-membered ring having at least one O, S, N or NR$^5$ atom directly attached to the boron atom, wherein the 5- to 8-membered ring is optionally substituted with one or more hydrogen, —SO$_2$R$^{11}$, —SOR$^{11}$, —C(O)R$^{11}$, —CO$_2$R$^{11}$, —C(O)N(R$^{11}$)$_2$, —C(O)NH(R$^{11}$), optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl groups, or two groups present on the ring are joined to form a 5- to 8-membered monocylic or bicyclic ring optionally containing one or more heteroatoms selected from O, S, N or NR$^5$, wherein each instance of R$^{18}$ is independently, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl.

In certain embodiments, the 5- to 8-membered ring is optionally substituted with one or more —C(=O)R$^{18}$, —C(=O)OR$^{18}$, —C(=O)NH(R$^{18}$), —C(=O)N(R$^{18}$)$_2$ and optionally substituted $C_{1-8}$ alkyl groups.

For example, in certain embodiments, $Z^1$ and $Z^2$, taken together with the boron atom to which they are bound, form a 5-membered ring having at least one O, S, N or NR$^5$ atom directly attached to the boron atom. Exemplary 5-membered rings include, but are not limited to:

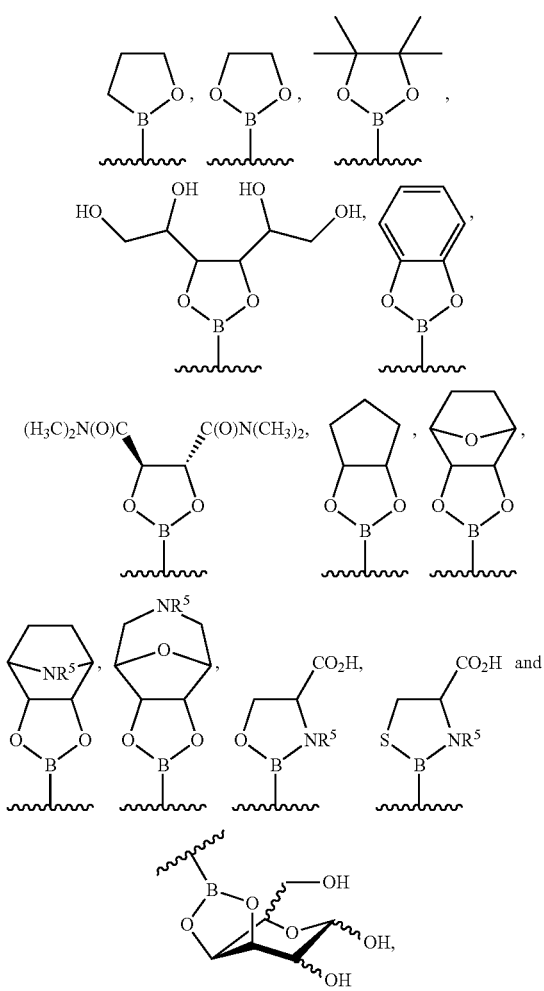

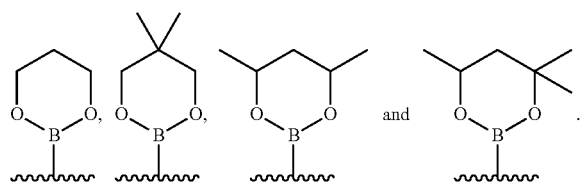

wherein each $R^5$ is as defined above and herein.

In other embodiments, $Z^1$ and $Z^2$, taken together with the boron atom to which they are bound, form a 6-membered ring having at least one O, S, N or $NR^5$ atom directly attached to the boron atom. Exemplary 6-membered rings include, but are not limited to:

In yet other embodiments, $Z^1$ and $Z^2$ form an 8-membered ring having at least one O, S, N or $NR^5$ atom directly attached to the boron atom. Exemplary 8-membered ring structures include, but are not limited to:

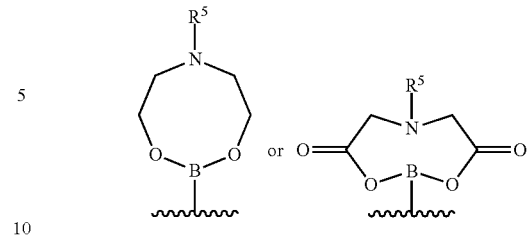

wherein each $R^5$ is as defined above and herein.

Furthermore, as generally defined above, in certain embodiments, $Z^1$ is —OH or —$OR^3$, and $Z^2$ and Ring A taken together form an optionally substituted 5- to 7-membered ring.

For example, in certain embodiments, $Z^1$ is —OH or —$OR^3$, and $Z^2$ and Ring A taken together form an optionally substituted 6-membered ring. Exemplary ring structures include, but are not limited to:

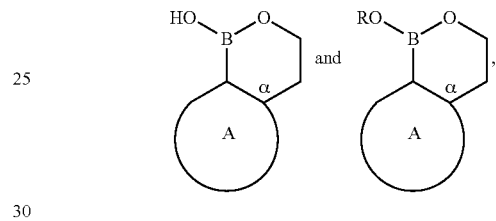

wherein Ring A is as defined above and herein.

(ii) $L^1$

As defined generally above, in certain embodiments, $L^1$ is a covalent bond, an optionally substituted straight or branched $C_{1-6}$ alkylene or an optionally substituted straight or branched $C_{2-6}$ alkenylene moiety.

In certain embodiments $L^1$ is a covalent bond.

In some embodiments, $L^1$ is an optionally substituted $C_{1-6}$ alkylene moiety. In some embodiments, $L^1$ is an optionally substituted $C_{1-3}$ alkylene moiety. In other embodiments, $L^1$ is an optionally substituted $C_{1-2}$ alkylene moiety. In certain embodiments, $L^1$ is a —$CH_2$— group. In other embodiments, $L^1$ is a —$CH_2CH_2$— group. In yet other embodiments, $L^1$ is a —CH═CH— group.

(iii) Ring A

As defined generally above, Ring A is an optionally substituted $C_{3-10}$ carbocyclyl, optionally substituted 3-10 membered heterocyclyl, optionally substituted $C_{6-10}$ aryl, or optionally substituted 5-10 membered heteroaryl. Ring A is monocyclic or bicyclic. In certain embodiments, Ring A is aromatic. In certain embodiments, Ring A is saturated or partially unsaturated.

In certain embodiments, Ring A is an optionally substituted $C_6$ or $C_8$ monocyclic aryl group. Such monocyclic ring systems include, but are not limited to:

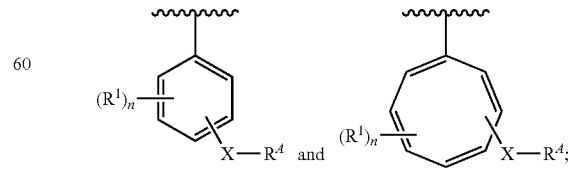

wherein each of X, $R^4$, $R^1$ and n is as defined above and herein.

In certain embodiments, Ring A is an optionally substituted phenyl ring system of formula:

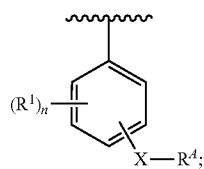

wherein each of X, $R^A$, $R^1$ and n is as defined above and herein.

In certain embodiments, Ring A is phenyl and has at least one fluorine substituent (i.e., n is at least one and $R^1$ is F). In certain embodiments, Ring A has at least two fluorine substituents (i.e., n is at least 2 and each $R^1$ is F). In certain embodiments, Ring A has at least three fluorine substituents (i.e., n is at least 3 and each $R^1$ is F). In certain embodiments, at least one $R^1$ group is fluoro in the ortho position relative to the boron atom. However, in certain embodiments, compounds containing fluorine substituents on Ring A are specifically excluded (i.e., when $R^1$ is F). In certain embodiments, compounds containing fluorine substituents ortho to the boron atom on Ring A are specifically excluded (i.e., when $R^1$ is F at the ortho position of Ring A with respect to the boron atom).

In certain embodiments, Ring A is an optionally substituted phenyl ring system of any one of formulae:

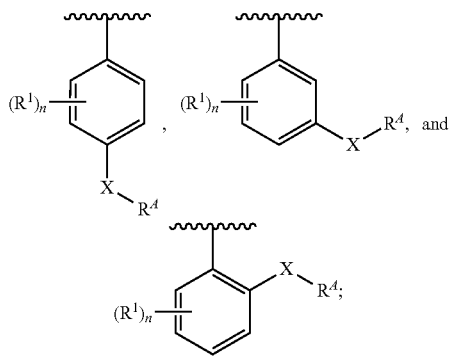

wherein each of X, $R^A$, $R^1$ and n is as defined above and herein.

In other embodiments, Ring A is an optionally substituted phenyl ring system having an —$XR^A$ group para to the boron atom, i.e., a phenyl ring of any one of formulae:

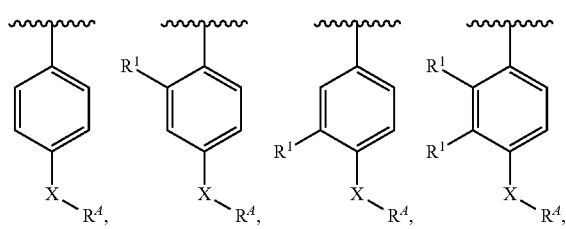

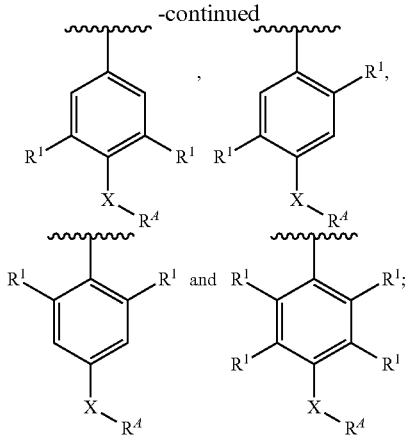

wherein each of X, $R^A$, and $R^1$ is as defined above and herein.

In yet other embodiments, Ring A is an optionally substituted phenyl ring system having an —$XR^A$ group meta to the boron atom, i.e., a phenyl ring of any one of formulae:

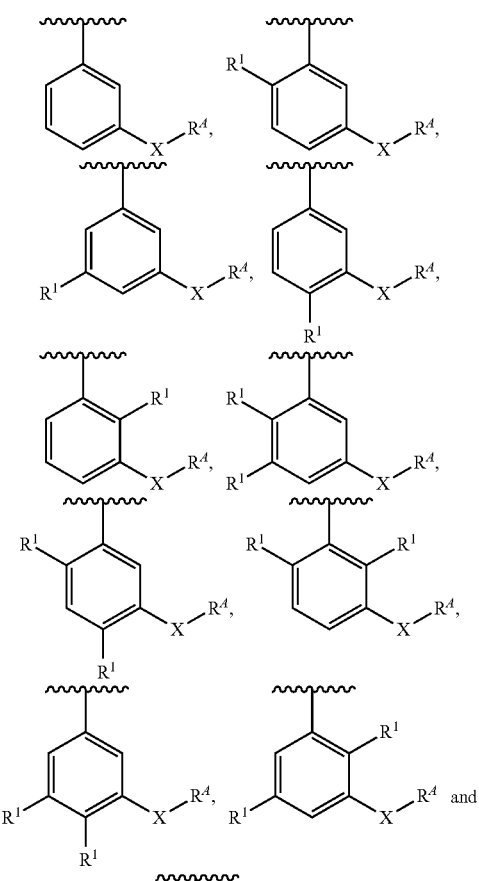

wherein each of X, $R^A$, and $R^1$ is as defined above and herein.

In yet other embodiments, Ring A is an optionally substituted phenyl ring system having an —XR$^A$ group ortho to the boron atom, i.e., a phenyl ring of any one of formulae:

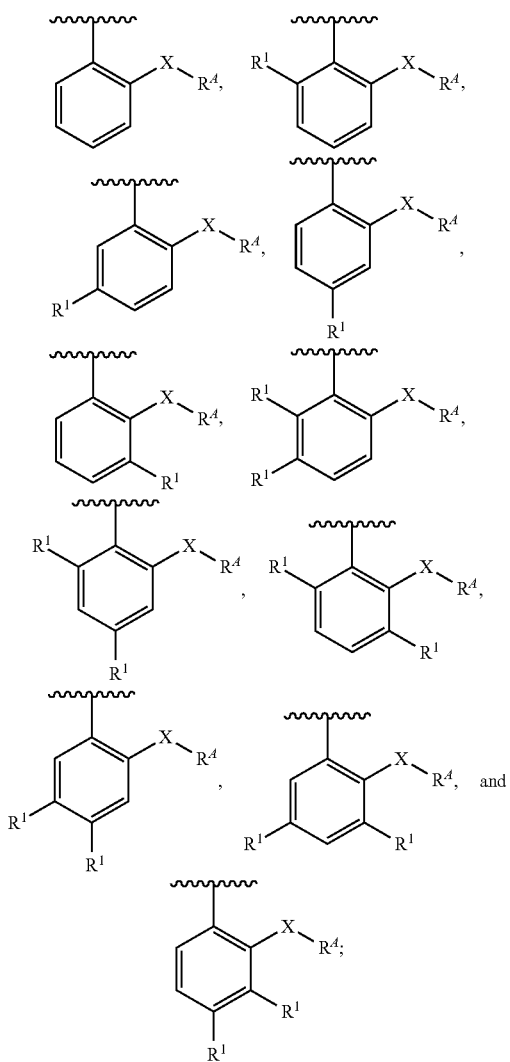

wherein each of X, R$^A$, and R$^1$ is as defined above and herein.

In certain embodiments, Ring A is phenyl, X is a covalent bond and R$^A$ is hydrogen, i.e., Ring A is an optionally substituted phenyl ring system of formula:

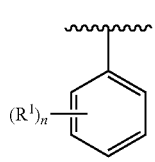

wherein each of R$^1$ and n is as defined above and herein. Examples of such ring systems include:

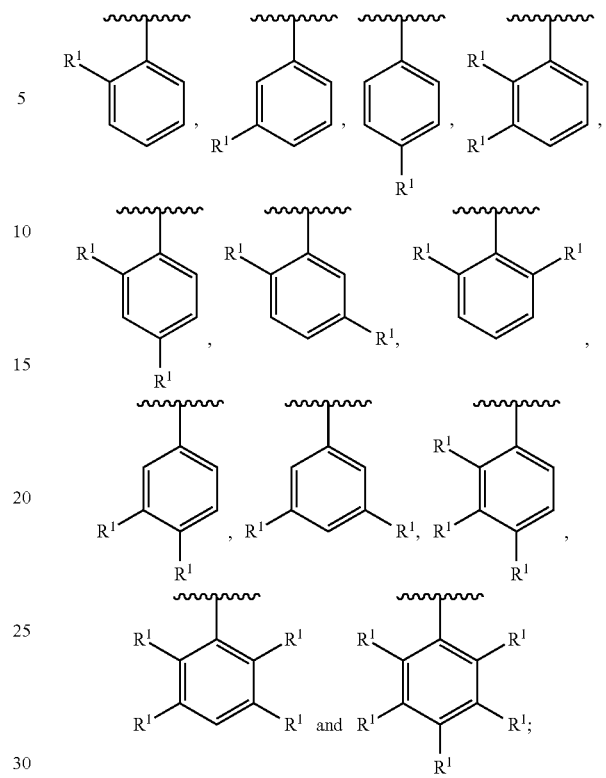

wherein each R$^1$ is as defined above and herein.

In other embodiments, Ring A is an optionally substituted saturated or partially unsaturated $C_{3-10}$ or $C_{3-8}$ monocyclic ring system. Such monocyclic ring systems include, but are not limited to:

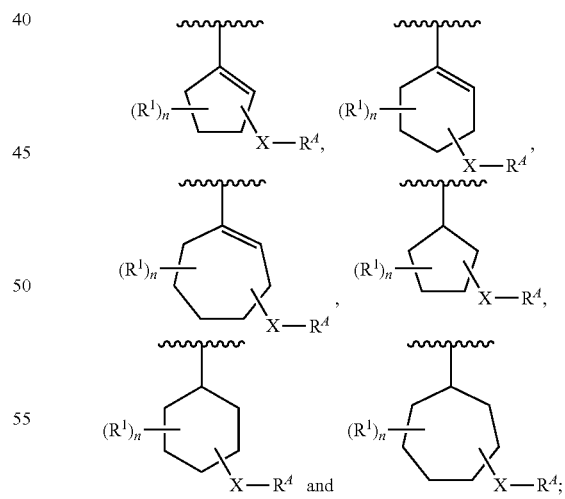

wherein each of X, R$^A$, R$^1$ and n is as defined above and herein.

In certain embodiments, Ring A is an optionally substituted 5-8 membered or 5-6 membered monocyclic heteroaryl group. Such aromatic monocyclic ring systems include, but are not limited to, 5-membered rings of any of following formulae:

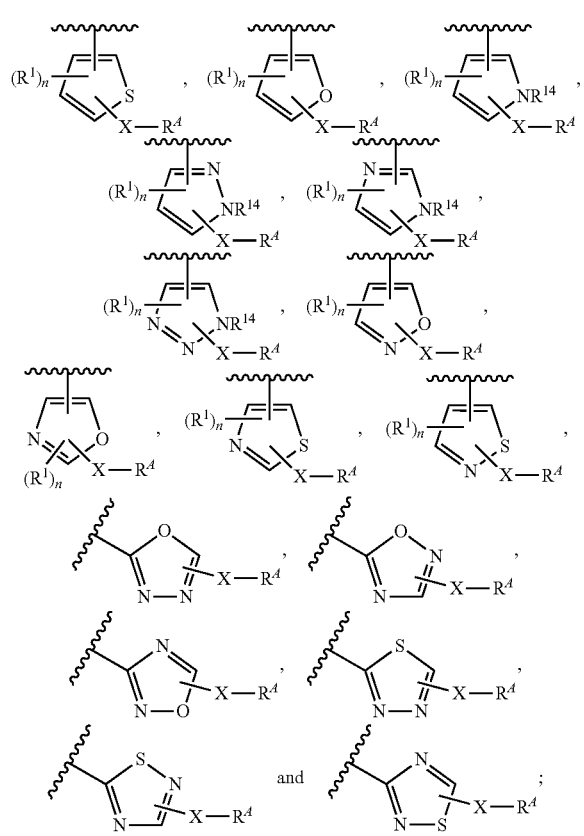

and 6-membered rings of the formulae:

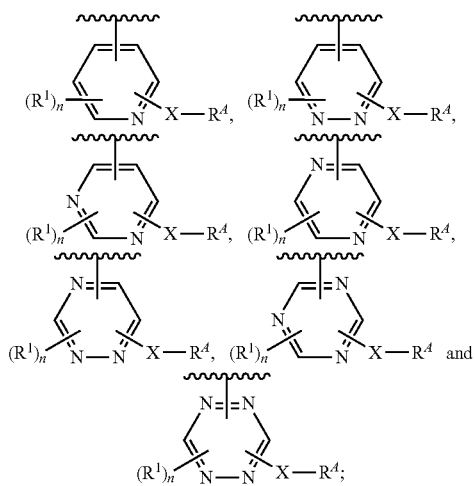

wherein each of X, $R^4$, $R^1$ and n is as defined above and herein, $R^{14}$ is hydrogen, $-SO_2R^{11}$, $-SOR^{11}$, $-C(O)R^{11}$, $-CO_2R^{11}$, $-C(O)N(R^{11})_2$, $-C(O)NH(R^{11})$, $-C(O)NH_2$, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl, and each instance of $R^{11}$ is, independently, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl.

In certain embodiments, Ring A is an optionally substituted furanyl group. In certain embodiments, Ring A is a furanyl group of the formula:

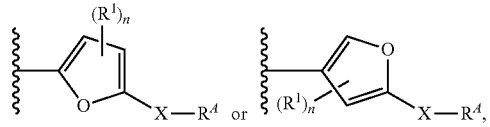

wherein each of X, $R^4$, $R^1$ and n is as defined above and herein.

In certain embodiments, Ring A is an optionally substituted thiophenyl group. In certain embodiments, Ring A is a thiophenyl group of the formula:

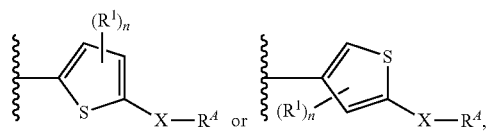

wherein each of X, $R^4$, $R^1$ and n is as defined above and herein.

In certain embodiments, Ring A is an optionally substituted pyridinyl group. In certain embodiments, Ring A is pyridinyl group of the formula:

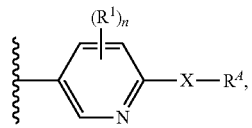

wherein each of X, $R^4$, $R^1$ and n is as defined above and herein.

In other embodiments, Ring A is an optionally substituted saturated or partially unsaturated 3-8 membered or 5-8-membered monocyclic heterocyclyl group. Examples of such saturated or partially unsaturated monocyclic ring systems include, but are not limited to:

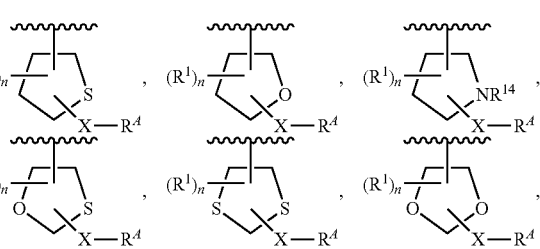

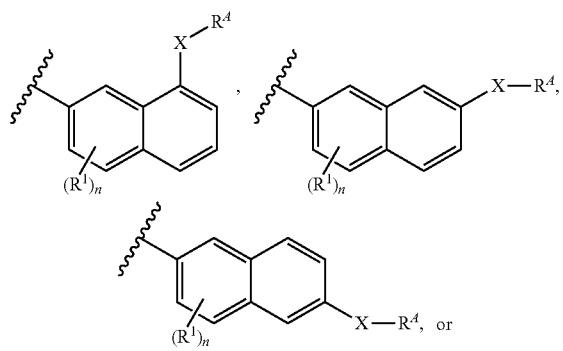

wherein each of X, $R^A$, $R^1$, $R^{14}$ and n is as defined above and herein.

In certain embodiments, Ring A is an optionally substituted bicyclic aryl group. Such bicyclic ring systems include, but are not limited to:

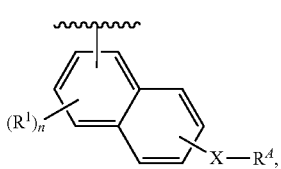

wherein each of X, $R^A$, $R^1$ and n is as defined above and herein. For example, in certain embodiments, Ring A is a bicyclic group of any of formulae:

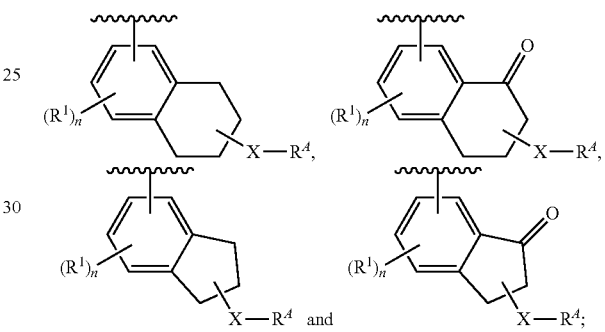

wherein each of X, $R^A$, $R^1$ and n is as defined above and herein.

In other embodiments, Ring A is an optionally substituted bicyclic $C_{8-10}$ carbocyclyl group. In some embodiments, both rings of the bicyclic $C_{8-10}$ carbocyclyl group are saturated or partially saturated. In other embodiments, one ring of the bicyclic $C_{8-10}$ carbocyclyl group is saturated or partially saturated and the other ring is aromatic. Such bicyclic $C_{8-10}$ carbocyclyl ring systems include, but are not limited to:

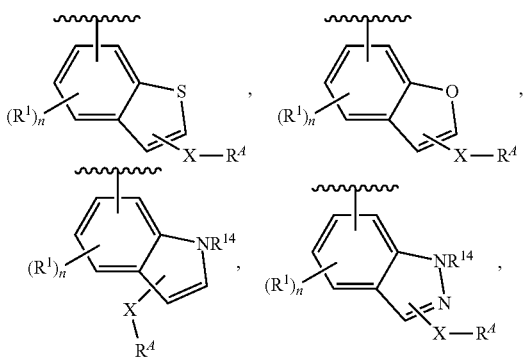

wherein each of X, $R^A$, $R^1$ and n is as defined above and herein.

In certain embodiments, Ring A is an optionally substituted 6-10 membered bicyclic heteroaryl group. In certain embodiments, Ring A is an optionally substituted 9-10 membered bicyclic heteroaryl group. In certain embodiments, Ring A is an optionally substituted 9 membered bicyclic heteroaryl group. In certain embodiments, the optionally substituted 9-membered bicyclic heteroaryl is a 6,5-fused heteroaryl ring. In certain embodiments, the optionally substituted 10-membered bicyclic heteroaryl is a 6,6-fused heteroaryl ring.

For example, in certain embodiments, Ring A is a 6,5-fused heteroaryl ring of any of formulae:

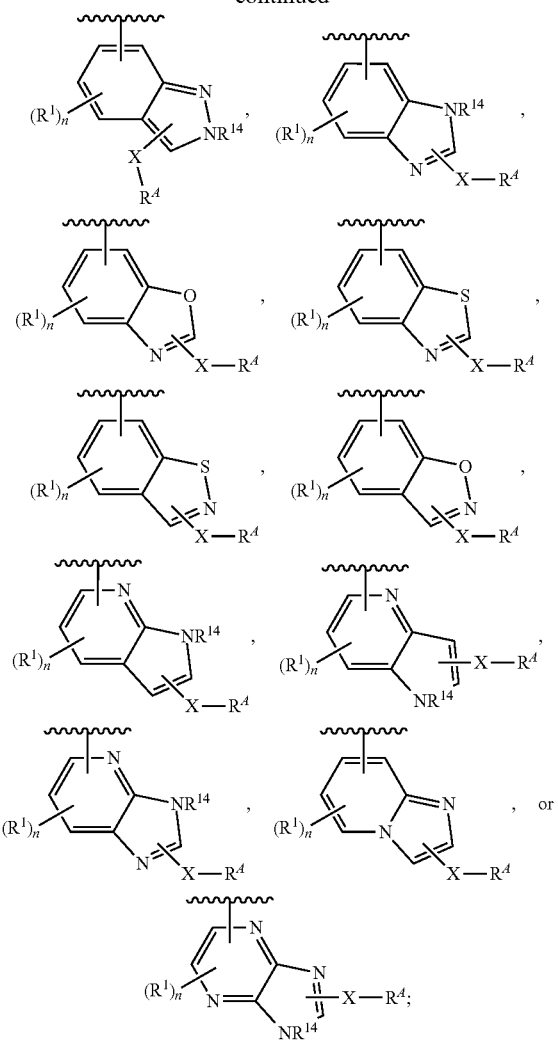

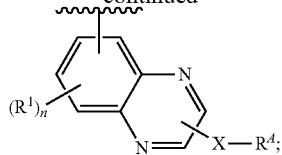

wherein each of X, $R^A$, $R^1$ and n is as defined above and herein.

In other embodiments, Ring A is an optionally substituted bicyclic 6-10 membered heterocyclyl group. In some embodiments, both rings of the bicyclic 6-10 membered heterocyclyl group are saturated or partially saturated. In other embodiments, one ring of the bicyclic 6-10 membered heterocyclyl group is saturated or partially saturated and the other ring is aromatic. Such bicyclic heterocyclyl ring systems include, but are not limited to:

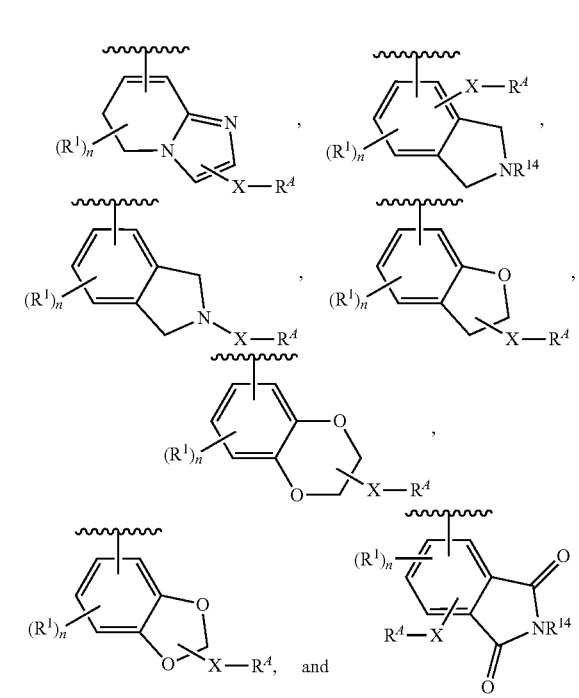

wherein each of X, $R^A$, $R^1$, $R^{14}$ and n is as defined above and herein.

In certain embodiments, Ring A is a 6,6-fused heteroaryl ring of any of formulae:

wherein each of X, $R^A$, $R^1$, $R^{14}$ and n is as defined above and herein.

It will be appreciated that in any of the above drawings of bicyclic Ring A having one or more floating substituents (e.g., —$R^1$ and/or —X—$R^A$) that the floating substituent may be present on any substitutable carbon atom on either ring of the fused ring system.

(iv) X

As is also defined generally above, X is a covalent bond, —O—, —N=N—, —C=N—, —$NR^6$—, —C($NR^6$)—, —S—, —C(O)—, —S(O)—, —S(O)$_2$—, optionally substituted $C_{1-6}$ alkylene, or optionally substituted $C_{2-6}$ alkenylene, wherein one, two or three methylene units of the $C_{1-6}$ alkylene or $C_{2-6}$ alkenylene are optionally and independently replaced with one or more —O—, —N=N—, —C=N—, —$NR^6$—, —C(NR)—, —S—, —C(O)—, —S(O)—, or —S(O)$_2$—.

In certain embodiments, X is a covalent bond.
In certain embodiments, X is —O—.
In certain embodiments, X is —$NR^6$—.
In certain embodiments, X is —S—.

In certain embodiments, X is an optionally substituted C$_{1-6}$ alkylene. In other embodiments, X is an optionally substituted C$_{1-4}$ alkylene. In yet other embodiments, X is an optionally substituted C$_{1-2}$ alkylene. In certain embodiments, X is —(CH$_2$)$_4$—. In certain embodiments, X is —(CH$_2$)$_3$—. In certain embodiments, X is —(CH$_2$)$_2$—. In certain embodiments, X is —CH$_2$—.

In certain embodiments, X is an optionally substituted C$_{2-6}$ alkenylene. In other embodiments, X is an optionally substituted C$_{2-4}$ alkenylene. In yet other embodiments, X is an optionally substituted C$_2$ alkenylene. In certain embodiments, X is —CH=CH—.

In certain embodiments, X is an optionally substituted C$_{1-6}$ alkylene, wherein one methylene unit is replaced with —O—. In certain embodiments, X is —CH$_2$O— or —OCH$_2$—.

In certain embodiments, X is an optionally substituted C$_{1-6}$ alkylene, wherein one methylene unit is replaced with —NR$^6$—. In certain embodiments, X is —CH$_2$NR$^6$— or —NR$^6$CH$_2$—.

In certain embodiments, X is a covalent bond, C(O), —O—, —CH$_2$O—, —OCH$_2$—, —NR$^6$—, or —CH$_2$NR$^6$—, or —NR$^6$CH$_2$—.

In certain embodiments, X is a covalent bond, —O—, or optionally substituted C$_{1-6}$ alkylene.

(v) R$^4$

As is defined generally above, R$^4$ is hydrogen, halogen, —OR$^7$, —CF$_3$, —CN, —NO$_2$, —SO$_2$R$^7$, —SOR$^7$, —C(O)R$^7$, —CO$_2$R$^7$, —C(O)N(R$^7$)$_2$, —CHO, —N$_3$, —N$_2$R$^7$, —N(R$^7$)$_2$, or Ring B having formula:

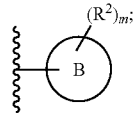

wherein Ring B is optionally substituted C$_{3-10}$ carbocyclyl, optionally substituted 3-10 membered heterocyclyl, optionally substituted C$_{6-10}$ aryl, or optionally substituted 5-10 membered heteroaryl, and R$^2$, R$^7$ and m are as defined herein.

In certain embodiments, R$^4$ is hydrogen.

In certain embodiments, R$^4$ is Ring B, as defined above and herein.

(vi) Ring B

As described herein, Ring B is optionally substituted C$_{3-10}$ carbocyclyl, optionally substituted 3-10 membered heterocyclyl, optionally substituted C$_{6-10}$ aryl, or optionally substituted 5-10 membered heteroaryl. Ring B is monocyclic or bicyclic. In certain embodiments, Ring B is aromatic.

In some embodiments, Ring B is an optionally substituted C$_6$ or C$_8$ monocyclic aryl group. Such monocyclic aryl ring systems include, but are not limited to:

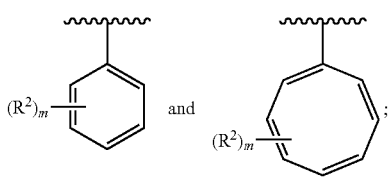

wherein each of R$^2$ and m is as defined above and herein.

In certain embodiments, Ring B is an optionally substituted phenyl ring of formula:

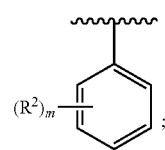

wherein each of R$^2$ and m is as defined above and herein.

In certain embodiments, Ring B is an optionally substituted phenyl ring of any one of formulae:

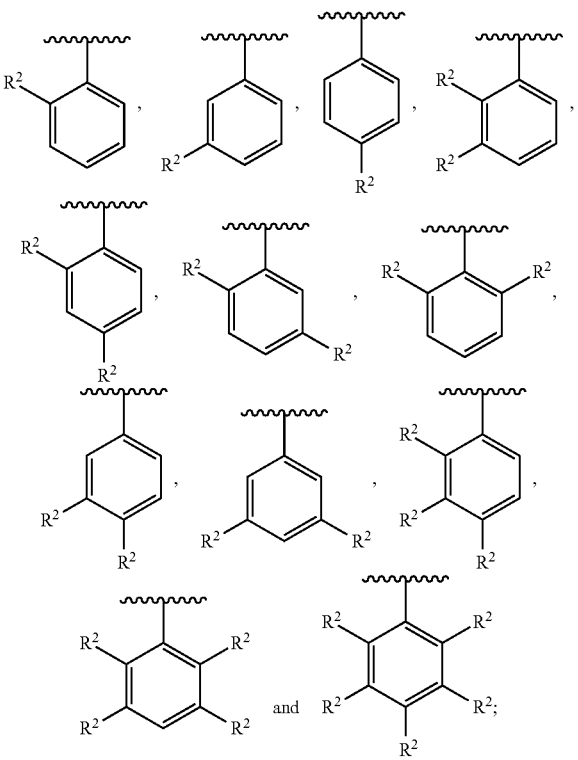

wherein R$^2$ is as defined above and herein.

In certain embodiments, both of Ring B and Ring A are phenyl.

In other embodiments, Ring B is an optionally substituted saturated or partially unsaturated C$_{3-10}$ or C$_{5-8}$ monocyclic carbocyclyl group. Such monocyclic ring systems include, but are not limited to:

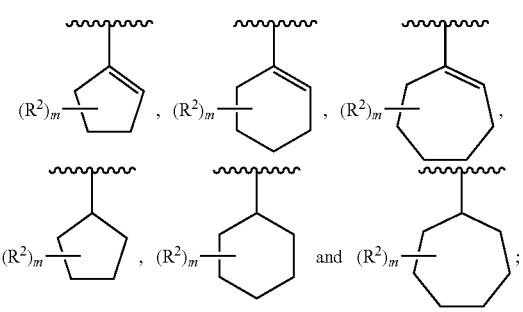

wherein each of R$^2$ and m is as defined above and herein.

In certain embodiments, Ring B is an optionally substituted 5-8 membered or 5-6 membered monocyclic heteroaryl group.

In certain embodiments, Ring B is an optionally substituted 5-membered heteroaryl group. Such monocyclic heteroaryl systems include, but are not limited to, any of formulae:

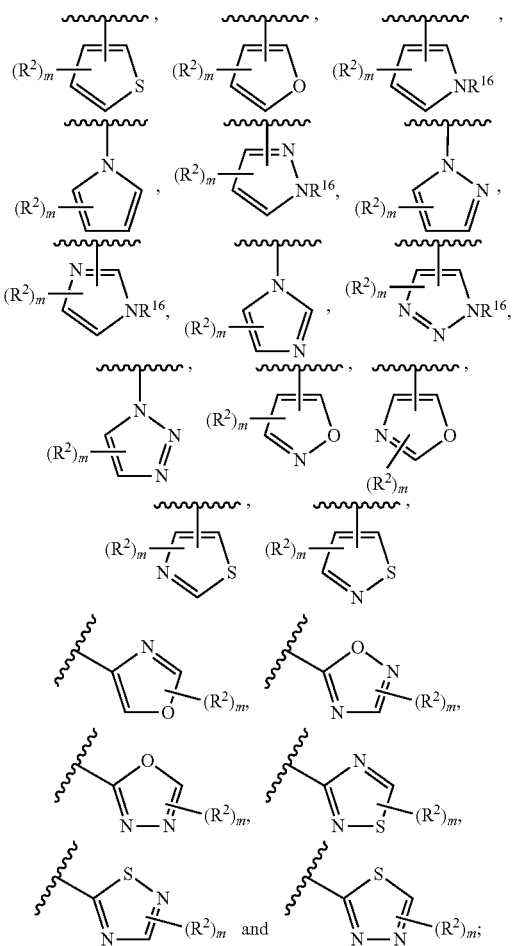

wherein each of $R^2$ and m is as defined above and herein,
$R^{16}$ is hydrogen, $-SO_2R^{11}$, $-SOR^{11}$, $-C(O)R^{11}$, $-CO_2R^{11}$, $-C(O)NH_2$, $-C(O)NH(R^{11})$, $-C(O)N(R^{11})_2$, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl, and
each instance of $R^{11}$ is, independently, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl.

In certain embodiments, Ring B is an optionally substituted 6-membered monocyclic heteroaryl group. Such monocyclic heteroaryl systems include, but are not limited to, 6-membered rings of any of formulae:

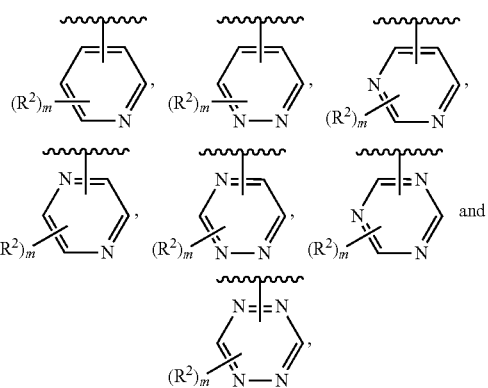

wherein each of $R^2$ and m is as defined above and herein.

In other embodiments, Ring B is an optionally substituted saturated or partially unsaturated monocyclic 3 to 10 membered heterocyclyl group. Such saturated or partially unsaturated monocyclic heterocyclyl systems include, but are not limited to:

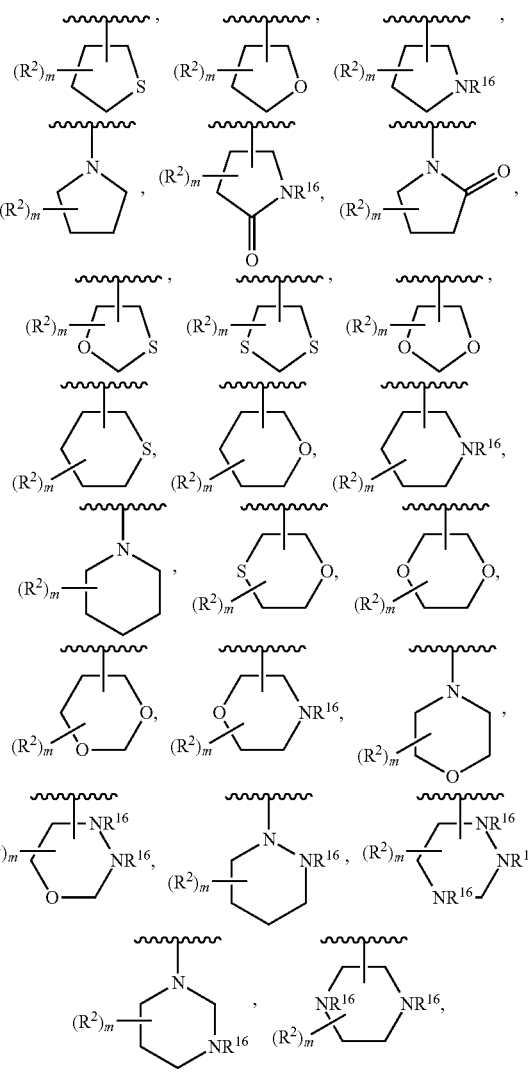

-continued

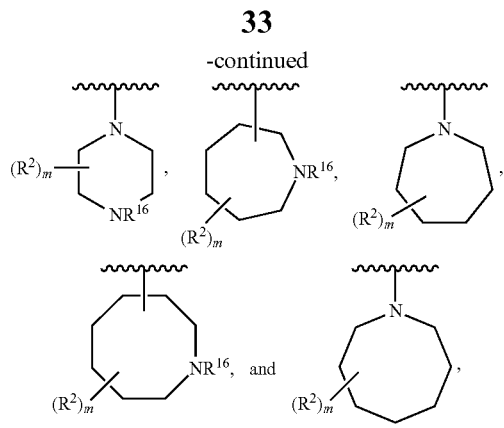

wherein each of $R^2$, $R^{16}$ and m is as defined above and herein.

In certain embodiments, Ring B is an optionally substituted $C_{10}$ bicyclic aryl group (i.e., naphthyl) having the formula:

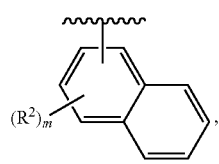

wherein each of $R^2$ and m is as defined above and herein.

In other embodiments, Ring B is a bicyclic $C_{8-10}$ carbocyclyl group. In some embodiments, both rings of the bicyclic $C_{8-10}$ carbocyclyl group are saturated or partially saturated. In other embodiments, one ring of the bicyclic $C_{8-10}$ carbocyclyl group is saturated or partially saturated and the other ring is aromatic. Such bicyclic ring systems include, but are not limited to:

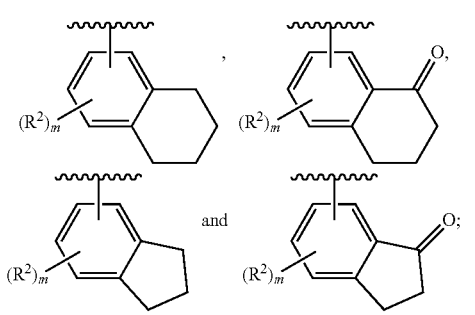

wherein each of $R^2$ and m is as defined above and above and described herein.

In certain embodiments, Ring B is an optionally substituted 6-10 membered bicyclic heteroaryl group. In certain embodiments, Ring B is an optionally substituted 9-10 membered bicyclic heteroaryl group. In certain embodiments, an optionally substituted 9-membered bicyclic heteroaryl group is a 6,5-fused bicyclic heteroaryl group. In certain embodiments, an optionally substituted 10-membered bicyclic heteroaryl group is a 6,6-fused bicyclic heteroaryl group.

Exemplary heteroaryl systems include, but are not limited to, 6,5-fused ring systems of any of formulae:

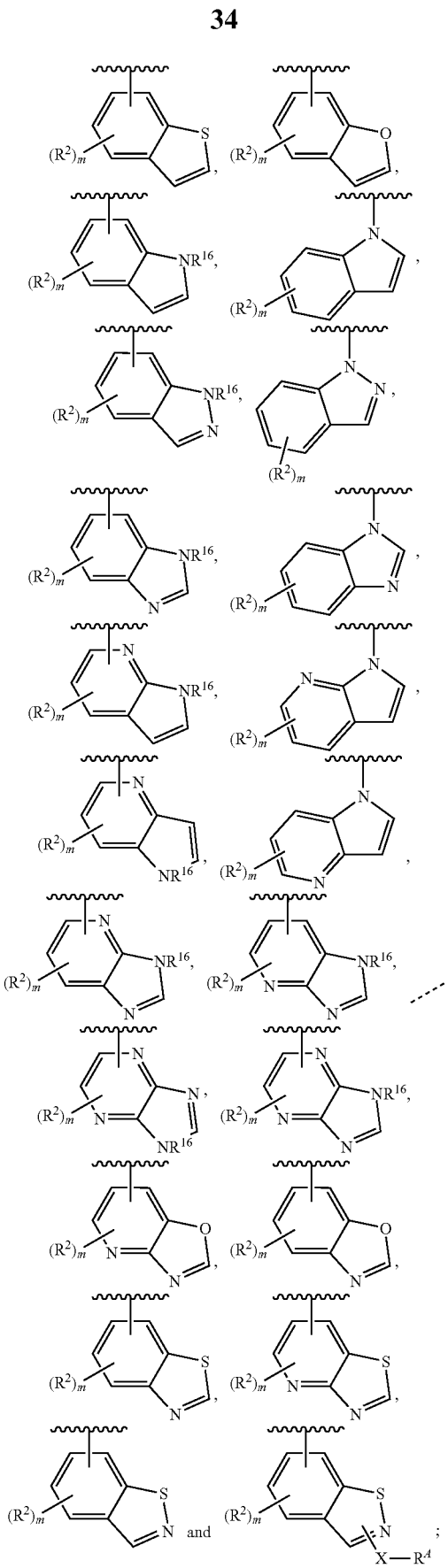

and 6,6-fused ring systems of any of formulae:

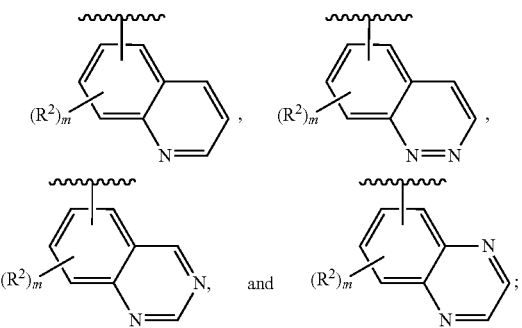

wherein each of $R^2$, $R^{16}$ and m is as defined above and herein.

In certain embodiments, Ring B is an optionally substituted saturated or partially saturated 9-10 membered bicyclic heterocyclyl group. Such bicyclic heterocyclyl systems include, but are not limited to:

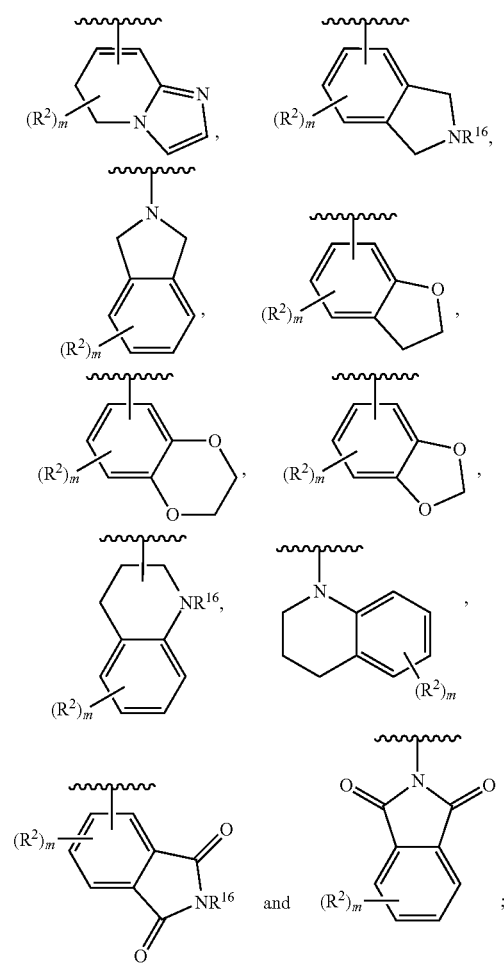

wherein each of $R^2$, $R^{16}$ and m is as defined above and herein.

It will be appreciated that in any of the above drawings of bicyclic Ring B having one or more floating substituents (e.g., —$R^2$) that the floating substituent may be present on any substitutable carbon atom on either ring of the fused bicyclic ring system.

(vii) $R^1$ and n

As defined generally above, each instance of $R^1$ is, independently, halogen, —$OR^8$, —$CF_3$, —CN, —$NO_2$, —$SO_2R^8$, —$SOR^8$, —$C(O)R^8$, —$CO_2R^8$, —$C(O)N(R^8)_2$, —$N_3$, —$N_2R^8$, —$N(R^8)_2$, —$B(OH)_2$, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or an optionally substituted 5-10 membered heteroaryl group; and wherein $R^8$ is as described herein.

In certain embodiments, each instance of $R^1$ is, independently, halogen, —$OR^8$, —$CF_3$, —CN, —$NO_2$, —$SO_2R^8$, —$SOR^8$, —$C(O)R^8$, —$CO_2R^8$, —$C(O)N(R^8)_2$, —$N_3$, —$N_2R^8$, or —$N(R^8)_2$, optionally substituted $C_{1-8}$ alkyl, optionally substituted $C_{2-8}$ alkenyl, or optionally substituted $C_{2-8}$ alkynyl.

In certain embodiments, each instance of $R^1$ is, independently, halogen, —$OR^8$ or optionally substituted $C_{1-8}$ alkyl. In some embodiments, $R^1$ is halogen. In other embodiments, $R^1$ is —F or —Cl. In certain embodiments, $R^1$ is —Cl. In other embodiments, $R^1$ is —F.

In certain embodiments, at least one $R^1$ is ortho to the boron atom. In other embodiments, at least one $R^1$ is meta to the boron atom. In yet other embodiments, at least one $R^1$ is para to the boron atom.

In certain embodiments, at least one $R^1$ is alpha to the boron atom. In other embodiments, at least one $R^1$ is beta to the boron atom. In yet other embodiments, at least one $R^1$ is gamma to the boron atom.

In certain embodiments, n is 0, 1, 2 or 3. In some embodiments, n is 0, 1 or 2. In other embodiments, n is 1 or 2. In yet other embodiments, n is 3. In yet other embodiments, n is 2. In still yet other embodiments, n is 1. In still yet other embodiments, n is 0.

It is understood that when n is 0 then Ring A is not substituted with an $R^1$ group, but instead is substituted with hydrogen. It is also understood that when n is 0, X is a covalent bond and $R^A$ is hydrogen, then Ring A is unsubstituted.

(viii) $R^2$ and m

As defined generally above, each instance of $R^2$ is, independently, halogen, —$OR^9$, —$CF_3$, —CN, —$NO_2$, —$SO_2R^9$, —$SOR^9$, —$C(O)R^9$, —$CO_2R^9$, —$C(O)N(R^9)_2$, —$N_3$, —$N_2R^9$, —$N(R^9)_2$, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl group; and wherein $R^9$ is as described herein.

In certain embodiments, each instance of $R^2$ is, independently, halogen, —$OR^9$, —$CF_3$, —CN, —$NO_2$, —$SO_2R^9$, —$SOR^9$, —$C(O)R^9$, —$CO_2R^9$, —$C(O)N(R^9)_2$, —$N_3$, —$N_2R^9$, —$N(R^9)_2$, optionally substituted $C_{1-8}$ alkyl, optionally substituted $C_{2-8}$ alkenyl, or optionally substituted $C_{2-8}$ alkynyl.

In certain embodiments, each instance of $R^2$ is, independently, halogen or —$OR^9$. In some embodiments, $R^2$ is halogen. In other embodiments, $R^2$ is —F or —Cl. In certain embodiments, $R^2$ is —Cl. In yet other embodiments, $R^2$ is —F.

In certain embodiments, at least one $R^2$ is ortho to X. In other embodiments, at least one $R^2$ is meta to X. In yet other embodiments, at least one $R^2$ is para to X.

In certain embodiments, at least one $R^2$ is alpha to X. In other embodiments, at least one $R^2$ is beta to X. In yet other embodiments, at least one $R^2$ is gamma to X.

In certain embodiments, m is 0, 1, 2, 3, 4 or 5. In some embodiments, m is 0, 1, 2 or 3. In some embodiments, m is 0, 1 or 2. In other embodiments, m is 1 or 2. In yet other embodiments, m is 3. In still other embodiments, m is 2. In still yet other embodiments, m is 1. In still other embodiments, m is 0.

It is understood that when m is 0, then Ring B is not substituted with an $R^2$ group, but instead is substituted with hydrogen.

(ix) Compounds of Formula (II) Wherein Ring A is Bicyclic

In certain embodiments, the present invention provides compounds of formula (I):

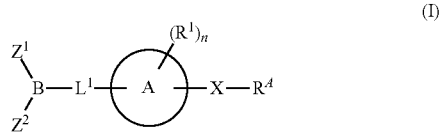

(I)

or a pharmaceutically acceptable salt or prodrug thereof, wherein $Z^1$, $Z^2$, $L^1$, X, $R^1$, $R^4$, and n are as defined above and herein, and wherein Ring A is an optionally substituted $C_{10}$ bicyclic aryl or an optionally substituted 9-10 membered bicyclic heteroaryl.

In certain embodiments, Ring A is an optionally substituted $C_{10}$ bicyclic aryl group. In certain embodiments, Ring A is an optionally substituted naphthyl group.

In certain embodiments, Ring A is an optionally substituted 9-10 membered bicyclic heteroaryl group.

In certain embodiments, Ring A is an optionally substituted 10-membered bicyclic heteroaryl group. In certain embodiments, Ring A is a 6,6-fused bicyclic heteroaryl. In certain embodiments, Ring A is a 6,6-fused bicyclic heteroaryl containing 1 to 2 N atoms. In certain embodiments, Ring A is a 6,6-fused bicyclic heteroaryl containing 1 N atom. In certain embodiments, Ring A is a 6,6-fused bicyclic heteroaryl containing 2 N atoms.

In certain embodiments, Ring A is an optionally substituted isoquinoline group. In certain embodiments, Ring A is an optionally substituted quinolinyl group. In certain embodiments, Ring A is an optionally substituted quinoxalinyl group.

In certain embodiments, the present invention provides 6,6-fused bicyclic compounds of formula (III):

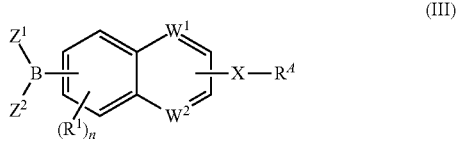

(III)

or a pharmaceutically acceptable salt or prodrug thereof, wherein:

(i) $Z^1$ is —OH or —OR$^3$ and $Z^2$ is —OH, —OR$^4$, an optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

(ii) $Z^1$ and $Z^2$ taken together form a 5- to 8-membered ring having at least one O, S, N or NR$^5$ directly bonded to the boron atom; or (iii) $Z^1$ is —OH or —OR$^3$, and $Z^2$ and Ring A taken together form an optionally substituted 5- to 7-membered ring;

$W^1$ and $W^2$ are independently selected from CR$^{12}$, C and N;

X is a covalent bond, —O—, —N=N—, —C=N—, —NR$^6$—, —C(NR$^6$)—, —S—, —C(O)—, —S(O)—, —S(O)$_2$—, or optionally substituted $C_{1-6}$ alkylene, wherein one, two or three methylene units of the $C_{1-6}$ alkylene are optionally and independently replaced with one or more groups selected from —O—, —N=N—, —C=N—, —NR$^6$—, —C(NR$^6$)—, —S—, —C(O)—, —S(O)—, and —S(O)$_2$—;

$R^4$ is hydrogen, halogen, —OR$^7$, —CF$_3$, —CN, —NO$_2$, —SO$_2$R$^7$, —SOR$^7$, —C(O)R$^7$, —CO$_2$R$^7$, —C(O)N(R$^7$)$_2$, —N$_3$, —N$_2$R$^7$, —N(R$^7$)$_2$, or Ring B having formula:

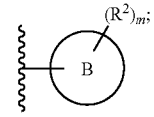

wherein Ring B is optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of $R^1$ is, independently, halogen, —OR$^8$, —CF$_3$, —CN, —NO$_2$, —SO$_2$R$^8$, —SOR$^8$, —C(O)R$^8$, —CO$_2$R$^8$, —C(O)N(R$^8$)$_2$, —N$_3$, —N$_2$R$^8$, —N(R$^8$)$_2$, —B(OH)$_2$, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of $R^2$ is, independently, halogen, —OR$^9$, —CF$_3$, —CN, —NO$_2$, —SO$_2$R$^9$, —SOR$^9$, —C(O)R$^9$, —CO$_2$R$^9$, —C(O)N(R$^9$)$_2$, —N$_3$, —N$_2$R$^9$, —N(R$^9$)$_2$, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of $R^3$ and $R^4$ is, independently, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of $R^5$, $R^6$, $R^7$, $R^8$, $R^9$, and $R^{10}$ is, independently, hydrogen, —C(O)R$^{11}$, —SO$_2$R$^{11}$, —SOR$^{11}$, —C(O)R$^{11}$, —CO$_2$R$^{11}$, —C(O)N(R$^{11}$)$_2$, —C(O)NH(R$^{11}$), —C(O)NH$_2$, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of $R^{11}$ is, independently, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of $R^{12}$ is, independently, hydrogen, halogen, —$CF_3$, optionally substituted $C_{1-8}$ alkyl, optionally substituted $C_{2-8}$ alkenyl, or optionally substituted $C_{2-8}$ alkynyl;

n is, independently, 0, 1, 2 or 3 and m is 0, 1, 2, 3, 4 or 5.

In certain embodiments, the present invention provides 6,6-fused bicyclic compounds of the formula (III-a), (III-b), (III-c), (III-d) or (III-e):

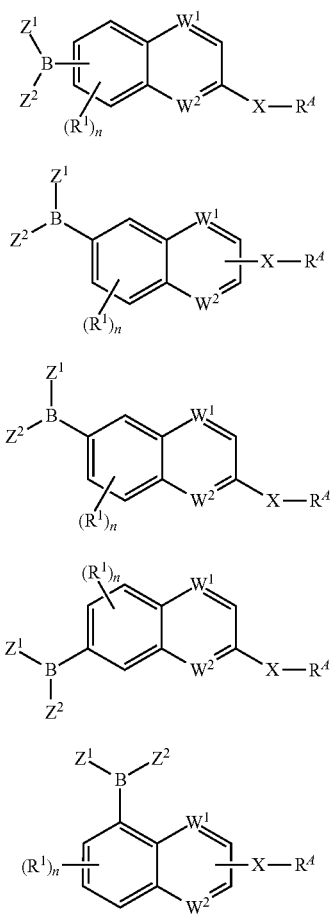

or a pharmaceutically acceptable salt or prodrug thereof, wherein $W^1$, $W^2$, $Z^1$, $Z^2$, X, $R^1$, $R^4$, and n are as defined above and herein.

In certain embodiments, n is 0. In certain embodiments, n is 1 or 2. In certain embodiments, n is 1.

In certain embodiments, $R^1$ is optionally substituted $C_{1-8}$ alkyl. In certain embodiments, $R^1$ is —$CH_3$.

In certain embodiments, X is a covalent bond, —(C=O)—, —O—, —$CH_2$O—, —O$CH_2$—, —NH—, —N($R^9$)—, —N($R^9$)$CH_2$—, —$CH_2$N($R^9$)— or an optionally substituted $C_{1-6}$ alkylene. In certain embodiments, X is a covalent bond, —(C=O)—, —O—, —$CH_2$O—, —O$CH_2$—, —NH—, —N($R^9$)—, —N($R^9$)$CH_2$—, —$CH_2$N($R^9$)—, —$CH_2$—, —($CH_2$)$_2$—, —($CH_2$)$_3$—, —($CH_2$)$_4$—, or —($CH_2$)$_5$—.

In certain embodiments, $R^4$ is hydrogen.

In certain embodiments, $R^4$ is Ring B. In certain embodiments, Ring B is an optionally substituted aryl, optionally substituted pyridinyl, optionally substituted pyrazinyl, optionally substituted pyrimidinyl, optionally substituted 1,2,3,4-tetrahydroquinolinyl, optionally substituted cyclopentyl or optionally substituted cyclohexyl.

In certain embodiments, m is 0. In certain embodiments, m is 1 or 2. In certain embodiments, m is 1.

In certain embodiments, $R^2$ is halogen, —$OR^9$, —CN, —$NO_2$, or —N($R^9$)$_2$. In certain embodiments, $R^2$ is —Cl, —CN, —$NO_2$, —OH, —$OCH_3$, —$OC_4H_9$, or —N($CH_3$)$_2$.

In certain embodiments, at least one of $W^1$ and $W^2$ is N.

In certain embodiments, $W^1$ is N and $W^2$ is C or $CR^{12}$. In certain embodiments, $W^2$ is N and $W^1$ is C or $CR^{12}$. In some embodiments, $W^1$ is N and $W^2$ is CH. In some embodiments, $W^2$ is N and $W^1$ is CH. In certain embodiments, wherein $W^1$ is N and $W^2$ is C, CH or $CR^{12}$, or wherein $W^2$ is N and $W^1$ is C, CH or $CR^{12}$, the following compounds are specifically excluded:

(i) compounds wherein n is 0, X is a covalent bond and $R^4$ is hydrogen;

(ii) compounds wherein n is 1, $R^1$ is fluoro, X is —$CH_2$—, and $R^4$ is hydrogen; and/or (iii) compounds wherein n is 1, $R^1$ is chloro, X is a covalent bond, and $R^4$ is hydrogen.

In certain embodiments, both $W^1$ and $W^2$ are N. In certain embodiments, wherein both $W^1$ and $W^2$ are N, the following compounds are specifically excluded:

(i) compounds wherein n is 0, X is a covalent bond and $R^4$ is hydrogen.

In certain embodiments, both $W^1$ and $W^2$ are, independently, C or $CR^{12}$. In certain embodiments, both $W^1$ and $W^2$ are CH. In certain embodiments, wherein both $W^1$ and $W^2$ are C, CH or $CR^{12}$, the following compounds are specifically excluded:

(i) compounds wherein n is 0, X is a covalent bond and $R^4$ is hydrogen, —OH, —$OCH_3$, —$OCH_2CH_3$ or —$OCH_2C_6H_5$;

(ii) compounds wherein n is 1, $R^1$ is —CHO or —$CH_2$N($R^9$)$C_6H_5$, X is a covalent bond, and $R^4$ is hydrogen;

(iii) compounds wherein n is 0, X is a covalent bond, and $R^4$ is an optionally substituted phenyl or napthyl ring (Ring B); and/or (iv) compounds wherein n is 0 and X is —C=N—NH—(C=S)— or —C=N—NH—(C=O)—.

In certain embodiments, the following compounds are specifically excluded:

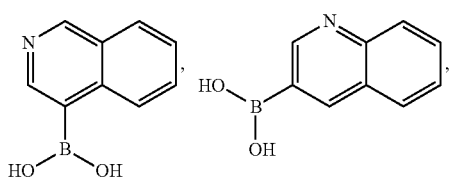

-continued

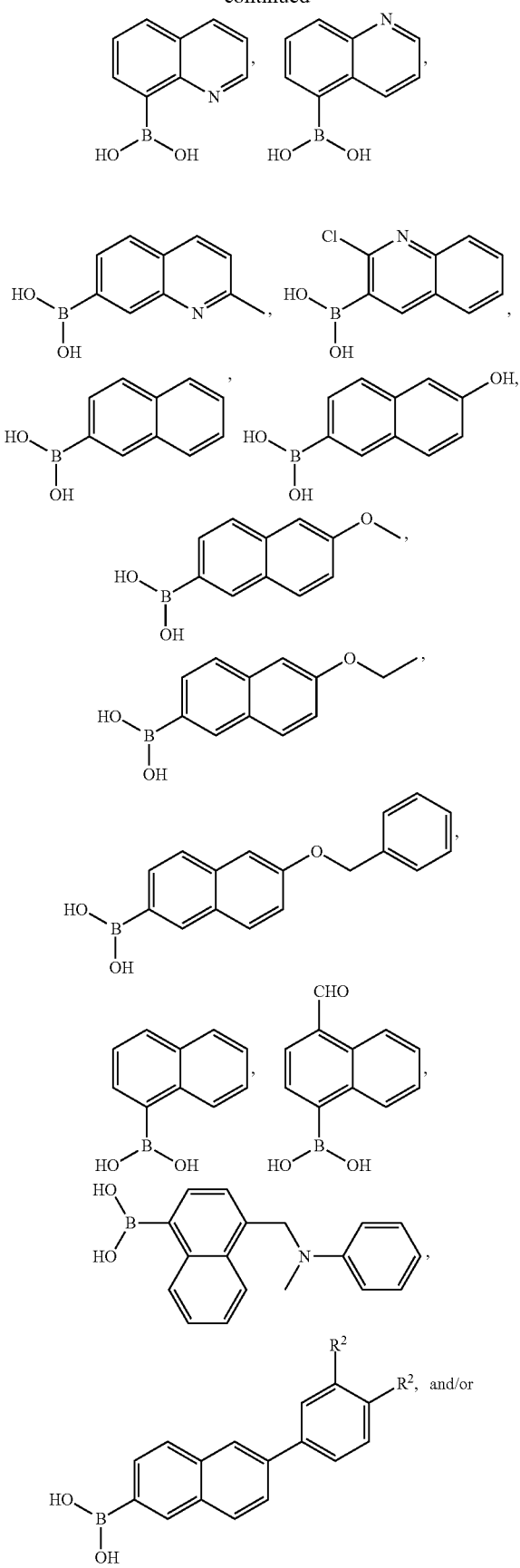

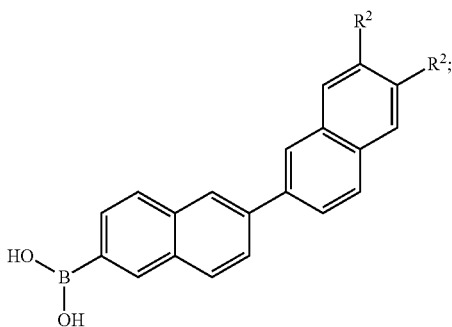

or a pharmaceutically acceptable salt or prodrug thereof.

In certain embodiments, $W^1$ is C or CH and $W^2$ is N, providing 6,6-fused bicyclic compounds of the formula (III-e):

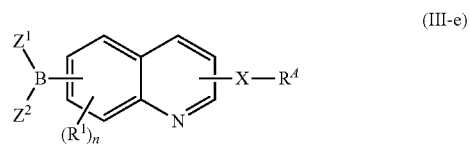
(III-e)

or a pharmaceutically acceptable salt or prodrug thereof, wherein $Z^1$, $Z^2$, $L^1$, X, $R^1$, $R^4$, and n are as defined above and herein. Examples of such compounds include compounds of any of formulae (III-e1), (III-e2), (III-e3), (III-e4) and (III-e5):

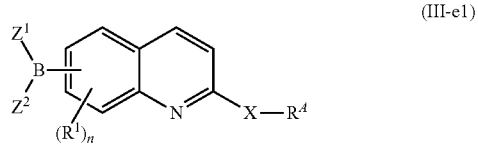
(III-e1)

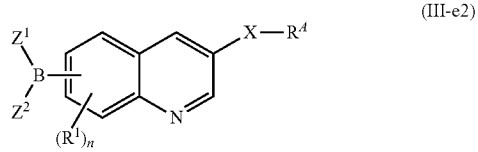
(III-e2)

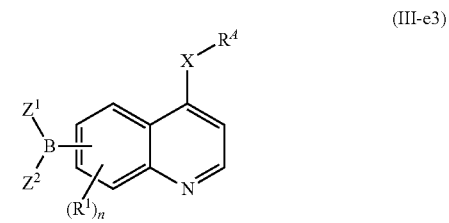
(III-e3)

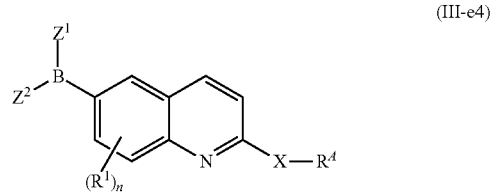
(III-e4)

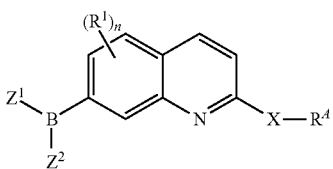
(III-e5)

or a pharmaceutically acceptable salt or prodrug thereof, wherein $Z^1$, $Z^2$, X, $R^1$, $R^4$, and n are as defined above and herein.

In certain embodiments, both $W^1$ and $W^2$ are N, providing 6,6-fused bicyclic compounds of the formula (III-f):

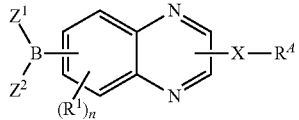
(III-f)

or a pharmaceutically acceptable salt or prodrug thereof, wherein $Z^1$, $Z^2$, $L^1$, X, $R^1$, $R^4$, and n are as defined above and herein. Examples of such compounds include compounds of any of formulae (III-f1), (III-f2), (III-f3) or (III-f4):

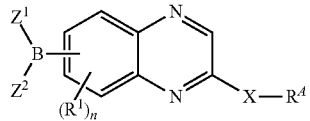
(III-f1)

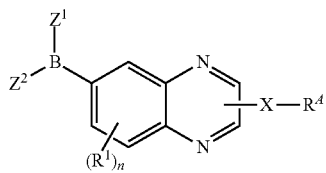
(III-f2)

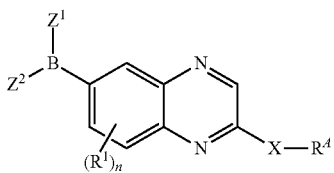
(III-f3)

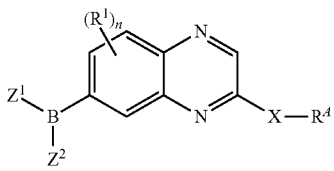
(III-f4)

or a pharmaceutically acceptable salt or prodrug thereof, wherein $Z^1$, $Z^2$, X, $R^1$, $R^4$, and n are as defined above and herein.

In certain embodiments, both $W^1$ and $W^2$ are C or CH, providing 6,6-fused bicyclic compounds of formula (III-g):

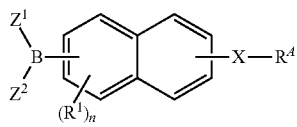
(III-g)

or a pharmaceutically acceptable salt or prodrug thereof, wherein $Z^1$, $Z^2$, $L^1$, X, $R^1$, $R^4$, and n are as defined above and herein. Examples of such compounds include compounds of any of formulae (III-g1), (III-g2), (III-g3), (III-g4), (III-g5), (III-g6) or (III-g7):

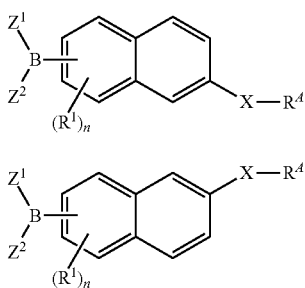
(III-g1)

(III-g2)

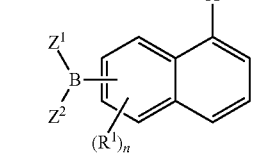
(III-g3)

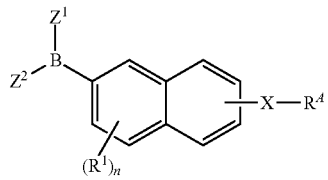
(III-g4)

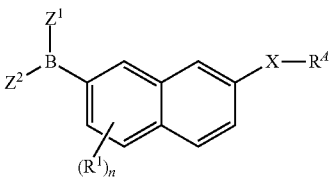
(III-g5)

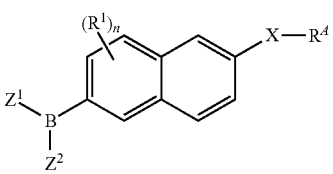
(III-g6)

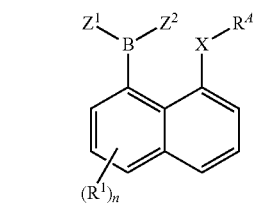
(III-g7)

or a pharmaceutically acceptable salt or prodrug thereof, wherein $Z^1$, $Z^2$, X, $R^1$, $R^4$, and n are as defined above and herein.
Exemplary 6,6-fused bicyclic compounds encompassed by formulae (I), (III), and subgenera thereof, are provided below in Tables 1-3.
TABLE 1
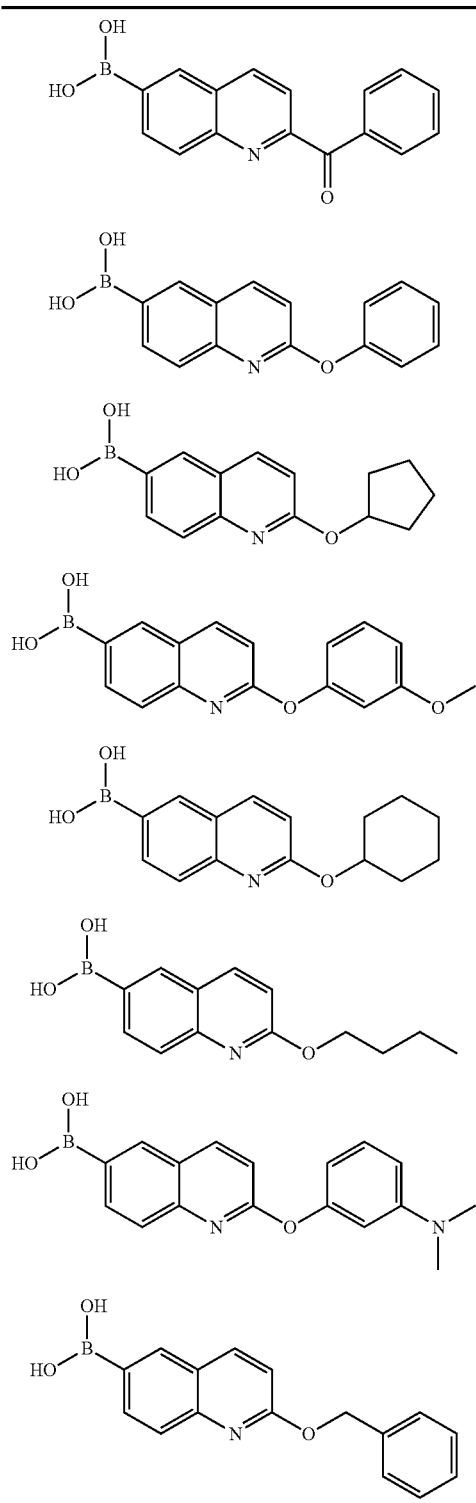
TABLE 1-continued
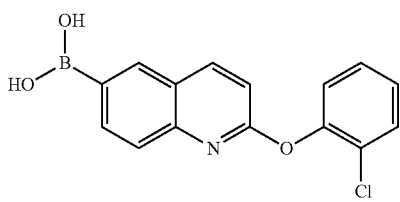 [SMILES: OB(O)c1ccc2nc(Oc3ccccc3Cl)ccc2c1]
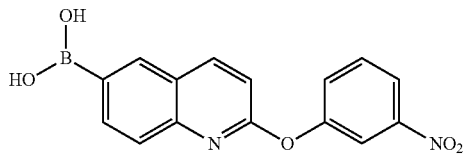 [SMILES: O=[N+]([O-])c1cccc(Oc2ccc3cc(B(O)O)ccc3n2)c1]
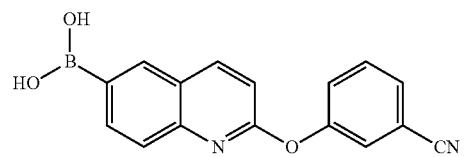 [SMILES: N#Cc1cccc(Oc2ccc3cc(B(O)O)ccc3n2)c1]
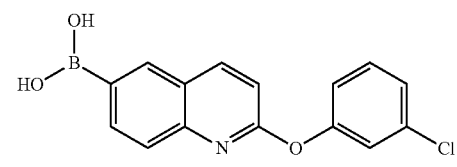 [SMILES: OB(O)c1ccc2nc(Oc3cccc(Cl)c3)ccc2c1]
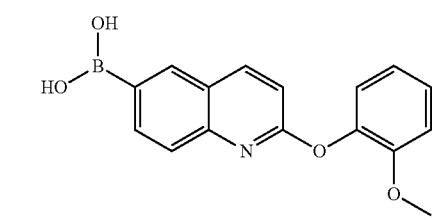 [SMILES: COc1ccccc1Oc1ccc2cc(B(O)O)ccc2n1]
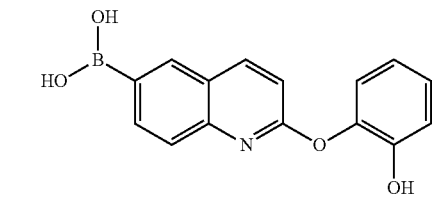 [SMILES: OB(O)c1ccc2nc(Oc3ccccc3O)ccc2c1]
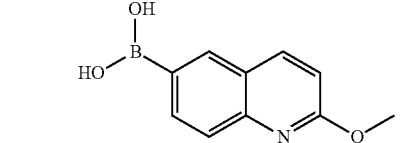
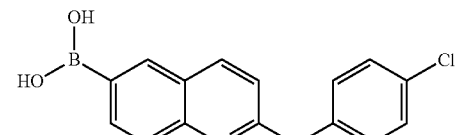

TABLE 1-continued
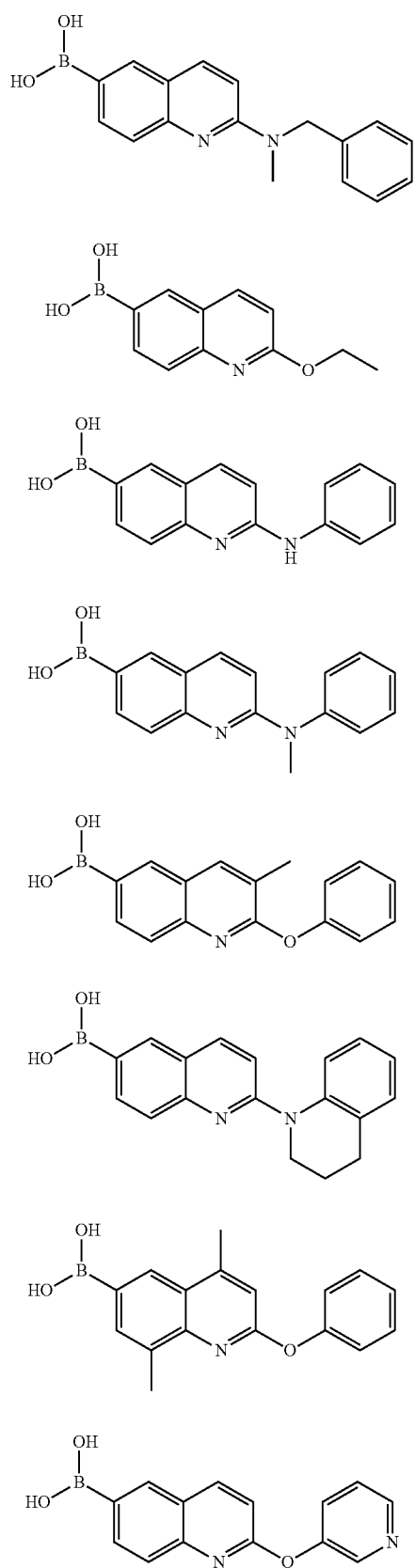
TABLE 1-continued
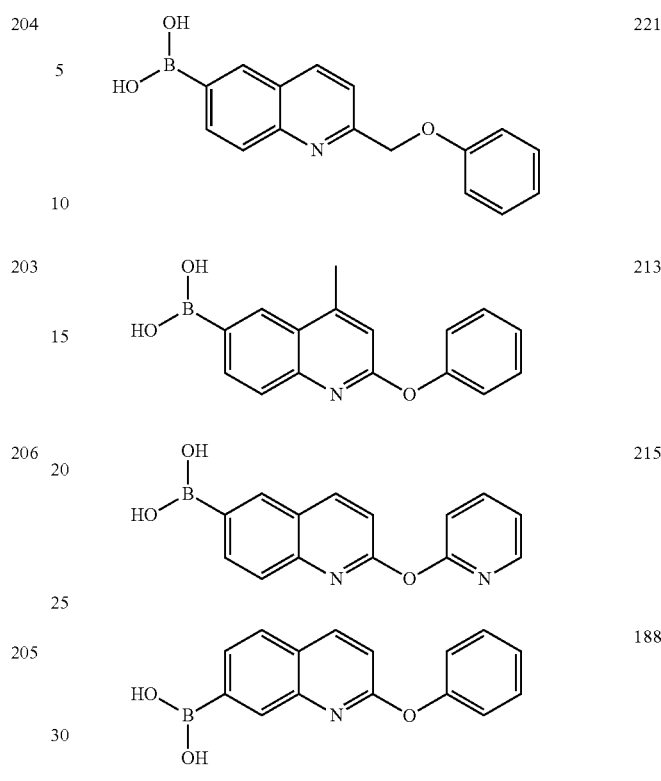
TABLE 2
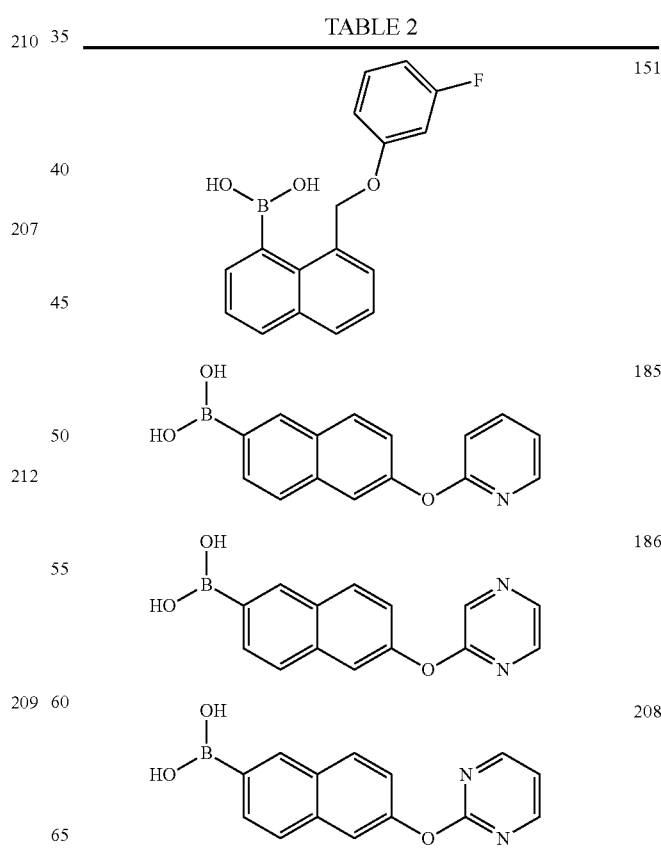

TABLE 2-continued

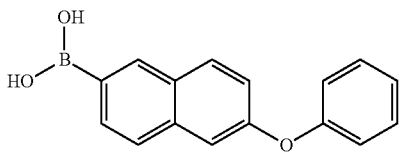 [SMILES: OB(O)c1ccc2cc(Oc3ccccc3)ccc2c1]
216

TABLE 3

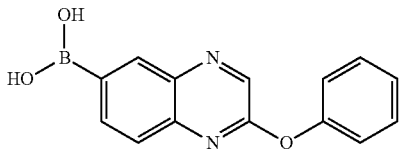 [SMILES: OB(O)c1ccc2nc(Oc3ccccc3)cnc2c1]
211

In certain embodiments, Ring A is an optionally substituted 9-membered bicyclic heteroaryl group. In certain embodiments, Ring A is a 6,5-fused bicyclic heteroaryl group. In certain embodiments, Ring A is a 6,5-fused bicyclic heteroaryl group containing 2-3 heteroatoms selected from O, S, N and $NR^{14}$, wherein:

$R^{14}$ is, independently, hydrogen, $-SO_2R^{11}$, $-SOR^{11}$, $-C(O)R^{11}$, $-CO_2R^{11}$, $-C(O)N(R^{11})_2$, $-C(O)NH(R^{11})$, $-C(O)NH_2$, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl; and each instance of $R^{11}$ is, independently, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl.

In certain embodiments, Ring A is a 6,5-fused bicyclic heteroaryl group containing 2 heteroatoms selected from O, S, N and $NR^{14}$. In certain embodiments, Ring A is a 6,5-fused bicyclic heteroaryl group containing 3 heteroatoms selected from O, S, N and $NR^{14}$.

In certain embodiments, Ring A is an optionally substituted benzoxazolyl, optionally substituted benzthiazolyl, optionally substituted benzimidazolyl, an optionally substituted indazolyl or an optionally substituted imidazopyridinyl group.

In certain embodiments, the present invention provides compounds of formula (IV):

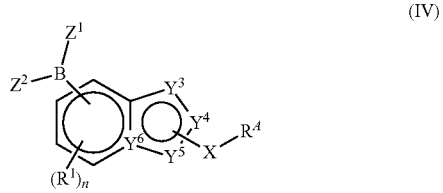
(IV)

or pharmaceutically acceptable salt or prodrug thereof, wherein:

(i) $Z^1$ is $-OH$ or $-OR^3$ and $Z^2$ is $-OH$, $-OR^4$, an optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

(ii) $Z^1$ and $Z^2$ taken together form a 5- to 8-membered ring having at least one O, S, N or $NR^5$ atom directly bonded to the boron atom; or (iii) $Z^1$ is $-OH$ or $-OR^3$, and $Z^2$ and Ring A taken together form an optionally substituted 5- to 7-membered ring;

each of $Y^3$, $Y^4$ and $Y^5$ is independently selected from C, $CR^{13}$, N, $NR^{14}$, O and S, with the proviso that at least one of $Y^3$, $Y^4$ or $Y^5$ is a heteroatom selected from N, $NR^{14}$, O or S;

$Y^6$ is C or N;

X is a covalent bond, $-O-$, $-N=N-$, $-C=N-$, $-NR^6-$, $-C(NR^6)-$, $-S-$, $-C(O)-$, $-S(O)-$, $-S(O)_2-$, or optionally substituted $C_{1-6}$ alkylene, wherein one, two or three methylene units of the $C_{1-6}$ alkylene are optionally and independently replaced with one or more groups selected from $-O-$, $-N=N-$, $-C=N-$, $-NR^6-$, $-C(NR^6)-$, $-S-$, $-C(O)-$, $-S(O)-$, and $-S(O)_2-$;

$R^4$ is hydrogen, halogen, $-OR^7$, $-CF_3$, $-CN$, $-NO_2$, $-SO_2R^7$, $-SOR^7$, $-C(O)R^7$, $-CO_2R^7$, $-C(O)N(R^7)_2$, $-N_3$, $-N_2R^7$, $-N(R^7)_2$, or Ring B having formula:

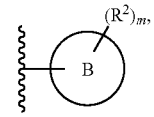

wherein Ring B is optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of $R^1$ is, independently, halogen, $-OR^8$, $-CF_3$, $-CN$, $-NO_2$, $-SO_2R^8$, $-SOR^8$, $-C(O)R^8$, $-CO_2R^8$, $-C(O)N(R^8)_2$, $-N_3$, $-N_2R^8$, $-N(R^8)_2$, $-B(OH)_2$, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of $R^2$ is, independently, halogen, $-OR^9$, $-CF_3$, $-CN$, $-NO_2$, $-SO_2R^9$, $-SOR^9$, $-C(O)R^9$, $-CO_2R^9$, $-C(O)N(R^9)_2$, $-N_3$, $-N_2R^9$, $-N(R^9)_2$, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of $R^3$ and $R^4$ is, independently, optionally substituted $C_{1-8}$ alkyl, optionally substituted $C_{2-8}$ alkenyl, optionally substituted $C_{2-8}$ alkynyl, optionally substituted C$_{1-8}$ heteroalkyl, optionally substituted C$_{2-8}$ heteroalkenyl, optionally substituted C$_{2-8}$ heteroalkynyl, optionally substituted C$_{3-10}$ carbocyclyl, optionally substituted 3-10 membered heterocyclyl, optionally substituted C$_{6-10}$ aryl, or optionally substituted 5-10 membered heteroaryl;

each instance of R$^5$, R$^6$, R$^7$, R$^8$, R$^9$, R$^{10}$, and R$^{14}$ is, independently, hydrogen, —SO$_2$R$^{11}$, —SOR$^{11}$, —C(O)R$^{11}$, —CO$_2$R$^{11}$, —C(O)N(R$^{11}$)$_2$, —C(O)NH(R$^{11}$), —C(O)NH$_2$, optionally substituted C$_{1-8}$ alkyl, optionally substituted C$_{2-8}$ alkenyl, optionally substituted C$_{2-8}$ alkynyl, optionally substituted C$_{1-8}$ heteroalkyl, optionally substituted C$_{2-8}$ heteroalkenyl, optionally substituted C$_{2-8}$ heteroalkynyl, optionally substituted C$_{3-10}$ carbocyclyl, optionally substituted 3-10 membered heterocyclyl, optionally substituted C$_{6-10}$ aryl, or optionally substituted 5-10 membered heteroaryl;

each instance of R$^{11}$ is, independently, optionally substituted C$_{1-8}$ alkyl, optionally substituted C$_{2-8}$ alkenyl, optionally substituted C$_{2-8}$ alkynyl, optionally substituted C$_{1-8}$ heteroalkyl, optionally substituted C$_{2-8}$ heteroalkenyl, optionally substituted C$_{2-8}$ heteroalkynyl, optionally substituted C$_{3-10}$ carbocyclyl, optionally substituted 3-10 membered heterocyclyl, optionally substituted C$_{6-10}$ aryl, or optionally substituted 5-10 membered heteroaryl;

each instance of R$^{13}$ is, independently, hydrogen, halogen, —CF$_3$, optionally substituted C$_{1-8}$ alkyl, optionally substituted C$_{2-8}$ alkenyl, or optionally substituted C$_{2-8}$ alkynyl;

n is 0, 1, 2 or 3; and m is 0, 1, 2, 3, 4 or 5.

In certain embodiments, the present invention provides compounds of any of formulae (IV-a), (IV-b), (IV-c), (IV-d) or (IV-e):

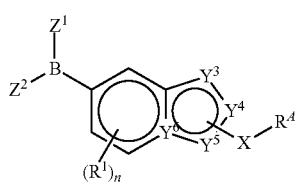
(IV-a)

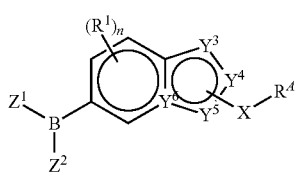
(IV-b)

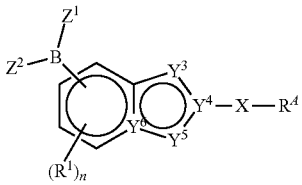
(IV-c)

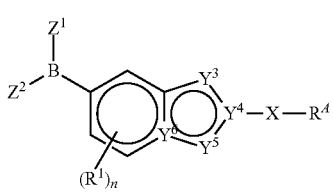
(IV-d)

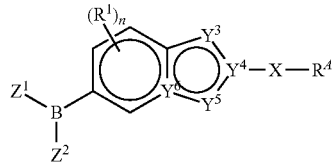
(IV-e)

or pharmaceutically acceptable salts or prodrugs thereof, wherein Y$^3$, Y$^4$, Y$^5$, Y$^6$, Z$^1$, Z$^2$, R$^1$, X, n and R$^A$ are as defined above and herein.

In certain embodiments, n is 0. In certain embodiments, n is 1 or 2. In certain embodiments, n is 1.

In certain embodiments, R$^1$ is halogen. In certain embodiments, R$^1$ is —F. In certain embodiments, R$^1$ is —Br.

In certain embodiments, X is a covalent bond or an optionally substituted C$_{1-6}$ alkylene. In certain embodiments, X is a covalent bond. In certain embodiments, X is —CH$_2$—, —(CH$_2$)$_2$—, —(CH$_2$)$_3$—, —(CH$_2$)$_4$—, —(CH$_2$)$_5$— or —(CH$_2$)$_5$(C=O)—.

In certain embodiments, R$^A$ is hydrogen. In certain embodiments, R$^A$ is —CF$_3$.

In certain embodiments, R$^A$ is Ring B. In certain embodiments, Ring B is an optionally substituted phenyl, optionally substituted pyrrolidinone or an optionally substituted piperidinyl.

In certain embodiments, m is 0. In certain embodiments, m is 1 or 2. In certain embodiments, m is 1.

In certain embodiments, R$^2$ is optionally substituted C$_{1-8}$ alkyl, optionally substituted C$_{6-10}$ aryl, —SO$_2$R$^9$, —SOR$^9$, —C(O)R$^9$, or —CO$_2$R$^9$. In certain embodiments, R$^2$ is —C$_3$H$_7$, —CH$_2$CH(CH$_3$)$_2$, —CO$_2$tBu, —C(O)(CH$_2$)$_2$C$_6$H$_5$, —C$_6$H$_5$, —CH$_2$C$_5$, or —SO$_2$C$_6$H$_5$.

In certain embodiments, two of Y$^3$, Y$^4$ and Y$^5$ are, independently, heteroatoms selected from N, NR$^{14}$, O or S, and Y$^6$ is C.

In certain embodiments, one of Y$^3$, Y$^4$, Y$^5$ is a heteroatom selected from N, NR$^{14}$, O or S, and Y$^6$ is C or N.

In certain embodiments, one of Y$^3$, Y$^4$, Y$^5$ is a heteroatom selected from N, NR$^{14}$, O or S, and Y$^6$ is N.

In certain embodiments, Y$^3$ is O or S. In certain embodiments, Y$^3$ is O. In certain embodiments, Y$^3$ is S.

In certain embodiments, Y$^6$ is C.

In certain embodiments, Y$^3$ is O or S, Y$^4$ is C, Y$^5$ is N and Y$^6$ is C. In certain embodiments, wherein Y$^3$ is O or S; Y$^4$ is C; Y$^5$ is N and Y$^6$ is C, the following compounds are specifically excluded:

(i) compounds wherein n is 0, X is a covalent bond, and R$^A$ is hydrogen; and/or (ii) compounds wherein n is 0, X is —CH$_2$—, and R$^A$ is hydrogen.

In certain embodiments, Y$^3$ is O or S, Y$^4$ and Y$^5$ are, independently, C or CR$^{13}$ and Y$^6$ is C. In certain embodiments, wherein Y$^3$ is O or S, Y$^4$ and Y$^5$ are, independently, C or CR$^{13}$ and Y$^6$ is C, the following compounds are specifically excluded:

(i) compounds wherein n is 0, X is a covalent bond or —CH$_2$—, and R$^A$ is hydrogen or chloro;

(ii) compounds wherein n is 0, X is —CH$_2$O— or —OCH$_2$— and R$^A$ is —C$_6$H$_5$; and/or (iii) compounds wherein n or is 0, X is —(C=O)—, and R$^A$ is —C$_6$H$_5$.

In certain embodiments, Y$^3$ and Y$^4$ are, independently, N or NR$^{14}$, Y$^5$ is C or CR$^{13}$ and Y$^6$ is C. In certain embodiments, wherein $Y^3$ and $Y^4$ are, independently, N or $NR^{14}$, $Y^5$ is C or $CR^{13}$ and $Y^6$ is C, the following compounds are specifically excluded:

(i) compounds wherein n is 0, X is a covalent bond, and $R^A$ is hydrogen.

In certain embodiments, $Y^3$ and $Y^5$ are, independently, N or $NR^{14}$, $Y^4$ is C or $CR^{13}$, and $Y^6$ is C. In certain embodiments, wherein $Y^3$ and $Y^5$ are, independently, N or $NR^{14}$, $Y^4$ is C or $CR^{13}$, and $Y^6$ is C, the following compounds are specifically excluded:

(i) compounds wherein n is 0, X is a covalent bond, and $R^A$ is hydrogen.

In certain embodiments, $Y^3$ and $Y^6$ are, independently, N and $Y^4$ and $Y^5$ are, independently, C or $CR^{13}$. In certain embodiments, wherein $Y^3$ and $Y^6$ are, independently, N and $Y^4$ and $Y^5$ are, independently, C or $CR^{13}$, the following compounds are specifically excluded:

(i) compounds wherein n is 0, X is a covalent bond, and $R^A$ is hydrogen.

In certain embodiments, $Y^3$ is N or $NR^{14}$, and $Y^4$, $Y^5$ and $Y^6$ are, independently, C or $CR^{13}$. In certain embodiments, wherein $Y^3$ is N or $NR^{14}$, and $Y^4$, $Y^5$ and $Y^6$ are, independently, C or $CR^{13}$, the following compounds are specifically excluded:

(i) compounds wherein n is 0, X is a covalent bond, and $R^A$ is hydrogen;
(ii) compounds wherein n is 0, X is —$OCH_2$— or —$CH_2O$—, and $R^A$ is —$C_6H_5$; and/or
(iii) compounds wherein n is 0, 1 or 2, $R^1$ is —OH or —$OCH_3$, X is —(C=O)— and $R^A$ is —$OR^7$.

In certain embodiments, the following compounds are specifically excluded:

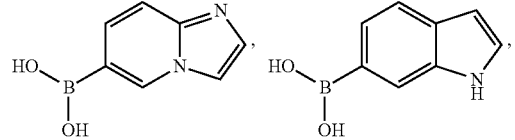

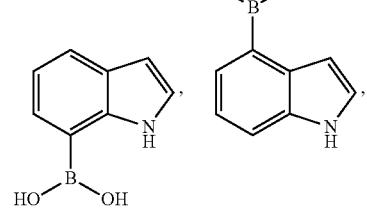

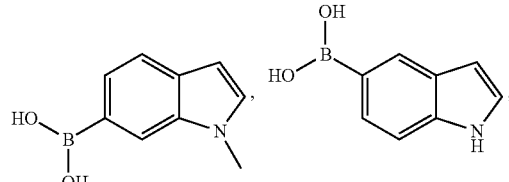

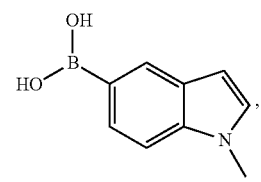

-continued

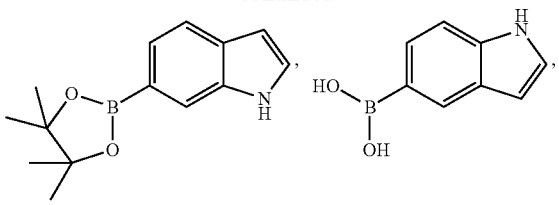

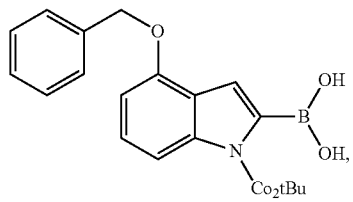

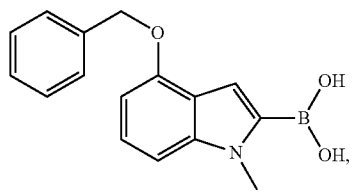

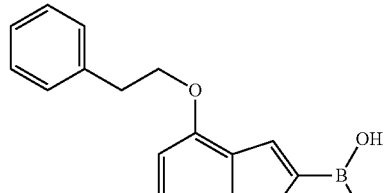

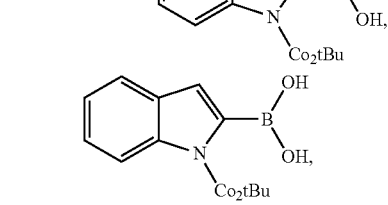

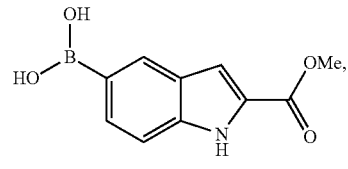

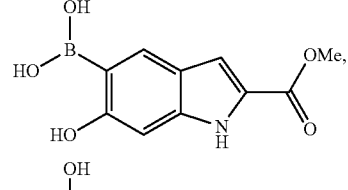

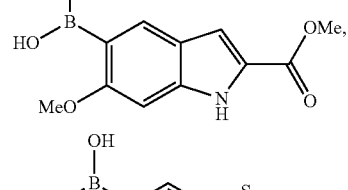

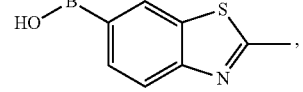

-continued

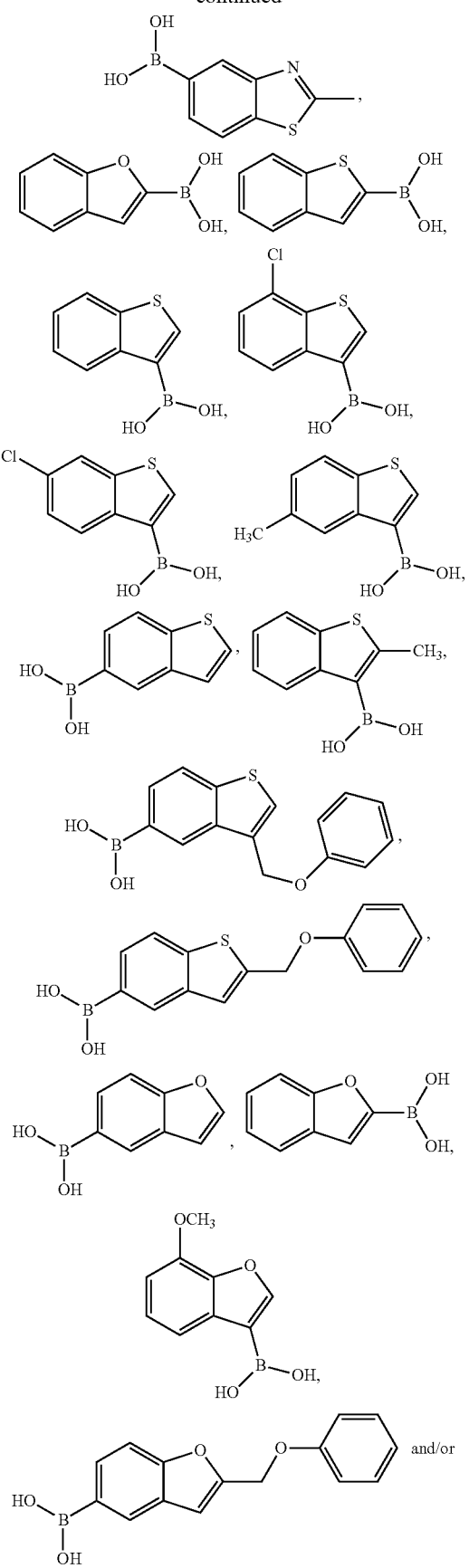

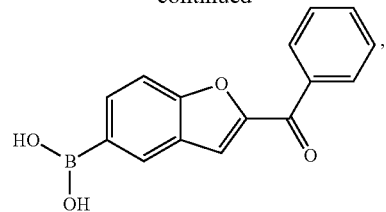

or pharmaceutically acceptable salts or prodrugs thereof.

In certain embodiments, the present invention provides compounds of the formula (IV-f):

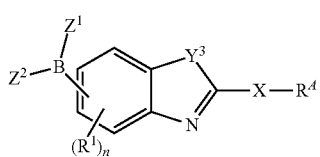

(IV-f)

or pharmaceutically acceptable salts or prodrugs thereof, wherein $Y^3$, $Z^1$, $Z^2$, $R^1$, X, n and $R^4$ are as defined above and herein. Examples of such compounds include compounds of the formulae (IV-f1) and (IV-f2):

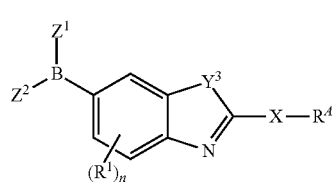

(IV-f1)

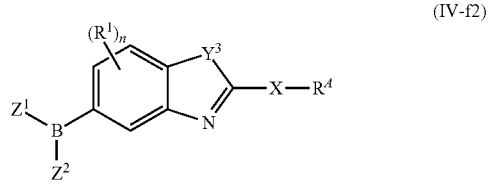

(IV-f2)

or a pharmaceutically acceptable salt or prodrug thereof, wherein $Y^3$, $Z^1$, $Z^2$, $R^1$, X, n and $R^4$ are as defined above and herein.

In certain embodiments, the present invention provides compounds of the formula (IV-g):

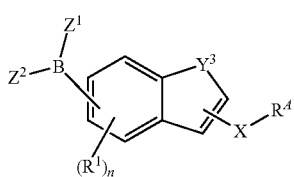

(IV-g)

or a pharmaceutically acceptable salt or prodrug thereof, wherein $Y^3$, $Z^1$, $Z^2$, $R^1$, X, n and $R^4$ are as defined above and herein. Examples of such compounds include compounds of either of formulae (IV-g1) and (IV-g2):

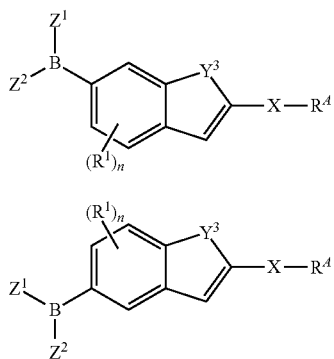

(IV-g1)

(IV-g2)

or a pharmaceutically acceptable salt or prodrug thereof, wherein $Y^3$, $Z^1$, $Z^2$, $R^1$, X, n and $R^A$ are as defined above and herein.

In certain embodiments, the present invention provides compounds of formula (IV-h):

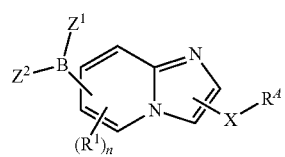

(IV-h)

or a pharmaceutically acceptable salt or prodrug thereof, wherein $Z^1$, $Z^2$, $R^1$, X, n and $R^A$ are as defined above and herein. Examples of such compounds include compounds of the formulae (IV-h1) and (IV-h2):

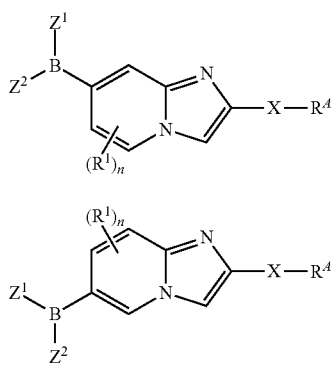

(IV-h1)

(IV-h2)

In certain embodiments, the present invention provides compounds of either of formulae (IV-i) or (IV-k):

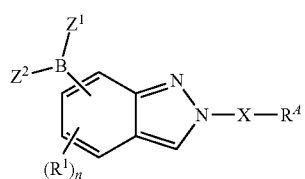

(IV-i)

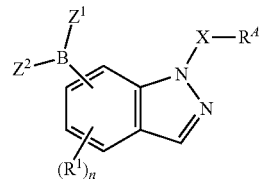

(IV-k)

or a pharmaceutically acceptable salt or prodrug thereof, wherein $Z^1$, $Z^2$, $R^1$, X, n and $R^A$ are as defined above and herein. Examples of such compounds include compounds of any of formulae (IV-i1), (IV-i2), (IV-k1) and (IV-k2):

(IV-i1)

(IV-i2)

(IV-k1)

(IV-k2)

or a pharmaceutically acceptable salt or prodrug thereof, wherein $Z^1$, $Z^2$, $R^1$, X, n and $R^A$ are as defined above and herein.

In certain embodiments, the present invention provides compounds of the formulae (IV-m) or (IV-n):

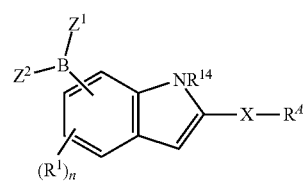

(IV-m)

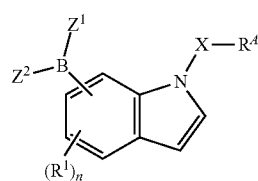
or a pharmaceutically acceptable salt or prodrug thereof, wherein $R^{14}$, $Z^1$, $Z^2$, $R^1$, X, n and $R^A$ are as defined above and herein.
Exemplary 6,5-fused bicyclic compounds encompassed by formulae (I), (IV), and subgenera thereof, are provided below in Tables 4-8.
TABLE 4
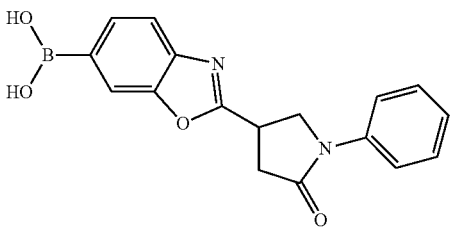 [SMILES: O=C1CC(c2nc3ccc(B(O)O)cc3o2)CN1c1ccccc1]
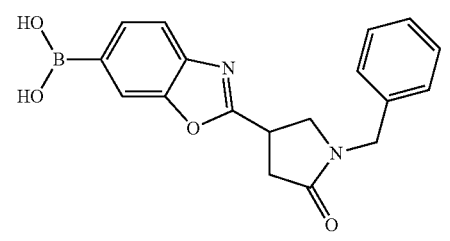 [SMILES: O=C1CC(c2nc3ccc(B(O)O)cc3o2)CN1Cc1ccccc1]
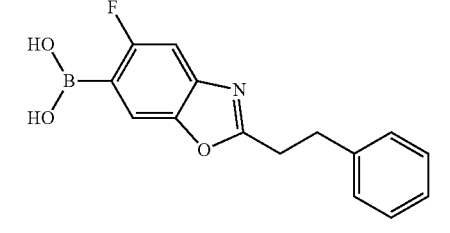 [SMILES: OB(O)c1cc2oc(CCc3ccccc3)nc2cc1F]
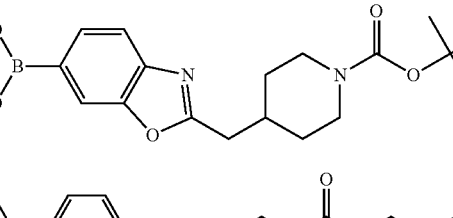
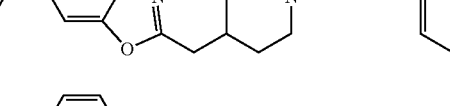
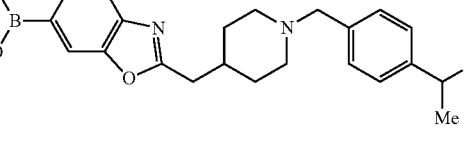
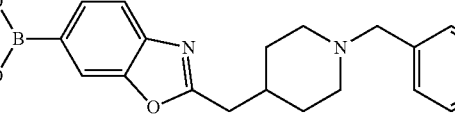
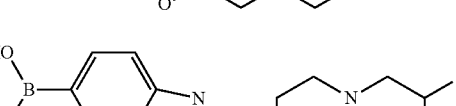
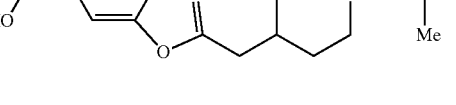

TABLE 4-continued

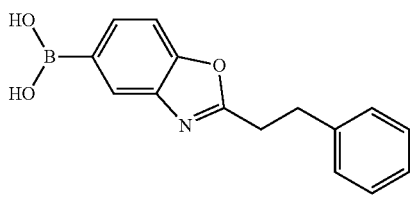 [SMILES: OB(O)c1ccc2oc(CCc3ccccc3)nc2c1] 242

TABLE 5

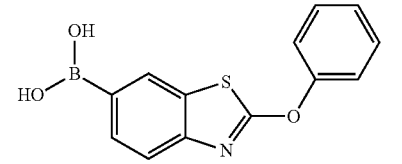 [SMILES: OB(O)c1ccc2nc(Oc3ccccc3)sc2c1] 214

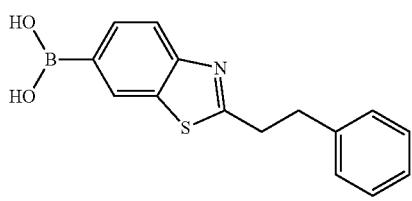 278

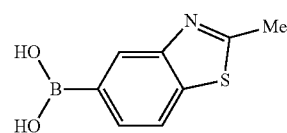 [SMILES: Cc1nc2cc(B(O)O)ccc2s1] 88

TABLE 6

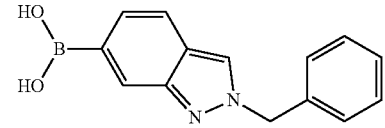 313

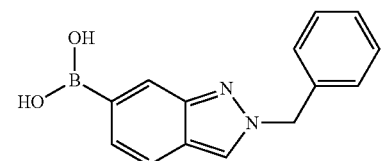 217

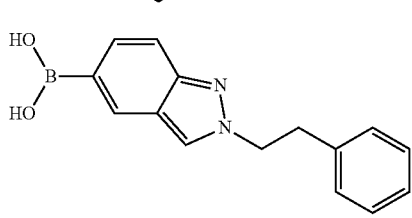 315

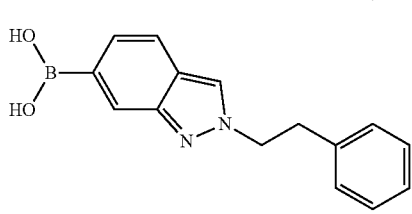 [SMILES: OB(O)c1ccc2cn(CCc3ccccc3)nc2c1] 314

TABLE 6-continued

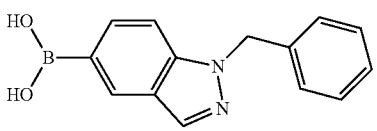 [SMILES: OB(O)c1ccc2c(cnn2Cc2ccccc2)c1] 316

TABLE 7

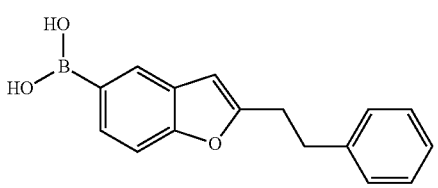 [SMILES: OB(O)c1ccc2oc(CCc3ccccc3)cc2c1] 291

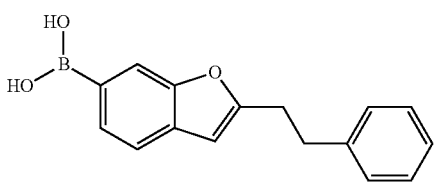 [SMILES: OB(O)c1ccc2cc(CCc3ccccc3)oc2c1] 293

TABLE 8

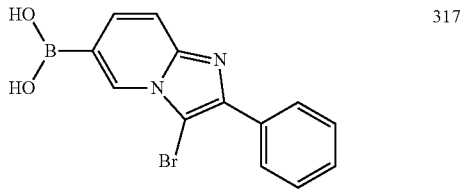 317

(x) Compounds of Formula II, Wherein Ring B is Het-B

In certain embodiments, the present invention provides compounds of formula (II):

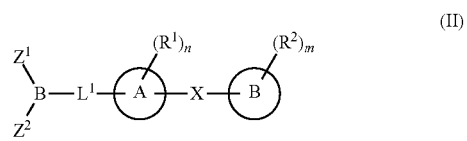 (II)

or a pharmaceutically acceptable salt or prodrug thereof, wherein $Z^1$, $Z^2$, $L^1$, X, Ring A, Ring B, $R^1$, $R^2$, n and m are as defined above and herein.

In certain embodiments, Ring B is optionally substituted 3-10 membered heterocyclyl or optionally substituted 5-10 membered heteroaryl (i.e., referred to as "Het-B"). Such ring systems are depicted and described in detail above and herein.

For example, in certain embodiments, the present invention provides compounds of formula (V):

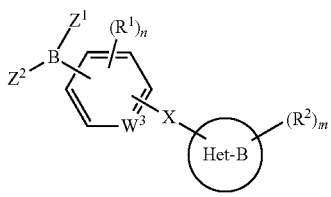

(V)

or a pharmaceutically acceptable salt or prodrug thereof;
wherein:

(i) $Z^1$ is —OH or —OR$^3$ and $Z^2$ is —OH, —OR$^4$, an optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

(ii) $Z^1$ and $Z^2$ taken together form a 5- to 8-membered ring having at least one O, S, N or NR$^5$ atom directly bonded to the boron atom; or (iii) $Z^1$ is —OH or —OR$^3$, and $Z^2$ and Ring A taken together form an optionally substituted 5- to 7-membered ring;

$W^3$ is C, CR$^{15}$, or N;

X is a covalent bond, —O—, —N=N—, —C=N—, —NR$^6$—, —C(NR$^6$)—, —S—, —C(O)—, —S(O)—, —S(O)$_2$—, or optionally substituted $C_{1-6}$ alkylene, wherein one, two or three methylene units of the $C_{1-6}$ alkylene are optionally and independently replaced with one or more groups selected from —O—, —N=N—, —C=N—, —NR$^6$—, —C(NR$^6$)—, —S—, —C(O)—, —S(O)—, and —S(O)$_2$—;

Het-B is an optionally substituted 3-10 membered heterocyclyl or an optionally substituted 5-10 membered heteroaryl ring;

each instance of R$^1$ is, independently, halogen, —OR$^8$, —CF$_3$, —CN, —NO$_2$, —SO$_2$R$^8$, —SOR$^8$, —C(O)R$^8$, —CO$_2$R$^8$, —C(O)N(R$^8$)$_2$, —N$_3$, —N$_2$R$^8$, —N(R$^8$)$_2$, —B(OH$_2$), optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of R$^2$ is, independently, halogen, —OR$^9$, —CF$_3$, —CN, —NO$_2$, —SO$_2$R$^9$, —SOR$^9$, —C(O)R$^9$, —CO$_2$R$^9$, —C(O)N(R$^9$)$_2$, —N$_3$, —N$_2$R$^9$, —N(R$^9$)$_2$, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of R$^3$ and R$^4$ is, independently, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of R$^5$, R$^6$, R$^7$, R$^8$, R$^9$, and R$^{10}$ is, independently, hydrogen, —SO$_2$R$^{11}$, —SOR$^{11}$, —C(O)R$^{11}$, —CO$_2$R$^{11}$, —C(O)N(R$^{11}$)$_2$, —C(O)NH(R$^{11}$), —C(O)NH$_2$, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of R$^{11}$ is, independently, hydrogen, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

R$^{15}$ is hydrogen, halogen, —CF$_3$, optionally substituted $C_{1-8}$ alkyl, optionally substituted $C_{2-8}$ alkenyl, or optionally substituted $C_{2-8}$ alkynyl;

n is 0, 1, 2 or 3; and m is 0, 1, 2, 3, 4, or 5.

In certain embodiments, each n is 0. In certain embodiments, each n is independently 1 or 2. In certain embodiments, each n is 1.

In certain embodiments, R$^1$ is halogen, —OR$^8$, —CF$_3$, optionally substituted $C_{1-8}$ alkyl or optionally substituted 5-membered heteroaryl. In certain embodiments, R$^1$ is —Cl, —F, —OCH$_3$, —OCH$_2$CH$_2$C$_6$H$_5$, —O(CH$_2$)$_3$CH$_3$, —CH$_2$C(CH$_3$)$_2$, or an optionally substituted oxadiazolyl.

In certain embodiments, X is a covalent bond or an optionally substituted $C_{1-6}$ alkylene. In certain embodiments, X is a covalent bond. In certain embodiments, X is —CH$_2$— or —CH=CH—.

In certain embodiments, each m is 0. In certain embodiments, each m is independently 1 or 2. In certain embodiments, each m is 1.

In certain embodiments, R$^2$ is selected from —OR$^9$, —N(R$^9$)$_2$, optionally substituted $C_{1-8}$ alkyl, optionally substituted $C_{2-8}$ alkenyl, optionally substituted $C_{1-8}$ heteroalkyl, optionally substituted $C_{6-10}$ aryl, or optionally substituted 5-10 membered heteroaryl. In certain embodiments, R$^2$ is selected from optionally substituted $C_{1-8}$ alkyl, optionally substituted $C_{6-10}$ aryl, or optionally substituted 5-10 membered heteroaryl.

In certain embodiments, R$^2$ is selected from —CH$_3$, —CH$_2$CH$_3$, —CH$_2$C(CH$_3$)$_3$, —(CH$_2$)$_2$CH$_3$, —C(CH$_3$)$_3$, —(CH$_2$)$_3$CH$_3$, —CH$_2$C(CH$_3$)$_3$, —(CH$_2$)$_4$CH$_3$, —(CH$_2$)$_5$CH$_3$, —(CH$_2$)$_3$C(CH$_3$)$_3$, —(CH$_2$)$_6$CH$_3$, —(CH$_2$)$_4$CH$_3$, —CH$_2$CH$_2$CF$_3$, —CH(CH$_3$)(CH$_2$)$_3$CH$_3$, —CH=CH(CH$_2$)$_2$CH$_3$, —(CH$_2$)$_2$CH(CH$_3$)CH$_2$CH$_3$, —CH$_2$CH$_2$CH$_2$CF$_3$, —CH$_2$CH$_2$CF$_2$CF$_3$, —C(OH)(CH$_3$)$_2$, —CH$_2$CH$_2$CH$_2$(C=O)-(oxadiazole), optionally substituted pyridinyl, —C$_6$H$_5$, optionally substituted phenyl, optionally substituted benzyl, —CH$_2$CH$_2$Ph, optionally substituted furanyl, optionally substituted imidazolyl, optionally substituted thiazolyl, —OCH$_3$, —OCH$_2$CH$_3$, —CH$_2$OCH$_3$, —CH$_2$OCH$_2$CH$_3$, —CH$_2$CH$_2$CH$_2$OCH$_3$, —CH$_2$NHBoc, —CH$_2$CH$_2$NHBoc, —CH$_2$CH$_2$NHAc, —CH$_2$CH$_2$NH(C=O)OCH$_3$, —N(CH$_3$)$_2$, —CH$_2$CH$_2$N(C=O)OCH$_2$CH$_2$CH$_2$—), —CH$_2$CH$_2$(C=O)N(CH$_2$CH$_2$CH$_2$CH$_2$—), —CH$_2$C$_5$H$_9$, —CH$_2$C$_6$H$_{11}$, —CH$_2$CH$_2$C$_5$H$_9$, —CH$_2$CH$_2$C$_6$H$_{11}$, —CH$_2$(furanyl), —CH$_2$(thiophenyl), and —CH$_2$(indanyl). In certain embodiments, R$^2$ is selected from —(CH$_2$)$_4$CH$_3$, —CH$_2$CH$_2$CF$_2$CF$_3$, optionally substituted pyridinyl and optionally substituted phenyl. In certain embodiments, R$^2$ is selected from —(CH$_2$)$_4$CH$_3$, —CH$_2$CH$_2$CF$_2$CF$_3$, -pyridinyl or —C$_6$H$_5$.

In certain embodiments, W$^3$ is C or CR$^{15}$. In certain embodiments, W$^3$ is C or CH. In certain embodiments, W$^3$ is CH. In certain embodiments, W$^3$ is N.

In certain embodiments, the present invention provides compounds of formula (V-a):

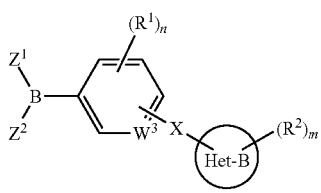
(V-a)

or a pharmaceutically acceptable salt or prodrug thereof, wherein W$^3$, Z$^1$, Z$^2$, X, Het-B, R$^1$, R$^2$, m and n are as defined above and herein. Examples of such compounds, wherein Ring A is substituted ortho, meta, or para to the boron atom with the group X-HetB, are provided in compounds of any of formulae (V-b), (V-c) or (V-d):

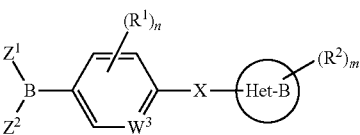
(V-b)

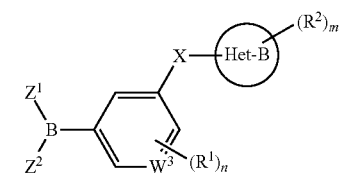
(V-c)

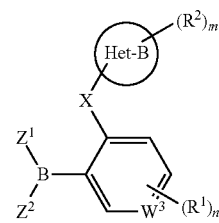
(V-d)

or a pharmaceutically acceptable salt or prodrug thereof, wherein W$^3$, Z$^1$, Z$^2$, X, Het-B, R$^1$, R$^2$, m and n are as defined above and herein.

Exemplary Het-B rings include, but are not limited to,

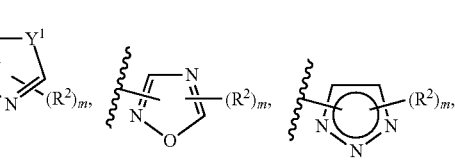

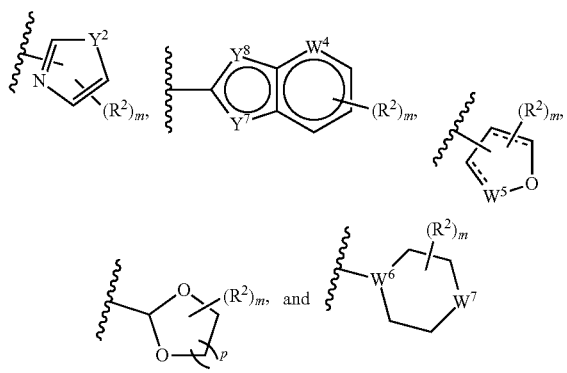

wherein Y$^1$, Y$^2$, Y$^7$, Y$^8$, W$^4$, W$^5$, W$^6$, W$^7$ and p are as defined below, and R$^2$ and m are as defined above and herein.

For example, in certain embodiments, the present invention provides compounds of formula (V-e):

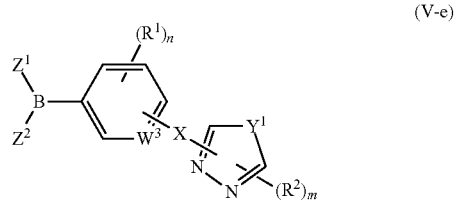
(V-e)

or a pharmaceutically acceptable salt or prodrug thereof, wherein W$^3$, Z$^1$, Z$^2$, X, Het-B, R$^1$, R$^2$, m and n are as defined above and herein, and Y$^1$ is O, S or NR$^{16}$.

In certain embodiments, Y$^1$ is O or S. In certain embodiments, Y$^1$ is O. In certain embodiments, Y$^1$ is S. For example, in certain embodiments, the present invention provides compounds of any of formulae (V-e1), (V-e2), (V-e3), (V-e4), (V-e5), (V-e6), or (V-e7):

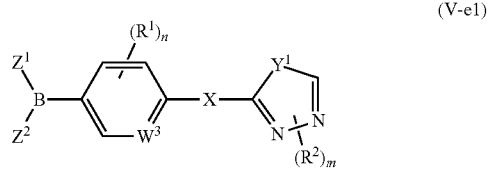
(V-e1)

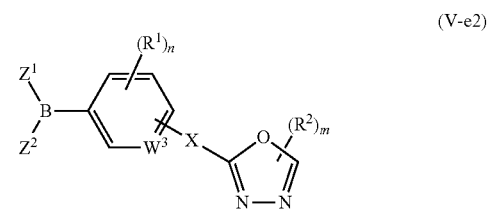
(V-e2)

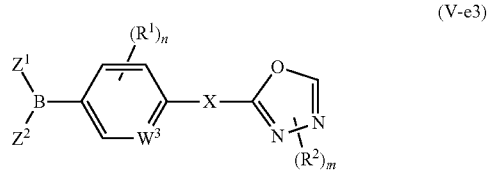
(V-e3)

-continued

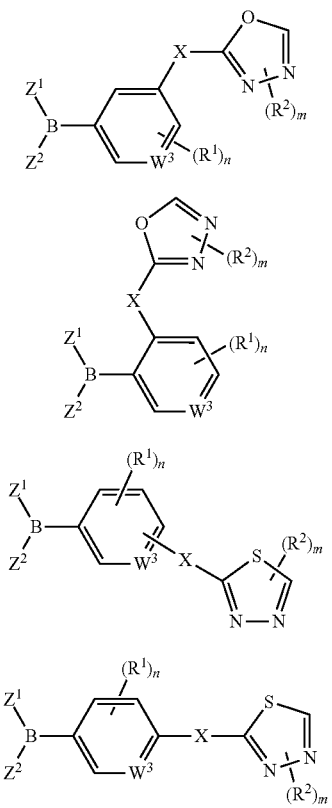

(V-e4)
(V-e5)
(V-e6)
(V-e7)

or a pharmaceutically acceptable salt or prodrug thereof, wherein $W^3$, $Z^1$, $Z^2$, X, Het-B, $R^1$, $R^2$, m and n are as defined above and herein.

In certain embodiments, the present invention provides compounds of formula (V-f):

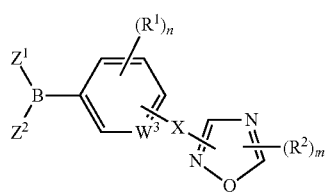

(V-f)

or a pharmaceutically acceptable salt or prodrug thereof, wherein $W^3$, $Z^1$, $Z^2$, X, $R^1$, $R^2$, m and n are as defined above and herein. For example, in certain embodiments, the present invention provides compounds of any of formulae (V-f1), (V-f2), (V-f3) or (V-f4):

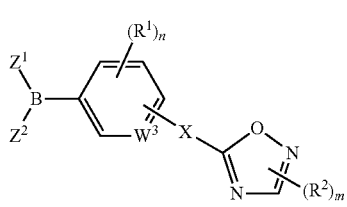

(V-f1)

-continued

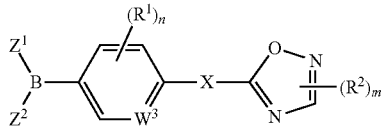

(V-f2)

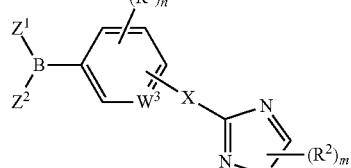

(V-f3)

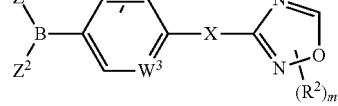

(V-f4)

or a pharmaceutically acceptable salt or prodrug thereof, wherein $W^3$, $Z^1$, $Z^2$, X, Het-B, $R^1$, $R^2$, m and n are as defined above and herein.

In certain embodiments, the present invention provides compounds of formula (V-g):

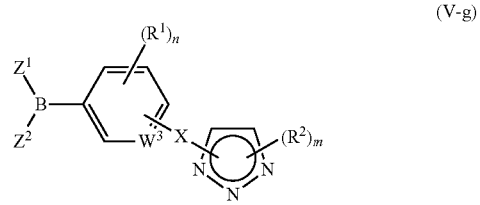

(V-g)

or a pharmaceutically acceptable salt or prodrug thereof, wherein $W^3$, $Z^1$, $Z^2$, X, $R^1$, $R^2$, and m and n are as defined above and herein. For example, in certain embodiments, the present invention provides compounds of either of formulae (V-g1) and (V-g2):

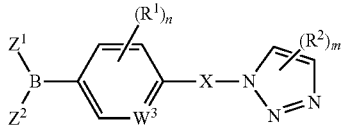

(V-g1)

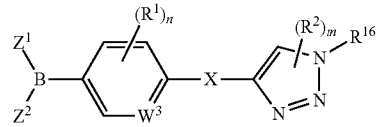

(V-g2)

or a pharmaceutically acceptable salt or prodrug thereof, wherein $W^3$, $R^{16}$, $Z^1$, $Z^2$, X, $R^1$, $R^2$, m and n are as defined above and herein.

In certain embodiments, the present invention provides compounds of formula (V-h):

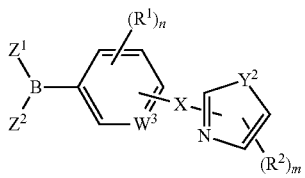
(V-h)

or a pharmaceutically acceptable salt or prodrug thereof, wherein $W^3$, $Z^1$, $Z^2$, X, $R^1$, $R^2$, m and n are as defined above and herein, and $Y^2$ is O, S or $NR^{16}$.

In certain embodiments, the present invention provides compounds of formulae (V-h1) or (V-h2):

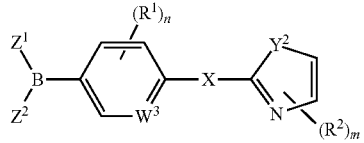
(V-h1)

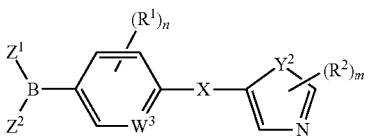
(V-h2)

or a pharmaceutically acceptable salt or prodrug thereof, wherein $Y^2$, $W^3$, $Z^1$, $Z^2$, X, $R^1$, $R^2$, m and n are as defined above and herein.

In certain embodiments, $Y^2$ is O or S. In certain embodiments, $Y^2$ is O. In certain embodiments, $Y^2$ is S. For example, in certain embodiments, the present invention provides compounds of any of formulae (V-h3), (V-h4), (V-h5), (V-h6), (V-h7), (V-h8), (V-h9) or (V-h10):

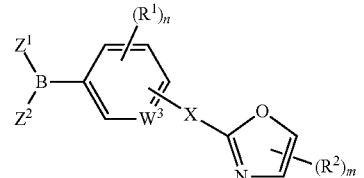
(V-h3)

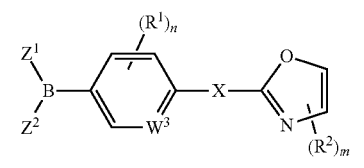
(V-h4)

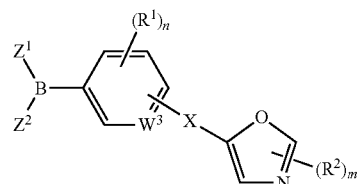
(V-h5)

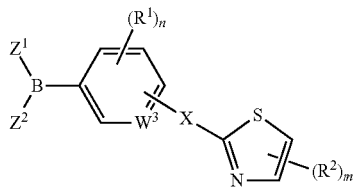
(V-h6)

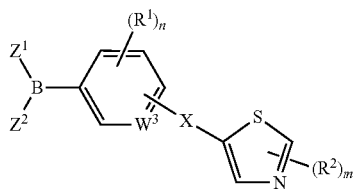
(V-h7)

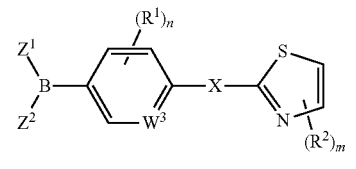
(V-h8)

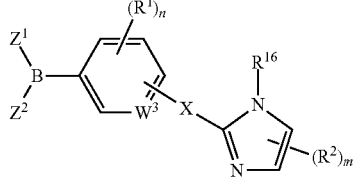
(V-h9)

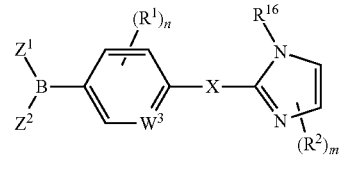
(V-h10)

or a pharmaceutically acceptable salt or prodrug thereof, wherein $W^3$, $R^{16}$, $Z^1$, $Z^2$, X, $R^1$, $R^2$, m and n are as defined above and herein.

In certain embodiments, the present invention provides compounds of formula (V-i):

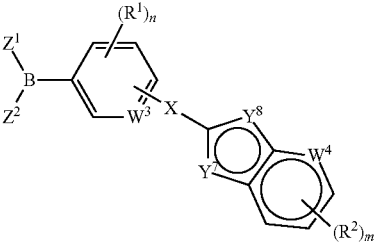
(V-i)

or pharmaceutically acceptable salts or prodrugs thereof, wherein $W^3$, $Z^1$, $Z^2$, $R^1$, $R^2$, m and n are as defined above and herein, $Y^7$ and $Y^8$ are independently selected from N, $NR^{16}$, O and S, and $W^4$ is C, $CR^{17}$ or N, wherein $R^{17}$ is hydrogen, halogen, —$CF_3$, optionally substituted $C_{1-8}$ alkyl, optionally substituted $C_{2-8}$ alkenyl, or optionally substituted $C_{2-8}$ alkynyl.

In certain embodiments, $Y^7$ is O or S and $Y^8$ is N. In certain embodiments, $Y^7$ is O and $Y^8$ is N. In certain embodiments, $Y^7$ is S and $Y^8$ is N.

In certain embodiments, $W^4$ is N.

In certain embodiments, $W^4$ is C or $CR^{17}$. In certain embodiments, $W^4$ is C or CH.

In certain embodiments, the present invention provides compounds of formulae (V-i1):

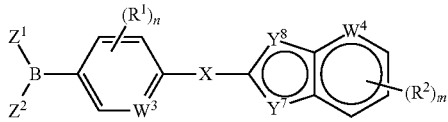

(V-i1)

or pharmaceutically acceptable salts or prodrugs thereof, wherein $W^3$, $Z^1$, $Z^2$, X, $R^1$, $R^2$, m, n, $W^4$, $Y^7$ and $Y^8$, are as defined above and herein.

In certain embodiments, the present invention provides compounds of the formula (V-j):

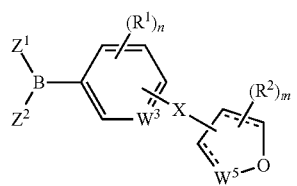

(V-j)

or a pharmaceutically acceptable salt or prodrug thereof, wherein $W^3$, $Z^1$, $Z^2$, X, $R^1$, $R^2$, m and n are as defined above and herein, $W^5$ is N or $N^{16}$, and the dashed line represents a single or double bond. In certain embodiments, the dashed line is a single bond. In certain embodiments, the dashed line is a double bond. For example, in certain embodiments, the present invention provides compounds of formulae (V-j1), (V-j2), (V-j3), (V-j4), (V-j5) or (V-j6):

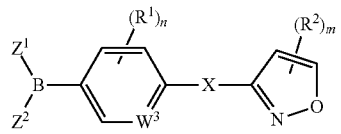

(V-j1)

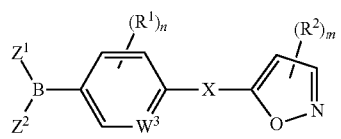

(V-j2)

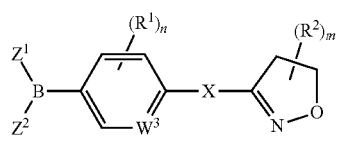

(V-j3)

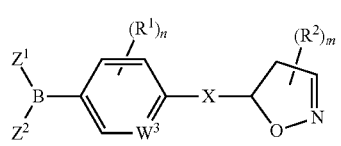

(V-j4)

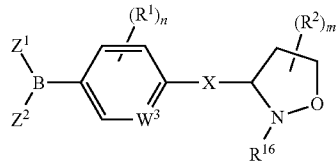

(V-j5)

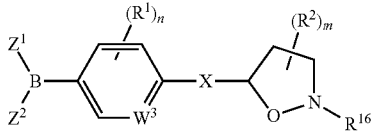

(V-j6)

or a pharmaceutically acceptable salt or prodrug thereof, wherein $W^3$, $Z^1$, $Z^2$, X, $R^1$, $R^2$, $R^{16}$, m and n are as defined above and herein.

In certain embodiments, the present invention provides compounds of formula (V-k):

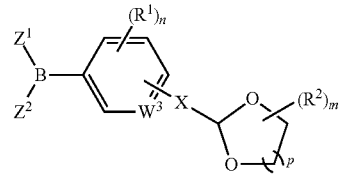

(V-k)

or a pharmaceutically acceptable salt or prodrug thereof, wherein $W^3$, $Z^1$, $Z^2$, $R^1$, $R^2$, m and n are as defined above and herein, and p is 1 or 2. For example, in certain embodiments, the present invention provides compounds of either of formulae (V-k1) or (V-k2):

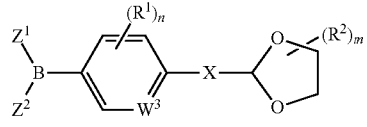

(V-k1)

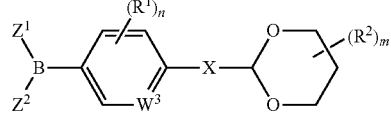

(V-k2)

or a pharmaceutically acceptable salt or prodrug thereof, wherein $W^3$, $Z^1$, $Z^2$, $R^1$, $R^2$, m and n are as defined above and herein.

In certain embodiments, the present invention provides compounds of formula (V-m):

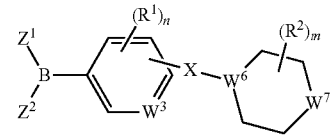

(V-m)

or pharmaceutically acceptable salts or prodrugs thereof, wherein $W^3$, $Z^1$, $Z^2$, X, $R^1$, $R^2$, $R^{16}$, m, and n, are as defined above and herein, and W⁶ and W⁷ are selected from N or CH, with the proviso that one or both of W⁶ and W⁷ is N. For example, in certain embodiments, the present invention provides compounds of either of formulae (V-m1), (V-m2) or (V-m3):

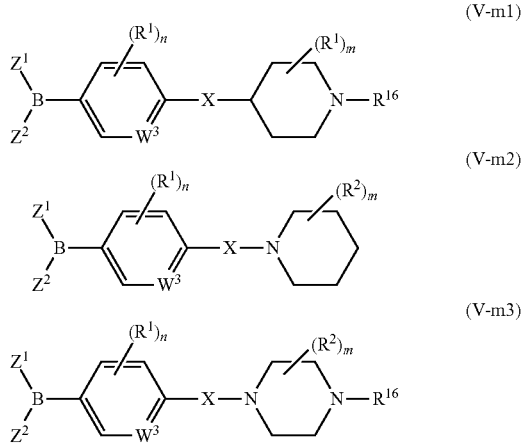

or pharmaceutically acceptable salts or prodrugs thereof, wherein $W^3$, $W^6$, $Z^1$, $Z^2$, X, $R^1$, $R^2$, $R^{16}$, m, and n, are as defined above and herein.

Additional Embodiments Wherein Het-B is an Optionally Substituted 3-10 Membered Heterocyclyl Ring As generally defined above, in certain embodiments, Het-B is an optionally substituted 3-10 membered heterocyclyl ring.

In certain embodiments, Het-B is an optionally substituted 3-10 membered heterocyclyl ring, wherein said heterocyclyl ring has 1 to 3 heteroatoms selected from N, $NR^{16}$, O and S, and $R^{16}$ is, independently, hydrogen, $-SO_2R^{11}$, $-SOR^{11}$, $-C(O)R^{11}$, $-CO_2R^{11}$, $-C(O)N(R^{11})_2$, $-C(O)NH(R^{11})$, $-C(O)NH_2$, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl.

In certain embodiments, Het-B is an optionally substituted 5-6 membered monocyclic heterocyclyl ring.

In certain embodiments, Het-B is an optionally substituted 5-membered monocyclic heterocyclyl ring. In certain embodiments, Het-B is an optionally substituted 5-membered monocyclic heterocyclyl ring containing 1 to 3 heteroatoms selected from N, $NR^{16}$, O and S. In certain embodiments, Het-B is an optionally substituted 5-membered monocyclic heterocyclyl ring containing 1 heteroatom selected from N, $NR^{16}$, O and S. In certain embodiments, Het-B is an optionally substituted 5-membered monocyclic heterocyclyl ring containing 2 heteroatoms selected from N, $NR^{16}$, O and S. In certain embodiments, Het-B is an optionally substituted 5-membered monocyclic heterocyclyl ring containing 3 heteroatoms selected from N, $NR^{16}$, O and S. In certain embodiments, Het-B is an optionally substituted 5-membered monocyclic heterocyclyl ring selected from the group consisting of optionally substituted 1,3-dioxolanyl, optionally substituted 4,5-dihydroisoxazolyl, optionally substituted isoxazolidinyl, optionally substituted oxazolidinyl, optionally substituted tetrahydrofuranyl, optionally substituted pyrrolidinyl and optionally substituted pyrrolyl-2,5-dione.

In certain embodiments, wherein Het-B is an optionally substituted pyrrolidinyl (i.e., containing 1 heteroatom selected from N or $NR^{16}$), the following compounds are specifically excluded:
  (i) compounds wherein $W^3$ is CH, n is 0, m is 0 and X is a covalent bond or $-CH_2OCH_2-$;
  (ii) compounds wherein $W^3$ is CH, n is 1 and $R^1$ is $CH_2OH$; and/or
  (iii) compounds wherein $Z^1$ is $-OH$ or $-OR^3$, and $Z^2$ and Ring A taken together form a 5-membered ring containing 1 O atom.

In certain embodiments, Het-B is an optionally substituted 6-membered monocyclic heterocyclyl ring containing 1 to 3 heteroatoms selected from N, $NR^{16}$, O and S. In certain embodiments, Het-B is an optionally substituted 6-membered monocyclic heterocyclyl ring containing 1 heteroatom selected from N, $NR^{16}$, O and S. In certain embodiments, Het-B is an optionally substituted 6-membered monocyclic heterocyclyl ring containing 2 heteroatoms selected from N, $NR^{16}$, O and S. In certain embodiments, Het-B is an optionally substituted 6-membered monocyclic heterocyclyl ring containing 3 heteroatoms selected from N, $NR^{16}$, O and S. In certain embodiments, Het-B is an optionally substituted 6-membered monocyclic heterocyclyl ring selected from the group consisting of optionally substituted 1,3-dioxanyl, optionally substituted piperidinyl, optionally substituted piperazinyl, optionally substituted morpholinyl, and optionally substituted tetrahydropyranyl.

In certain embodiments, wherein Het-B is an optionally substituted piperidinyl (i.e., containing 1 heteroatom selected from N or $NR^{16}$), the following compounds are specifically excluded:
  (i) compounds wherein $W^3$ is CH, n is 0, m is 0 and X is $-(C=O)-$ or a covalent bond;
  (ii) compounds wherin $W^3$ is CH, n is 1, $R^1$ is fluoro, and X is $-OCH_2CH_2-$ or $-CH_2CH_2O-$;
  (iii) compounds wherein $W^3$ is CH, n is 0 and X is $-(C=O)-$;
  (iv) compounds wherein $W^3$ is CH, n is 1 and $R^1$ is $CH_2OH$; and/or
  (v) compounds wherein $Z^1$ is $-OH$ or $-OR^3$, and $Z^2$ and Ring A taken together form a 5-membered ring containing 1 O atom.

In certain embodiments, wherein Het-B is an optionally substituted piperazinyl (i.e., containing 2 heteroatoms selected from N or $NR^{16}$), the following compounds are specifically excluded:
  (i) compounds wherein $W^3$ is CH, n is 1, and X is a covalent bond, $-OCH_2(C=O)-$ or $-(C=O)CH_2O-$;
  (ii) compounds wherein $W^3$ is N, n is 1, $R^1$ is $-CH_3$ and X is a covalent bond;
  (iii) compounds wherein $W^3$ is CH, n is 1 and $R^1$ is $CH_2OH$; and/or
  (iv) compounds wherein $Z^1$ is $-OH$ or $-OR^3$, and $Z^2$ and Ring A taken together form a 5-membered ring containing 1 O atom.

In certain embodiments, wherein Het-B is an optionally substituted morpholynyl (i.e., containing 1 heteroatom selected from O and 1 heteroatom selected from N or $NR^{16}$), the following compounds are specifically excluded:
  (i) compounds wherein $W^3$ is CH, n is 0 or 1, m is 0 and X is $-(C=O)-$ or a covalent bond;
  (ii) compounds wherein $W^3$ is N, n is 1, $R^1$ is $-CH_3$ and X is a covalent bond;

(iii) compounds wherein W³ is CH, n is 1 and R¹ is CH₂OH; and/or
(iv) compounds wherein Z¹ is —OH or —OR³, and Z² and Ring A taken together form a 5-membered ring containing 1 O atom.

In certain embodiments, wherein Het-B is an optionally substituted tetrahydropyranyl (i.e., containing 2 O heteroatoms), the following compounds are specifically excluded:
(i) compounds wherein W³ is CH, n is 0, m is 0 and X is —O— or —CH₂OCH₂—;
(ii) compounds wherein W³ is CH, n is 1 and R¹ is CH₂OH; and/or
(iii) compounds wherein Z¹ is —OH or —OR³, and Z² and Ring A taken together form a 5-membered ring containing 1 O atom.

In certain embodiments, Het-B is an optionally substituted 9-10 membered bicyclic heterocyclyl ring.

In certain embodiments, Het-B is an optionally substituted 9-membered bicyclic heterocyclyl ring containing 1 to 3 heteroatoms selected from N, NR¹⁶, O and S. In certain embodiments, Het-B is an optionally substituted 9-membered bicyclic heterocyclyl ring containing 1 heteroatom selected from N, NR¹⁶, O and S. In certain embodiments, Het-B is an optionally substituted 9-membered bicyclic heterocyclyl ring containing 2 heteroatoms selected from N, NR¹⁶, O and S. In certain embodiments, Het-B is an optionally substituted 9-membered bicyclic heterocyclyl ring containing 3 heteroatoms selected from N, NR¹⁶, O and S. In certain embodiments, Het-B is an optionally substituted 9-membered bicyclic heterocyclyl ring selected from the group consisting of optionally substituted indolinyl, optionally substituted isoindolinyl-1,3-dione, and optionally substituted benzo[d][1,3]dioxolyl.

In certain embodiments, wherein Het-B is an optionally substituted indolinyl (i.e., containing 1 heteroatom selected from N or NR¹⁶), the following compounds are specifically excluded:
(i) compounds wherein W³ is CH, n is 0, m is 0, and X is —CH₂—;
(ii) compounds wherein W³ is CH, n is 1, R¹ is fluoro, m is 0, and X is —CH₂—;
(iii) compounds wherein W³ is CH, n is 1 and R¹ is CH₂OH; and/or
(iv) compounds wherein Z¹ is —OH or —OR³, and Z² and Ring A taken together form a 5-membered ring containing 1 O atom.

In certain embodiments, wherein Het-B is an optionally substituted isoindolinyl-1,3-dione (i.e., containing 1 heteroatom selected from N or NR¹⁶), the following compounds are specifically excluded:
(i) compounds wherein W³ is CH, n is 0, m is 0 and X is —CH₂—;
(ii) compounds wherein W³ is CH, n is 1 and R¹ is CH₂OH; and/or
(iii) compounds wherein Z¹ is —OH or —OR³, and Z² and Ring A taken together form a 5-membered ring containing 1 O atom.

In certain embodiments, wherein Het-B is an optionally substituted benzo[d][1,3]dioxolyl (i.e., containing 2 O heteroatoms), the following compounds are specifically excluded:
(i) compounds wherein W³ is CH, n is 0, m is 0 and X is —O—;
(ii) compounds wherein W³ is CH, n is 1 and R¹ is CH₂OH; and/or
(iii) compounds wherein Z¹ is —OH or —OR³, and Z² and Ring A taken together form a 5-membered ring containing 1 O atom.

In certain embodiments, Het-B is an optionally substituted 10-membered bicyclic heterocyclyl ring containing 1 to 3 heteroatoms selected from N, NR¹⁶, O and S. In certain embodiments, Het-B is an optionally substituted 10-membered bicyclic heterocyclyl ring containing 1 heteroatom selected from N, NR¹⁶, O and S. In certain embodiments, Het-B is an optionally substituted 10-membered bicyclic heterocyclyl ring containing 2 heteroatoms selected from N, NR¹⁶, O and S. In certain embodiments, Het-B is an optionally substituted 10-membered bicyclic heterocyclyl ring containing 3 heteroatoms selected from N, NR¹⁶, O and S. In certain embodiments, Het-B is an optionally substituted 9-membered bicyclic heterocyclyl ring selected from the group consisting of optionally substituted 1,2,3,4-tetrahydroquinolinyl.

In certain embodiments, wherein Het-B is an optionally substituted 1,2,3,4-tetrahydroquinolinyl (i.e., containing 1 heteroatom selected from N or NR¹⁶), the following compounds are specifically excluded:
(iv) compounds wherein W³ is CH, n is 0, m is 0 and X is —CH₂—;
(v) compounds wherein W³ is CH, n is 1 and R¹ is CH₂OH; and/or
(vi) compounds wherein Z¹ is —OH or —OR³, and Z² and Ring A taken together form a 5-membered ring containing 1 O atom.

Additional Embodiments Wherein Het-B is an Optionally Substituted 5-10 Membered Heteroaryl Ring As generally defined above, in certain embodiments, Het-B is an optionally substituted 5-10 membered heteroaryl ring.

In certain embodiments, Het-B is an optionally substituted 5-10 membered heteroaryl ring, wherein said heteroaryl ring has 1 to 3 heteroatoms selected from N, NR¹⁶, O and S, and R¹⁶ is, independently, hydrogen, —SO₃R¹¹, —SOR¹¹, —C(O)R¹¹, —CO₂R¹¹, —C(O)N(R¹¹)₂, —C(O)NH(R¹¹), —C(O)NH₂, optionally substituted C₁₋₈ alkyl, optionally substituted C₂₋₈ alkenyl, optionally substituted C₂₋₈ alkynyl, optionally substituted C₁₋₈ heteroalkyl, optionally substituted C₂₋₈ heteroalkenyl, optionally substituted C₂₋₈ heteroalkynyl, optionally substituted C₃₋₁₀ carbocyclyl, optionally substituted 3-10 membered heterocyclyl, optionally substituted C₆₋₁₀ aryl, or optionally substituted 5-10 membered heteroaryl.

In certain embodiments, Het-B is an optionally substituted 5-6 membered monocyclic heteroaryl ring.

In certain embodiments, Het-B is an optionally substituted 5-membered monocyclic heteroaryl ring containing 1 to 3 heteroatoms selected from N, NR¹⁶, O and S. In certain embodiments, Het-B is an optionally substituted 5-membered monocyclic heteroaryl ring containing 1 heteroatom selected from N, NR¹⁶, O and S. In certain embodiments, Het-B is an optionally substituted 5-membered monocyclic heteroaryl ring containing 2 heteroatoms selected from N, NR¹⁶, O and S. In certain embodiments, Het-B is an optionally substituted 5-membered monocyclic heteroaryl ring containing 3 heteroatoms selected from N, NR¹⁶, O and S. In certain embodiments, Het-B is an optionally substituted 5-membered monocyclic heteroaryl ring selected from the group consisting of optionally substituted triazolyl, optionally substituted oxadiazolyl, optionally substituted thiadiazolyl, optionally substituted imidazolyl, optionally substituted pyrazolyl, optionally substituted thiazolyl, optionally substituted isothiazolyl, optionally substituted oxazolyl, optionally substituted isoxazolyl, optionally substituted thiophenyl, optionally substituted furanyl and optionally substituted pyrrolyl.

In certain embodiments, wherein Het-B is an optionally substituted oxadiazolyl group (i.e., containing one O and two N atoms), the following compounds are specifically excluded:
(i) compounds wherein $W^3$ is CH, X is a covalent bond, n is 0 and m is 0;
(ii) compounds wherein $W^3$ is CH, X is a covalent bond, n is 0, m is 1 and $R^2$ is an unsubstituted furanyl group;
(iii) compounds wherein $W^3$ is CH, X is a covalent bond, n is 0, m is 1 and $R^2$ is —$CH_3$;
(iv) compounds wherein $W^3$ is CH, n is 1 and $R^1$ is $CH_2OH$; and/or
(v) compounds wherein $Z^1$ is —OH or —$OR^3$, and $Z^2$ and Ring A taken together form a 5-membered ring containing 1 O atom.

In certain embodiments, wherein Het-B is an optionally substituted thiadiazolyl group (i.e., containing one S and two N atoms), the following compounds are specifically excluded:
(i) compounds wherein $W^3$ is CH, X is a covalent bond, n is 0 and m is 0;
(ii) compounds wherein $W^3$ is CH, n is 1 and $R^1$ is $CH_2OH$; and/or
(iii) compounds wherein $Z^1$ is —OH or —$OR^3$, and $Z^2$ and Ring A taken together form a 5-membered ring containing 1 O atom.

In certain embodiments, wherein Het-B is an optionally substituted triazolyl group (i.e., containing three heteroatoms selected from N and $NR^{16}$), the following compounds are specifically excluded:
(i) compounds wherein $W^3$ is CH, X is a covalent bond, n is 0 and m is 0;
(ii) compounds wherein $W^3$ is CH, X is —$OCH_2$— or —$CH_2O$—, n is 1, $R^1$ is fluoro, m is 1 and $R^2$ is a cyclohexyl group;
(iii) compounds wherein $W^3$ is CH, n is 1 and $R^1$ is $CH_2OH$; and/or
(iv) compounds wherein $Z^1$ is —OH or —$OR^3$, and $Z^2$ and Ring A taken together form a 5-membered ring containing 1 O atom.

In certain embodiments, wherein Het-B is an optionally substituted oxazolyl group (i.e., containing one N atom and one O atom), the following compounds are specifically excluded:
(i) compounds wherein $W^3$ is CH, X is a covalent bond, n is 0 and m is 0;
(ii) compounds wherein $W^3$ is CH, n is 1, $R^1$ is fluoro, X is —$OCH_2$— or —$CH_2O$—, and m is 0;
(iii) compounds wherein $W^3$ is CH, X is a covalent bond, n is 0, m is 2 and each $R^2$ is independently —$CH_3$, an optionally substituted $C_{1-8}$ alkyl or $C_{1-8}$ heteroalkyl group;
(iv) compounds wherein $W^3$ is CH, n is 1 and $R^1$ is $CH_2OH$; and/or
(v) compounds wherein $Z^1$ is —OH or —$OR^3$, and $Z^2$ and Ring A taken together form a 5-membered ring containing 1 O atom.

In certain embodiments, wherein Het-B is an optionally substituted thiazolyl group (i.e., containing one S atom and one N atom), the following compounds are specifically excluded:
(i) compounds wherein W is CH, n is 0, X is a covalent bond, m is 1 and $R^2$ is —$CH_3$;
(ii) compounds wherein W is CH, n is 1, $R^1$ is fluoro, X is —$OCH_2$— or —$CH_2O$— and m is 0;
(iii) compounds wherein $W^3$ is CH, n is 1 and $R^1$ is $CH_2OH$; and/or
(iv) compounds wherein $Z^1$ is —OH or —$OR^3$, and $Z^2$ and Ring A taken together form a 5-membered ring containing 1 O atom.

In certain embodiments, wherein Het-B is an optionally substituted pyrazolyl group (i.e., containing two heteroatoms selected from N or $NR^{16}$), the following compounds are specifically excluded:
(i) compounds wherein $W^3$ is CH, n is 1, $R^1$ is fluoro, X is —$OCH_2$— or —$CH_2O$—, and m is 0;
(ii) compounds wherein $W^3$ is CH, n is 0, X is —$OCH_2CH_2$— or —$CH_2CH_2O$— and m is 0;
(iii) compounds wherein $W^3$ is CH, n is 1 and $R^1$ is $CH_2OH$; and/or
(iv) compounds wherein $Z^1$ is —OH or —$OR^3$, and $Z^2$ and Ring A taken together form a 5-membered ring containing 1 O atom.

In certain embodiments, wherein Het-B is an optionally substituted imidazolyl group (i.e., containing two heteroatoms selected from N or $NR^{16}$), the following compounds are specifically excluded:
(i) compounds wherein $W^3$ is CH, n is 1, $R^1$ is fluoro, X is —$OCH_2$— or —$CH_2O$—, and m is 0;
(ii) compounds wherein $W^3$ is CH, n is 0, X is —$OCH_2CH_2$— or —$CH_2CH_2O$— and m is 0;
(iii) compounds wherein $W^3$ is CH, n is 1 and $R^1$ is $CH_2OH$; and/or
(iv) compounds wherein $Z^1$ is —OH or —$OR^3$, and $Z^2$ and Ring A taken together form a 5-membered ring containing 1 O atom.

In certain embodiments, wherein Het-B is an optionally substituted thiophenyl group (i.e., containing one S atom), the following compounds are specifically excluded:
(i) compounds wherein $W^3$ is CH, n is 0, m is 0 and X is a covalent bond;
(ii) compounds wherein $W^3$ is CH, n is 1 and $R^1$ is $CH_2OH$; and/or
(iii) compounds wherein $Z^1$ is —OH or —$OR^3$, and $Z^2$ and Ring A taken together form a 5-membered ring containing 1 O atom.

In certain embodiments, wherein Het-B is an optionally substituted furanyl group (i.e., containing one O atom), the following compounds are specifically excluded:
(i) compounds wherein $W^3$ is CH, n is 0, X is —(C=O)$NHCH_2$— or —$CH_2NH(C=O)$— and m is 0;
(ii) compounds wherein $W^3$ is CH, n is 0, m is 0 and X is a covalent bond;
(iii) compounds wherein $W^3$ is CH, n is 1 and $R^1$ is $CH_2OH$; and/or
(iv) compounds wherein $Z^1$ is —OH or —$OR^3$, and $Z^2$ and Ring A taken together form a 5-membered ring containing 1 O atom.

In certain embodiments, wherein Het-B is an optionally substituted pyrrolyl group (i.e., containing one heteroatom selected from N or $NR^{16}$), the following compounds are specifically excluded:
(i) compounds wherein $W^3$ is CH, n is 0 and X is a covalent bond;
(ii) compounds wherein $W^3$ is CH, n is 0 and X is —$SO_2$—;
(iii) compounds wherein $W^3$ is CH, n is 1 and $R^1$ is $CH_2OH$; and/or
(iv) compounds wherein $Z^1$ is —OH or —$OR^3$, and $Z^2$ and Ring A taken together form a 5-membered ring containing 1 O atom.

In certain embodiments, Het-B is an optionally substituted 6-membered monocyclic heteroaryl ring containing 1 to 3 heteroatoms selected from N, $NR^{16}$, O and S. In certain embodiments, Het-B is an optionally substituted 6-membered monocyclic heteroaryl ring containing 1 heteroatom selected from N, $NR^{16}$, O and S. In certain embodiments, Het-B is an optionally substituted 6-membered monocyclic heteroaryl ring containing 2 heteroatoms selected from N, $NR^{16}$, O and S. In certain embodiments, Het-B is an optionally substituted 6-membered monocyclic heteroaryl ring containing 3 heteroatoms selected from N, $NR^{16}$, O and S. In certain embodiments, Het-B is an optionally substituted pyridinyl group (e.g., 2-pyridinyl, 3-pyridinyl, 4-pyridinyl).

However, in certain embodiments, Het-B is not an optionally substituted 6-membered monocyclic heteroaryl ring. In certain embodiments, Het-B is not an optionally substituted pyridinyl. Alternatively, in certain embodiments, wherein Het-B is an optionally substituted pyridinyl group, the following compounds are specifically excluded:
- (i) 3-pyridinyl compounds wherein $W^3$ is CH, n is 1, $R^1$ is a fluoro group ortho to the boron atom, X is a covalent bond, —O—, —$CH_2O$—, —$OCH_2$—, —$OCH_2CH_2$— or —$CH_2CH_2O$—, and m is 0;
- (ii) 3-pyridinyl compounds wherein $W^3$ is CH, n is 0, X is a covalent bond and m is 0;
- (iii) 2-pyridinyl compounds wherein $W^3$ is CH, n is 1, $R^1$ is fluoro ortho to the boron atom, X is —$OCH_2CH_2CH_2O$—, —$CH_2O$—, —$OCH_2$—, —$OCH_2CH_2$— or —$CH_2CH_2O$—, and m is 0;
- (iv) 2-pyridinyl compounds wherein $W^3$ is CH, n is 0, X is —(C=O)NH— or —NH(C=O)— and m is 0;
- (v) 4-pyridinyl compounds wherein $W^3$ is CH, n is 1, $R^1$ is fluoro ortho to the boron atom, X is —$CH_2O$— or —$OCH_2$—, and m is 0;
- (vi) 4-pyridinyl compounds wherein $W^3$ is CH, n is 0, X is a covalent bond and m is 0;
- (vii) compounds wherein $W^3$ is CH, n is 1 and $R^1$ is $CH_2OH$; and/or
- (viii) compounds wherein $Z^1$ is —OH or —$OR^3$, and $Z^2$ and Ring A taken together form a 5-membered ring containing 1 O atom.

In certain embodiments, Het-B is an optionally substituted 9-10 membered bicyclic heteroaryl ring.

In certain embodiments, Het-B is an optionally substituted 9-membered bicyclic heteroaryl ring containing 1 to 3 heteroatoms selected from N, $NR^{16}$, O and S (e.g., a 6-5 fused heteroaryl ring). In certain embodiments, Het-B is an optionally substituted 9-membered bicyclic heteroaryl ring containing 1 heteroatom selected from N, $NR^{16}$, O and S. In certain embodiments, Het-B is an optionally substituted 9-membered bicyclic heteroaryl ring containing 2 heteroatoms selected from N, $NR^{16}$, O and S. In certain embodiments, Het-B is an optionally substituted 9-membered bicyclic heteroaryl ring containing 3 heteroatoms selected from N, $NR^{16}$, O and S. In certain embodiments, Het-B is an optionally substituted 9-membered bicyclic heteroaryl ring selected from the group consisting of optionally substituted benzthiazolyl, optionally substituted benzoxazolyl, optionally substituted benzisoxazolyl, optionally substituted benzimidazolyl, optionally substituted indazolyl, optionally substituted benzofuranyl, optionally substituted benzothiophenyl and optionally substituted indolyl.

In certain embodiments, wherein Het-B is an optionally substituted benzoxazolyl group (i.e., containing one N atom and one O atom), the following compounds are specifically excluded:
- (i) compounds wherein $W^3$ is CH, X is a covalent bond, n is 0 and m is 0;
- (ii) compounds wherein $W^3$ is CH, n is 1 and $R^1$ is $CH_2OH$; and/or
- (iii) compounds wherein $Z^1$ is —OH or —$OR^3$, and $Z^2$ and Ring A taken together form a 5-membered ring containing 1 O atom.

In certain embodiments, wherein Het-B is an optionally substituted benzisoxazolyl group (i.e., containing one N atom and one O atom), the following compounds are specifically excluded:
- (i) compounds wherein $W^3$ is CH, X is a covalent bond, n is 0 and m is 0;
- (ii) compounds wherein $W^3$ is CH, n is 1 and $R^1$ is $CH_2OH$; and/or
- (iii) compounds wherein $Z^1$ is —OH or —$OR^3$, and $Z^2$ and Ring A taken together form a 5-membered ring containing 1 O atom.

In certain embodiments, wherein Het-B is an optionally substituted benzthiazolyl group (i.e., containing one N atom and one S atom), the following compounds are specifically excluded:
- (i) compounds wherein $W^3$ is CH, X is a covalent bond, n is 0 and m is 0;
- (ii) compounds wherein $W^3$ is CH, n is 1 and $R^1$ is $CH_2OH$; and/or
- (iii) compounds wherein $Z^1$ is —OH or —$OR^3$, and $Z^2$ and Ring A taken together form a 5-membered ring containing 1 O atom.

In certain embodiments, wherein Het-B is an optionally substituted benzimidazolyl group (i.e., containing two heteroatoms selected from N or $NR^{16}$), the following compounds are specifically excluded:
- (i) compounds wherein $W^3$ is CH, X is a covalent bond, n is 0 and m is 0;
- (ii) compounds wherein $W^3$ is CH, n is 1 and $R^1$ is $CH_2OH$; and/or
- (iii) compounds wherein $Z^1$ is —OH or —$OR^3$, and $Z^2$ and Ring A taken together form a 5-membered ring containing 1 O atom.

In certain embodiments, wherein Het-B is an optionally substituted indazolyl group (i.e., containing two heteroatoms selected from N or $NR^{16}$), the following compounds are specifically excluded:
- (i) compounds wherein $W^3$ is CH, X is a covalent bond, n is 0 and m is 0;
- (ii) compounds wherein $W^3$ is CH, n is 1 and $R^1$ is $CH_2OH$; and/or
- (iii) compounds wherein $Z^1$ is —OH or —$OR^3$, and $Z^2$ and Ring A taken together form a 5-membered ring containing 1 O atom.

In certain embodiments, wherein Het-B is an optionally substituted indolyl group (i.e., containing one heteroatom selected from N or $NR^{16}$), the following compounds are specifically excluded:
- (i) compounds wherein $W^3$ is CH, X is —$CH_2$—, n is 0 and m is 0;
- (ii) compounds wherein $W^3$ is CH, n is 1 and $R^1$ is $CH_2OH$; and/or
- (iii) compounds wherein $Z^1$ is —OH or —$OR^3$, and $Z^2$ and Ring A taken together form a 5-membered ring containing 1 O atom.

In certain embodiments, Het-B is an optionally substituted 10-membered bicyclic heteroaryl ring containing 1 to 3 heteroatoms selected from N, $NR^{16}$, O and S (e.g., a 6,6-fused heteroaryl ring). In certain embodiments, Het-B is an optionally substituted 10-membered bicyclic heteroaryl ring containing 1 heteroatom selected from N, $NR^{16}$, O and S. In certain embodiments, Het-B is an optionally substituted 10-membered bicyclic heteroaryl ring containing 2 heteroatoms selected from N, $NR^{16}$, O and S. In certain embodiments, Het-B is an optionally substituted 10-membered bicyclic heteroaryl ring containing 3 heteroatoms selected from N, $NR^{16}$, O and S. In certain embodiments, Het-B is an optionally substituted 10-membered bicyclic heteroaryl ring selected from the group consisting of optionally substituted quinolinyl, optionally substituted isoquinolinyl or optionally substituted quinoxalinyl.

In certain embodiments, wherein Het-B is an optionally substituted quinolinyl group (i.e., containing one heteroatom selected from N), the following compounds are specifically excluded:

(iv) compounds wherein $W^3$ is CH, X is a covalent bond, n is 0, m is 1 and $R^2$ is —$CO_2H$;
(v) compounds wherein $W^3$ is CH, n is 1 and $R^1$ is $CH_2OH$; and/or
(vi) compounds wherein $Z^1$ is —OH or —$OR^3$, and $Z^2$ and Ring A taken together form a 5-membered ring containing 1 O atom.

In certain embodiments, the following compounds are specifically excluded:

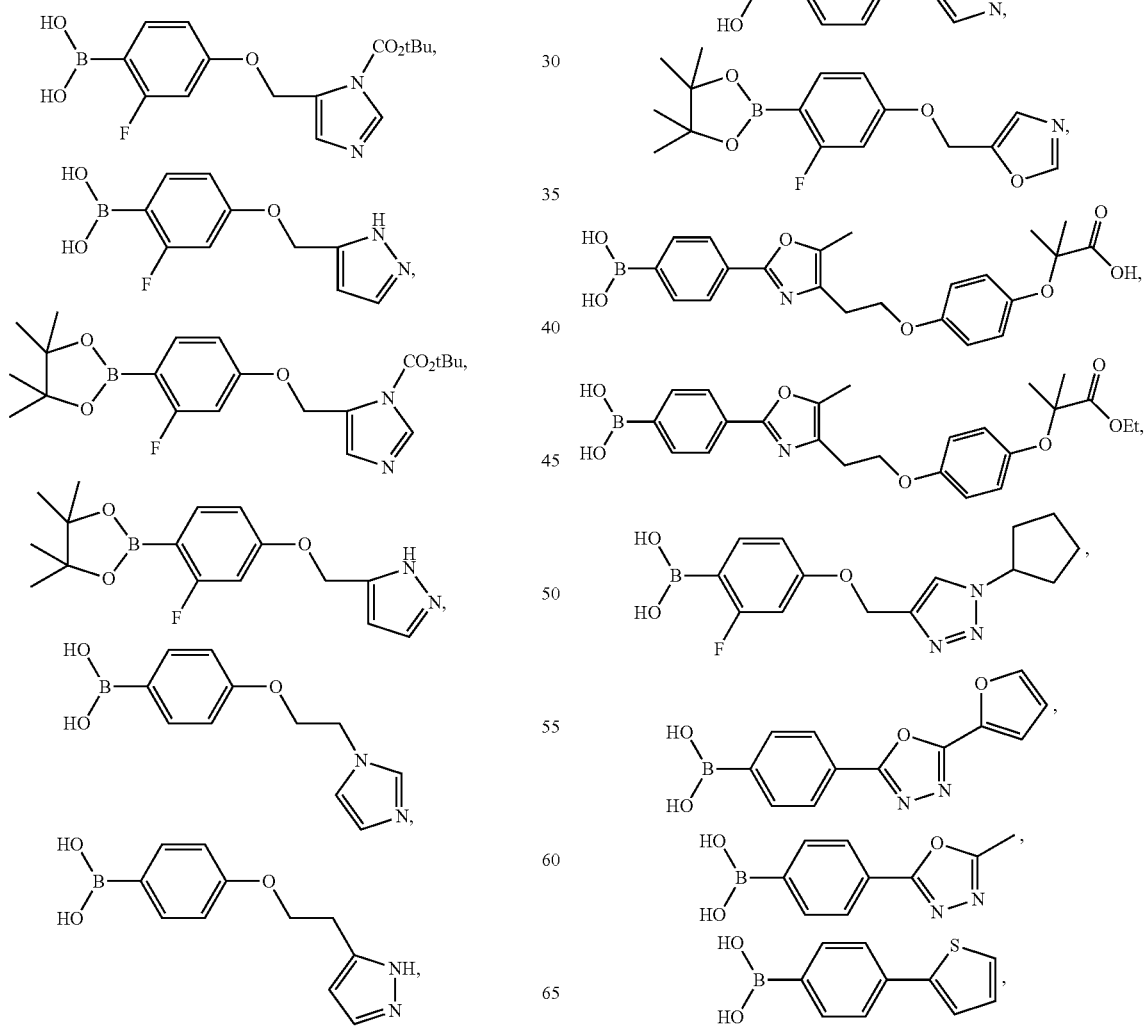

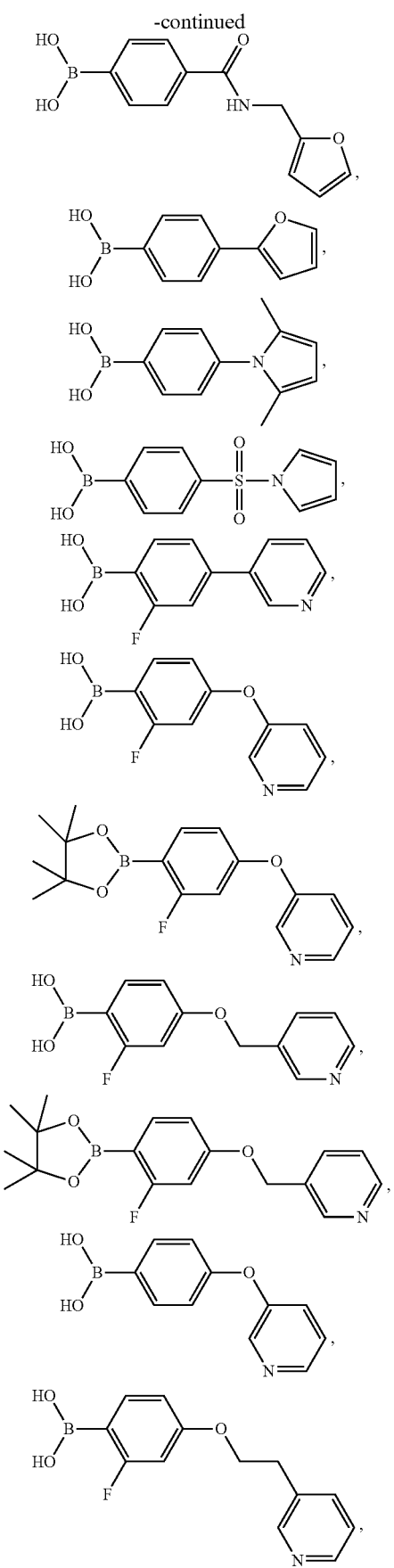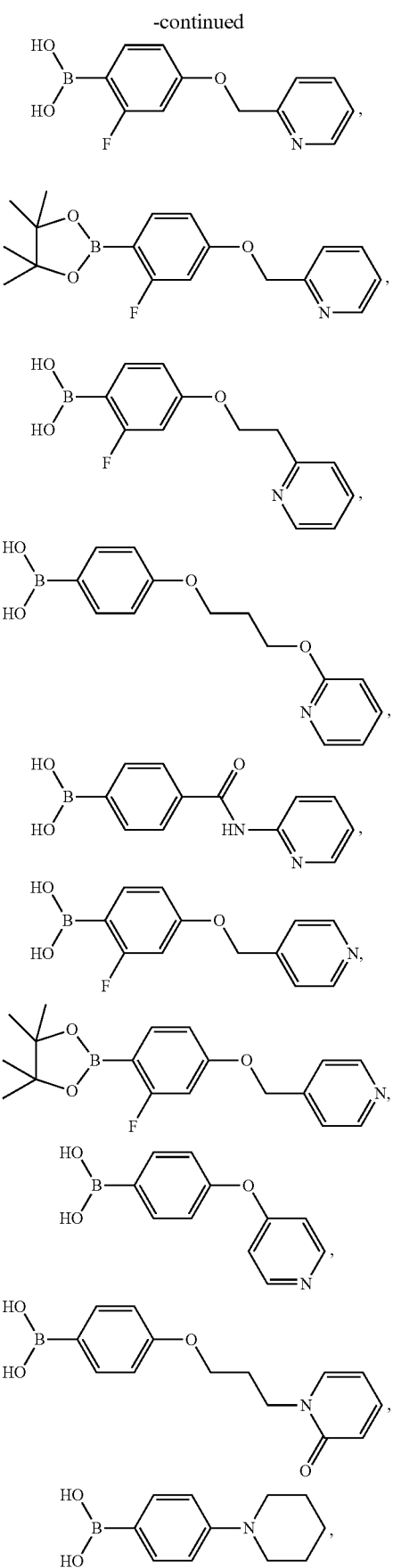

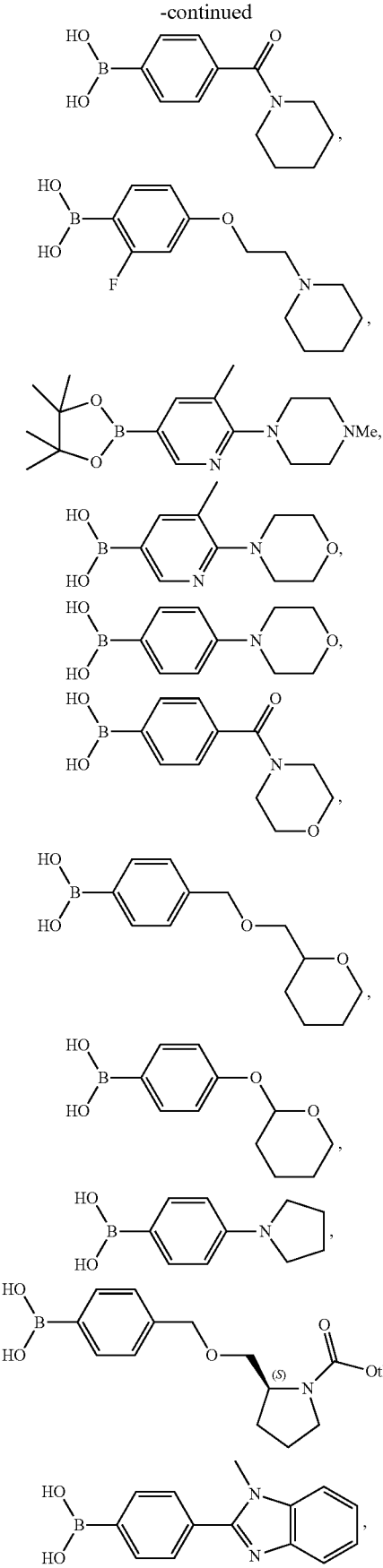
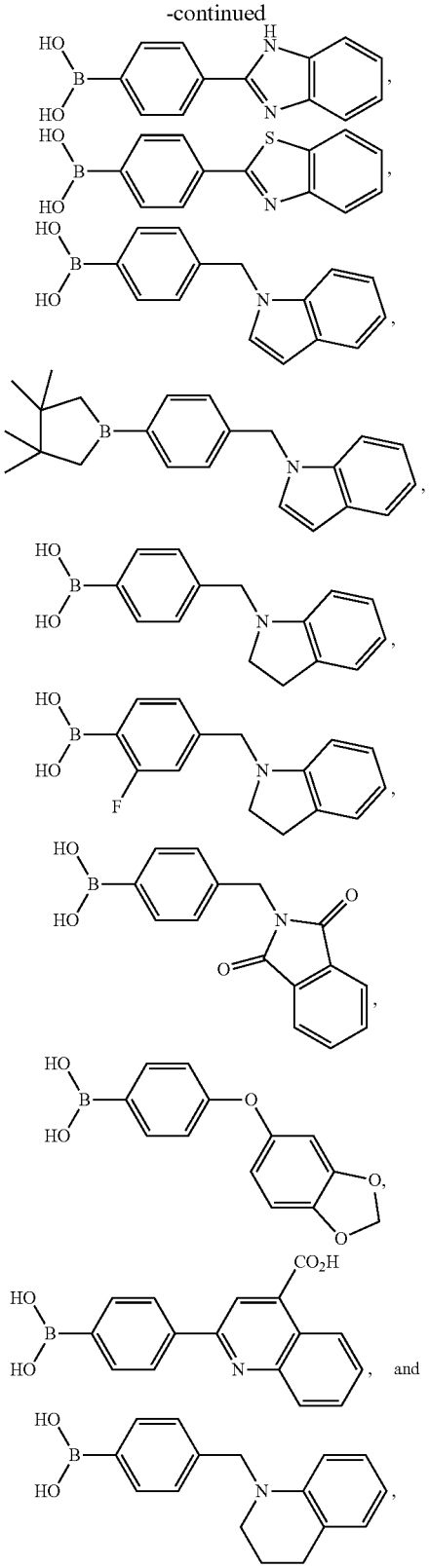
and pharmaceutically acceptable salts or prodrugs thereof.
Exemplary compounds encompassed by formulae (II), (V), and subgenera thereof, are provided below in Tables 9-20.

TABLE 9
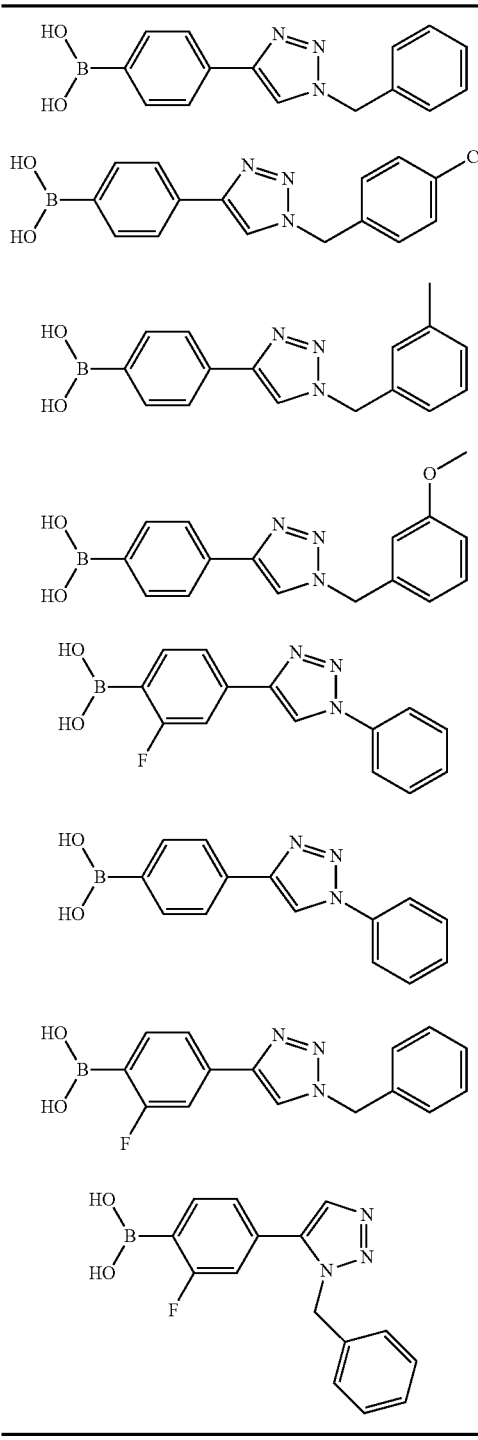
TABLE 10
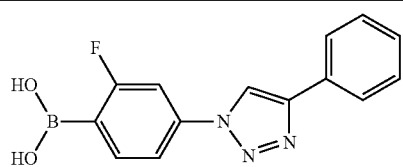
TABLE 10-continued
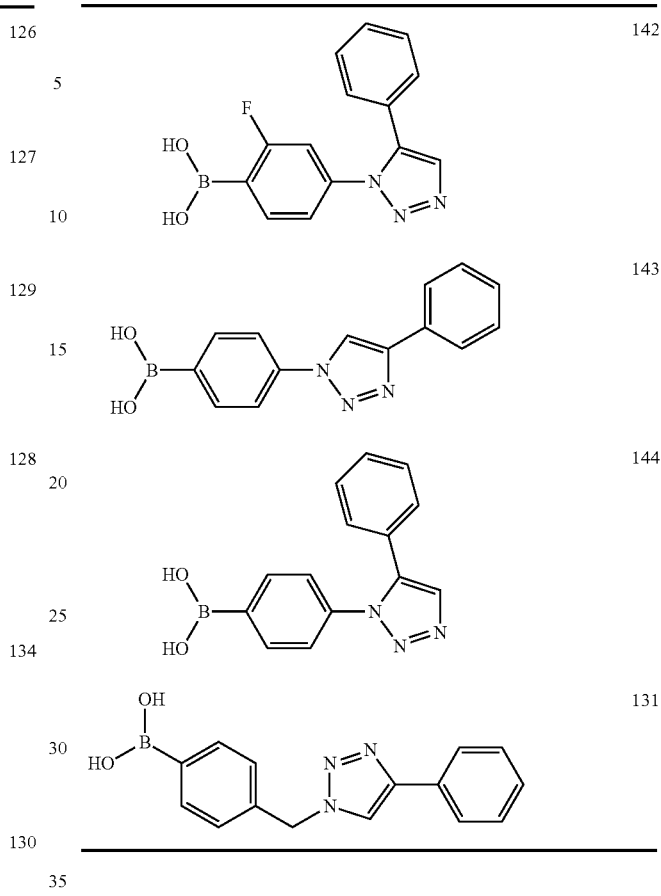
TABLE 11
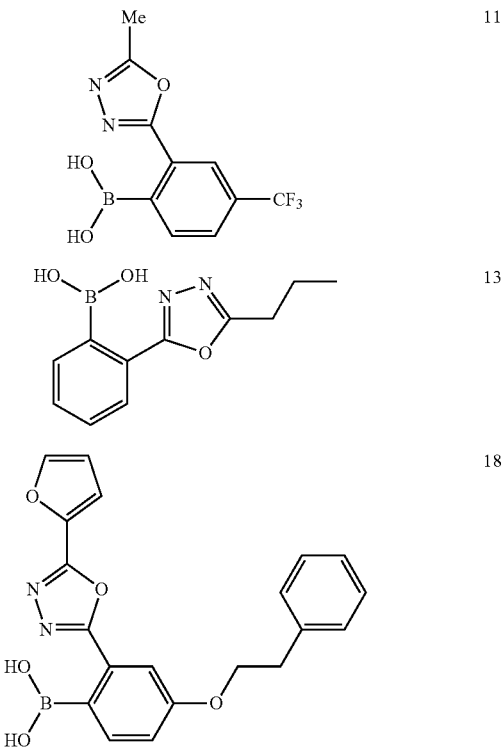

TABLE 11-continued
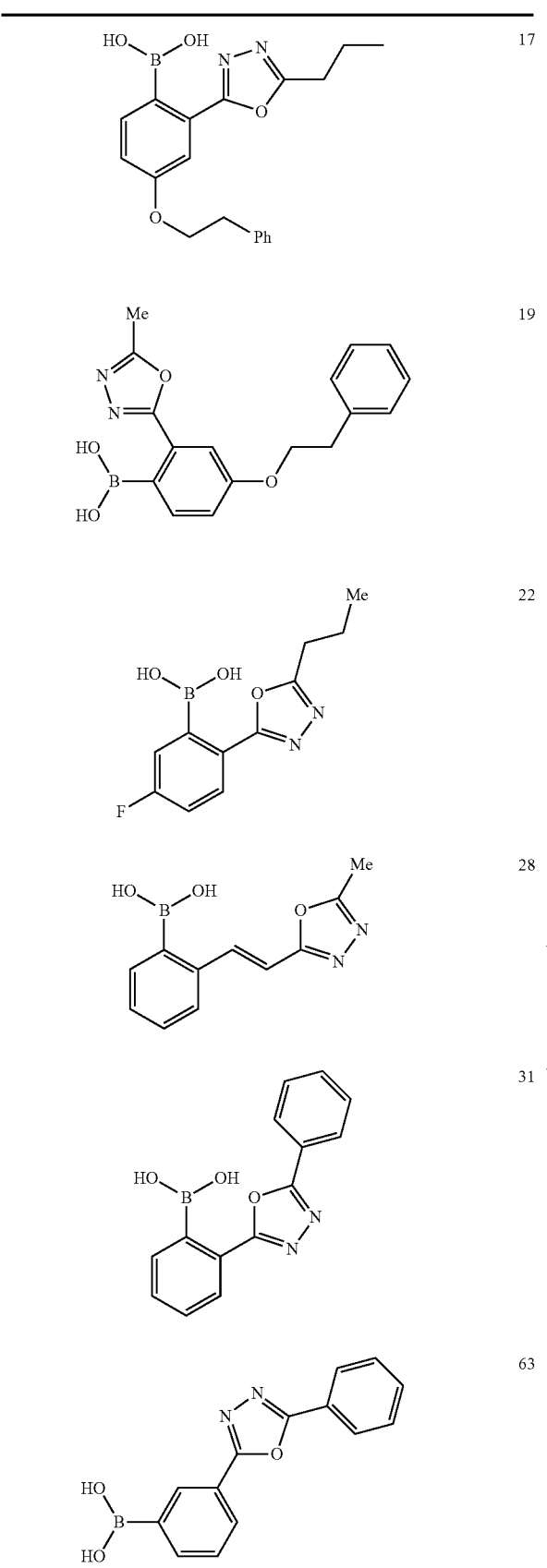
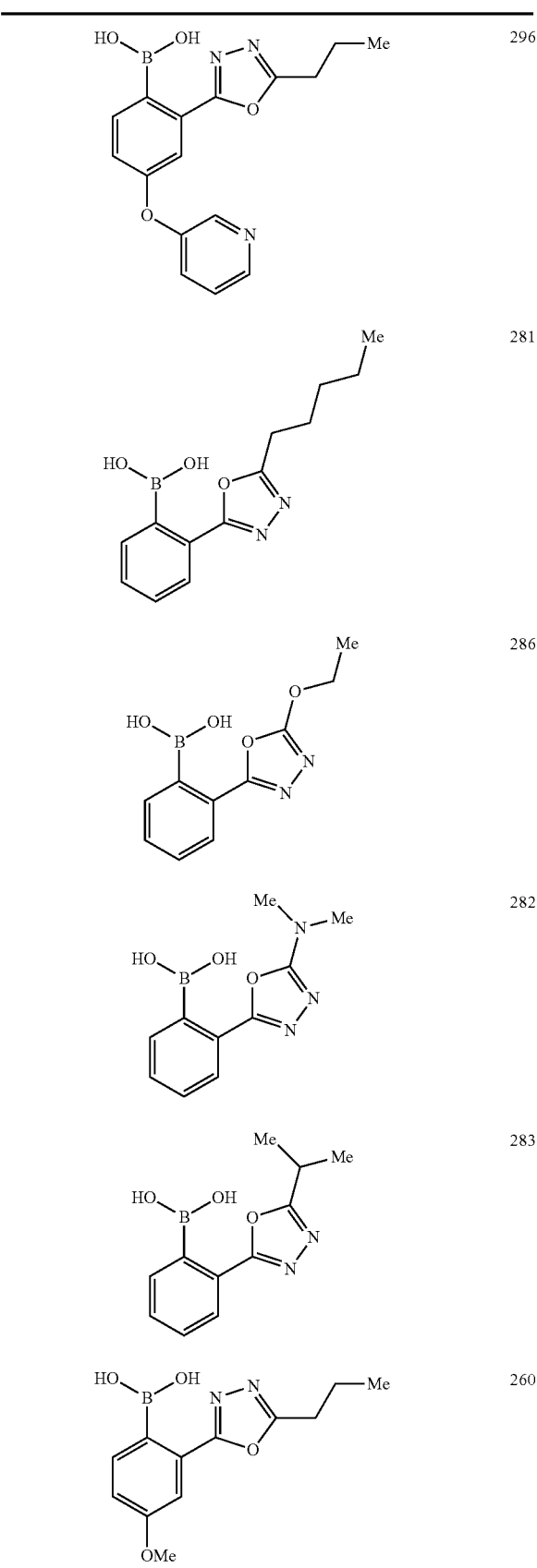

TABLE 11-continued
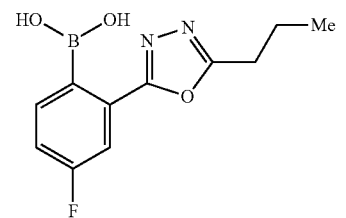 [SMILES: CCCc1nnc(-c2cc(F)ccc2B(O)O)o1] 261
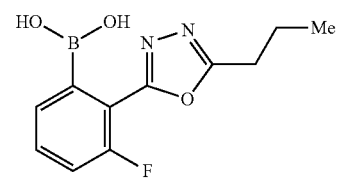 [SMILES: CCCc1nnc(-c2c(F)cccc2B(O)O)o1] 262
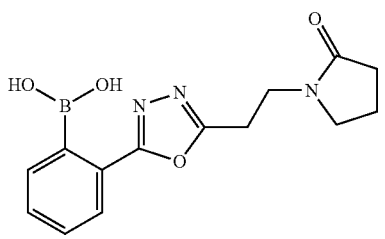 [SMILES: O=C1CCCN1CCc1nnc(-c2ccccc2B(O)O)o1] 263
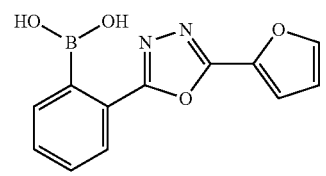 [SMILES: OB(O)c1ccccc1-c1nnc(-c2ccco2)o1] 264
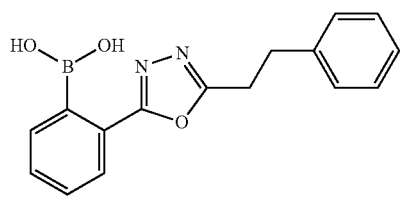 [SMILES: OB(O)c1ccccc1-c1nnc(CCc2ccccc2)o1] 265
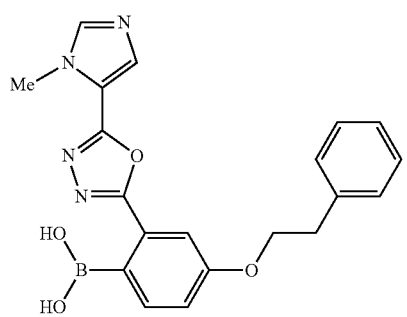 [SMILES: Cn1cncc1-c1nnc(-c2cc(OCCc3ccccc3)ccc2B(O)O)o1] 268
TABLE 11-continued
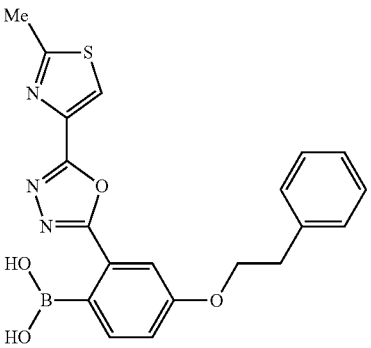 [SMILES: Cc1nc(-c2nnc(-c3cc(OCCc4ccccc4)ccc3B(O)O)o2)cs1] 269
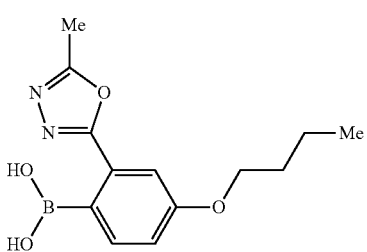 [SMILES: CCCCOc1ccc(B(O)O)c(-c2nnc(C)o2)c1] 272
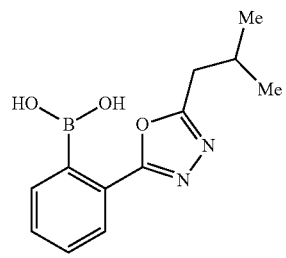 [SMILES: CC(C)Cc1nnc(-c2ccccc2B(O)O)o1] 284
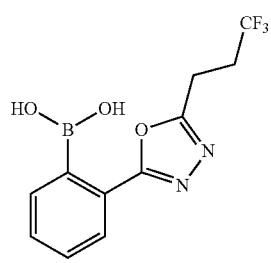 [SMILES: OB(O)c1ccccc1-c1nnc(CCC(F)(F)F)o1] 285
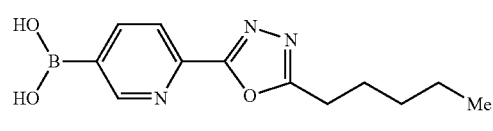 [SMILES: CCCCCc1nnc(-c2ccc(B(O)O)cn2)o1] 9
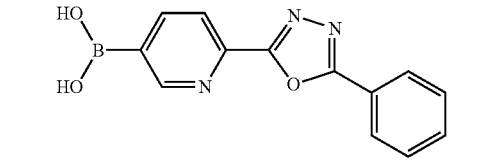 [SMILES: OB(O)c1ccc(-c2nnc(-c3ccccc3)o2)nc1] 12
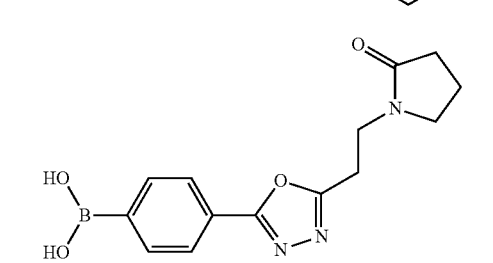 10

TABLE 11-continued
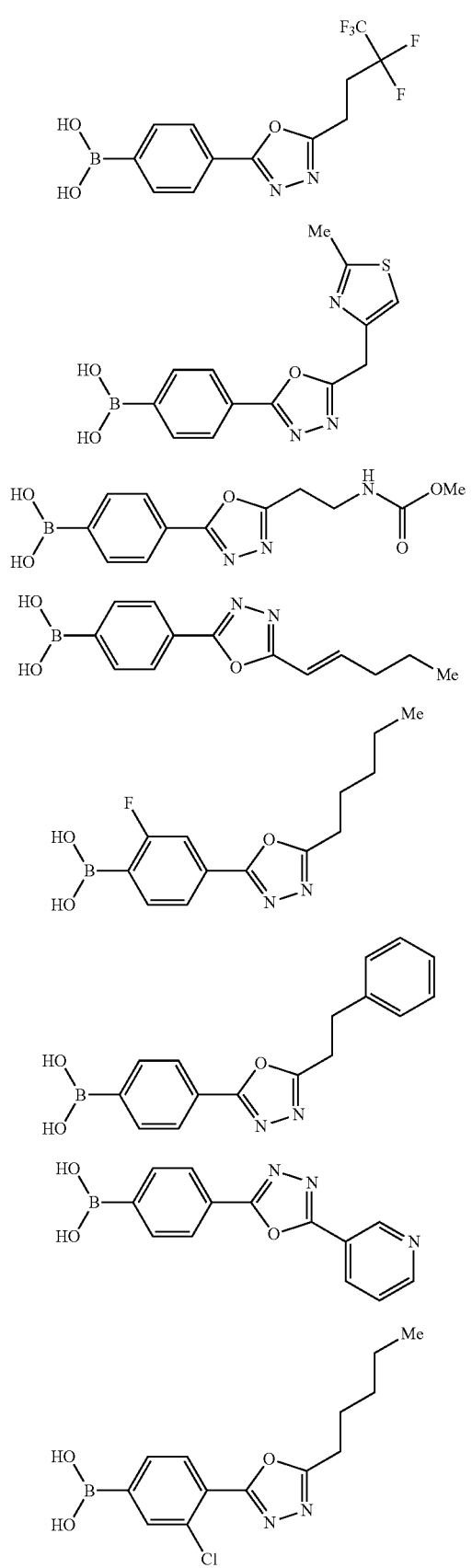
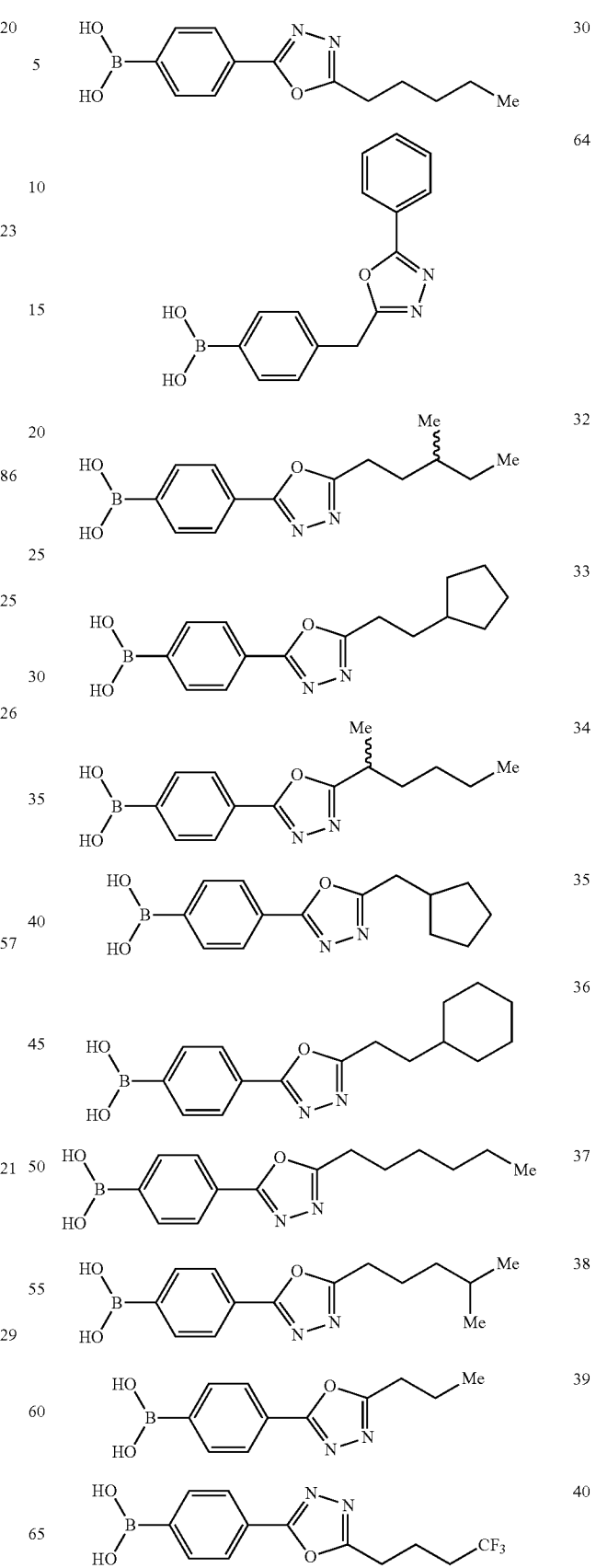

TABLE 11-continued
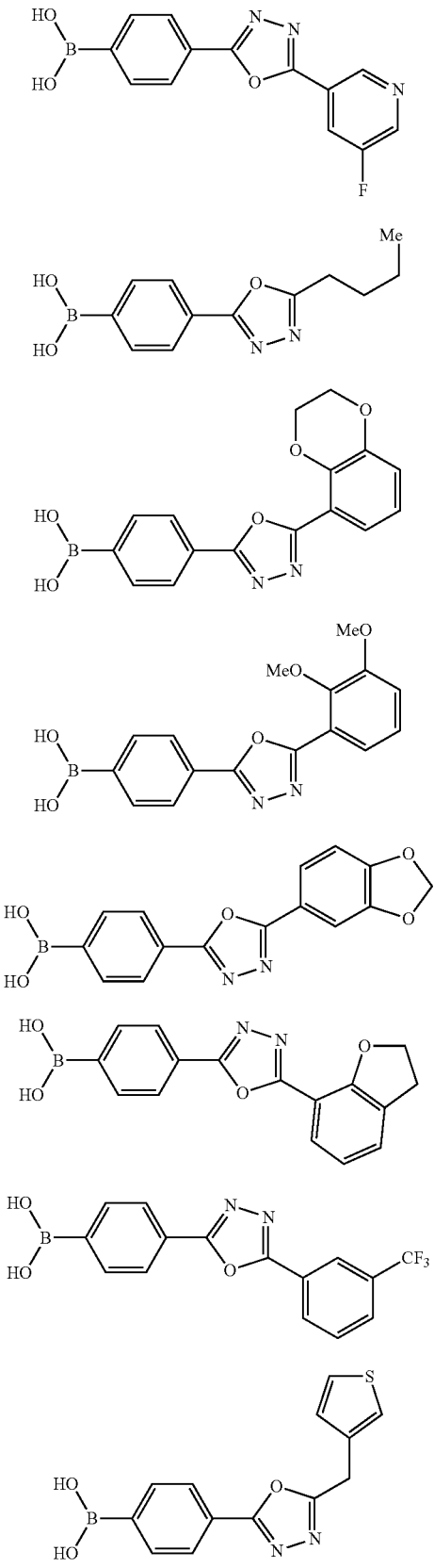
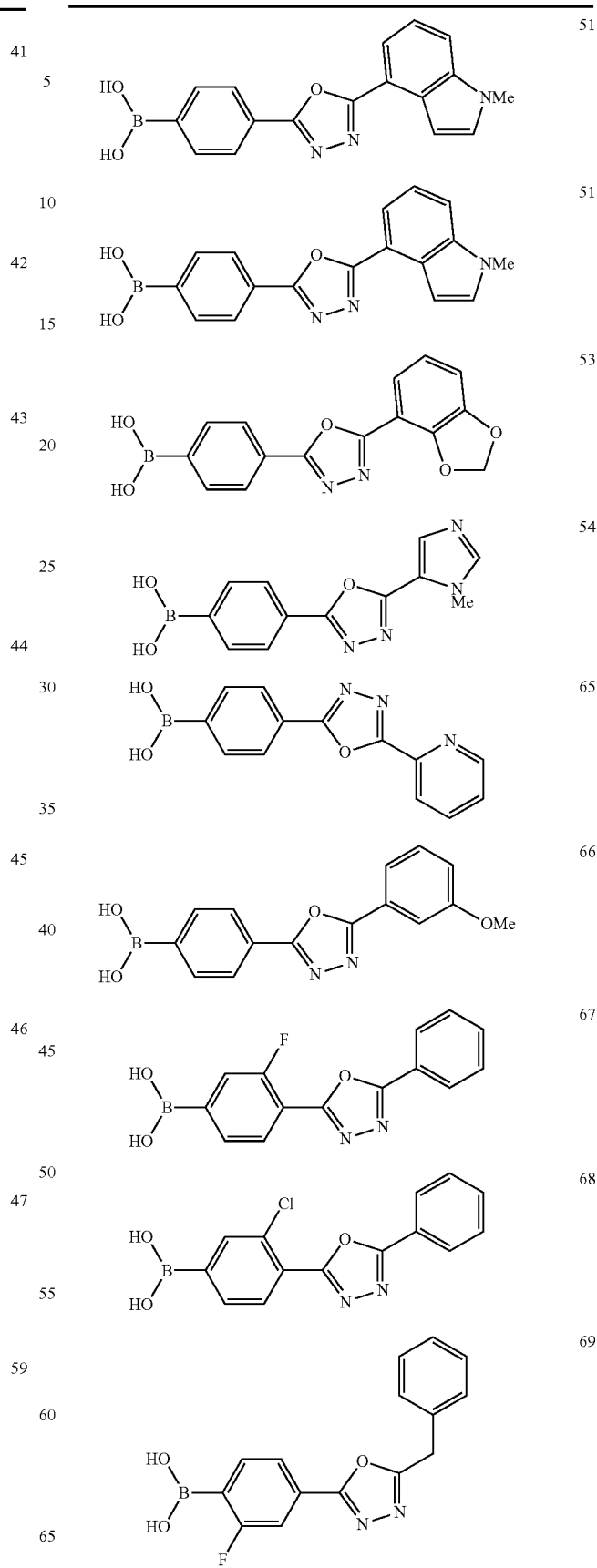

TABLE 11-continued
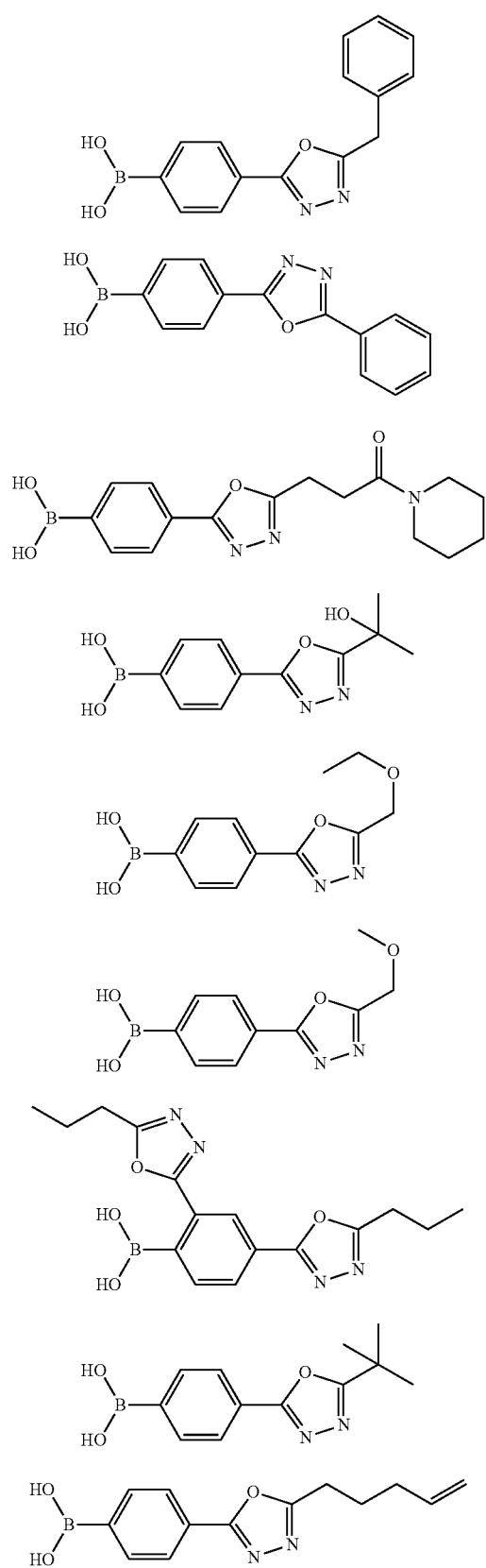
TABLE 11-continued
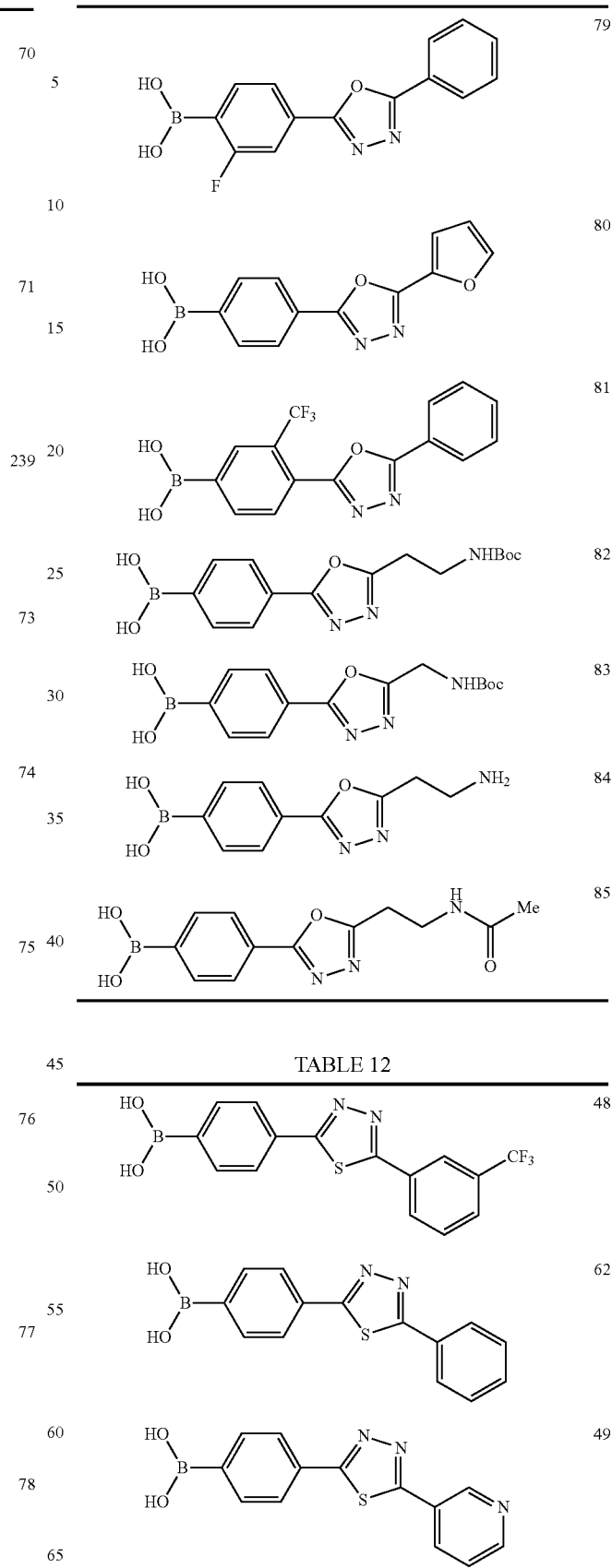
TABLE 12
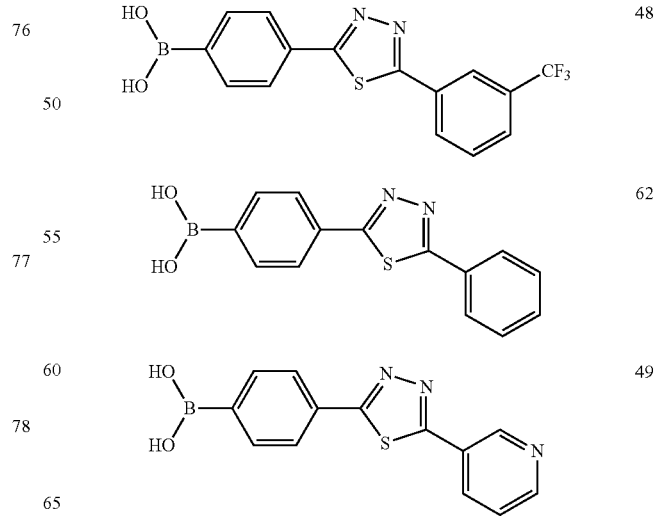

TABLE 12-continued
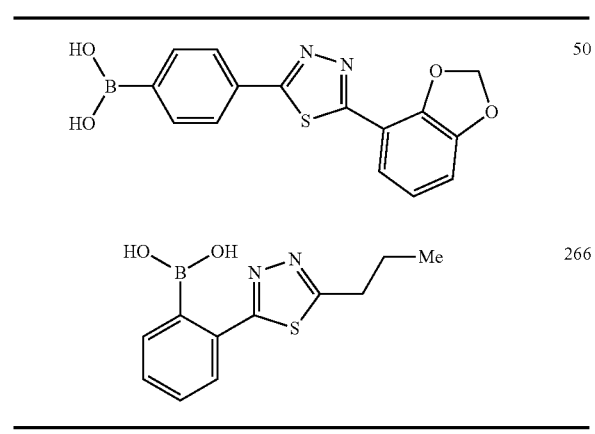
TABLE 13
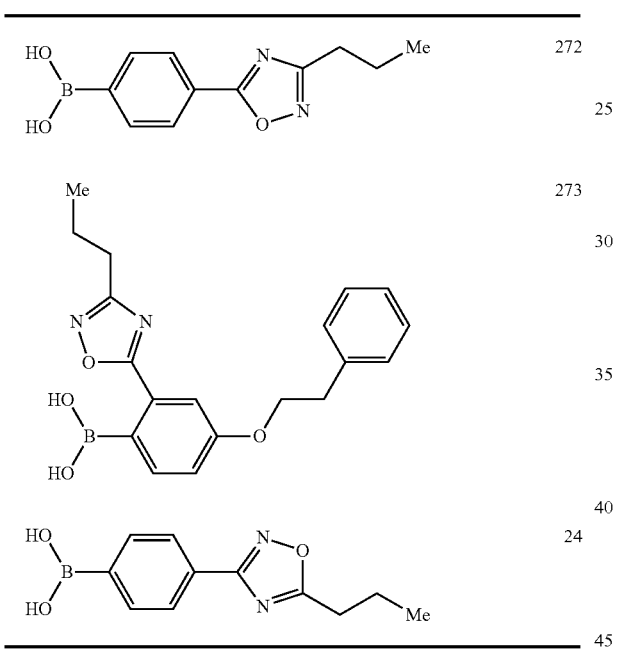
TABLE 14
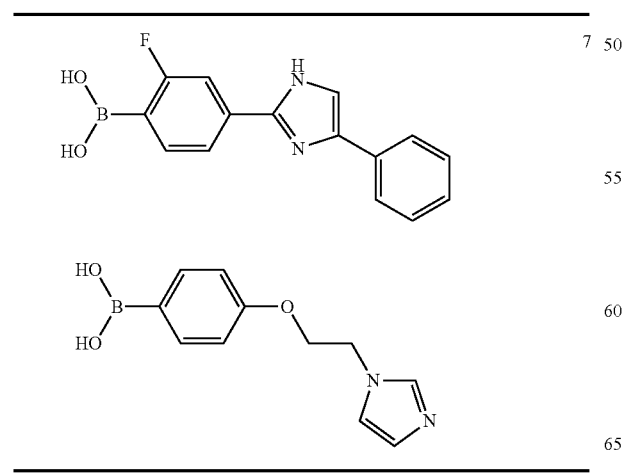
TABLE 15
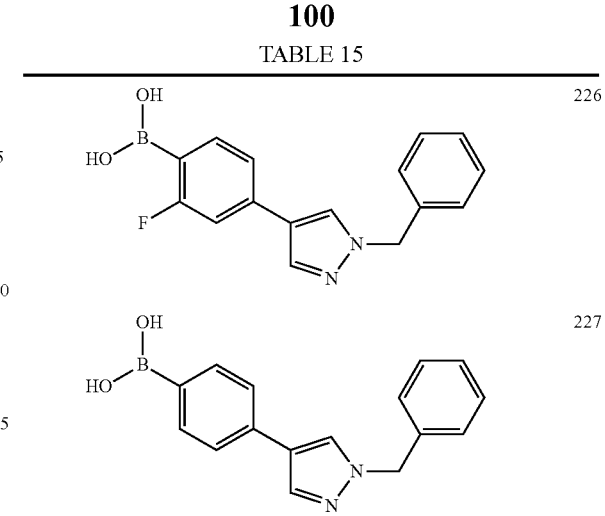
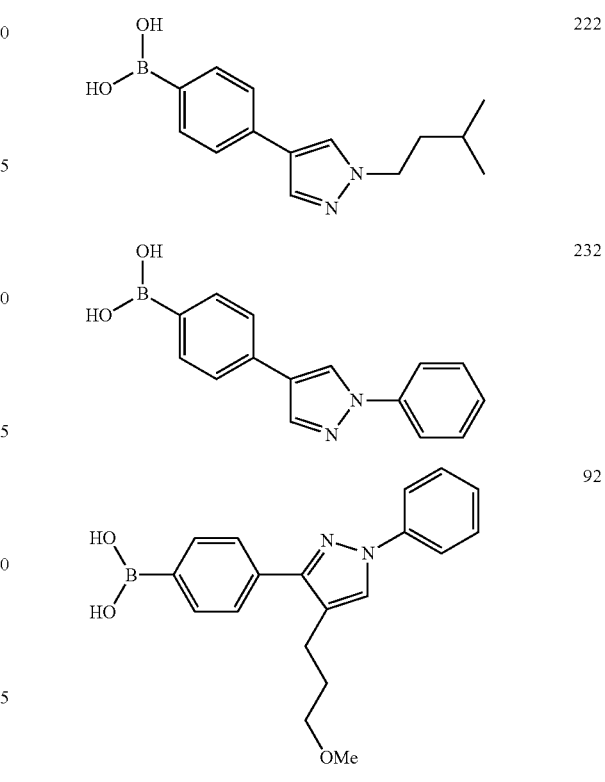
TABLE 16
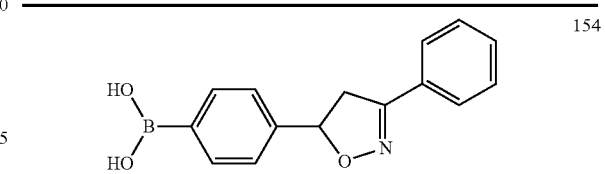

TABLE 16-continued
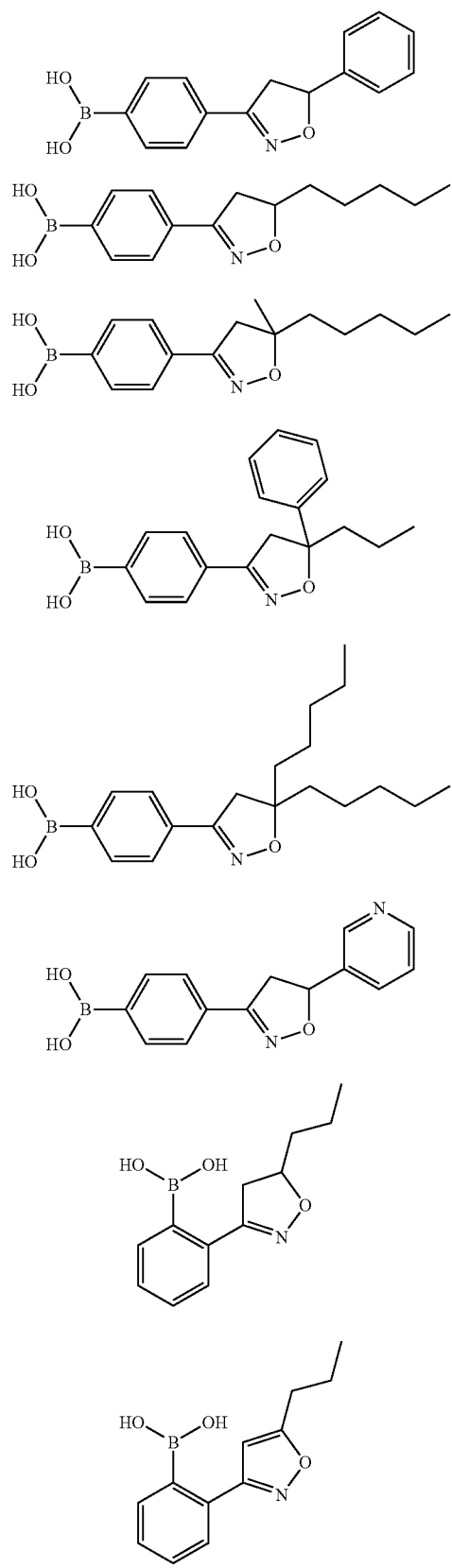
TABLE 16-continued
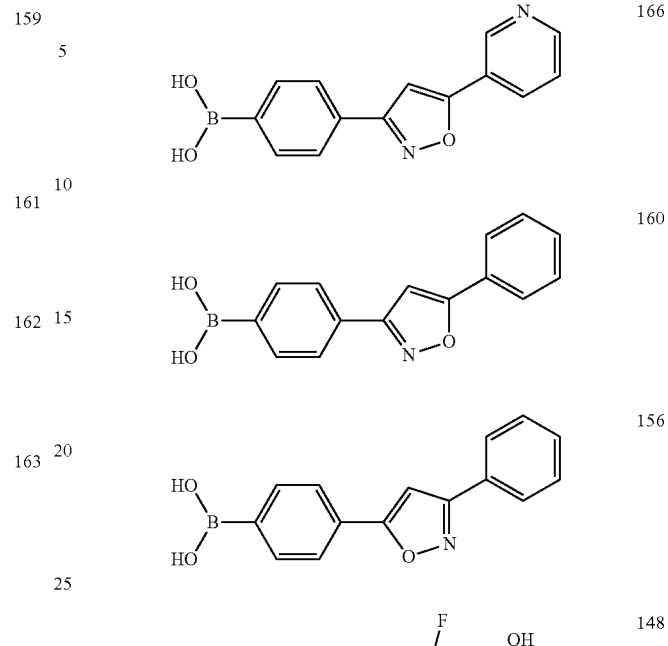
TABLE 17
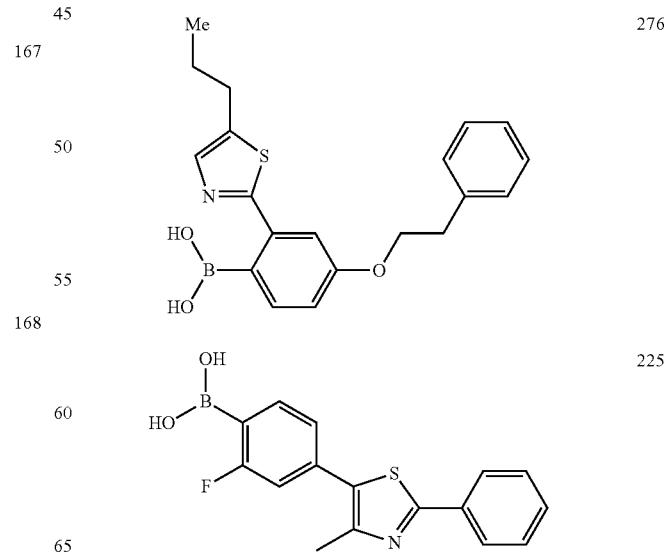

TABLE 17-continued
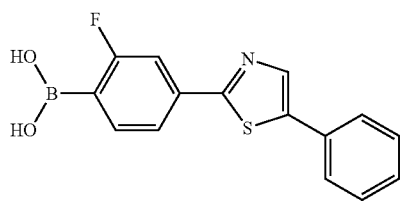
3
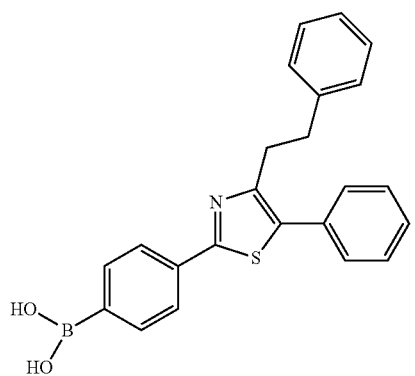 [SMILES: OB(O)c1ccc(-c2nc(CCc3ccccc3)c(-c3ccccc3)s2)cc1]
8
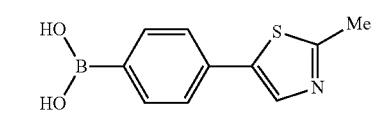 [SMILES: Cc1ncc(-c2ccc(B(O)O)cc2)s1]
89
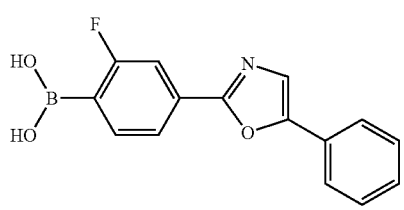 [SMILES: OB(O)c1ccc(-c2ncc(-c3ccccc3)o2)cc1F]
1
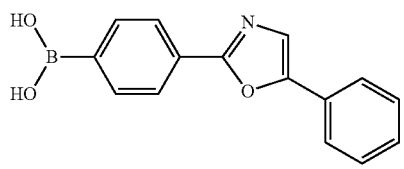 [SMILES: OB(O)c1ccc(-c2ncc(-c3ccccc3)o2)cc1]
2
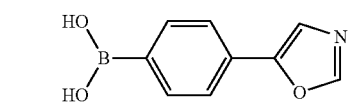 [SMILES: OB(O)c1ccc(-c2cnco2)cc1]
90
TABLE 18
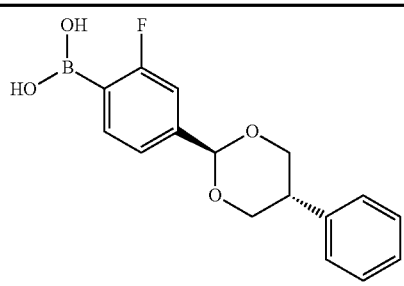
173
TABLE 18-continued
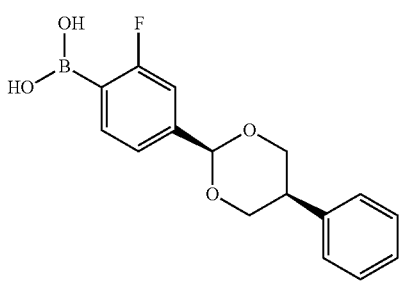 [SMILES: OB(O)c1ccc([C@H]2OC[C@@H](c3ccccc3)CO2)cc1F]
174
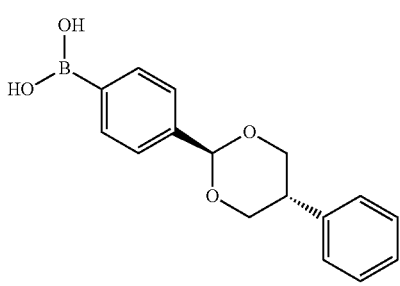 [SMILES: OB(O)c1ccc([C@H]2OC[C@H](c3ccccc3)CO2)cc1]
175
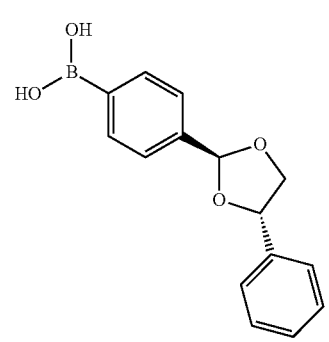 [SMILES: OB(O)c1ccc([C@H]2OC[C@H](c3ccccc3)O2)cc1]
179
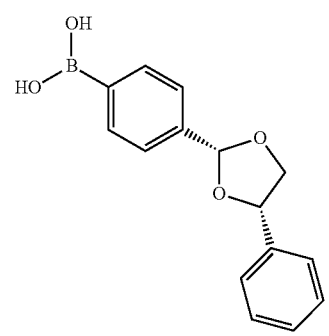 [SMILES: OB(O)c1ccc([C@@H]2OC[C@H](c3ccccc3)O2)cc1]
180
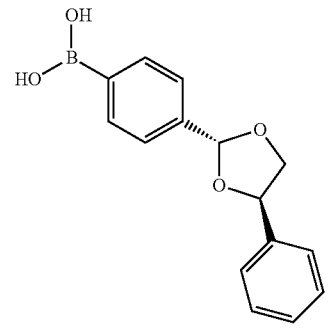
181

TABLE 18-continued
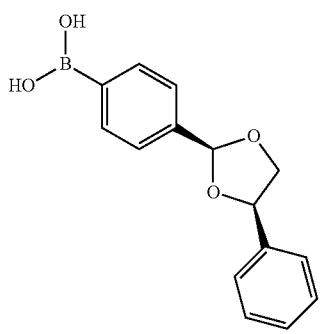 [SMILES: OB(O)c1ccc([C@H]2OC[C@@H](c3ccccc3)O2)cc1]
182
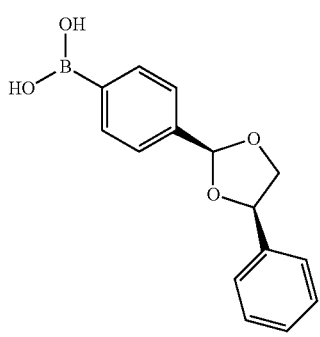 [SMILES: OB(O)c1ccc([C@H]2OC[C@@H](c3ccccc3)O2)cc1]
182
TABLE 19
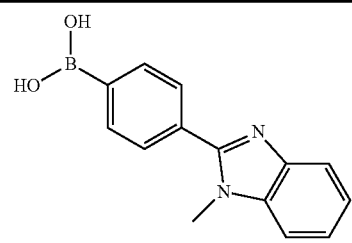
224
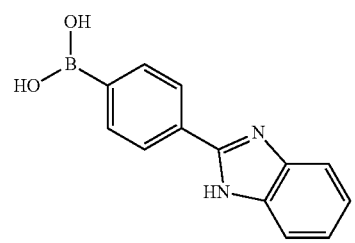 [SMILES: OB(O)c1ccc(-c2nc3ccccc3[nH]2)cc1]
223
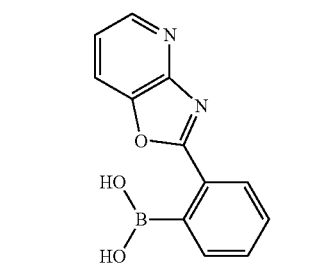 [SMILES: OB(O)c1ccccc1-c1nc2ncccc2o1]
259
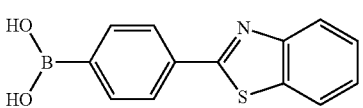
87
TABLE 20
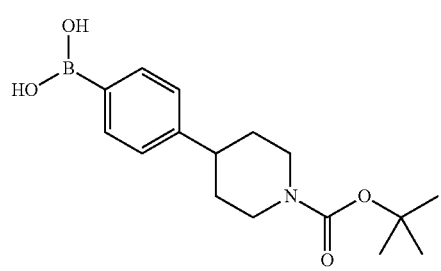 [SMILES: CC(C)(C)OC(=O)N1CCC(c2ccc(B(O)O)cc2)CC1]
233
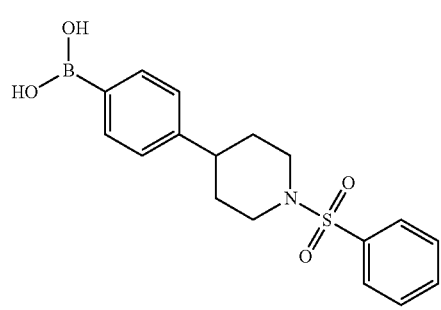 [SMILES: O=S(=O)(c1ccccc1)N1CCC(c2ccc(B(O)O)cc2)CC1]
236
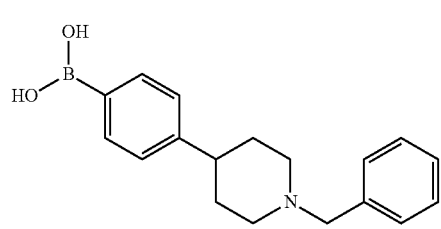
279
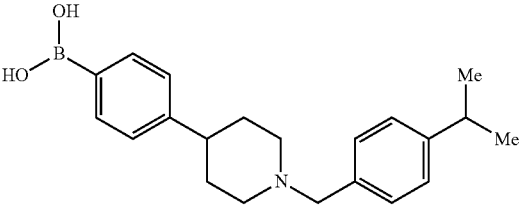 [SMILES: CC(C)c1ccc(CN2CCC(c3ccc(B(O)O)cc3)CC2)cc1]
280
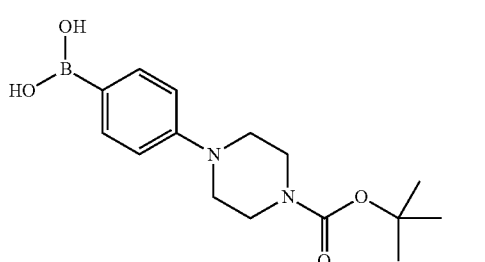
318
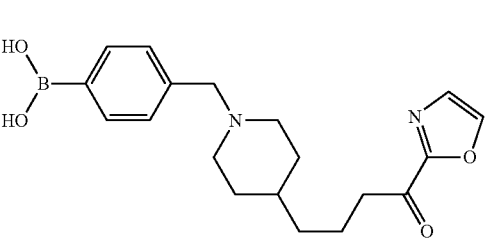 [SMILES: O=C(CCCC1CCN(Cc2ccc(B(O)O)cc2)CC1)c1ncco1]
329
Additionally, in certain embodiments, the present invention provides compounds of formula (VI):

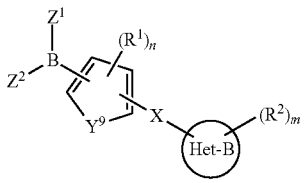

(VI)

or a pharmaceutically acceptable salt or prodrug thereof, wherein:

(i) $Z^1$ is —OH or —OR$^3$ and $Z^2$ is —OH, —OR$^4$, an optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

(ii) $Z^1$ and $Z^2$ taken together form a 5- to 8-membered ring having at least one O, S, N or NR$^5$ atom directly bonded to the boron atom; or (iii) $Z^1$ is —OH or —OR$^3$, and $Z^2$ and Ring A taken together form an optionally substituted 5- to 7-membered ring;

$Y^9$ is an S or O;

X is a covalent bond, —O—, —N=N—, —C=N—, —NR$^6$—, —C(NR$^6$)—, —S—, —C(O)—, —S(O)—, —S(O)$_2$—, or optionally substituted $C_{1-6}$ alkylene, wherein one, two or three methylene units of the $C_{1-6}$ alkylene are optionally and independently replaced with one or more groups selected from —O—, —N=N—, —C=N—, —NR$^6$—, —C(NR$^6$)—, —S—, —C(O)—, —S(O)—, and —S(O)$_2$—;

Het-B is an optionally substituted 3-10 membered heterocyclyl or an optionally substituted 5-10 membered heteroaryl ring;

each instance of R$^1$ is, independently, halogen, —OR$^8$, —CF$_3$, —CN, —NO$_2$, —SO$_2$R$^8$, —SOR$^8$, —C(O)R$^8$, —CO$_2$R$^8$, —C(O)N(R$^8$)$_2$, —N$_3$, —N$_2$R$^8$, —N(R$^8$)$_2$, —B(OH$_2$), optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of R$^2$ is, independently, halogen, —OR$^9$, —CF$_3$, —CN, —NO$_2$, —SO$_2$R$^9$, —SOR$^9$, —C(O)R$^9$, —CO$_2$R$^9$, —C(O)N(R$^9$)$_2$, —N$_3$, —N$_2$R$^9$, —N(R$^9$)$_2$, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of R$^3$ and R$^4$ is, independently, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of R$^5$, R$^6$, R$^7$, R$^8$, R$^9$, and R$^{10}$ is, independently, hydrogen, —SO$_2$R$^{11}$, —SOR$^{11}$, —C(O)R$^{11}$, —CO$_2$R$^{11}$, —C(O)N(R$^{11}$)$_2$, —C(O)NH(R$^{11}$), —C(O)NH$_2$, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

each instance of R$^{11}$ is, independently, optionally substituted $C_{1-8}$ alkyl, optionally substituted $C_{2-8}$ alkenyl, optionally substituted $C_{2-8}$ alkynyl, optionally substituted $C_{1-8}$ heteroalkyl, optionally substituted $C_{2-8}$ heteroalkenyl, optionally substituted $C_{2-8}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;

n is 0, 1, 2 or 3 and m is 0, 1, 2, 3, 4, or 5.

In certain embodiments, the present invention provides compounds of any of formulae (VI-a), (VI-b), (VI-c), (VI-d) or (VI-e):

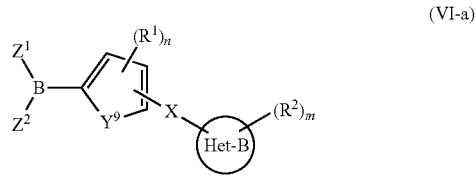

(VI-a)

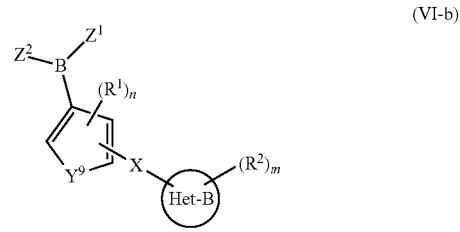

(VI-b)

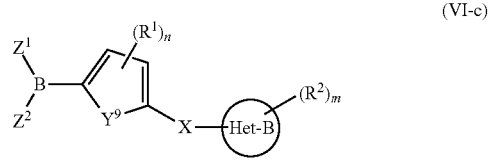

(VI-c)

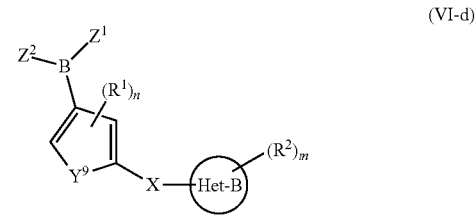

(VI-d)

or a pharmaceutically acceptable salt or prodrug thereof, wherein $Y^9$, $Z^1$, $Z^2$, Het-B, X, R$^1$, R$^2$, m and n are as defined above and herein.

Exemplary Het-B rings include, but are not limited to,

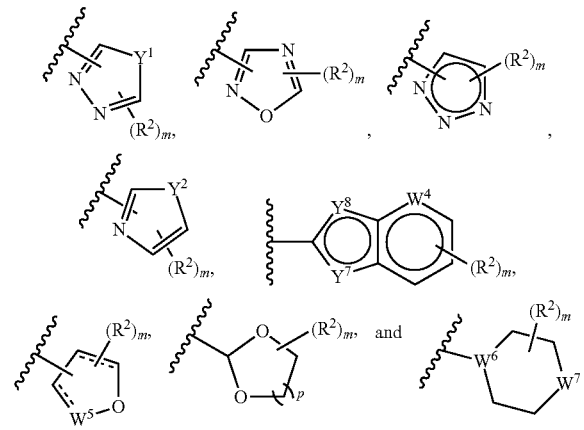

wherein $Y^1$, $Y^2$, $Y^7$, $Y^8$, $W^5$, $W^6$, $W^7$, p, $R^2$ and m are as defined above and herein.

In certain embodiments, Het-B of formula (VI), and subgenera thereof, is selected from

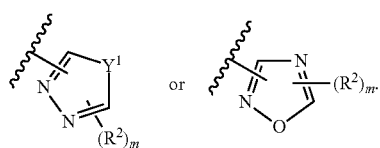

In certain embodiments, Het-B of formula (VI), and subgenera thereof, is selected from

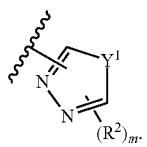

For example, in certain embodiments, the present invention provides compounds of formula (VI-e):

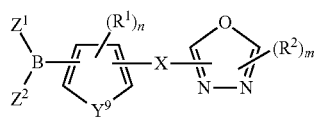

(VI-e)

or a pharmaceutically acceptable salt or prodrug thereof, wherein $Y^9$, $Z^1$, $Z^2$, X, $R^1$, $R^2$, m and n are as defined above and herein. For example, in certain embodiments, the present invention provides compounds of any of formulae (VI-e1), (VI-e2), (VI-e3), (VI-e4) or (VI-e5):

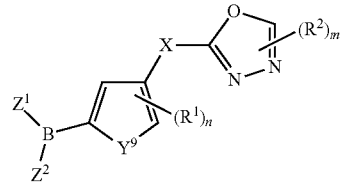

(VI-e1)

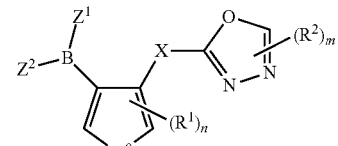

(VI-e2)

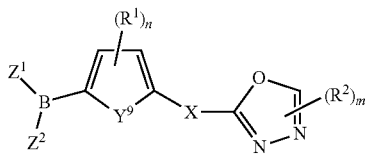

(VI-e3)

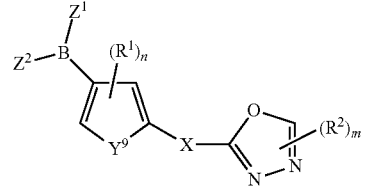

(VI-e4)

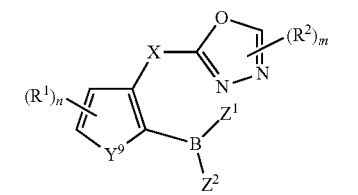

(VI-e5)

or a pharmaceutically acceptable salt or prodrug thereof, wherein $Y^9$, $Z^1$, $Z^2$, X, $R^1$, $R^2$, m and n are as defined above and herein.

In certain embodiments, n is 0.

In certain embodiments, X is a covalent bond.

In certain embodiments, m is 1. In certain embodiments, $R^2$ is selected from optionally substituted $C_{1-8}$ alkyl or optionally substituted $C_{6-10}$ aryl. In certain embodiments, $R^2$ is selected from —$CH_3$, —$CH_2CH_3$, —$(CH_2)_2CH_3$, —$(CH_2)_3CH_3$, —$(CH_2)_4CH_3$, optionally substituted phenyl, optionally substituted benzyl, and —$(CH_2)_2C_6H_5$.

In certain embodiments, $Y^9$ is a S atom. In certain embodiments, $Y^9$ is an O atom.

In certain embodiments, Het-B is an optionally substituted 3-10 membered heterocyclyl ring having 2 to 3 heteroatoms selected from N, $NR^{16}$, O and S. In certain embodiments, Het-B is an optionally substituted 5-10 membered heteroaryl ring having 2 to 3 heteroatoms selected from N, $NR^{16}$, O and S. In certain embodiments, Het-B is an optionally substituted 5-membered heteroaryl ring having 2 to 3 heteroatoms selected from N, $NR^{16}$, O and S.

In certain embodiments, Het-B is an optionally substituted 5-membered monocyclic heteroaryl ring selected from the group consisting of an optionally substituted triazolyl, optionally substituted oxadiazolyl, optionally substituted thiadiazolyl, optionally substituted imidazolyl, optionally substituted pyrazolyl, optionally substituted thiazolyl, optionally substituted isothiazolyl, optionally substituted oxazolyl and optionally substituted isoxazolyl.

In certain embodiments, compounds of formula (VI) or subgenera thereof, wherein $Y^9$ is S, X is a covalent bond, n is 0, m is 0 and Het-B is $C_6H_5$ or unsubstituted thiophenyl, are specifically excluded.

In certain embodiments, the following compounds are specifically excluded:

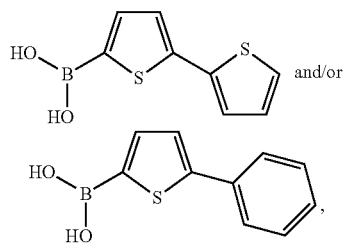

or a pharmaceutically acceptable salt or prodrug thereof.

Exemplary compounds encompassed by formulae (II), (VI), and subgenera thereof, are provided below in Table 21.

TABLE 21

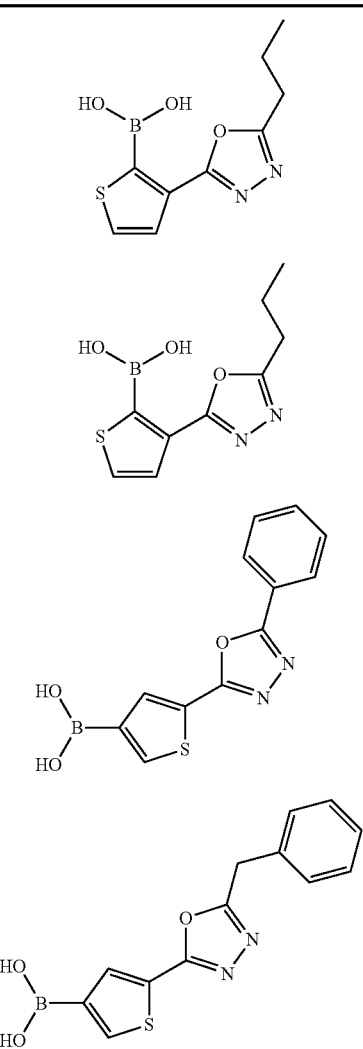

TABLE 21-continued

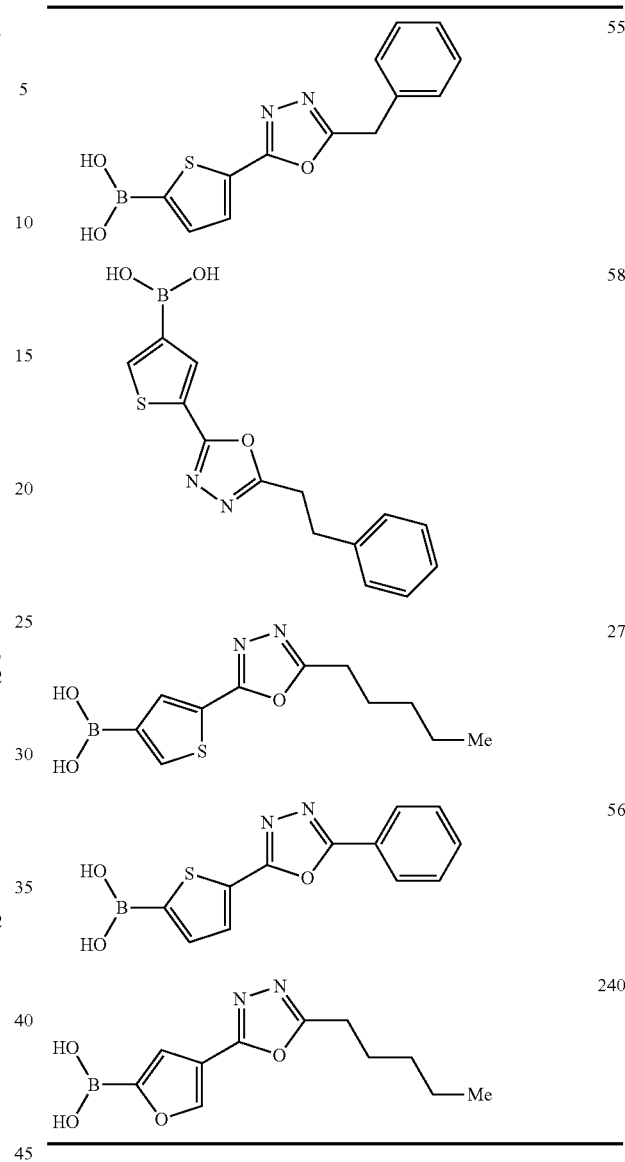

4. Pharmaceutically Acceptable Compositions and Formulations

In certain embodiments, the present invention provides a pharmaceutically acceptable composition comprising a compound of any of formulae (I), (II), (III), (IV), (V), or (VI), or subgenera thereof, or a pharmaceutically acceptable salt or prodrug thereof, and a pharmaceutically acceptable excipient, medium, or carrier.

In some embodiments, the present invention provides a pharmaceutically acceptable composition comprising a compound of any of formulae (I), (II), (III), (IV), (V), or (VI), or subgenera thereof, or a pharmaceutically acceptable salt or prodrug thereof, as provided in any of Tables 1 through 20, and a pharmaceutically acceptable excipient, medium, or carrier.

In some embodiments, the present invention provides a pharmaceutically acceptable composition comprising a compound of any of formulae (I), (II), (III), (IV), (V), or (VI), or subgenera thereof, or a pharmaceutically acceptable salt or prodrug thereof, as provided in the Examples, and a pharmaceutically acceptable excipient, medium, or carrier.

In other embodiments, the present invention provides a pharmaceutically acceptable composition comprising a compound of any of formulae (I), (II), (III), (IV), (V), or (VI), or subgenera thereof, or a pharmaceutically acceptable salt or prodrug thereof, as provided in the Examples having a K, of less than or equal to 0.01 microM or having a K, of between 0.01 microM and 0.1 microM (i.e., compounds with activities designated "A" and "B"), and a pharmaceutically acceptable excipient, medium, or carrier.

In yet other embodiments, the present invention provides a pharmaceutically acceptable composition comprising a compound of any of formulae (I), (II), (III), (IV), (V), or (VI), or subgenera thereof, or a pharmaceutically acceptable salt or prodrug thereof, as provided in the Examples having a $K_i$ of less than or equal to 0.01 microM (i.e., compounds with activities designated "A") and a pharmaceutically acceptable excipient, medium, or carrier.

In still yet other embodiments, the present invention provides a pharmaceutically acceptable composition comprising a compound of any of formulae (I), (II), (III), (IV), (V), or (VI), or subgenera thereof, or a pharmaceutically acceptable salt or prodrug thereof, and a pharmaceutically acceptable excipient, medium, or carrier, wherein said compound is selected from the any compound depicted in the Examples.

As described above, pharmaceutically acceptable compositions of the present invention additionally comprise a pharmaceutically acceptable excipient, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human scrum albumin, buffer substances such as phosphates, glycinc, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Provided formulations of pharmaceutically acceptable compositions described herein may be prepared by any method known or hereafter developed in the art of pharmacology. In general, such preparatory methods include the step of bringing the active ingredient into association with a carrier and/or one or more other accessory ingredients, and then, if necessary and/or desirable, shaping and/or packaging the product into a desired single- or multi-dose unit.

A pharmaceutically acceptable composition of the invention may be prepared, packaged, and/or sold in bulk, as a single unit dose, and/or as a plurality of single unit doses. As used herein, a "unit dose" is discrete amount of the pharmaceutically acceptable composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable carrier, and/or any additional ingredients in a pharmaceutically acceptable composition of the invention will vary, depending upon the identity, size, and/or condition of the subject treated and further depending upon the route by which the composition is to be administered. By way of example, the composition may comprise between 0.1% and 100% (w/w) active ingredient.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of provided pharmaceutically acceptable compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidonc), sodium carboxymethyl starch (sodium starch glycolatc), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol, etc.); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives.

Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include, but are not limited to, ethanol, polyethylene glycol, phenol, phenolic compounds, bisphenol, chlorobutanol, hydroxybenzoate, and phenylethyl alcohol.

Exemplary acidic preservatives include, but are not limited to, vitamin A, vitamin C, vitamin E, beta-carotene, citric acid, acetic acid, dehydroacetic acid, ascorbic acid, sorbic acid, and phytic acid.

Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phcnonip, methylparaben, German 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microcmulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as may be required. Additionally, the present invention contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutically acceptable compositions described herein include short needle devices such as those described in U.S. Pat. Nos.

4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutically acceptable composition of the invention may be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutically acceptable compositions of the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutically acceptable composition of the invention. Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the flares.

Formulations suitable for nasal administration may, for example, comprise from about as little as 0.1% (w/w) and as much as 100% (w/w) of the active ingredient, and may comprise one or more of the additional ingredients described herein. A pharmaceutically acceptable composition of the invention may be prepared, packaged, and/or sold in a formulation suitable for buccal administration. Such formulations may, for example, be in the form of tablets and/or lozenges made using conventional methods, and may, for example, 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutically acceptable composition of the invention may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* $21^{st}$ ed., Lippincott Williams & Wilkins, 2005.

Although the descriptions of pharmaceutically acceptable compositions provided herein are principally directed to pharmaceutical compositions which are suitable for administration to humans, it will be understood by the skilled artisan that such compositions are generally suitable for administration to animals of all sorts. Modification of pharmaceutically acceptable compositions suitable for administration to humans in order to render the compositions suitable for administration to various animals is well understood, and the ordinarily skilled veterinary pharmacologist can design and/or perform such modification with merely ordinary, if any, experimentation.

5. Kits

Still further encompassed by the invention are kits comprising one or more compounds of the invention (or pharmaceutically acceptable salts or prodrugs thereof), and/or one or more pharmaceutically acceptable compositions as described herein. Kits are typically provided in a suitable container (e.g., for example, a foil, plastic, or cardboard package).

In certain embodiments, an inventive kit may include one or more pharmaceutical excipients, pharmaceutical additives, therapeutically active agents, and the like, as described herein. In certain embodiments, an inventive kit may include means for proper administration, such as, for example, graduated cups, syringes, needles, cleaning aids, and the like. In certain embodiments, an inventive kit may include instructions for proper administration and/or preparation for proper administration.

6. Methods of Treatment

The present invention also provides methods for treating an FAAH-mediated disease, disorder or condition by administering a therapeutically effective amount of a compound of any of formulae (I), (II), (III), (IV), (V), or (VI), or subgenera thereof, or a pharmaceutically acceptable composition thereof, to a patient in need thereof.

Additionally, the present invention provides methods for inhibiting FAAH in a patient by administering a therapeutically effective amount of a compound of any of formulae (I), (II), (III), (IV), (V), or (VI), or subgenera thereof, or a pharmaceutically acceptable composition thereof, to a patient in need thereof.

A patient to which administration is contemplated includes, but is not limited to, humans (e.g., male, female, infant, child, adolescant, adult, elderly, etc.) and/or other primates; mammals, including commercially relevant mammals such as cattle, pigs, horses, sheep, cats, and/or dogs; and/or birds, including commercially relevant birds such as chickens, ducks, geese, and/or turkeys.

"Treating," as used herein, refers to partially or completely inhibiting or reducing the condition from which the patient is suffering.

"Therapeutically effective amount," as used herein, refers to the minimal amount or concentration of an inventive compound, or pharmaceutically acceptable composition thereof, that, when administered, is sufficient in treating the patient. Treating may be via prophylactic or therapeutic therapy.

In other embodiments, the present invention provides a method for inhibiting FAAH in a biological sample comprising the step of contacting said sample with a compound of any of formulae (I), (II), (III), (IV), (V), or (VI), or subgenera thereof, or with a compound set forth in the Examples.

FAAH-mediated diseases, disorders or conditions include, but are not limited to, painful conditions, inflammatory disorders, immune disorders, depression, anxiety, anxiety-related disorders, sleep disorders, feeding behaviors, movement disorders, glaucoma, neuroprotection and cardiovascular disease.

In certain embodiments, the FAAH-mediated disease, disorder or condition is a painful condition, disease or disorder. As used herein, a "painful condition, disease or disorder" includes, but is not limited to, neuropathic pain (e.g., peripheral neuropathic pain), central pain, deafferentiation pain, chronic pain (e.g., chronic nociceptive pain, and other forms of chronic pain such as post-operative pain), stimulus of nociceptive receptors, acute pain (e.g., phantom and transient acute pain), non-inflammatory pain, inflammatory pain, pain associated with cancer, wound pain, burn pain, post-operative pain, pain associated with medical procedures, arthritic pain (e.g., pain associated with rheumatoid arthritis, osteoarthritis), lumbosacral pain, musculo-skeletal pain, headache, migraine, muscle ache, lower back and neck pain, toothache and the like.

In certain embodiments, the painful condition, disease or disorder is neuropathic pain. The term "neuropathic pain" refers to pain resulting from injury to a nerve. Neuropathic pain is distinguished from nociceptive pain, which is the pain caused by acute tissue injury involving small cutaneous nerves or small nerves in muscle or connective tissue. Neuropathic pain typically is long-lasting or chronic and often develops days or months following an initial acute tissue injury. Neuropathic pain can involve persistent, spontaneous pain as well as allodynia, which is a painful response to a stimulus that normally is not painful. Neuropathic pain also can be characterized by hyperalgesia, in which there is an accentuated response to a painful stimulus that usually is trivial, such as a pin prick. Neuropathic pain conditions can develop following neuronal injury and the resulting pain may persist for months or years, even after the original injury has healed. Neuronal injury may occur in the peripheral nerves, dorsal roots, spinal cord or certain regions in the brain. Neuropathic pain conditions include: diabetic neuropathy; sciatica; non-specific lower back pain; multiple sclerosis pain; fibromyalgia; HIV-related neuropathy; neuralgia, such as post-herpetic neuralgia and trigeminal neuralgia; and pain resulting from physical trauma, amputation, cancer, chemotherapy-induced pain, chemotherapy, surgery, invasive medical procedures, toxins burns, infection, or chronic inflammatory conditions. Neuropathic pain can result from a peripheral nerve disorder such as neuroma; nerve compression; nerve crush, nerve stretch or incomplete nerve transsection; mononeuropathy or polyneuropathy. Neuropathic pain can also result from a disorder such as dorsal root ganglion compression; inflammation of the spinal cord; contusion, tumor or hemisection of the spinal cord; tumors of the brainstem, thalamus or cortex; or trauma to the brainstem, thalamus or cortex.

The symptoms of neuropathic pain are heterogeneous and are often described as spontaneous shooting and lancinating pain, or ongoing, burning pain. In addition, there is pain associated with normally non-painful sensations such as "pins and needles" (paraesthesias and dyscsthesias), increased sensitivity to touch (hyperesthesia), painful sensation following innocuous stimulation (dynamic, static or thermal alodynia), in creased sensitivity to noxious stimuli (thermal, cold, mechanical hyperalgesia), continuing pain sensation after removal of the stimulation (hyperpathia) or an absence of or deficit in selective sensory pathways (hypoalgesia).

In certain embodiments, the painful condition, disease or disorder is non-inflammatory pain and/or inflammatory pain. The types of non-inflammatory pain include, without limitation, peripheral neuropathic pain (e.g., pain caused by a lesion or dysfunction in the peripheral nervous system), central pain (e.g., pain caused by a lesion or dysfunction of the central nervous system), deafferentation pain (e.g., pain due to loss of sensory input to the central nervous system), chronic nociceptive pain (e.g., certain types of cancer pain), noxious stimulus of nociceptive receptors (e.g., pain felt in response to tissue damage or impending tissue damage), phantom pain (e.g., pain felt in a part of the body that no longer exists, such as a limb that has been amputated), pain felt by psychiatric patients (e.g., pain where no physical cause may exist), and wandering pain (e.g., wherein the pain repeatedly changes location in the body). In certain embodiments, non-inflammatory pain and/or inflammatory pain are associated with disorders such as inflammatory diseases (e.g., autoimmune disease).

In certain embodiments, the FAAH-mediated disease, disorder or condition is an inflammatory disorder. The term "inflammatory disorders" refers to those diseases or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which may be partial or complete, temporary or permanent). Inflammatory disorders include, without limitation, those affecting the blood vessels (e.g., polyarteritis, temporal arteritis); joints (e.g, arthritis: crystalline, osteo-, psoriatic, reactive, rheumatoid, Reiter's syndrome); gastrointestinal tract (e.g, Crohn's disease, ulcerative colitis); skin (e.g, dermatitis); or multiple organs and tissues (e.g, systemic lupus erythematosus). Inflammatory disorders include, but are not limited to, inflammation associated with vascular diseases, migraine headaches, tension headaches, arteritis, thyroiditis, aplastic anemia, Hodgkin's disease, scleroderma, rheumatic fever, type I diabetes, myasthenia gravis, sarcoidosis, nephrotic syndrome, Behcet's syndrome, polymyositis, gingivitis, hypersensitivity, conjunctivitis, multiple sclerosis, and ischemia (e.g., myocardial ischemia), and the like. The compounds and compositions may be useful for treating neuroinflammation associated with brain disorders (e.g., Parkinson's disease and Alzheimer's disease) and chronic inflammation associated with cranial radiation injury. The compounds may be useful for treating acute inflammatory conditions (e.g., conditions resulting from infection) and chronic inflammatory conditions (e.g., conditions resulting from asthma, arthritis and inflammatory bowel disease). The compounds may also be useful in treating inflammation associated with trauma and non-inflammatory myalgia. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

In certain embodiments, the FAAH-mediated disease, disorder or condition is an immune disorder. Immune disorders, such as auto-immune disorders, include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin inflammation disorders (e.g., psoriasis, eczema, burns, dermatitis), enuresis, eosinophilic disease, gastrointestinal disorders (e.g., inflammatory bowel disease (IBD), peptic ulcers, regional enteritis, diverticulitis, gastrointestinal bleeding, Crohn's disease, gastritis, diarrhea, irritable bowel syndrome and ulcerative colitis), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In certain embodiments, the immune disorder is a gastrointestinal disorder. In some embodiments, the immune disorder is inflammatory bowel disease (e.g., Crohn's disease and/or ulcerative colitis), peptic ulcers, regional enteritis, diverticulitis, gastrointestinal bleeding, Crohn's disease, gastritis, diarrhea, irritable bowel syndrome and ulcerative colitis. In other embodiments, the immune disorder is inflammatory bowel disease (IBD).

In certain embodiments, the FAAH-mediated disease, disorder or condition is a skin disorder. In some embodiments, the skin disorder is pruritus (itch), psoriasis, eczema, burns or dermatitis. In certain embodiments, the skin disorder is psoriasis. In certain embodiments, the skin disorder is pruritus.

In certain embodiments, the FAAH-mediated disease, disorder or condition is anxiety. "Anxiety," as used herein, includes, but is not limited to anxiety and anxiety disorders or conditions, such as, for example, clinical anxiety, panic disorder, agoraphobia, generalized anxiety disorder, specific phobia, social phobia, obsessive-compulsive disorder, acute stress disorder, and post-traumatic stress disorder; and adjustment disorders with anxious features, anxiety disorders associated with depression, anxiety disorders due to general medical conditions, and substance-induced anxiety disorders. This treatment may also be to induce or promote sleep in a patient (e.g., for example, a patient with anxiety).

In certain embodiments, the FAAH-mediated disease, disorder or condition is a sleep disorder. "Sleep disorders" include, but are not limited to, insomia, sleep apnea, restless legs syndrome (RLS), delayed sleep phase syndrome (DSPS), periodic limb movement disorder (PLMD), hypopnea syndrome, rapid eye movement behavior disorder (RBD), shift work sleep disorder (SWSD), and sleep problems (e.g., parasomnias) such as nightmares, night terrors, sleep talking, head banging, snoring, and clenched jaw and/or grinding of teeth (bruxism).

In certain embodiments, the FAAH-mediated disease, disorder or condition is depression. "Depression," as used herein, includes, but is not limited to, depressive disorders or conditions, such as, for example, major depressive disorders (unipolar depression), dysthymic disorders (chronic, mild depression) and bipolar disorders (manic-depression). The depression may be clinical or subclinical depression.

In certain embodiments, the FAAH-mediated disease, disorder or condition is feeding behavior. "Feeding behavior," as used herein, includes but is not limited to, eating disorders (e.g., anorexias and cachexias of various natures, over-eating leading to obesity), weight loss associated with cancer, weight loss associated with other general medical conditions, weight loss associated with failure to thrive, and other wasting conditions. The compounds disclosed herein can also be used to reduce body fat and for treating or preventing obesity in a mammal. The compounds disclosed herein can also be used for preventing or treating the diseases associated with these health conditions.

In certain embodiments, the FAAH-mediated disease, disorder or condition is a movement disorder. In other embodiments, the FAAH-mediated disease, disorder or condition is glaucoma. In yet other embodiments, the FAAH-mediated disease, disorder or condition is neuroprotection. In still yet other embodiments, the FAAH-mediated disease, disorder or condition is cardiovascular disease.

In certain embodiments, the above methods provide administering a compound of any of formulae (I), (II), (III), (IV), (V), or (VI), or subgenera thereof, or a pharmaceutically acceptable salt or prodrug thereof, to a patient in need thereof.

In some embodiments, the above methods provide administering a compound of any of formulae (I), (II), (III), (IV), (V), or (VI), or subgenera thereof, or a pharmaceutically acceptable salt or prodrug thereof, as provided in the Examples.

In other embodiments, the above methods provide administering a compound of any of formulae (I), (II), (III), (IV), (V), or (VI), or subgenera thereof, or a pharmaceutically acceptable salt or prodrug thereof, having a $K_i$ of less than or equal to 0.01 microM or having a $K_i$ of between 0.01 microM and 0.1 microM (i.e., compounds with activities designated "A" or "B").

In yet other embodiments, the above methods provide administering a compound of any of formulae (I), (II), (III), (IV), (V), or (VI), or subgenera thereof, or a pharmaceutically acceptable salt or prodrug thereof, having a $K_i$ of less than or equal to 0.01 microM (i.e., compounds with activities designated "A").

7. Administration

Provided compounds may be administered using any amount and any route of administration effective for treatment. The exact amount required will vary from subject to subject, depending on the species, age, and general condition of the subject, the severity of the infection, the particular composition, its mode of administration, its mode of activity, and the like.

Compounds of the present invention are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

Provided compounds and compositions of the present invention may be administered by any route. In some embodiments, provided compounds and compositions are administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration), etc. At present the oral and/or nasal spray and/or aerosol route is most commonly used to deliver therapeutic agents directly to the lungs and/or respiratory system. However, the invention encompasses the delivery of a provided pharmaceutically acceptable composition by any appropriate route taking into consideration likely advances in the sciences of drug delivery.

The exact amount of a compound required to achieve a therapeutically effective amount will vary from subject to subject, depending on species, age, and general condition of a subject, severity of the side effects or disorder, identity of the particular compound(s), mode of administration, and the like. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

In certain embodiments of the present invention, a therapeutically effective amount of an inventive compound for administration one or more times a day to a 70 kg adult human may comprise about 0.0001 mg to about 1000 mg of an inventive compound per unit dosage form. It will be appreciated that dose ranges as described herein provide guidance for the administration of provided pharmaceutically acceptable compositions to an adult. The amount to be administered to, for example, a child or an adolescent can be determined by a medical practitioner or person skilled in the art and can be lower or the same as that administered to an adult.

It will be also appreciated that an inventive compound or composition, as described above and herein, can be administered in combination with one or more additional therapeutically active agents.

By "in combination with," it is not intended to imply that the agents must be administered at the same time and/or formulated for delivery together, although these methods of delivery are certainly within the scope of the invention. The compositions can be administered concurrently with, prior to, or subsequent to, one or more other additional therapeutically active agents. In general, each agent will be administered at a dose and/or on a time schedule determined for that agent. In will further be appreciated that the additional therapeutically active agent utilized in this combination may be administered together in a single composition or administered separately in different compositions. The particular combination to employ in a regimen will take into account compatibility of the inventive compound with the additional therapeutically active agent and/or the desired therapeutic effect to be achieved.

In general, it is expected that additional therapeutically active agents utilized in combination be utilized at levels that do not exceed the levels at which they are utilized individually. In some embodiments, the levels utilized in combination will be lower than those utilized individually.

By a "therapeutically active agent" or "active agent" refers to any substance that is useful for therapy, including prophylactic and therapeutic treatment.

The invention encompasses the delivery of provided pharmaceutically acceptable compositions in combination with agents that may improve their bioavailability, reduce and/or modify their metabolism, inhibit their excretion, and/or modify their distribution within the body. It will also be appreciated that therapy employed may achieve a desired effect for the same disorder (for example, an inventive compound may be administered in combination with an anti-inflammatory, anti-anxiety and/or anti-depressive agent, etc.), and/or they may achieve different effects (e.g., control of any adverse side-effects).

Exemplary active agents include, but are not limited to, anti-cancer agents, antibiotics, anti-viral agents, anesthetics, anti-coagulants, inhibitors of an enzyme, steroidal agents, steroidal or non-steroidal anti-inflammatory agents, antihistamine, immunosuppressant agents, anti-neoplastic agents, antigens, vaccines, antibodies, decongestants sedatives, opioids, pain-relieving agents, analgesics, anti-pyretics, hormones, prostaglandins, progestational agents, anti-glaucoma agents, ophthalmic agents, anti-cholinergics, anti-depressants, anti-psychotics, hypnotics, tranquilizers, anti-convulsants, muscle relaxants, anti-spasmodics, muscle contractants, channel blockers, miotic agents, anti-secretory agents, anti-thrombotic agents, anticoagulants, anti-cholinergics, β-adrenergic blocking agents, diuretics, cardiovascular active agents, vasoactive agents, vasodilating agents, anti-hypertensive agents, angiogenic agents, modulators of cell-extracellular matrix interactions (e.g. cell growth inhibitors and anti-adhesion molecules), or inhibitors/intercalators of DNA, RNA, protein-protein interactions, protein-receptor interactions, etc. Active agents include small organic molecules such as drug compounds (e.g., compounds approved by the Food and Drugs Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

In certain embodiments, the additional therapeutically active agent is a pain-relieving agent. In other embodiments, the additional therapeutically active agent is an anti-inflammatory agent.

8. Methods of Determining Biological Activity

Methods of determining the activity of compounds of the present invention for various therapeutic uses are well known in the art. These include, but are not limited to, high throughput screening to identify compounds that bind to and/or modulate the activity of isolated FAAH, as well as animal and cellular models of therapies.

Assays for compounds described herein are amenable to high throughput screening. Assays useful for screening the compounds of the present invention may detect the binding of the inhibitor to FAAH or the release of a reaction product (e.g., fatty acid amide or ethanolamine) produced by the hydrolysis of a substrate such as oleoylethanolamide or anandamide. The substrate may be labeled to facilitate detection of the released reaction products. U.S. Pat. No. 5,559,410 discloses high throughput screening methods for proteins, and U.S. Pat. Nos. 5,576,220 and 5,541,061 disclose high throughput methods of screening for ligand/antibody binding.

Methods for screening FAAH inhibitors for an antinociceptive effect are well known to one of ordinary skill in the art. For instance, the test compounds can be administered to the subject animals in the mouse hot-plate test and the mouse formalin test and the nociceptive reactions to thermal or chemical tissue damage measured (for example, see U.S. Pat. No. 6,326,156 which teaches methods of screening for antinociceptive activity; see also Cravatt et al. *Proc. Natl. Acad. Sci. U.S.A.* (2001) 98:9371-9376).

Two pharmacologically validated animal models of anxiety are the elevated zero maze test, and the isolation-induced ultrasonic emission test. The zero maze consists of an elevated annular platform with two open and two closed quadrants and is based on the conflict between an animal's instinct to explore its environment and its fear of open spaces, where it may be attacked by predators (see, for example, Bickerdike, M. J. et al., *Eur. J. Pharmacol.*, (994) 271, 403-411; Shepherd, J. K. et al., *Psychopharmacology*, (1994) 116, 56-64). Clinically used anxiolytic drugs, such as the benzodiazepines, increase the proportion of time spent in, and the number of entries made into, the open compartments.

A second test for an anti-anxiety compound is the ultrasonic vocalization emission model, which measures the number of stress-induced vocalizations emitted by rat pups removed from their nest (see, for example, Insel, T. R. et al., Pharmacol. Biochem. Behav., 24, 1263-1267 (1986); Miczek, K. A. et al., Psychopharmacology, 121, 38-56 (1995); Winslow, J. T. et al., Biol. Psychiatry, 15, 745-757 (1991).

The effect of the compound of the invention in the treatment of depression can be tested in the model of chronic mild stress induced anhedonia in rats. This model is based on the observation that chronic mild stress causes a gradual decrease in sensitivity to rewards, for example consumption of sucrose, and that this decrease is dose-dependently reversed by chronic treatment with antidepressants. The method has previously been described and more information with respect to the test appears from Willner, Paul, Psychopharmacology, 1997, 134, 319-329.

Another test for antidepressant activity is the forced swimming test (Nature 266, 730-732, 1977). In this test, animals are administered an agent, preferably by the intraperitoneal route or by the oral route, 30 or 60 minutes before the test. The animals are placed in a crystallizing dish filled with water and the time during which they remain immobile is clocked. The immobility time is then compared with that of the control group treated with distilled water. Imipramine 25 mg/kg. can be used as the positive control. The antidepressant compounds decrease the immobility time of the mice thus immersed.

Another test for antidepressant activity is the caudal suspension test on the mouse (Psychopharmacology, 85, 367-370, 1985). In this test, animals are preferably treated with the study compound by the intraperitoneal route or by the oral route 30 or 60 minutes before the test. The animals are then suspended by the tail and their immobility time is automatically recorded by a computer system. The immobility times are then compared with those of a control group treated with distilled water. Imipramine 25 mg/kg can be used as the positive control. Antidepressant compounds decrease the immobility time of the mice.

Animal models are available to one of ordinary skill in the art for studying anticonvulsant activity of test compounds. See for instance, U.S. Pat. No. 6,309,406 and U.S. Pat. No. 6,326,156 which describe methods for performing such tests.

Inhibition of FAAH has been reported to induce sleep in test animals (U.S. Pat. No. 6,096,784). Methods for studying sleep inducing compounds are well known to one of ordinary skill in the art. In particular, methods for testing the ability of a FAAH inhibitory compound to induce sleep or treat insomnia are disclosed in U.S. Pat. No. 6,096,784 and U.S. Pat. No. 6,271,015. Most obviously, the compounds can be administered to a test animal (e.g., rat or mouse) or a human and the subsequent time (e.g., onset, duration) spent sleeping (e.g., eyes closed, motor quiescence) can be monitored. See also WO 98/24396.

Methods for screening FAAH inhibitors which induce catalepsy are also well known to one of ordinary skill in the art. See Quistand et al. in Toxicology and Applied Pharmacology 173: 48-55 (2001). See Cravatt et al. Proc. Natl. Acad. Sci. U.S.A. 98:9371-9376 (2001).

Methods of assessing appetitive behavior are known to one of ordinary skill in the art. For instance, Maruani et al. (U.S. Pat. No. 6,344,474) teach two such assays. One method of assessing the effect on appetite behavior is to administer a FAAH inhibitor to a rat and assess its effect on the intake of a sucrose solution. This method is taught in W. C. Lynch et al., Physiol. Behav., 1993, 54, 877-880.

9. Covalent Complex Formation Between Serine-241 of FAAH and Boronic Acid Inhibitors Compounds provided herein can form reversible covalent complexes with the nucleophilic side chain of Ser-241 FAAH.

Thus, compounds of any of formulae (I), (II), (III), (IV), (V), or (VI), or subgenera thereof, as described above and herein, associated with (e.g., complexed with) a serine residue of a protein are also provided.

For example, in certain embodiments, compounds of any of formulae (III), (IV), (V), or (VI), or subgenera thereof, as described above and herein, are associated with a serine residue of a protein:

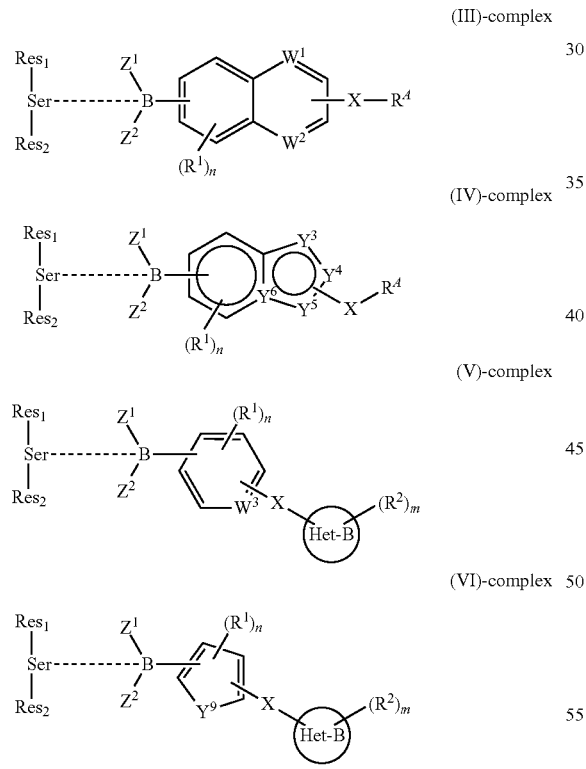

wherein Res$_1$-Ser-Res$_2$ is a protein having a length between about 400 to about 600 residues.

By "Ser" is meant a serine residue. In certain embodiments, Ser is Ser$_{241}$ of FAAH protein. In some embodiments, the protein is rat FAAH. In other embodiments, the protein is human FAAH (SEQ ID NO. 1). In certain embodiments, the active site of the protein has a Lys at 142; a Ser at 217; and a Ser at 241. In certain embodiments, the compound binds at Ser$_{241}$.

By Res$_1$ is meant the residue(s) closer to the N-terminus than Ser. By Res$_2$ is meant the residue(s) closer to the C-terminus than Ser. In certain embodiments, Res$_1$ has a serine residue that is 24 amino acids closer to the N terminus than (Ser) and a lysine residue that is 99 amino acids closer to the N terminus than (Ser).

In certain embodiments, Z$^1$ and Z$^2$ are both —OH. Thus, in certain embodiments, the compound is a boronic acid compound.

10. Methods of Synthesis

A number of methods are known in the art to synthesize the compounds provided herein. A recognized method of synthesizing boronate esters is the reaction of an organometallic species with an organic borate, such as trimethyl borate. Suitable organometallic species include, but are not limited to, alkyl lithium and Grignard reagents. Other methods for the synthesis of boronates are employed when the boronate contains sensitive functionality that may not tolerate alkyl lithium reagents or Grignard reagents. These methods include palladium coupling reactions of aryl or akenyl halides and diboronates or dialkoxy boranes and hydroboration of alkenes or alkynes. Using these methods a diverse collection of boronates can be synthesized. Boronates can be readily transformed in to boronic acids by hydrolyzing the boronate under aqueous acidic conditions using a suitable acid. Suitable acids include, but are not limited to HCl, H$_2$SO$_4$, and HBr. Another method of hydrolyzing boronates is an oxidative hydrolysis employing an oxidizing agent, such as NaIO$_4$, as exemplified in Example 5. The boronic acid compounds of the present invention readily form boronic esters when exposed to alcohols. The resulting boronic esters may also be used in the methods provided herein. Cyclic boronates are formed when certain diols (e.g., 1,2- and 1,3-diols) are used. Boronic acid compounds provided herein readily form oligomeric anhydrides by dehydration of the boronic acid moiety to form dimers, trimers, and tetramers, and mixtures thereof. These species in the presence of water and under physiological conditions convert back to the boronic acid by hydrolysis.

EXEMPLIFICATION

The invention now being generally described, it will be more readily understood by reference to the following examples, which are included merely for purposes of illustration of certain aspects and embodiments of the present invention, and are not intended to limit the invention.

Exemplary compounds are set forth in the Examples provided below. Compounds were assayed as inhibitors of human FAAH using the method described in detail in Example 286. Activity of exemplified compounds are provided in the Examples, wherein activity designated as "A" refers to compounds having a K$_i$ of less than or equal to 0.01 microM, "B" refers to compounds having a K$_i$ of between 0.01 microM and 0.1 microM, "C" refers to compounds having a K$_i$ of between 0.1 microM and 1 microM, and "D" refers to compounds having a K$_i$ of greater than 1 microM.

General Synthetic Methods

Preparation of Boronic Acids:

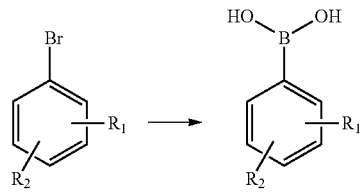

Method 1

General conditions for the preparation of boronic acids: under an argon atmosphere, 0.1 M aryl bromide (1.0 equiv) dissolved in 4:1 toluene/tetrahydrofuran was cooled to −78° C. Triisopropylborate (1.3 equiv) was added, and the mixture was treated dropwise with nBuLi in hexanes (1.2 equiv). After stirring for 30 min, the mixture was warmed to 0° C. and stirred for an additional 30 min. The mixture was quenched with 2N aqueous HCl (10 equiv) and stirred for 1 h at 23° C. The mixture was diluted with water and extracted with ethyl acetate. The organic layer was washed with brine and then dried over sodium sulfate. The residue upon concentration was purified either by recrystallization/trituration (heptanes, acetonitrile, or other) or by flash silica gel chromatography (1→10% methanol/dichloromethane) to generally produce a white solid.

Method 2

General conditions for the preparation of boronic acids: under an argon atmosphere, 0.1 M aryl bromide (1.0 equiv) dissolved in 4:1 toluene/tetrahydrofuran was cooled to −78° C. nBuLi in hexanes (2.5M, 1.2 equiv) was added dropwise, and the mixture was stirred for 60 min. Triisopropylborate (1.3 equiv) was then added dropwise to the clear stirring solution. After 15 min, the mixture was warmed to 0° C. and stirred for an additional 30 min. The mixture was quenched with 2N aqueous HCl (10 equiv) and stirred for 1 h at 23° C. The mixture was diluted with water and extracted with ethyl acetate. The organic layer was washed with brine and then dried over sodium sulfate. The residue upon concentration was purified either by recrystallization/trituration (heptanes, acetonitrile, or other) or by flash silica gel chromatography (1→10% methanol/dichloromethane) to generally produce a white solid.

Preparation of Boronic Acid Pinacol Esters:

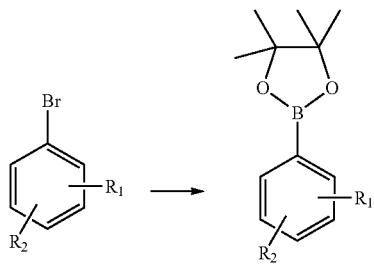

Method 3

General conditions for the preparation of boronic acid pinacol esters: a dry flask under argon atmosphere was charged with aryl bromide (1.0 equiv), 1,1"-Bis(diphenylphosphino)-ferrocenedichloropalladium(II) (0.05 equiv), potassium acetate (1.0 equiv), cesium carbonate (3 equiv), and bis(pinacolato)diboron (2.0 equiv). The mixture was suspended with dimethylsulfoxide (0.1 M with respect to aryl bromide) and heated at 80° C. for 2-8 h. Upon completion as judged by thin layer chromatography analysis, the reaction was split between water and ethyl acetate, and the organic layer was washed with brine, dried over sodium sulfate, and concentrated in vacuo. The concentrated reaction mixture was purified by flash silica gel chromatography (ethyl acetate/hexanes) to provide boronic acid pinacol ester.

Method 4

General conditions for the preparation of boronic acid pinacol esters: a dry flask under argon atmosphere was charged with aryl bromide (1.0 equiv), bis(triphenylphosphine)palladium(II) dichloride (0.05 equiv), potassium acetate (2.0 equiv), and bis(pinacolato)diboron (1.5 equiv). The mixture was suspended with 1,4-dioxane (0.1 M with respect to aryl bromide) and heated at 80° C. for 2-8 h. Upon completion as judged by thin layer chromatography analysis, the reaction was split between water and ethyl acetate, and the organic layer was washed with brine, dried over sodium sulfate, and concentrated in vacuo. The concentrated reaction mixture was purified by flash silica gel chromatography (ethyl acetate/hexanes) to provide boronic acid pinacol ester.

Conversion of Boronate Esters to Boronic Acids:

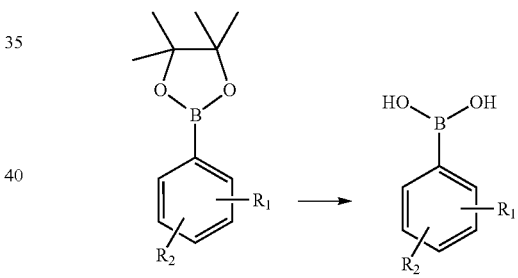

Method 5

General conditions for the conversion of boronate esters to boronic acids: the boronate ester (1.0 eq), sodium periodate (5.0 eq) and ammonium acetate (5.0 eq) were dissolved in acetone/water 2:1 (0.05 M boronate ester) and stirred for 12 h at 23° C. until TLC or LCMS indicated conversion to the boronic acid was complete. One option for isolation is to precipitate the product by dilution of the mixture with 1N aqueous HCl and collection by filtration of the solid boronic acid. Alternately, the mixture was split between water and ethyl acetate, and the organic layer was washed with brine, dried over sodium sulfate, and concentrated in vacuo. The residue was purified either by recrystallization and trituration (heptane, acetonitrile, or other solvents) or by flash silica gel chromatography (0.5%→10% methanol/dichloromethane) to afford pure boronic acid.

Method 6

General conditions for the conversion of boronate esters to boronic acids: the boronate ester was treated with concentrated sulfuric acid (0.2 M final ester concentration) and stirred until the mixture became a clear solution, about 10 min, at 23° C. The solution was diluted with water 15 fold, and the precipitated boronic acid collected by filtration and washed with water.

Preparation of Oxadiazoles:

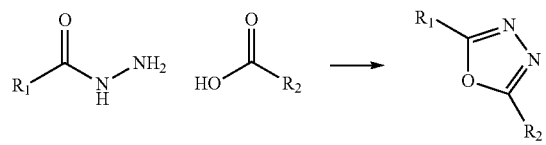

Method 7

General conditions for the preparation of oxadiazoles: in a microwave reactor tube, (hydrazinocarbonyl)arylboronic acid pinacol ester (1.0 equiv) and carboxylic acid (1.0 equiv) were dissolved in dry acetonitrile (0.1 M each). Polystyrene—supported triphenylphosphine (3.0 equiv) and trichloroacetonitrile (2.0 equiv) were added, and the mixture was sealed and heated in a microwave reactor at 130° C. for 2 hours. The concentrated reaction mixture was purified by flash silica gel chromatography (hexanes/ethyl acetate) to provide oxadiazole-aryl boronic acid pinacol ester.

Method 8

General conditions for the preparation of oxadiazoles: the oxadiazole was formed as in Method 7, except that the reactants are a carboxyarylboronic acid pinacol ester and either an alkyl or aryl hydrazide.

Preparation of Thiadiazoles:

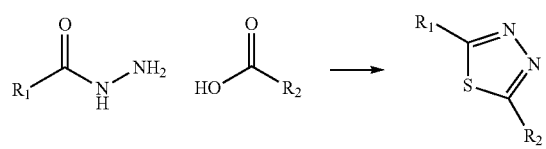

Method 9

General conditions for the preparation of thiadiazoles: (hydrazinocarbonyl)arylboronic acid pinacol ester (1.0 equiv) and carboxylic acid (1 equiv) were dissolved in dry DCM (0.1 M each) and treated with EDC (1.05 equiv) and DMAP (0.10 equiv). The mixture was stirred for 6 h at 23° C., and then diluted into a separatory funnel with DCM and washed twice each with 0.5 M aqueous citric acid and saturated aqueous sodium bicarbonate. The organic layer was dried over magnesium sulfate and concentrated to a clear oil.

This oil was dissolved in dry THF and 1.2 equiv Lawesson's reagent added. The mixture was sealed in a tube and heated in a microwave reactor at 115° C. for 30 min. The concentrated reaction mixture was purified by flash silica gel chromatography (hexanes/ethyl acetate) to provide thiadiazole-aryl boronic acid pinacol ester.

Method 10

General conditions for the preparation of thiadiazoles: the thiadiazole was formed as in Method 9, except that the reactants are a carboxyarylboronic acid pinacol ester and either an alkyl or aryl hydrazide.

Preparation of quinoline-2-ethers:

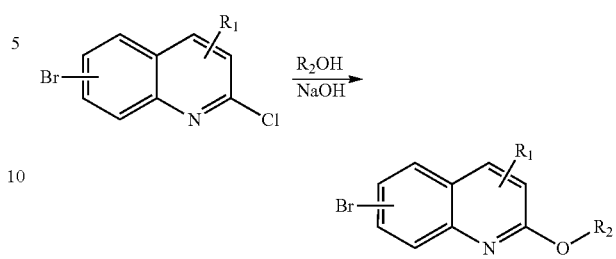

Method 11

Conditions for the preparation of quinoline-2-ethers: substituted 2-chloroquinolin e (1.0 eq.), alcohol (3.0 eq.), and crushed NaOH (2.0 eq.) were suspended in NMP (0.3 M quinoline) and subjected to microwave heating at a temperature of ca. 160° C. during 15 min. When done by 1 c/ms, the reaction mixture was diluted into 0.1M NaOH and MTBE and separated. The organic phase was washed with brine, dried on $Na_2SO_4$, and treated with silica gel. After removal of the solvent, the residue was chromatographed (2→10% EtOAc/hexanes) to give clean ether product.

Preparation of Isoxazolines and Isoxazoles:

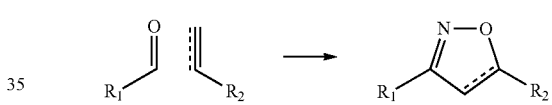

Method 12

General conditions for the preparation of isoxazolines and isoxazoles: Aldehyde (1.0 equiv.) was added to the solution of hydroxylamine hydrochloride (1.0 equiv.) in 1:1 t-BuOH: H2O (0.1 M aldehyde). To this was added NaOH to pH 5, and after being stirred for 30 min at ambient temperature, TLC analysis indicated that oxime formation was complete. Chloramine-T trihydrate (1.0 equiv.) was added in small portions over 5 min, followed by $CuSO_4$ (0.045 equiv.) and copper turnings (ca. 0.01 equiv.). Alkene or alkyne (1.0 equiv.) was added, and the pH was adjusted to ca. 6 by addition of a few drops of 1 M NaOH, and stirring was continued for another 6 h. The reaction mixture was poured into ice/water, and dilute $NH_4OH$ was added to remove all copper salts. The desired product was collected by filtration and purified by flash silica gel chromatography.

Preparation of Benzoxazoles:

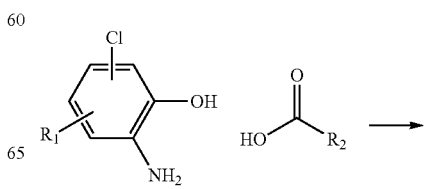

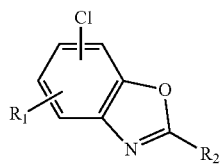

Method 13

General conditions for the preparation of benzoxazoles: in a microwave reactor tube, aminophenol (1.0 equiv) and carboxylic acid (1.0 equiv) were dissolved in dry acetonitrile (0.1 M each). Polystyrene—supported triphenylphosphine (3.0 equiv) and trichloroacetonitrile (2.0 equiv) were added, and the mixture was sealed and heated in a microwave reactor at 150° C. for 2 hours. The concentrated reaction mixture was purified by flash silica gel chromatography (hexanes/ethyl acetate) to provide the desired benzoxazole.

Method 14

General conditions for the preparation of benzoxazoles: in a sealed tube, aminophenol (1.0 equiv) and carboxylic acid (1.0 equiv) were dissolved in dry acetonitrile (0.1 M each). Polystyrene—supported triphenylphosphine (4.0 equiv) and trichloroacetonitrile (2.0 equiv) were added, and the mixture was sealed and heated at 100° C. for 20-36 h. The concentrated reaction mixture was purified by flash silica gel chromatography (hexanes/ethyl acetate) to provide the desired benzoxazole.

Preparation of Boronic Acid Pinacol Esters from Aryl Chlorides:

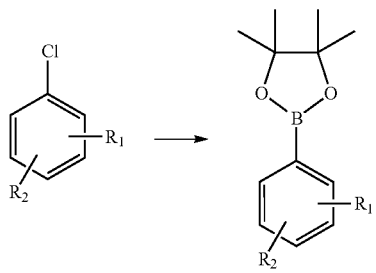

Method 15

General conditions for the preparation of boronic acid pinacol esters from aryl chlorides: a dry flask under argon atmosphere was charged with aryl chloride (1.0 equiv) and dissolved in tetrahydrofuran (0.1 M with respect to aryl chloride). Bis(pinacolato)diboron (2.5 equiv) was added followed by potassium acetate (2.5 equiv), palladium diacetate (0.2 equiv) and 1,3-bis(2,6-di-iso-propylphenyl)imidazolium chloride (0.4 equiv). The reaction was heated to 95° C. in a sealed tube for 14-36 h. Upon completion as judged by thin layer chromatography analysis the mixture was then filtered through a plug of celite with some silica gel on top. The celite was washed with ethyl acetate. The combined solution was concentrated in vacuo and purified by flash silica gelchromatography (ethyl acetate/hexanes) to provide the desired boronic acid pinacol ester.

Synthesis of Exemplary Compounds:

Example 1

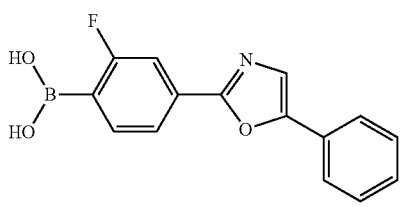

3-Fluoro-4-(4,4,5,5-tetramethyl-1,3,2-dioxaborolan-2-yl)benzoic acid (470 mg, 1.77 mmol) and 2-aminoacetophenone hydrochloride (318 mg, 1.89 mmol) were dissolved in 10 mL anhydrous dichloromethane. HOBt (286 mg, 2.12 mmol) and EDC (406 mg, 2.12 mmol) were added followed by triethylamine (741 uL, 5.30 mmol). The reaction was allowed to stir for 12 h at room temperature after which point it was transferred to a separatory funnel with excess dichloromethane and washed with 0.5 M citric acid (2×75 mL) and saturated $NaHCO_3$ (2×75 mL). The organic layer was then dried over $MgSO_4$, filtered and concentrated to provide the desired ketoamide as a yellow solid in quantitative yield (680 mg) which was used directly to form the oxazole the in the following step.

The crude ketoamide (100 mg, 0.261 mmol) was dissolved in 2 mL concentrated $H_2SO_4$. The reaction solution first turns bright orange, then a brown solid forms. The reaction was allowed to stir at room temperature for 10 minutes after which it was poured into 75 mL water at which point a white solid forms that was isolated using vacuum filtration. The solid was washed with excess water and dried under vacuum for 12 h to provide 45 mg of oxazole 1 in 61% yield. $[M-H]^-=282.1$ m/z. Activity: B

Example 2

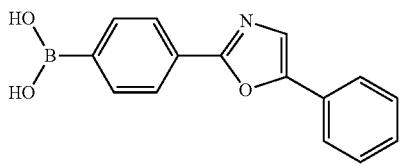

Oxazole 2 was prepared using conditions described for example 1. $[M-H]^-=264.1$ m/z. Activity: B

Example 3

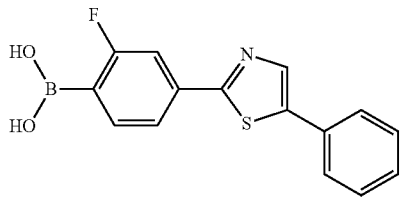

The ketoamide that was used to prepare 2 (223 mg, 0.58 mmol) was dissolved in 5 mL anhydrous tetrahydrofuran and Lawesson's reagent (282 mg, 0.70 mmol) was then added. The reaction was heated to 70° C. for 14 h after which point it was loaded directly onto silica gel and purified using silica gel chromatography using a gradient of 20-70% ethyl acetate/ hexanes to provide 200 mg of the desired thiazole in 90% yield.

The resulting pinacol ester (2-(3-fluoro-4-(4,4,5,5-tetramethyl-1,3,2-dioxaborolan-2-yl)phenyl)-5-phenylthiazole) was then converted to thiazole 3 using Method 5 and was isolated after precipitation from the reaction mixture. [M−H]⁻=298.1 m/z. Activity: D

Example 4

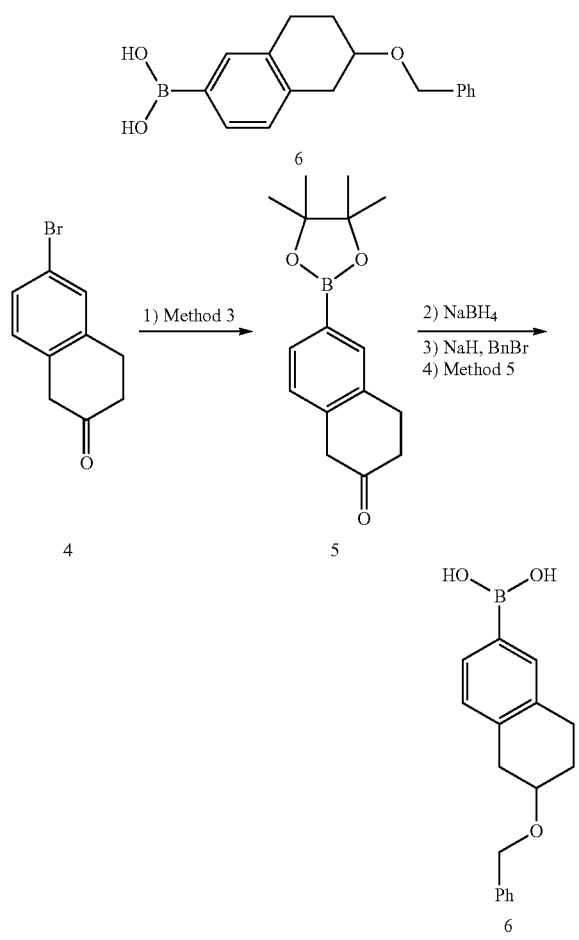

6-Bromo-2-tetralone (4) was converted to its corresponding pincol ester boronate (5) using Method 3. This ketone (6-(4,4,5,5-tetramethyl-1,3,2-dioxaborolan-2-yl)-3,4-dihydronaphthalen-2(1H)-one) (600 mg, 2.21 mmol) was dissolved in 10 mL 1:1 v/v methanol/tetrahydrofuran and cooled to 0° C. in an ice bath. Sodium borohydride (250 mg, 6.63 mmol) was added portion wise and the reaction was allowed to stir for 2 h after which point there was no more starting material as indicated by TLC analysis. Saturated NaCl (100 mL) was added to reaction and the mixture was transferred to a separatory funnel with excess water and methylene chloride. The water layer was washed with methylene chloride (2×75 mL). The organic layers were combined, washed with saturated NaCl (1×75 mL), dried over $Na_2SO_4$ and concentrated under reduced pressure to provide the corresponding secondary alcohol in quantitative yield (600 mg).

This secondary alcohol (110 mg, 0.40 mmol) was dissolved in 2 mL anhydrous N,N-dimethylforamide and cooled to 0° C. in an ice bath. Sodium hydride (48 mg, 1.20 mmol, 60% in dispersion oil) was added with some fizzing. After 10 min, benzyl bromide (95 μL, 0.80 mmol) was added and the reaction was allowed to stir at room temperature for 2 h. A large amount of starting material was still remaining at this point so sodium hydride and benzyl bromide was added in 3 additional portions and the reaction was allowed to stir for an additional 48 h. After this point, the reaction was quenched with saturated $NH_4Cl$ (75 mL) and transferred to a separatory funnel with excess water and ethyl acetate. The water layer was washed with ethyl acetate (2×75 mL). The combined organic layers were washed with saturated NaCl (2×75 mL), dried over $MgSO_4$, concentrated directly onto silica gel and purified by silica gel chromatography using a gradient of 5-10% ethyl acetate/hexanes to provide the desired ether as an oil (57 mg) in 39% yield.

The resulting pinacol ester (2-(6-(benzyloxy)-5,6,7,8-tetrahydronaphthalen-2-yl)-4,4,5,5-tetramethyl-1,3,2-dioxaborolane) was then converted to tetrahydronaphthalene 6 using Method 5 and was isolated after precipitation from the reaction mixture. [M−H]⁻=281.1 m/z. Activity: A

Example 5

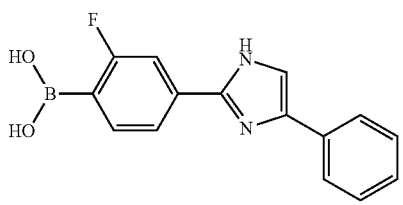

The ketoamide used to prepare 2 (100 mg, 0.26 mmol) and ammonium acetate (1.00 g, 13.0 mmol) was added to a 5 mL microwave reaction vial. Acetic acid (2 mL) is added and the reaction is heated for 30 min at 175° C. in a microwave reactor. Water (100 mL) is added to the crude reaction mixture at which point a small amount of solid crashes out which is isolated using vacuum filtration and dried under vacuum overnight to provide 6 mg of imidazole 7 in 8% yield. [M−H]⁻=281.1 m/z. Activity: D

Example 6

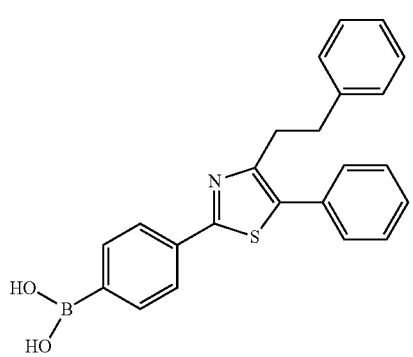

8

4-(4,4,5,5-Tetramethyl-1,3,2-dioxaborolan-2-yl)benzoic acid (160 mg, 0.645 mmol) and 2-amino-1,4-diphenylbutan-1-one hydrochloride (178 mg, 0.645 mmol) were dissolved in 10 mL anhydrous dichloromethane. HOBt (105 mg, 0.774 mmol) and EDC (148 mg, 0.774 mmol) were added followed by triethylamine (270 uL, 1.94 mmol). The reaction was allowed to stir for 12 h at room temperature after which point it was transferred to a separatory funnel with excess dichloromethane and washed with 0.5 M citric acid (2×75 mL) and saturated NaHCO$_3$ (2×75 mL). The organic layer was then dried over MgSO$_4$, filtered and concentrated to provide the desired ketoamide as a white solid in 93% yield (281 mg) which was used directly to form the thiazole in the following step.

The ketoamide (140 mg, 0.298 mmol) was dissolved in 4 mL anhydrous tetrahydrofuran and followed by the addition of Lawesson's reagent (145 mg, 0.358 mmol). The reaction was heated to 115° C. in a microwave reactor for 90 min after which point the crude mixture was loaded directly onto silica gel and purified using a gradient of 25-50% ethyl acetate/hexanes to isolate 90 mg of the desired compound in 65% yield. The resulting pinacol ester (4-phenethyl-5-phenyl-2-(4-(4,4,5,5-tetramethyl-1,3,2-dioxaborolan-2-yl)phenyl)thiazole) was then converted to thiazole 8 by Method 5 and was isolated after precipitation from the reaction mixture. [M−H]$^-$=384.1 m/z. Activity: D

Example 7

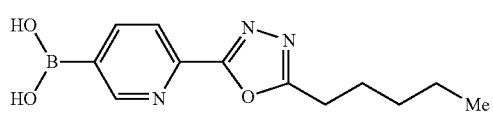

9

Oxadiazole 9 was prepared in 2 steps starting with oxadiazole formation between 5-bromopicolic acid and hexanoic hydrazide using Method 7 followed by the lithiation conditions of Method 1. [M−H]=260.1 m/z. Activity: A

Example 8

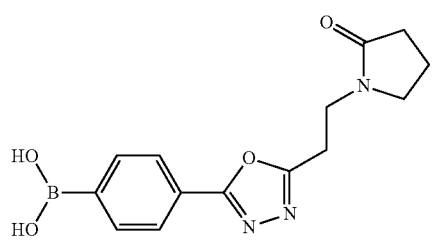

10

Oxadiazole 10 was prepared in 2 steps by first forming the oxadiazole from 4-(4,4,5,5-tetramethyl-1,3,2-dioxaborolan-2-yl)benzohydrazide and 3-(2-oxo-pyrrolidin-1-yl)-propionic acid using Method 7 followed by Method 5 and was isolated after precipitation from the reaction mixture. [M−H]$^-$=300.1 m/z. Activity: C

Example 9

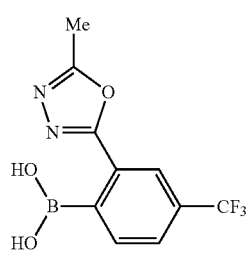

11

Oxadiazole 11 was prepared in 2 steps starting with oxadiazole formation between 2-bromo-5-(trifluoromethyl)benzoic acid and acetic hydrazide using Method 7 followed by lithiation using Method 1. [M−H]$^-$=271.0 m/z. Activity: C

Example 10

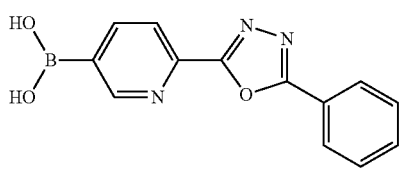

12

Oxadiazole 12 was prepared in 2 steps starting with oxadiazole formation between 5-bromopicolic acid and benzoic hydrazide using Method 7 followed by lithiation using Method 1. [M−H]$^-$=266.1 m/z. Activity: B

Example 11

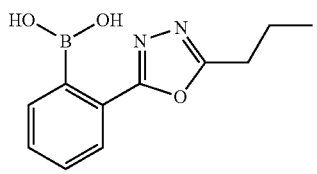
13

Oxadiazole 13 was prepared by Method 8 followed by Method 5. [M−H]−—231.1 m/z. Activity: D

Example 12

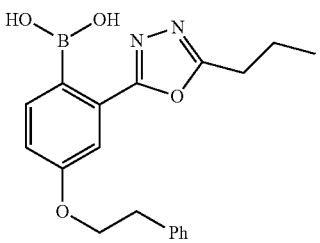
17

Part A

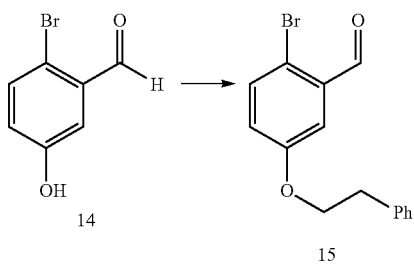 [SMILES: O=Cc1cc(O)ccc1Br ; O=Cc1cc(OCCc2ccccc2)ccc1Br]

2-Bromo-5-hydroxybenzaldehyde 14 (1.0 g, 5 mmol. 1.0 equiv), phenethyl bromide (2.76 g, 15 mmol, 3.0 equiv), and potassium carbonate (2.75 g, 20 mmol, 4.0 equiv) were suspended in dimethylformamide (15 ml) and heated at 80° C. for 14 h. The mixture was cooled and split between water (150 ml) and ethyl acetate (150 ml), and the organic layer was washed with brine and dried over sodium sulfate. The oil from concentration in vacuo was purified by flash silica gel chromatography (1→30% ethyl acetate/hexanes) to give phenethyl ether 15 as a clear oil (550 mg).

Part B

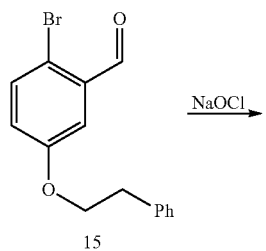

-continued

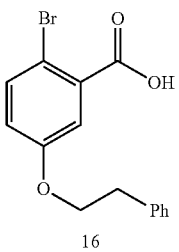
16

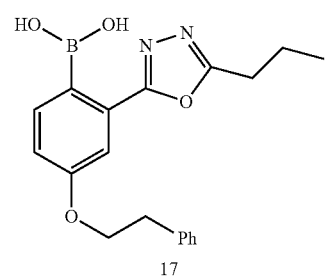
17

Bromobenzaldehyde 15 (3.0 g, 9.83 mmol, 1.0 equiv) dissolved in 2:1 tetrahydrofuran/water (75 ml) was treated with 2-methyl-2-butene (6.9 g, 98 mmol, 10 equiv), sodium phosphate monobasic, dihydrate, (4.6 g, 29.5 mmol, 3.0 equiv), and sodium chlorite (2.1 g, 24 mmol, 2.4 equiv). The mixture was stirred at 23° C. for 6 h and was then split between ethyl acetate (200 ml) and 1N aqueous HCl (100 ml). The organic layer was washed with brine (100 ml) and concentrated in vacuo. The resulting oil was purified by flash silica gel chromatography (1→30% ethyl acetate/hexanes) to give the carboxylic acid 16 (56% yield).

The acid 16 was converted to the oxadiazole-arylboronic acid 17 by Method 8 followed by Method 1. [M−H]−=351.1 m/z. Activity: A

Example 13

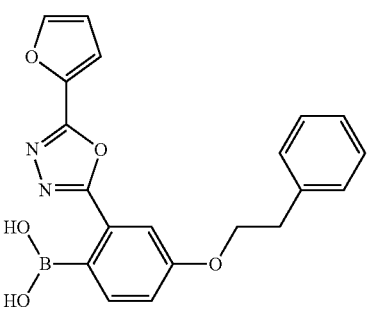
18

Oxadiazole 18 was prepared in 2 steps starting with oxadiazole formation between 2-bromo-5-phenethoxybenzoic acid 16 and furoic hydrazide using Method 7 followed by lithiation using Method 1. [M−H]−=375.1 m/z. Activity: A

Example 14

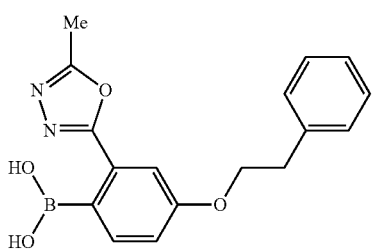

19

Oxadiazole 19 was prepared in 2 steps starting with oxadiazole formation between 2-bromo-5-phenethoxybenzoic acid 16 and acetic hydrazide using Method 7 followed by lithiation using Method 1. [M−H]⁻=323.1 m/z. Activity: A

Example 15

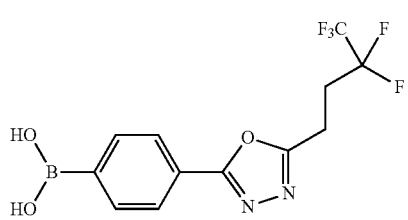

20

Oxadiazole 20 was prepared in 2 steps by first forming the oxadiazole from 4-(4,4,5,5-tetramethyl-1,3,2-dioxaborolan-2-yl)benzohydrazide and 4,4,5,5,5-pentafluoropentanoic acid using Method 7 followed by Method 5 and was isolated after precipitation from the reaction mixture. [M−H]⁻=335.1 m/z. Activity: A

Example 16

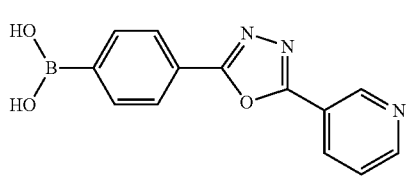

21

Oxadiazole 21 was prepared in 2 steps by first forming the oxadiazole from 4-(4,4,5,5-tetramethyl-1,3,2-dioxaborolan-2-yl)benzoic acid and nicotinic hydrazide using Method 8 followed by Method 6. [M−H]⁻=266.1 m/z. Activity: A

Example 17

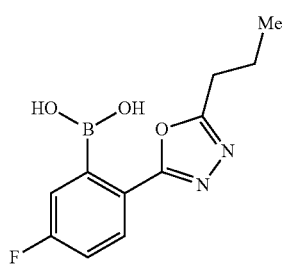

22

Oxadiazole 22 was prepared in 2 steps by first forming the oxadiazole from 4-fluoro-2-(4,4,5,5-tetramethyl-1,3,2-dioxaborolan-2-yl)benzoic acid and butyric hydrazide using Method 8 followed by Method 5 and was isolated after precipitation from the reaction mixture followed by purification using flash silica gel chromatography. [M−H]=249.1 m/z. Activity: D

Example 18

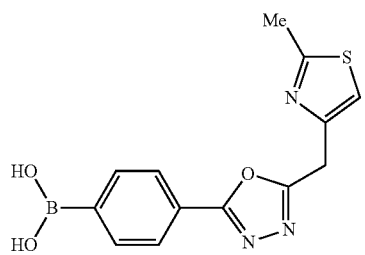

23

Oxadiazole 23 was prepared in 2 steps by first forming the oxadiazole from 4-(4,4,5,5-tetramethyl-1,3,2-dioxaborolan-2-yl)benzoic acid and (2-methyl-thiazol-4-yl)acetic acid hydrazide using Method 8 followed by Method 6. [M−H]⁻=300.1 m/z. Activity: B

Example 19

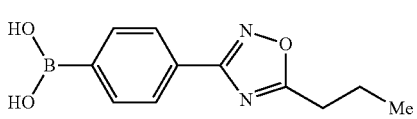

24

Oxadiazole 24 was prepared in 2 steps from the corresponding aryl bromide using Method 3 followed by Method 5 and was isolated after precipitation from the reaction mixture. [M−H]⁻=231.1 m/z. Activity: A

Example 20

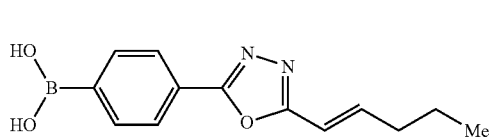

25

Oxadiazole 25 was prepared in 2 steps by first forming the oxadiazole from 4-(4,4,5,5-tetramethyl-1,3,2-dioxaborolan-2-yl)benzohydrazide and 2-hexenoic acid using Method 7 followed by Method 5 and was isolated after precipitation from the reaction mixture. [M−H]⁻=257.1 m/z. Activity: A

Example 21

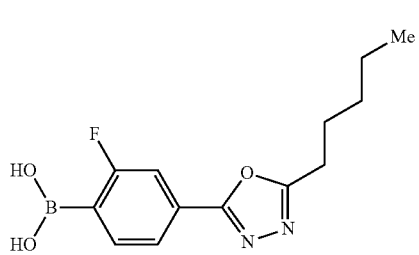

26

Oxadiazole 26 was prepared in 2 steps by first forming the oxadiazole from 3-fluoro-4-(4,4,5,5-tetramethyl-1,3,2-dioxaborolan-2-yl)benzoic acid and hexanoic hydrazide using Method 8 followed by Method 5 and was isolated after precipitation from the reaction mixture. [M−H]⁻=279.1 m/z. Activity: A

Example 22

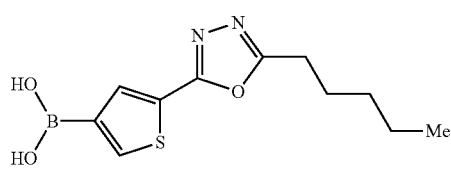

27

Oxadiazole 27 was prepared in 2 steps by first forming the oxadiazole from 4-(4,4,5,5-tetramethyl-1,3,2-dioxaborolan-2-yl)thiophene-2-carboxylic acid and hexanoic hydrazide using Method 8 followed by Method 5 and was isolated after precipitation from the reaction mixture. [M−H]⁻=265.1 m/z. Activity: A

Example 23

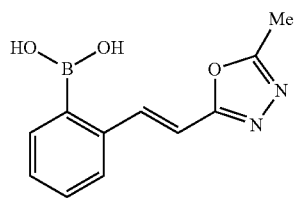

28

Oxadiazole 28 was prepared in 2 steps by first forming the oxadiazole from (E)-3-(2-(4,4,5,5-tetramethyl-1,3,2-dioxaborolan-2-yl)phenyl)acrylic acid and acetic hydrazide using Method 8 followed by Method 5 and was isolated after precipitation from the reaction mixture. [M−H]⁻=229.1 m/z. Activity: C

Example 24

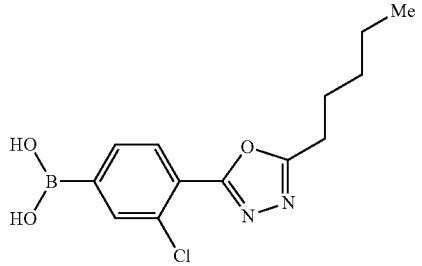

29

Oxadiazole 29 was prepared in 2 steps by first forming the oxadiazole from 3-chloro-4-(4,4,5,5-tetramethyl-1,3,2-dioxaborolan-2-yl)benzoic acid and hexanoic hydrazide using Method 8 followed by Method 5 and was isolated after precipitation from the reaction mixture. [M−H]⁻=293.1 m/z. Activity: A

Example 25

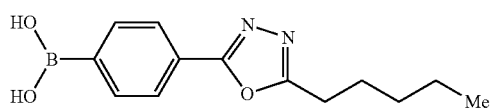

30

Oxadiazole 30 was prepared in 2 steps by first forming the oxadiazole from 4-(4,4,5,5-tetramethyl-1,3,2-dioxaborolan-2-yl)benzohydrazide and hexanoic acid using Method 7 followed by Method 5 and was isolated after precipitation from the reaction mixture. [M−H]⁻=259.1 m/z. Activity: A

Example 26

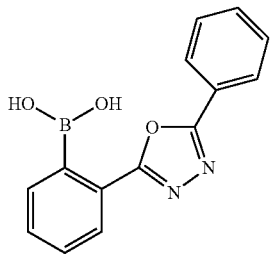

31

Oxadiazole 31 was prepared in 2 steps by first forming the oxadiazole from 2-(4,4,5,5-tetramethyl-1,3,2-dioxaborolan-2-yl)benzoic acid and benzoic hydrazide using Method 8 followed by Method 5 and was isolated after precipitation from the reaction mixture followed by purification using flash silica gel chromatography. [M–H]⁻=265.1 m/z. Activity: D

Example 27

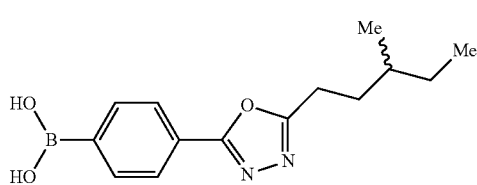

32

Oxadiazole 32 was prepared in 2 steps by first forming the oxadiazole from 4-(4,4,5,5-tetramethyl-1,3,2-dioxaborolan-2-yl)benzohydrazide and 4-methylhexanoic acid using Method 7 followed by Method 5 and was isolated after precipitation from the reaction mixture. [M–H]⁻=273.1 m/z. Activity: A

Example 28

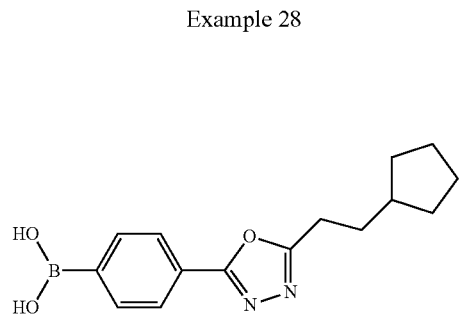

33

Oxadiazole 33 was prepared in 2 steps by first forming the oxadiazole from 4-(4,4,5,5-tetramethyl-1,3,2-dioxaborolan-2-yl)benzohydrazide and 3-cyclopentylpropionic acid using Method 7 followed by Method 5 and was isolated after precipitation from the reaction mixture. [M–H]⁻=285.1 m/z. Activity: A

Example 29

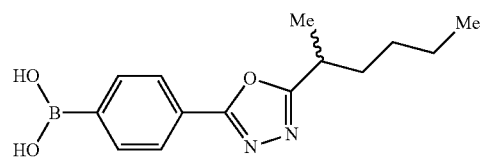

34

Oxadiazole 34 was prepared in 2 steps by first forming the oxadiazole from 4-(4,4,5,5-tetramethyl-1,3,2-dioxaborolan-2-yl)benzohydrazide and 2-methylhexanoic acid using Method 7 followed by Method 5 and was isolated after precipitation from the reaction mixture. [M–H]⁻=273.1 m/z. Activity: A

Example 30

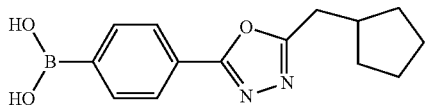

35

Oxadiazole 35 was prepared in 2 steps by first forming the oxadiazole from 4-(4,4,5,5-tetramethyl-1,3,2-dioxaborolan-2-yl)benzohydrazide and cyclopentylacetic acid using Method 7 followed by Method 5 and was isolated after precipitation from the reaction mixture. [M–H]⁻=271.1 m/z. Activity: A

Example 31

36

Oxadiazole 36 was prepared in 2 steps by first forming the oxadiazole from 4-(4,4,5,5-tetramethyl-1,3,2-dioxaborolan-2-yl)benzohydrazide and 3-cyclohexylpropionic acid using Method 7 followed by Method 5 and was isolated after precipitation from the reaction mixture. [M–H]⁻=299.1 m/z. Activity: A

Example 32

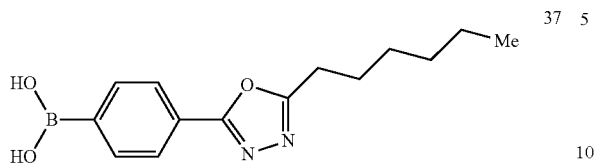

37

Oxadiazole 37 was prepared in 2 steps by first forming the oxadiazole from 4-(4,4,5,5-tetramethyl-1,3,2-dioxaborolan-2-yl)benzohydrazide and heptanoic acid using Method 7 followed by Method 5 and was isolated after precipitation from the reaction mixture. [M–H]⁻=273.1 m/z. Activity: A

Example 33

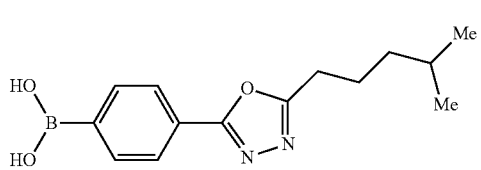

38

Oxadiazole 38 was prepared in 2 steps by first forming the oxadiazole from 4-(4,4,5,5-tetramethyl-1,3,2-dioxaborolan-2-yl)benzohydrazide and 5-methylhexanoic acid using Method 7 followed by Method 5 and was isolated after precipitation from the reaction mixture. [M–H]⁻=273.1 m/z. Activity: A

Example 34

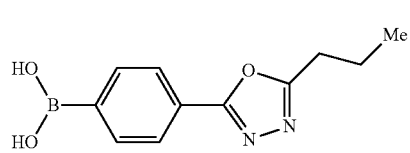

39

Oxadiazole 39 was prepared in 2 steps by first forming the oxadiazole from 4-(4,4,5,5-tetramethyl-1,3,2-dioxaborolan-2-yl)benzoic acid and butyric hydrazide using Method 8 followed by Method 5 and was isolated after precipitation from the reaction mixture. [M–H]=231.1 m/z. Activity: A

Example 35

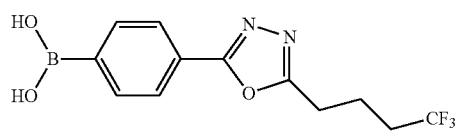

40

Oxadiazole 40 was prepared in 2 steps by first forming the oxadiazole from 4-(4,4,5,5-tetramethyl-1,3,2-dioxaborolan-2-yl)benzohydrazide and 5,5,5-trifluoropentanoic acid using Method 7 followed by Method 5 and was isolated after precipitation from the reaction mixture. [M–H]⁻=299.1 m/z. Activity: A

Example 36

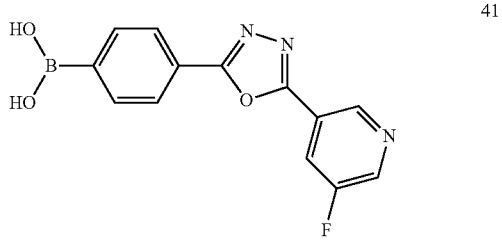 [SMILES: OB(O)c1ccc(-c2nnc(-c3cncc(F)c3)o2)cc1]

41

Oxadiazole 41 was prepared in 2 steps by first forming the oxadiazole from 4-(4,4,5,5-tetramethyl-1,3,2-dioxaborolan-2-yl)benzohydrazide and 5-fluoronicotinic acid using Method 7 followed by Method 6. [M–H]⁻=284.1 m/z. Activity: B

Example 37

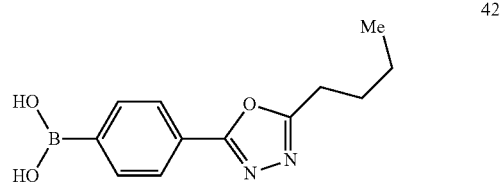 [SMILES: CCCCc1nnc(-c2ccc(B(O)O)cc2)o1]

42

Oxadiazole 42 was prepared in 2 steps by first forming the oxadiazole from 4-(4,4,5,5-tetramethyl-1,3,2-dioxaborolan-2-yl)benzoic acid and valeric hydrazide using Method 8 followed by Method 5 and was isolated after precipitation from the reaction mixture. [M–H]⁻=245.1 m/z. Activity: A

Example 38

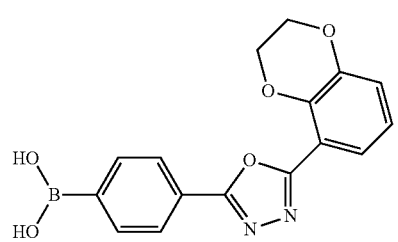

43

Oxadiazole 43 was prepared in 2 steps by first forming the oxadiazole from 4-(4,4,5,5-tetramethyl-1,3,2-dioxaborolan-2-yl)benzohydrazide and 1,4-benzodioxan-5-carboxylic acid using Method 7 followed by Method 5 and was isolated after precipitation from the reaction mixture. [M–H]⁻=323.1 m/z. Activity: A

Example 39

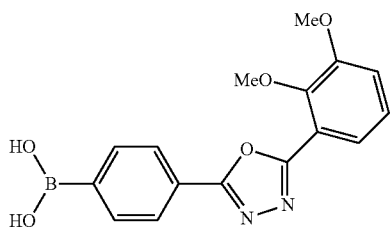

44

Oxadiazole 44 was prepared in 2 steps by first forming the oxadiazole from 4-(4,4,5,5-tetramethyl-1,3,2-dioxaborolan-2-yl)benzohydrazide and 2,3-dimethoxybenzoic acid using Method 7 followed by Method 5 and was isolated after precipitation from the reaction mixture. [M–H]⁻=325.1 m/z. Activity: A

Example 40

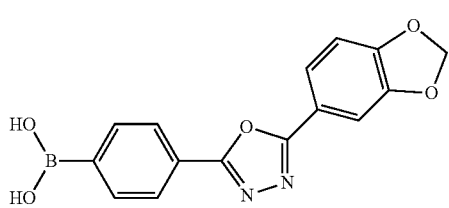

45

Oxadiazole 45 was prepared in 2 steps by first forming the oxadiazole from 4-(4,4,5,5-tetramethyl-1,3,2-dioxaborolan-2-yl)benzohydrazide and piperonylic acid using Method 7 followed by Method 5 and was isolated after precipitation from the reaction mixture. [M–H]⁻=309.0 m/z. Activity: A

Example 41

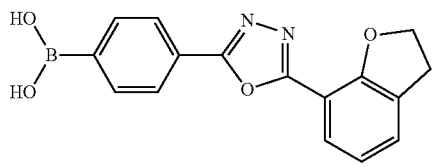

46

Oxadiazole 46 was prepared in 2 steps by first forming the oxadiazole from 4-(4,4,5,5-tetramethyl-1,3,2-dioxaborolan-2-yl)benzohydrazide and 2,3-dihydro-1-benzofuran-7-carboxylic acid using Method 7 followed by Method 5 and was isolated after precipitation from the reaction mixture. [M–H]⁻=307.1 m/z. Activity: A

Example 42

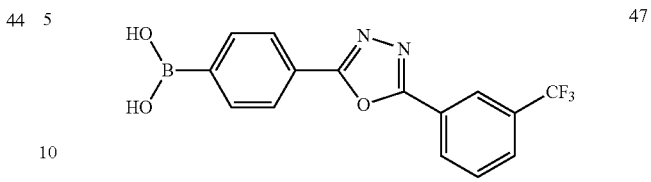

47

Oxadiazole 47 was prepared in 2 steps by first forming the oxadiazole from 4-(4,4,5,5-tetramethyl-1,3,2-dioxaborolan-2-yl)benzohydrazide and 3-trifluoromethylbenzoic acid using Method 7 followed by Method 6. [M–H]⁻=333.0 m/z. Activity: A

Example 43

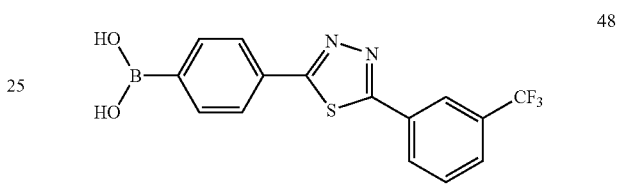

48

Thiadiazole 48 was prepared in 2 steps by first forming the oxadiazole from 4-(4,4,5,5-tetramethyl-1,3,2-dioxaborolan-2-yl)benzohydrazide and 3-trifluoromethylbenzoic acid using Method 9 followed by Method 6. [M–H]⁻=349.1 m/z. Activity: A

Example 44

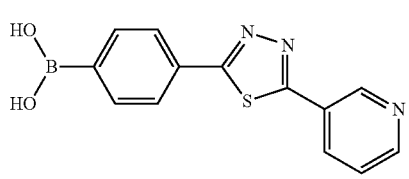

49

Thiadiazole 49 was prepared in 2 steps by first forming the oxadiazole from 4-(4,4,5,5-tetramethyl-1,3,2-dioxaborolan-2-yl)benzoic acid and nicotinic hydrazide using Method 9 followed by Method 6. [M–H]=282.1 m/z. Activity: A

Example 45

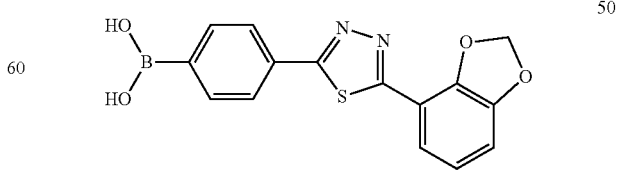

50

Thiadiazole 50 was prepared in 2 steps by first forming the oxadiazole from 4-(4,4,5,5-tetramethyl-1,3,2-dioxaborolan- 2-yl)benzohydrazide and 3-trifluoromethylbenzoic acid using Method 9 followed by Method 5 and was isolated after precipitation from the reaction mixture. [M−H]=325.1 m/z. Activity: A Example 46

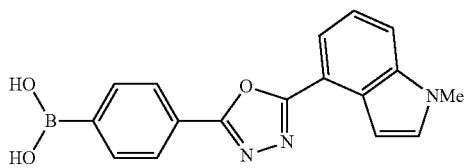

51

Oxadiazole 51 was prepared in 2 steps by first forming the oxadiazole from 4-(4,4,5,5-tetramethyl-1,3,2-dioxaborolan-2-yl)benzohydrazide and 1-methyl-1H-indole-4-carboxylic acid using Method 7 followed by Method 5 and was isolated after precipitation from the reaction mixture. [M−H]=318.1 m/z. Activity: A Example 47

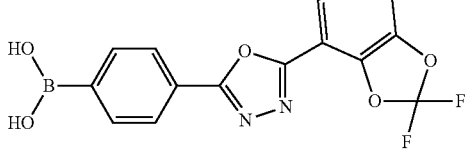

52

Oxadiazole 52 was prepared in 2 steps by first forming the oxadiazole from 4-(4,4,5,5-tetramethyl-1,3,2-dioxaborolan-2-yl)benzohydrazide and 2,2-difluoro-1,3-benzodioxole-4-carboxylic acid using Method 7 followed by Method 5 and was isolated after precipitation from the reaction mixture. [M−H]$^-$=345.1 m/z. Activity: A Example 48

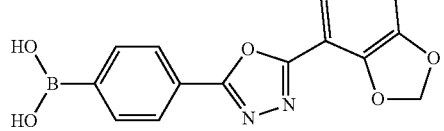

53

Oxadiazole 53 was prepared in 2 steps by first forming the oxadiazole from 4-(4,4,5,5-tetramethyl-1,3,2-dioxaborolan-2-yl)benzohydrazide and 1,3-benzodioxole-4-carboxylic acid using Method 7 followed by Method 5 and was isolated after precipitation from the reaction mixture. [M−H]$^-$=309.1 m/z. Activity: A Example 49

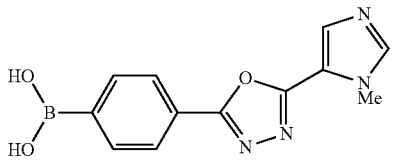

54

Oxadiazole 54 was prepared in 2 steps by first forming the oxadiazole from 4-(4,4,5,5-tetramethyl-1,3,2-dioxaborolan-2-yl)benzoic acid and 1-methyl-1H-imidazole-5-carbohydrazide using Method 8 followed by Method 6. [M−H]$^-$=269.1 m/z. Activity: B Example 50

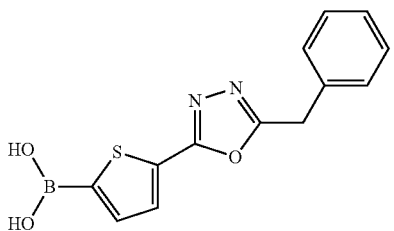

55

Oxadiazole 55 was prepared in 2 steps by first forming the oxadiazole from 5-(4,4,5,5-tetramethyl-1,3,2-dioxaborolan-2-yl)thiophene-2-carboxylic acid and phenylacetic hydrazide using Method 8 followed by Method 5 and was isolated after precipitation from the reaction mixture. [M−H]$^-$=285.1 m/z. Activity: B Example 51

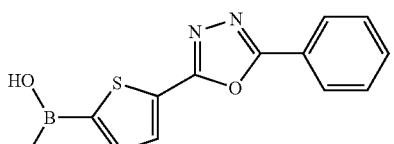

56

Oxadiazole 56 was prepared in 2 steps by first forming the oxadiazole from 5-(4,4,5,5-tetramethyl-1,3,2-dioxaborolan-2-yl)thiophene-2-carboxylic acid and benzoic hydrazide using Method 8 followed by Method 5 and was isolated after precipitation from the reaction mixture. [M−H]$^-$=271.1 m/z. Activity: B

Example 52

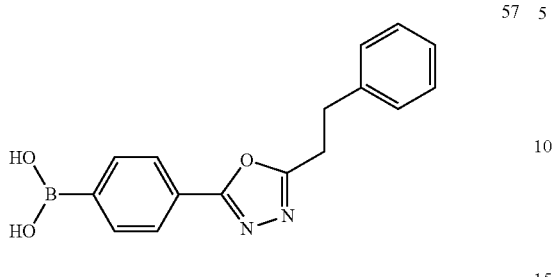

57

Oxadiazole 57 was prepared in 2 steps by first forming the oxadiazole from 4-(4,4,5,5-tetramethyl-1,3,2-dioxaborolan-2-yl)benzoic acid and 3-phenylpropionic acid hydrazide using Method 8 followed by Method 5 and was isolated after precipitation from the reaction mixture. [M−H]⁻=293.1 m/z. Activity: A

Example 53

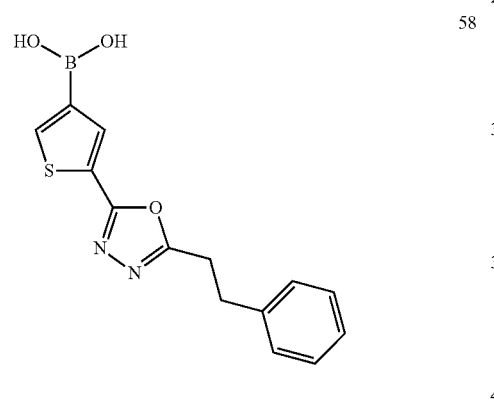

58

Oxadiazole 58 was prepared in 2 steps by first forming the oxadiazole from 4-(4,4,5,5-tetramethyl-1,3,2-dioxaborolan-2-yl)thiophene-2-carboxylic acid and 3-phenylpropionic acid hydrazide using Method 8 followed by Method 5 and was isolated after precipitation from the reaction mixture. [M−H]⁻=299.1 m/z. Activity: A

Example 54

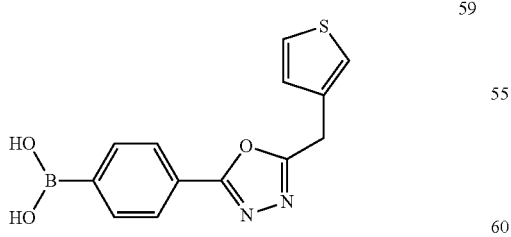

59

Oxadiazole 59 was prepared in 2 steps by first forming the oxadiazole from 4-(4,4,5,5-tetramethyl-1,3,2-dioxaborolan-2-yl)benzoic acid and 2-(3-thienyl)ethanohydrazide using Method 8 followed by Method 5 and was isolated after precipitation from the reaction mixture. [M−H]⁻=285.1 m/z. Activity: A

Example 55

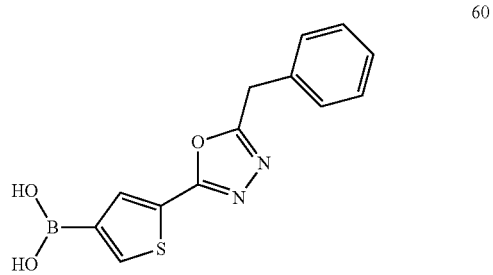 [SMILES: OB(O)c1csc(-c2nnc(Cc3ccccc3)o2)c1]

60

Oxadiazole 60 was prepared in 2 steps by first forming the oxadiazole from 4-(4,4,5,5-tetra-methyl-1,3,2-dioxaborolan-2-yl)thiophene-2-carboxylic acid and phenylacetic hydrazide using Method 8 followed by Method 5 and was isolated after precipitation from the reaction mixture. [M−H]⁻=285.1 m/z. Activity: A

Example 56

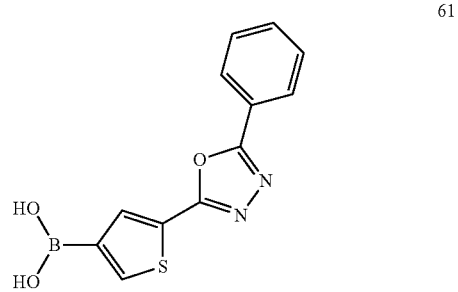 [SMILES: OB(O)c1csc(-c2nnc(-c3ccccc3)o2)c1]

61

Oxadiazole 61 was prepared in 2 steps by first forming the oxadiazole from 4-(4,4,5,5-tetra-methyl-1,3,2-dioxaborolan-2-yl)thiophene-2-carboxylic acid and benzoic hydrazide using Method 8 followed by Method 5 and was isolated after precipitation from the reaction mixture. [M−H]⁻=271.1 m/z. Activity: B

Example 57

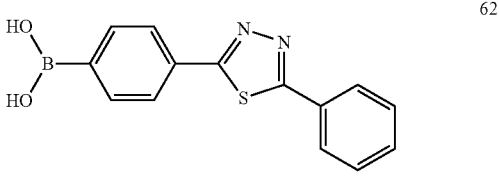

62

Thiadiazole 62 was prepared in 2 steps by first forming the oxadiazole from 4-(4,4,5,5-tetra-methyl-1,3,2-dioxaborolan-2-yl)benzohydrazide and benzoic acid using Method 9 followed by Method 5 and was isolated after precipitation from the reaction mixture. [M−H]⁻=281.1 m/z. Activity: A

Example 58

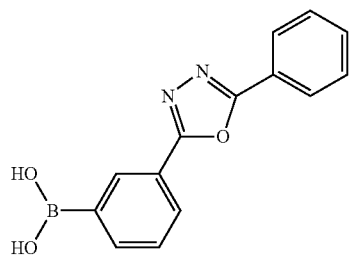
63

Oxadiazole 63 was prepared in 2 steps by first forming the oxadiazole from 3-(4,4,5,5-tetra-methyl-1,3,2-dioxaborolan-2-yl)benzoic acid and benzoic hydrazide using Method 8 followed by Method 5 and was isolated after precipitation from the reaction mixture. [M–H]⁻=265.1 m/z. Activity: C

Example 59

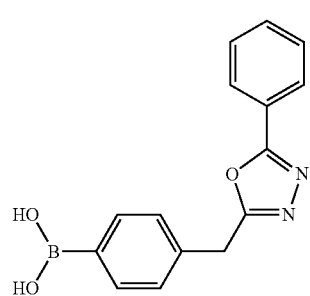
64

Oxadiazole 64 was prepared in 2 steps by first forming the oxadiazole from 4-(4,4,5,5-tetramethyl-1,3,2-dioxaborolane)phenylacetic acid and benzoic hydrazide using Method 8 followed by Method 5 and was isolated after precipitation from the reaction mixture. [M–H]⁻=279.1 m/z. Activity: B

Example 60

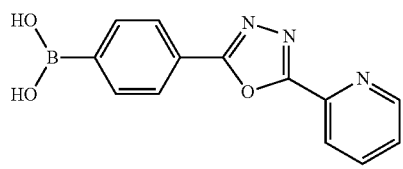
65

Oxadiazole 65 was prepared in 2 steps by first forming the oxadiazole from 4-(4,4,5,5-tetramethyl-1,3,2-dioxaborolan-2-yl)benzoic acid and 2-picolinyl hydrazide using Method 8 followed by Method 6. [M–H]⁻=266.1 m/z. Activity: B

Example 61

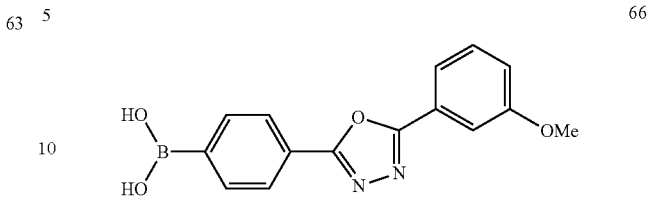
66

Oxadiazole 66 was prepared in 2 steps by first forming the oxadiazole from 4-(4,4,5,5-tetramethyl-1,3,2-dioxaborolan-2-yl)benzoic acid and 3-methoxybenzoic hydrazide using Method 8 followed by Method 5 and was isolated after precipitation from the reaction mixture. [M–H]⁻=295.1 m/z. Activity: A

Example 62

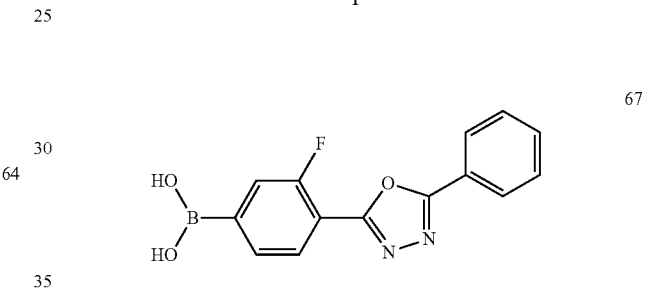
67

Oxadiazole 67 was prepared in 2 steps by first forming the oxadiazole from 2-fluoro-4-(4,4,5,5-tetramethyl-1,3,2-dioxaborolan-2-yl)benzoic acid and benzoic hydrazide using Method 8 followed by Method 5 and was isolated after precipitation from the reaction mixture. [M–H]⁻=283.1 m/z. Activity: B

Example 63

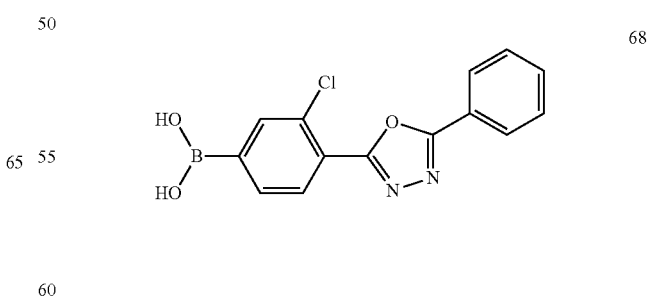
68

Oxadiazole 68 was prepared in 2 steps by first forming the oxadiazole from 2-chloro-4-(4,4,5,5-tetramethyl-1,3,2-dioxaborolan-2-yl)benzoic acid and benzoic hydrazide using Method 8 followed by Method 5 and was isolated after precipitation from the reaction mixture. ESI-MS [M+H]⁺=301.2 m/z. Activity: A

Example 64

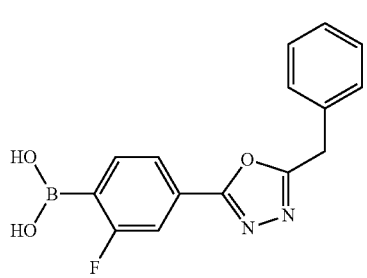

69

Oxadiazole 69 was prepared in 2 steps by first forming the oxadiazole from 3-fluoro-4-(4,4,5,5-tetramethyl-1,3,2-dioxaborolan-2-yl)benzoic acid and phenylacetic hydrazide using Method 8 followed by Method 5 and was isolated after precipitation from the reaction mixture. [M–H]⁻=297.1 m/z. Activity: B

Example 65

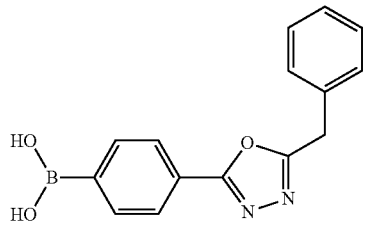

70

Oxadiazole 70 was prepared in 2 steps by first forming the oxadiazole from 4-(4,4,5,5-tetramethyl-1,3,2-dioxaborolan-2-yl)benzoic acid and phenylacetic hydrazide using Method 8 followed by Method 5 and was isolated after precipitation from the reaction mixture. [M–H]⁻=279.0 m/z. Activity: A

Example 66

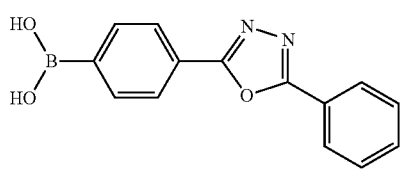

71

Oxadiazole 71 was prepared in 2 steps by from the corresponding aryl bromide using Method 1 followed by Method 6. [M–H]⁻=265.1 m/z. Activity: A

Example 67

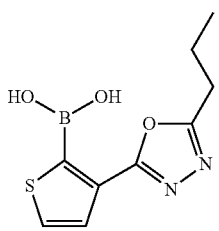

72

Oxadiazole 72 was prepared in 2 steps by first forming the oxadiazole from 2-(4,4,5,5-tetramethyl-1,3,2-dioxaborolan-2-yl)thiophene-3-carboxylic acid and butyric hydrazide using Method 8 followed by Method 5. [M–H]⁻=237.1 m/z. Activity: D

Example 68

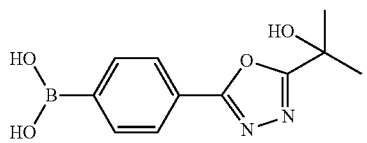

73

Oxadiazole 73 was prepared in 2 steps by first forming the oxadiazole from 4-(4,4,5,5-tetramethyl-1,3,2-dioxaborolan-2-yl)benzoic acid and 2-hydroxyisobutryic hydrazide using Method 8 followed by Method 5. [M–H]⁻=247.1 m/z. Activity: B

Example 69

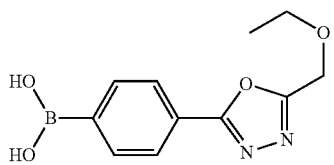

74

Oxadiazole 74 was prepared in 2 steps by first forming the oxadiazole from 4-(4,4,5,5-tetramethyl-1,3,2-dioxaborolan-2-yl)benzoic hydrazide and ethoxyacetic acid using Method 7 followed by Method 5. [M–H]⁻=247.1 m/z. Activity: B

Example 70

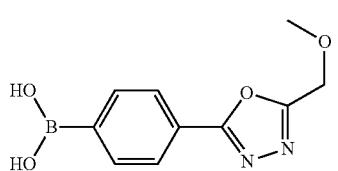
75

Oxadiazole 75 was prepared in 2 steps by first forming the oxadiazole from 4-(4,4,5,5-tetramethyl-1,3,2-dioxaborolan-2-yl)benzoic hydrazide and methoxyacetic acid using Method 7 followed by Method 5. [M–H]⁻=233.1 m/z. Activity: A

Example 71

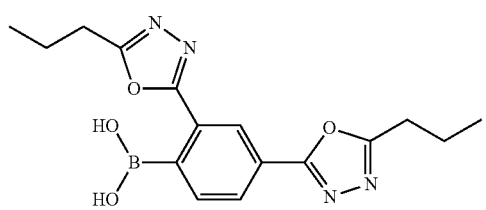
76

Oxadiazole 76 was prepared in 2 steps by first forming the bis-oxadiazole from bromobenzene-2,4-dicarboxylic acid and butryic hydrazide using Method 8 followed by Method 1. [M–H]⁻=341.1 m/z. Activity: A

Example 72

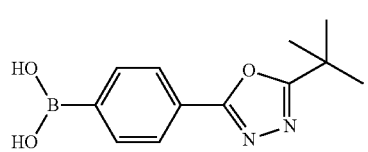
77

Oxadiazole 77 was prepared in 2 steps by first forming the oxadiazole from 4-(4,4,5,5-tetramethyl-1,3,2-dioxaborolan-2-yl)benzoic acid and pivaloic hydrazide using Method 8 followed by Method 5. [M–H]⁻=245.1 m/z. Activity: A

Example 73

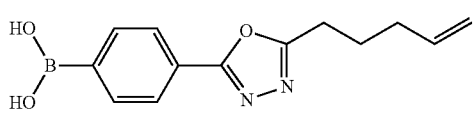
78

Oxadiazole 78 was prepared in 2 steps by first forming the oxadiazole from 4-(4,4,5,5-tetramethyl-1,3,2-dioxaborolan-2-yl)benzoic hydrazide and 5-hexenoic acid using Method 7 followed by Method 5. [M–H]⁻=257.1 m/z. Activity: A

Example 74

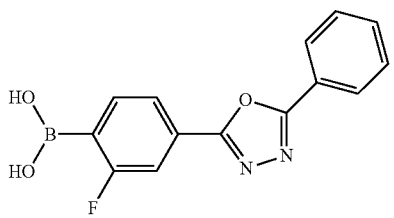
79

Oxadiazole 79 was prepared in 2 steps by first forming the oxadiazole from 3-fluoro-4-(4,4,5,5-tetramethyl-1,3,2-dioxaborolan-2-yl)benzoic acid and benzoic hydrazide using Method 8 followed by Method 5 and was isolated after precipitation from the reaction mixture. [M–H]⁻=283.1 m/z. Activity: B

Example 75

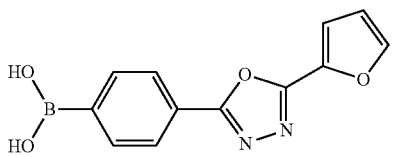
80

Oxadiazole 80 was prepared in 2 steps by first forming the oxadiazole from 4-(4,4,5,5-tetramethyl-1,3,2-dioxaborolan-2-yl)benzoic acid and furoic hydrazide using Method 8 followed by Method 5 and was isolated after precipitation from the reaction mixture. [M–H]⁻=255.0 m/z. Activity: A

Example 76

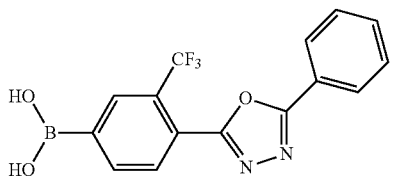
81

In a microwave reactor tube, 4-chloro-2-(trifluoromethyl)benzoic acid (300 mg, 1.34 mmol) and benzoic hydrazide (182 mg, 1.34 mmol) were dissolved in dry acetonitrile (6 mL). Polystyrene—supported triphenylphosphine (3.0 equiv, 1.80 g, 2.23 mmol/g loading) and trichloroacetonitrile (270 uL, 2.68 mmol) were added, and the mixture was sealed and heated in a microwave reactor at 130° C. for 2 hours. The reaction was then filtered and the resin was washed with excess tetrahydrofuran and methylene chloride. The filtrate was concentrated onto silica gel and purified by column chromatography using a gradient of 25-50% ethyl acetate/hexanes to provide the 300 mg of the desired oxadiazole in 70% yield.

2-(4-Chloro-2-(trifluoromethyl)phenyl)-5-phenyl-1,3,4-oxadiazole (296 mg, 0.921 mmol) was dissolved in 6 mL anhydrous tetrahydrofuran in a microwave reaction tube. Bis (pinacolato)diboron (278 mg, 1.09 mmol) was added followed by potassium acetate (206 mg, 2.10 mmol), palladium (II) acetate (12 mg, 0.055 mmol) and 1,3-bis(2,6-diisopropylphenyl)imidazolium chloride (46 mg, 0.11 mmol). The reaction was heated in a microwave reactor was heated to 110° C. for 20 min. A slurry of palladium(II) acetate and the imidazolum catalyst in 1 mL tetrahydrofuran was then added and the reaction was reheated under the same conditions. This was repeated a third time after which point the reaction was filtered through a plug of slica gel using 1:1 ethyl acetate/hexanes (v/v) as eluent. The filtrate was then concentrated onto silica gel and purified by column chromatography using a gradient of 25-50% ethyl acetate/hexanes to provide the 300 mg of the desired oxadiazole in 79% yield.

The resulting pinacol ester (2-phenyl-5-(4-(4,4,5,5-tetramethyl-1,3,2-dioxaborolan-2-yl)-2-(trifluoromethyl)phenyl)-1,3,4-oxadiazole) was then converted to boronic acid 81 using Method 5 and was isolated after precipitation from the reaction mixture. [M–H]⁻=333.1 m/z. Activity: C

Example 77

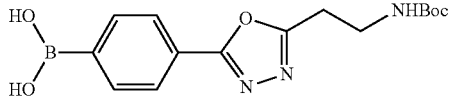

82

4-(4,4,5,5-Tetramethyl-1,3,2-dioxaborolan-2-yl)benzohydrazide (300 mg, 1.15 mmol) and N-Boc-β-alanine (227 mg, 1.20 mmol) were dissolved in 10 mL anhydrous dichloromethane. HOBt (187 mg, 1.37 mmol) and EDC (263 mg, 1.37 mmol) were added followed by triethylamine (480 uL, 3.43 mmol). The reaction was allowed to stir for 12 h at room temperature after which point it was transferred to a separatory funnel with excess dichloromethane and washed with 0.5 M citric acid (2×75 mL) and saturated NaHCO₃ (2×75 mL). The organic layer was then dried over MgSO₄, filtered and concentrated to provide the desired diacyl hydrazone as a while foamy solid in 93% yield (461 mg) which was used directly to form the oxadiazole in the following step.

The diacyl hydrazone (461 mg, 1.06 mmol) was dissolved in anhydrous tetrahydrofuran. Burgess' reagent (355 mg, 1.60 mmol) was added and the reaction was heated to 60° C. in a sealed tube for 20 h. After this point, the reaction was allowed to cool and transferred to a separatory funnel with excess saturated NaHCO₃ (50 mL) and ethyl acetate (50 mL). The organic layer is washed with saturated NaCl (50 mL), dried over MgSO₄, and concentrated under vacuum to provide a crude oil that is purified using silica gel chromatography with a gradient of 20-70% ethyl/hexanes to provide the 187 mg of the desired oxadiazole in 43% yield.

The resulting pinacol ester (tert-butyl 2-(5-(4-(4,4,5,5-tetramethyl-1,3,2-dioxaborolan-2-yl)phenyl)-1,3,4-oxadiazol-2-yl)ethylcarbamate) was then converted to boronic acid 82 using Method 5 and was isolated after precipitation from the reaction mixture. [M–H]⁻=332.1 m/z. Activity: B

Example 78

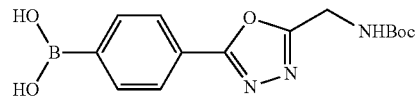

83

Carbamate 83 was prepared using the analogous procedure as Example 77 except that N-Boc glycine was used in place of N-Boc-β-alanine [M–H]⁻=318.1 m/z. Activity: B

Example 79

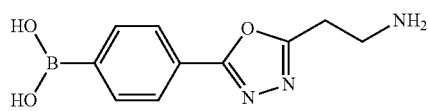

84

Carbamate 82 (20 mg, 0.060 mmol) was dissolved in 5 mL methylene chloride. Excess trifluoroacetic acid (5 mL) was added and the reaction was allowed to stir at room temperature for 10 min. The reaction was then diluted with toluene (40 mL) and azeotroped under vacuum to remove the excess acid. This was repeated 2 times and the resultant solid was dried under vacuum overnight to provide the desired amine 84 in quantitative yield (14 mg). [M–H]⁻=232.1 m/z. Activity: D

Example 80

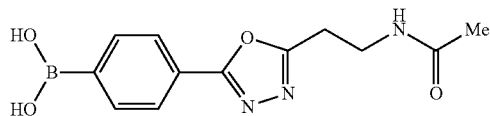

85

Amine 84 (17 mg, 0.050 mmol) was suspended in 5 mL methylene chloride. Acetic anhydride (49 μL, 0.49 mmol) was added followed by NaHCO₃ (29 mg, 0.25 mmol) and allowed to stir at room temperature for 10 min. An additional 49 uL of acetic anhydride and 29 mg of NaHCO₃ were then added and the reaction was allowed to stir for an additional hour at which point the reaction was determined to be complete by LC/MS. Methanol (1 mL) was added and the mixture was allowed to stir at room temperature for 20 min. The reaction mixture was then filtered and concentrated to provide 6 mg of amide 85 in 45% yield. [M–H]⁻=274.1 m/z. Activity: C

Example 81

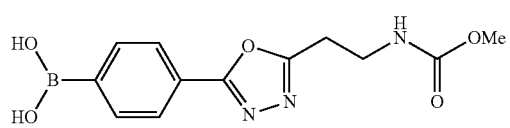

Tert-butyl 2-(5-(4-(4,4,5,5-tetramethyl-1,3,2-dioxaborolan-2-yl)phenyl)-1,3,4-oxadiazol-2-yl)ethylcarbamate (187 mg, 0.450 mmol) was dissolved in 10 mL 2N HCl in dioxane and allowed to stir at room temperature for 2 h. After this point the solvent was removed under vacuum to provide the desired free amine in quantitative yield as the HCl salt. A portion of this free amine (63 mg, 0.18 mmol) was dissolved in 3 ml anhydrous THF. Methyl chloroformate (18 µL, 0.23 mmol) was added followed by diisopropylethylamine (83 µL, 0.47 mmol) and the reaction was allowed to stir at room temperature for 2 h at which point there is no more starting material visible by LC/MS. Water (30 mL) was added and the mixture is acidified to pH<4 with 0.5 M citric acid. The solid that remains was collected via vacuum filtration and washed with excess water to provide the desired pinacol ester in 12% yield (8.0 mg).

The resulting pinacol ester (methyl 2-(5-(4-(4,4,5,5-tetramethyl-1,3,2-dioxaborolan-2-yl)phenyl)-1,3,4-oxadiazol-2-yl)ethylcarbamate) was then converted to amide 86 using Method 5 and was isolated after precipitation from the reaction mixture. [M–H]⁻=290.1 m/z. Activity: B

Example 82

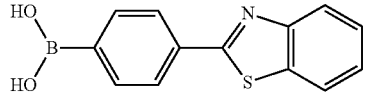

Benzothiazole 87 was prepared in two steps from the corresponding aryl bromide using Method 3 followed by Method 5 and purified using flash silica gel chromatography. [M–H]⁻=254.1 m/z. Activity: D

Example 83

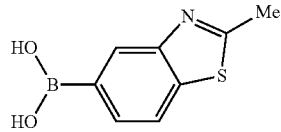

Benzothiazole 88 was prepared in two steps from the corresponding aryl bromide using Method 3 followed by Method 5 and purified using flash silica gel chromatography. [M–H]⁻=192.0 m/z. Activity: C

Example 84

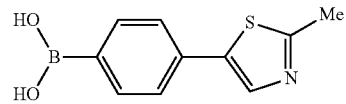

Thiazole 89 was prepared in two steps from the corresponding aryl bromide using Method 3 followed by Method 5 and purified using flash silica gel chromatography. [M–H]⁻=218.1 m/z. Activity D

Example 85

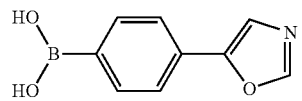

Oxazole 90 was prepared in two steps from the corresponding aryl bromide using Method 3 followed by Method 5 and purified using flash silica gel chromatography. [M–H]⁻=188.1 m/z. Activity: B

Example 86

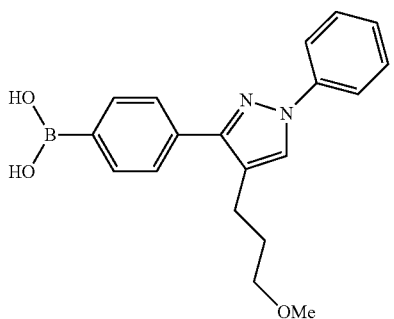

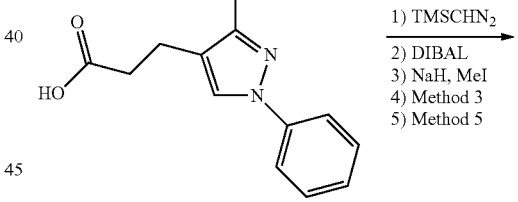

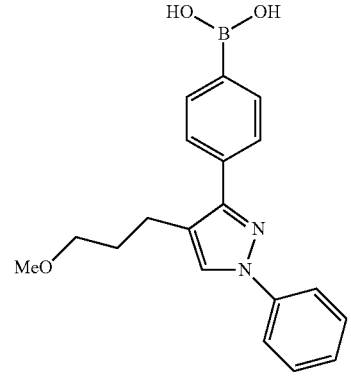

Pyrazole 92 was prepared in 5 steps from 3-(4-bromophenyl)-1-phenylpyrazole-4-propionic acid (1.00 g, 2.69 mmol) starting with the methylation of the free acid using trimethylsilyl-diazomethane (4.0 equiv in hexanes) in 1:1 toluene/methanol (0.05 M) for 1 h after which point the reaction was concentrated and dried under vacuum. The crude mixture was then redissolved in THF (0.15 M) and cooled to 0° C. in an ice bath under $N_2$. DIBAL (3.5 equiv, 1.0 M in toluene) was added drop wise and the reaction was allowed to warm to room temperature and allowed to stir for 2 h. The reaction was then quenched methanol (20 mL) followed by the addition of a saturated solution of Rochelle's salt (100 mL) After 1 h, the reaction was transferred to a separatory funnel with excess ethyl acetate and water after which the water layer was washed with ethyl acetate (2×75 mL). The organic layers were combined and washed with brine (2×75 mL), dried over $MgSO_4$, and concentrated to provide the desired product as a crude oil in quantitative yield.

The crude alcohol (340 mg, 0.95 mmol) was then redissolved in anhydrous N,N-dimethylforamide (0.20 M) and cooled to 0° C. in an ice bath. Sodium hydride (3.0 equiv) was added portion wise and allowed to stir for 10 min after which point iodomethane (2.0 equiv) was added and the reaction was allowed to stir for 2 h at room temperature. The reaction was then quenched with saturated $NH_4Cl$ and was transferred to a separatory funnel with excess ethyl acetate and water after which the water layer was washed with ethyl acetate (2×75 mL). The organic layers were combined and washed with brine (2×75 mL), dried over $MgSO_4$, and concentrated to provide the desired ether as a crude oil in quantitative yield.

The resulting methyl ether was then converted to the desired pyrazole 92 using Method 3 followed by Method 5 and purified using flash silica gel chromatography. [M–H]⁻=335.1 m/z. Activity: D Example 87

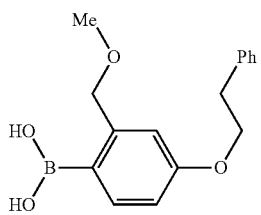

Part A

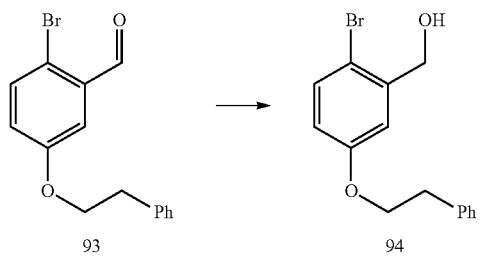 [SMILES: O=Cc1cc(OCCc2ccccc2)ccc1Br ; OCc1cc(OCCc2ccccc2)ccc1Br]

At 0° C., aldehyde 93 (15) (1.8 mmol, 1.0 equiv) was dissolved in 1:1 tetrahydrofuran/methanol (14 ml) and treated with sodium borohydride (136 mg, 3.6 mmol, 2.0 equiv). After stirring for 2 h, the mixture was diluted with water (100 ml) and extracted with ethyl acetate (100 ml). The organic layer was washed with brine, dried over sodium sulfate, and concentrated in vacuo. The resulting oil was purified by flash silica gel chromatography (5→30% ethyl acetate/hexanes) to give a colorless oil (500 mg).

Part B

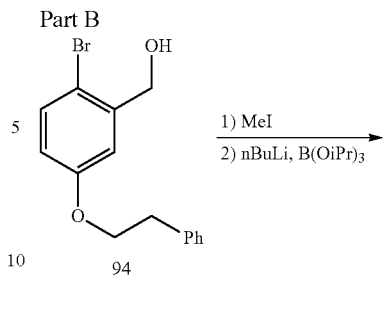

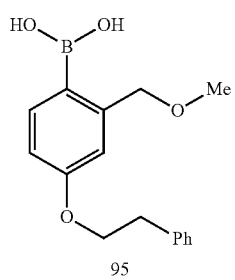

Benzylic alcohol 94 (185 mg, 0.6 mmol, 1.0 equiv) and iodomethane (128 mg, 0.9 mmol, 1.5 equiv) were dissolved in dimethylformamide (3 ml) and, at 0° C., were treated with sodium hydride (36 mg, 0.9 mmol, 1.5 equiv of a 60% dispersion in mineral oil). The mixture was stirred for 2 h and then quenched by addition of saturated aqueous ammonium chloride (1 ml). The mixture was split between water (100 ml) and extracted with ethyl acetate (100 ml). The organic layer was washed with brine, dried over sodium sulfate, and concentrated in vacuo. Purification by flash silica gel chromatography (1→5% ethyl acetate/hexanes) to give a colorless oil (143 mg). The resulting aryl bromide was converted to the boronic acid 95 by Method 1. [M–H]⁻=285.1 m/z. Activity: B Example 88

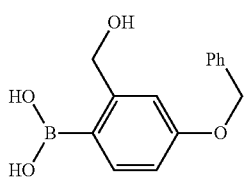

Benzyl alcohol 96 was prepared by reduction of the benzaldehyde-boronic acid as described for 94 and purified by flash silica gel chromatography (1→5% methanol/dichloromethane). [M–H]⁻=257.1 m/z. Activity: D Example 89

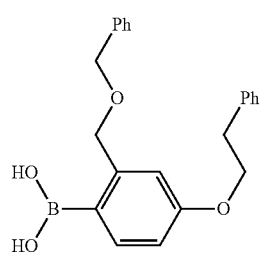

The benzyl ether 97 was made according to the procedures described for 95. [M−H]⁻=361.2 m/z. Activity: D

Example 90

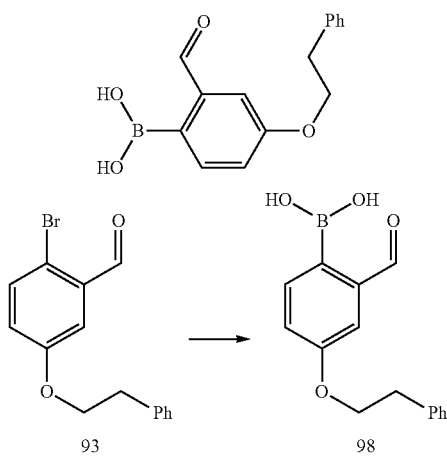

The bromobenzaldehyde 93 (15) (500 mg, 1.6 mmol, 1.0 equiv) and ethylene glycol (712 mg, 11.5 mmol, 7.0 equiv) with toluenesulfonic acid (9 mg, 3 mol %) were dissolved in toluene (35 ml) and heated at reflux 24 h with azeotropic removal of water with a Dean-Stark apparatus. After cooling, the mixture was split between 5% aqueous sodium bicarbonate (100 ml), and the organic layer was then washed with water (100 ml) and then brine (50 ml), dried over sodium sulfate, and concentrated in vacuo. The resultant clear oil was purified by flash silica gel chromatography (1→5% ethyl acetate/hexanes) to give a colorless oil (534 mg).

This pure acetal was then converted to the boronic acid 98 by Method 1. It was important to stir the mixture after the quench with 2N aqueous HCl for 1 h to ensure full hydrolysis of the acetal. [M−H]=269.1 m/z. Activity: A

Example 91

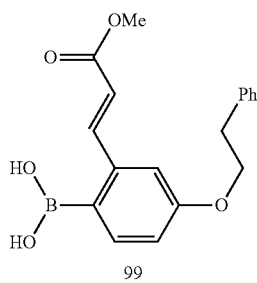

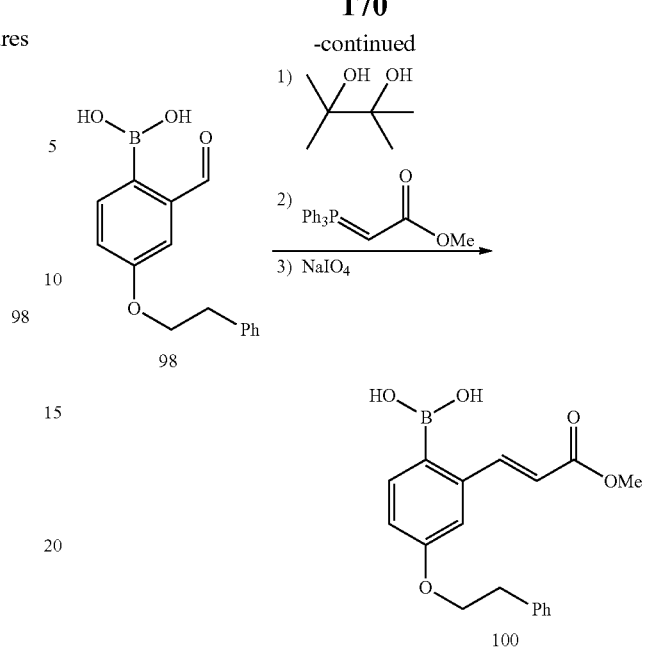

Benzaldehyde-boronic acid 98 (500 mg, 1.85 mmol, 1 equiv) and pinacol (263 mg, 2.2 mmol, 1.2 equiv) were heated at reflux in benzene (12 ml) for 5 h, with azeotropic removal of water using a Dean-Stark apparatus. The solution was concentrated and purification by flash silica gel chromatography (1→10% ethyl acetate/hexanes) gave pinacol ester (436 mg).

The product ester and methyl (triphenylphosphoranylidene)acetate (540 mg, 1.6 mmol, 1.3 equiv) were heated at 90° C. in dry toluene for 18 h. The mixture was cooled and split split between water (150 ml) and ethyl acetate (150 ml), and the organic layer was washed with brine and dried over sodium sulfate. The oil from concentration in vacuo was purified by flash silica gel chromatography (1→30% ethyl acetate/hexanes) to give a clear oil (70% yield). The pinacol ester was cleaved by Method 5 to produce boronic acid 100. [M−H]⁻=325.1 m/z. Activity: A

Example 92

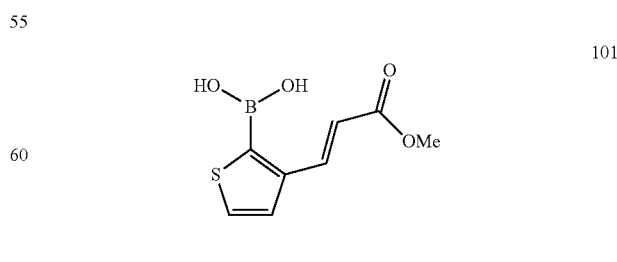

The thienyl—unsaturated ester boronic acid 101 was prepared by condition similar to those for compound 100. [M−H]⁻=211.0 m/z. Activity: C

Example 93

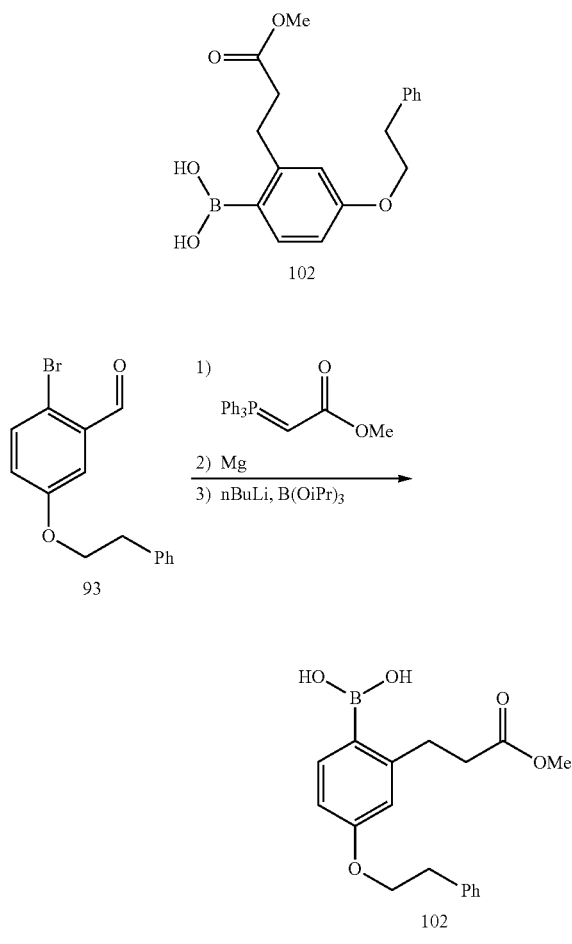

Example 94

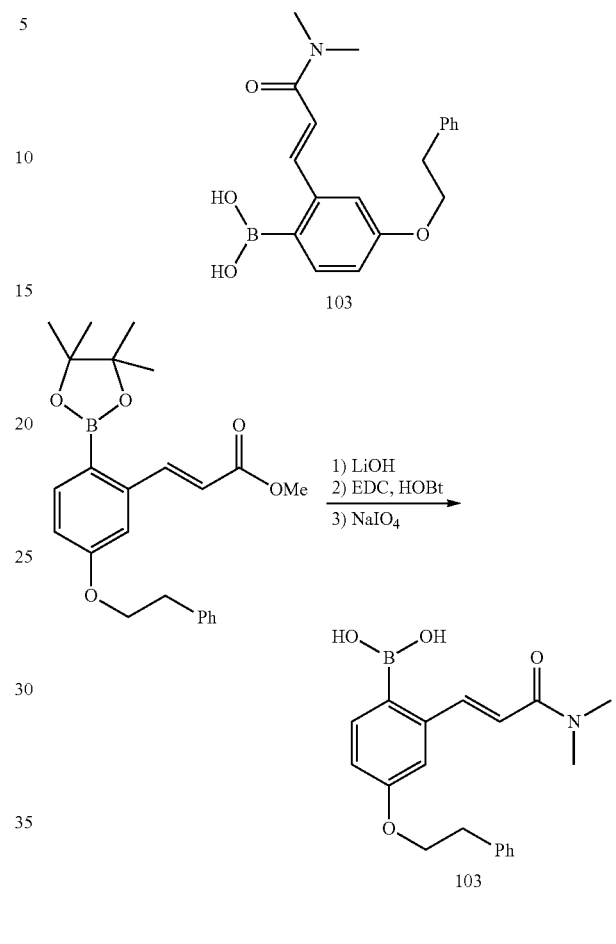

Bromobenzaldehyde 93 (15) (420 mg, 1.4 mmol, 1.0 equiv) and methyl (triphenylphos-phoranylidene)acetate (690 mg, 2.1 mmol, 1.5 equiv) were heated at 90° C. in dry toluene for 18 h. The mixture was cooled and split split between water (150 ml) and ethyl acetate (150 ml), and the organic layer was washed with brine and dried over sodium sulfate. The oil from concentration in vacuo was purified by flash silica gel chromatography (1→10% ethyl acetate/hexanes) to give a clear oil (55% yield).

The unsaturated ester (276 mg, 0.764, 1.0 equiv) in dry methanol (10 ml) was stirred under nitrogen atmosphere with magnesium turnings (279 mg, 11.5 mmol, 15 equiv) for 6 h at 23° C. The mixture was filtered, diluted with ethyl acetate (100 ml) and then washed with 1N aqueous HCl (100 ml) and brine (100 ml). The residue from concentration in vacuo was purified by flash silica gel chromatography (1→10% ethyl acetate/hexanes) to give the saturated ester (70% yield). The resulting aryl bromide was converted to the boronic acid pinacol ester 102 by Method 3 and the resultant pinacol ester cleaved by method 5. [M−H]⁻=327.1 m/z. Activity: B The pinacol ester of compound 100 (442 mg, 1.1 mmol, 1.0 equiv) was dissolved in 3:1 tetrahydrofuran/water (8 ml) and stirred with lithium hydroxide (78 mg, 3.25 mmol, 3.0 equiv) at 50° C. for 3 h. The mixture was diluted with ethyl acetate (50 ml), washed with 1N aqueous HCl (50 ml) and then brine (25 ml) and concentrated in vacuo. Purification by flash silica gel chromatography (1→20% ethyl acetate/hexanes) gave product (60% yield) which was used directly in the next step.

Carboxylic acid (133 mg, 0.34 mmol, 1.0 equiv) was dissolved in dry dichloromethane (5 ml) and treated with EDC-HCl (78 mg, 0.41 mmol, 1.2 equiv), HOBt (55 mg, 0.41 mmol, 1.2 equiv), iPr₂EtN (130 mg, 1.02 mmol, 3.0 equiv), dimethylamine (0.4 ml of a 2 M solution in tetrahydrofuran, 0.56 mmol, 2.2 equiv), and DMAP (2 mg, 0.02 mmol, 0.05 equiv). The mixture was stirred at 23° C. for 16 h and then split between 5% aqueous sodium bicarbonate and ethyl acetate (100 ml each). The organic layer was washed with brine (50 ml) and concentrated in vacuo. Purification by flash silica gel chromatography (1→10% methanol/dichloromethane) gave the desired amide (84% yield) which was cleaved by Method 5 to produce the arylboronic acid 103. [M−H]⁻=338.2 m/z. Activity: B

Example 95

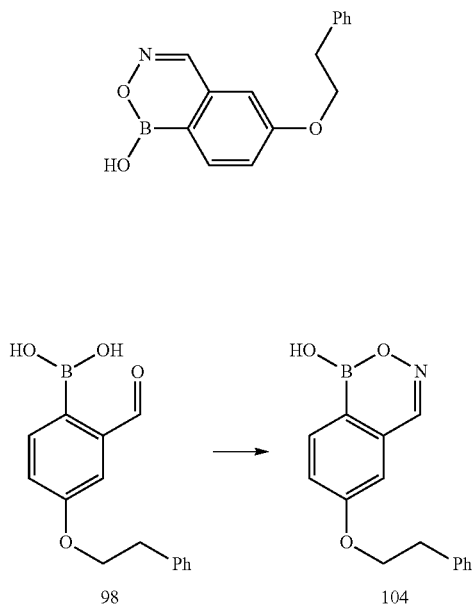

Benzaldehydeboronic acid 98 (240 mg, 0.89 mmol, 1.0 equiv) was suspended in water (10 ml) with hydroxylamine hydrochloride (195 mg, 2.80 mmol, 3.0 equiv) and sodium acetate (230 mg, 2.80 mmol, 3.0 equiv). The mixture was heated at 60° C. for 16 h and then cooled to room temperature. Addition of 1N HCl to achieve pH 1 produced (104) as a white precipitate that was collected and washed with water (64% yield). [M–H]⁻=266.1 m/z. Activity: B

Example 96

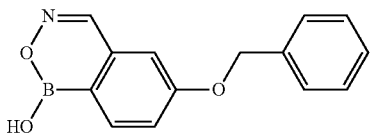

4-(Benzyloxy)-2-formylphenylboronic acid (72 mg, 0.28 mmol) was suspended in water (10 mL) followed by the addition of hydroxylamine hydrochloride (62 mg, 0.89 mmol). The pH was adjusted to 4 with 1N NaOH and the reaction was heated to 60° C. for 16 h after which point LC/MS analysis showed only the desired product. Additional water is added (50 mL) and the pH is adjusted to <2 with 6N HCl. The resultant solid is isolated using vacuum filtration, washed with excess water and dried under vacuum to provide 55 mg of benzoazaborine 105 in 77% yield. [M–H]⁻=252.1 m/z. Activity: B

Example 97

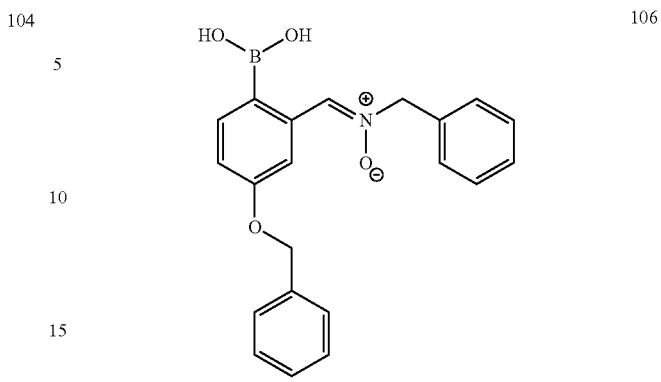

4-(Benzyloxy)-2-formylphenylboronic acid (100 mg, 0.391 mmol) was dissolved in 20 mL water/ethanol (1:1 v/v) followed by the addition of N-benzylhydroxylamine hydrochloride (62 mg, 0.391 mmol). The reaction was basified to pH=7 with 1N NaOH and stirred at room temperature for 6 h after which point there was no more starting material remaining by LC/MS analysis. The ethanol was removed under a stream of N₂ and 100 mL 1N HCl was added. The white solid that precipitated was collected using vacuum filtration, washed with excess water and dried under vacuum to provide 55 mg of nitrone 106 in 39% yield. [M–H]⁻=360.2 m/z. Activity: C

Example 98

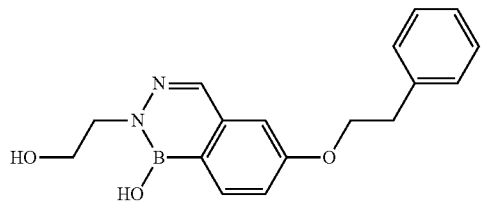

2-Formyl-4-phenethoxyphenylboronic acid (111 mg, 0.411 mmol) and 2-hydroxyethyl hydrazine (33 mL, 0.43 mmol) are dissolved in 10 mL ethanol and heated to 50° C. for 12 h. The reaction is allowed to cool and the solvent is removed under a stream of N₂ until there is only 2 mL of ethanol left. 1N HCl (50 mL) is then added until a solid crashes out which is isolated using vacuum filtration and washed with excess water. The resultant solid is dried under vacuum overnight to provide 10 mg of benzodiazoborine 107 in 8% yield. [M–H]⁻=309.1 m/z. Activity: D

Example 99

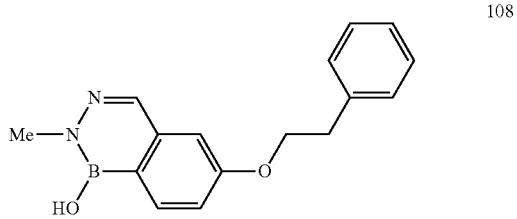 [SMILES: CN1N=Cc2cc(OCCc3ccccc3)ccc2B1O]

Benzodiazoborine 108 was prepared using the analogous procedure as example 98 except that N-methyhydrazine was used in place of 2-hydroxyethyl hydrazine. [M−H]⁻=279.1 m/z. Activity: D Example 100

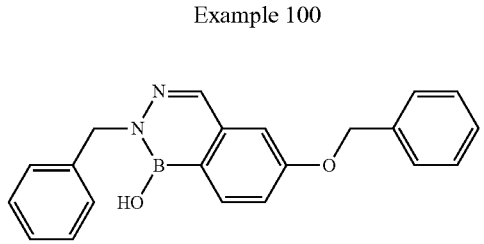

Benzodiazoborine 109 was prepared using the analogous procedure as example 98 except that N-benzylhydrazine was used in place of 2-hydroxyethyl hydrazine. [M−H]⁻=341.2 m/z. Activity: B Example 101

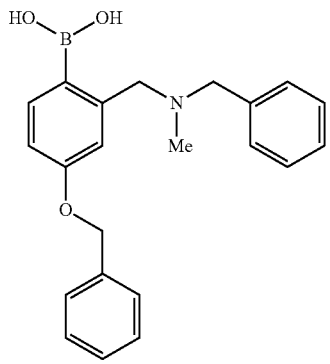

4-(Benzyloxy)-2-formylphenylboronic acid (78 mg, 0.31 mmol) is dissolved in 5 mL methylene chloride. N-Methyl-N-benzylamine (41 μL, 0.32 mmol) is added and the mixture is allowed to stir at room temperature for 20 min. Sodium triacetoxyborohydride (68 mg, 0.32 mmol) is then added and the reaction is allowed to stir at room temperature for 30 min after which point there is no starting material visible by LC/MS. The solvent is evaporated under a stream of N₂. The resultant solid is resuspended in a solution of 2% acetic acid in water (50 mL). The solid that forms is isolated using vacuum filtration, washed with excess water, and dried under vacuum to provide 93 mg of amine 110 in 85% yield. [M−H]⁻=360.2 m/z. Activity: C Example 102

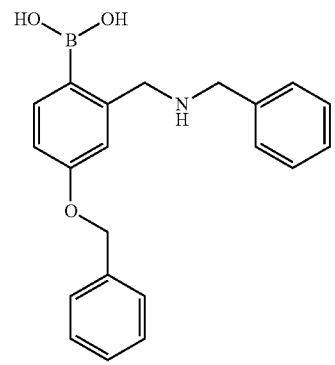

Amine 111 was prepared using the analogous procedure as example 101 except that benzylamine was used in place of N-methyl-N-benzylamine. [M−H]⁻=364.2 m/z. Activity: C.

Example 103

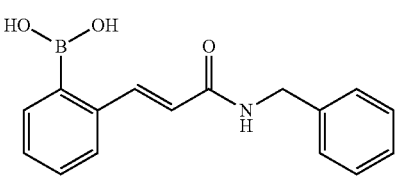

(E)-3-(2-(4,4,5,5-Tetramethyl-1,3,2-dioxaborolan-2-yl)phenyl)acrylic acid (80 mg, 0.29 mmol) was dissolved in 10 mL anhydrous dichloromethane and benzylamine (33 μL, 0.31 mmol) was added. HOBt (47 mg, 0.35 mmol) and EDC (67 mg, 0.35 mmol) were then added followed by triethylamine (59 uL, 58 mmol). The reaction was allowed to stir for 12 h at room temperature after which point it was transferred to a separatory funnel with excess dichloromethane and washed with 0.5 M citric acid (2×75 mL) and saturated NaHCO₃ (2×75 mL). The organic layer was then dried over MgSO₄, filtered and concentrated to provide the desired ketoamide as a white solid in 94% yield (100 mg) which was used directly in the following step.

The resulting pinacol ester ((E)-N-benzyl-3-(2-(4,4,5,5-tetramethyl-1,3,2-dioxaborolan-2-yl)phenyl)acrylamide) was then converted to amide 112 using Method 5 and was isolated after precipitation from the reaction mixture. [M−H]⁻=280.1 m/z. Activity: C Example 104

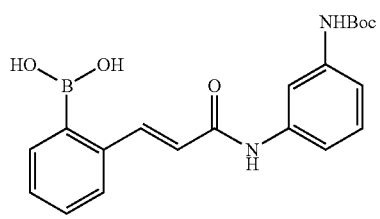

Amide 113 was prepared using the analogous procedure as example 103 except that N-Boc-m-phenylenediamine was used in place of benzylamine. [M−H]⁻=381.2 m/z. Activity: D

Example 105

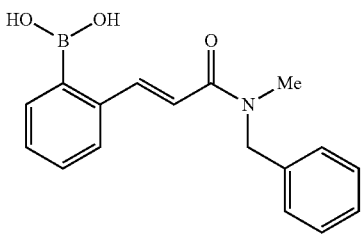

114

Amide 114 was prepared using the analogous procedure as example 103 except that N-methyl-N-benzylamine was used in place of benzylamine [M−H]=294.1 m/z. Activity: C

Example 106

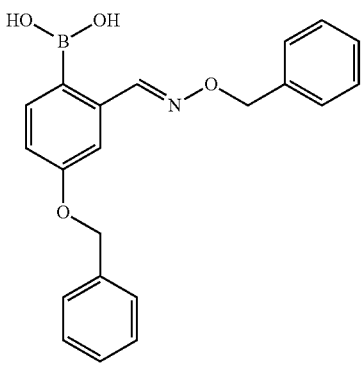

115

4-(Benzyloxy)-2-formylphenylboronic acid (100 mg, 0.39 mmol) and O-benzylhydroxylamine hydrochloride (62 mg, 0.39 mmol) were dissolved in 5 mL ethanol. The reaction was allowed to stir at room temperature for 14 h. The reaction was then added to 1N HCl (75 mL) and a solid crashed out which was collected via vacuum filtration and washed with excess water to provide 92 mg of the benzyloxyimine 115 after drying under vacuum overnight. [M−H]⁻=360.1 m/z. Activity: B

Example 107

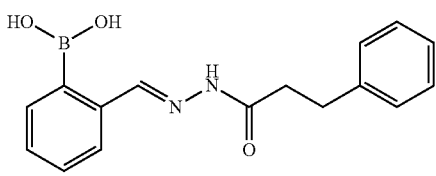

116

2-Formylphenylboronic acid (150 mg, 1.0 mmol) and 3-phenylpropionic hydrazide (164 mg, 1.0 mmol) were dissolved in 5 mL ethanol. The reaction was heated to 50° C. for 14 h after which point there was more starting material by LC/MS analysis. The reaction was allowed to cool after which point 100 mL 1N HCl was added to the reaction and the solid which crashes out is collected by vacuum filtration and washed with excess water. The solid is dried under vacuum overnight to provide 200 mg of acyl hydrazone 116 as a white solid in 68% yield. [M−H]⁻=295.1 m/z. Activity: D

Example 108

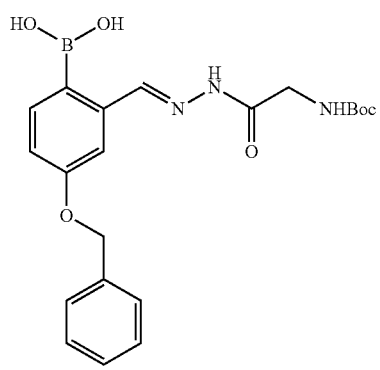

117

Acyl hydrazone 117 was prepared using the analogous procedure as example 107 except that N-Boc glycine hydrazide was used in place of 3-phenylpropionic hydrazide and 2-formyl-4-benzyloxyphenylboronic acid was used in place of 2-formylphenylboronic acid. [M−H]=426.1 m/z. Activity: B

Example 109

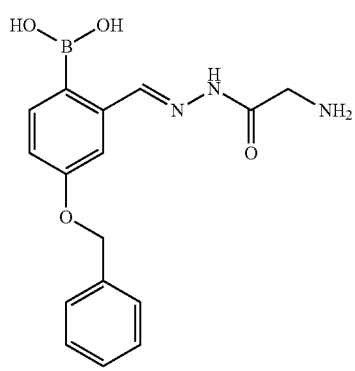

118

Acyl hydrazone 117 (58 mg, 0.14 mmol) is suspended in 10 mL ethyl acetate saturated with HCl. The reaction is allowed to stir for 30 min. The solvent is then removed under a stream of N₂ over the course of 1.5 h. The resulting oil is triturated with tert-butyl methylether until a solid forms, which is filtered and washed with excess tert-butyl methylether to provide 35 mg of acyl hydrazone 118 as the hydrochloride salt in 70% yield. [M−H]⁻=326.1 m/z. Activity: D

Example 110

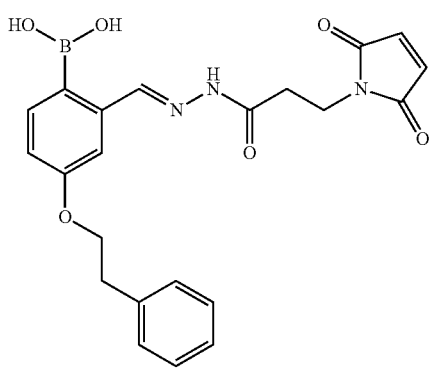

119

Acyl hydrazone 119 was prepared using the analogous procedure as example 107 except that 3-maleimidopropionic hydrazide was used in place of 3-phenylpropionic hydrazide and 2-formyl-4-phenethoxyphenylboronic acid was used in place of 2-formylphenylboronic acid. [M−H]⁻=434.1 m/z. Activity: A

Example 111

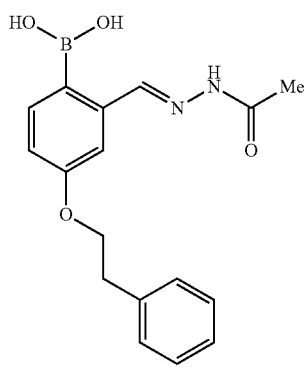

120

Acyl hydrazone 120 was prepared using the analogous procedure as example 107 except that acetic hydrazide was used in place of 3-phenylpropionic hydrazide and 2-formyl-4-benzyloxyphenylboronic acid was used in place of 2-formylphenylboronic acid. [M−H]⁻=325.1 m/z. Activity: A

Example 112

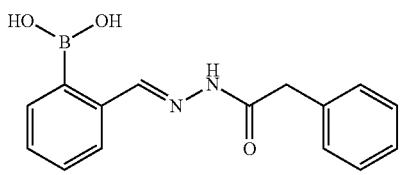

121

Acyl hydrazone 121 was prepared using the analogous procedure as example 107 except that pheylacetic hydrazide was used in place of 3-phenylpropionic hydrazide. [M−H]⁻=281.1 m/z. Activity: D

Example 113

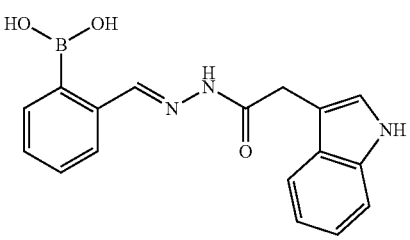

122

Acyl hydrazone 122 was prepared using the analogous procedure as example 107 except that indole-3-acetic acid hydrazide was used in place of 3-phenylpropionic hydrazide. [M−H]=320.1 m/z. Activity: D

Example 114

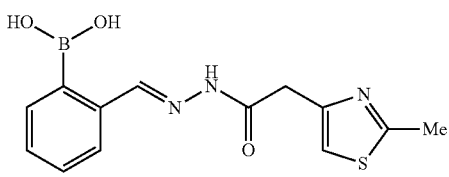

123

Acyl hydrazone 123 was prepared using the analogous procedure as example 107 except that (2-methyl-thiazol-4-yl)acetic acid hydrazide was used in place of 3-phenylpropionic hydrazide. [M−H]⁻=302.1 m/z. Activity: D

Example 115

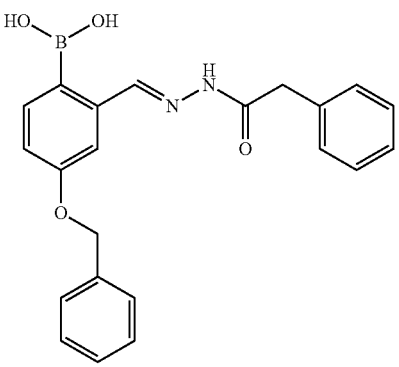

124

Acyl hydrazone 124 was prepared using the analogous procedure as example 107 except that pheylacetic hydrazide was used in place of 3-phenylpropionic hydrazide and 2-formyl-4-benzyloxyphenylboronic acid was used in place of 2-formylphenylboronic acid. [M−H]⁻=387.2 m/z. Activity: B

Example 116

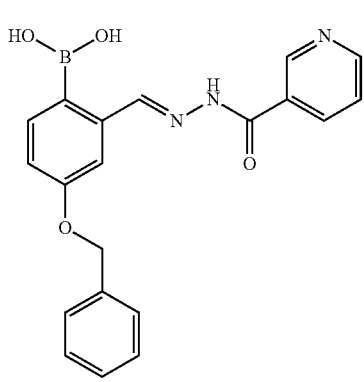

125

Acyl hydrazone 125 was prepared using the analogous procedure as example 107 except 2-picolinyl hydrazide was used in place of 3-phenylpropionic hydrazide and 2-formyl-4-benzyloxyphenylboronic acid was used in place of 2-formylphenylboronic acid. [M–H]⁻=374.1 m/z. Activity: B

Example 117

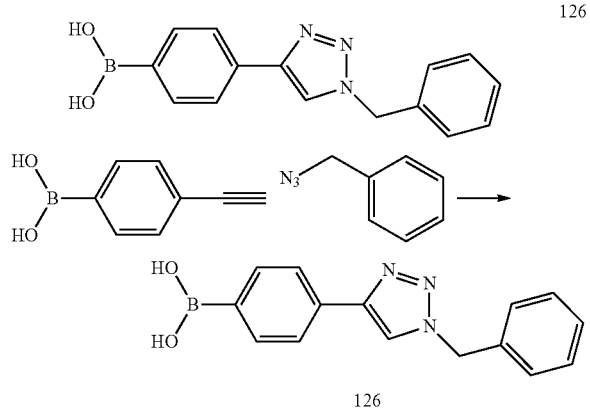

126

A mixture of 4-ethynylbenzeneboronic acid (42 mg, 0.289 mmol, 1.0 equiv), benzyl azide (38.5 mg, 0.289 mmol, 1.0 equiv), copper sulfate (0.5 mg, 0.003 mmol, 1 mol %), and sodium ascorbate (5 mg, 0.03 mmol, 0.1 equiv) were stirred in 2:1 tert-butanol/water (3 ml) for 14 h at 23° C. The mixture was split between ethyl acetate (25 ml) and water (25 ml), and the organic layer was washed with brine (20 ml) and dried over sodium sulfate. The residue upon concentration was purified by flash silica gel chromatography (1→30% methanol/dichloromethane) to give a white solid (70% yield). [2M–H₂O]⁻=539.1 m/z. Activity: A

Example 118

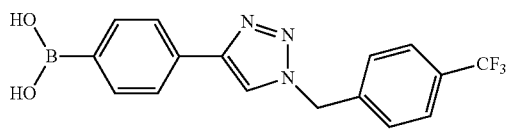

127

Compound 127 was prepared by methods described for Example 117. [M–H]⁻=346.1.1 m/z. Activity: C

Example 119

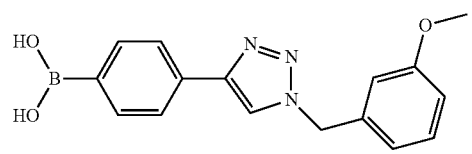

128

Compound 128 was prepared by methods described for Example 117. [M–H]⁻=308.1 m/z. Activity: B

Example 120

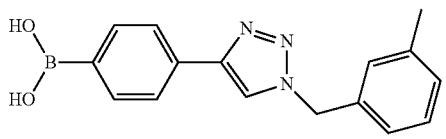

129

Compound 129 was prepared by methods described for Example 117. [M–H]⁻=292.1 m/z. Activity: A

Example 121

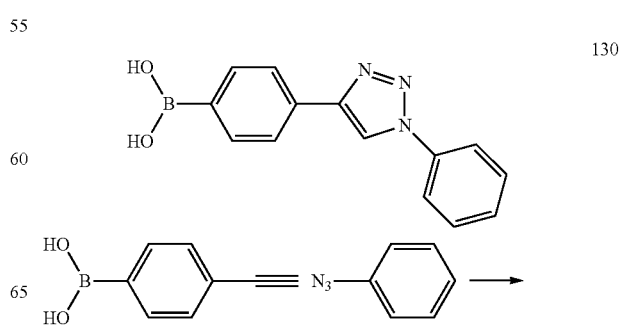

130

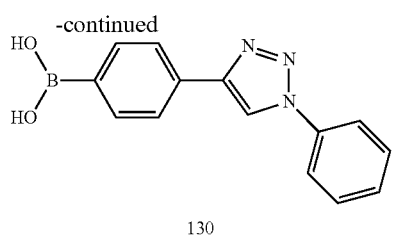

130

A mixture of 4-ethynylbenzeneboronic acid (180 mg, 1.23 mmol, 1.45 equiv), phenyl azide (100 mg, 0.84 mmol, 1.0 equiv), copper powder (0.5 mg, 0.003 mmol, 1 mol %), and sodium ascorbate (16 mg, 0.08 mmol, 0.1 equiv) were stirred in 1:1 tert-butanol/water (6 ml) for 14 h at 23° C. The mixture was split between ethyl acetate (25 ml) and water (25 ml), and the organic layer was washed with brine (20 ml) and dried over sodium sulfate. The residue upon concentration was purified by flash silica gel chromatography (1→10% methanol/dichloromethane) to give 130 as a white solid (30% yield). [M–H]⁻=264.1 m/z. Activity: B Example 122

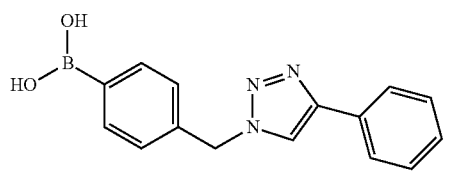

131

A 6 ml DMF solution of 4-bromomethylphenylboronic acid pinacol ester (150 mg, 0.5 mmol, 1.0 equiv) was heated with sodium azide (164 mg, 2.5 mmol, 5 equiv) at 60° C. for 24 h. The mixture was diluted with water (50 ml) and extracted with ethyl acetate (50 ml). The organic layer was washed with water (50 ml), then brine (30 ml) and then dried over sodium sulfate.

The clear oil produced upon concentration was then stirred with phenylacetylene (62 mg, 0.6 mmol, 1.0 equiv), copper sulfate (1 mg, 1 mol %), and sodium ascorbate (12 mg, 0.06 mmol, 0.1 equiv) in 2:1 tert-butanol/water (6 ml) for 16 h at 23° C. The mixture was diluted with water (50 ml) and extracted with ethyl acetate (50 ml). The organic layer was washed with water (50 ml), then brine (30 ml) and then dried over sodium sulfate. The residue from concentration in vacuo was purified by flash silica gel chromatography (5→60% ethyl acetate/hexanes) to give the pinacol ester as a clear oil. This resultant pinacol ester was cleaved by Method 5. [M–H]⁻=278.1 m/z. Activity: B Example 123

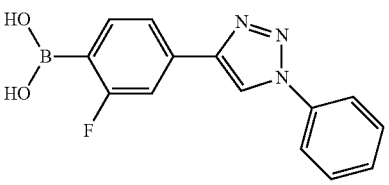

134

Part A

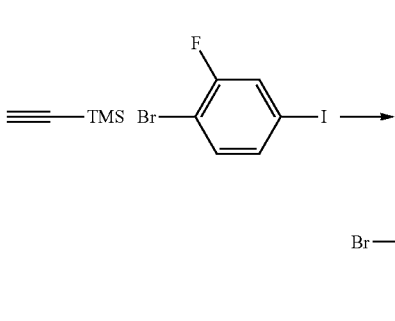

132

A flame—dried flask equipped with a rubber septum was charged with 4-bromo-3-fluoroiodobenzene (1.0 g, 3.3 mmol, 1.0 equiv), copper(I) iodide (63 mg, 0.33 mmol. 0.1 equiv), and bis(triphenylphosphine)palladium(II) dichloride (117 mg, 0.17 mmol, 0.05 equiv). Under argon atmosphere, the solids were suspended in dry THF (8 ml), and triethylamine (1.15 ml, 8.3 mmol, 2.5 equiv) and trimethylsilylacetylene (490 mg, 5 mmol, 1.5 equiv) were added. The mixture was stirred at 23° C. for 4 h, turning from orange to black, and was then split between ethyl acetate (50 ml) and water (50 ml). The organic layer was washed with brine (25 ml) and dried over sodium sulfate. The residue from concentration in vacuo was restored in methanol (15 ml) and stirred with potassium carbonate (1.4 g, 10 mmol, 3.0 equiv) for 1 h. The mixture was split between ethyl acetate (50 ml) and water (50 ml) and the organic layer was washed with brine (25 ml) and then dried over sodium sulfate and concentrated in vacuo. Purification by flash silica gel chromatography (hexanes) gave acetylene 132 as a pale yellow solid (60% yield).

Part B

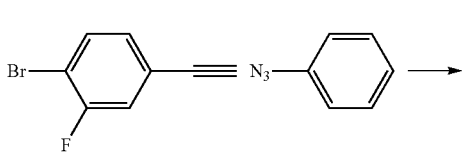

132

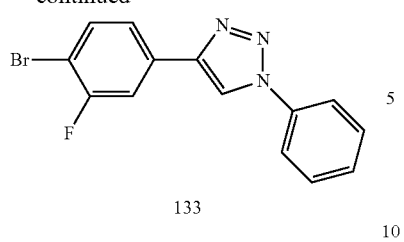

133

4-Bromo-3-fluorophenylacetylene (132) (400 mg, 2.0 mmol, 1.0 equiv), copper powder (126 mg, 2.0 mmol, 1.0 equiv), copper sulfate (6 mg, 0.1 mmol, 0.05 equiv), and sodium ascorbate (40 mg, 0.2 mmol, 0.1 equiv) in 2:1 tert-butanol/water (6 ml) were stirred for 16 h at 23° C. The mixture was diluted with water (50 ml) and extracted with ethyl acetate (50 ml). The organic layer was washed with water (50 ml), then brine (30 ml) and then dried over sodium sulfate. The residue from concentration in vacuo was purified by flash silica gel chromatography (5→60% ethyl acetate/hexanes) to give the triazole 133 as a white solid (35 mg).

Part C

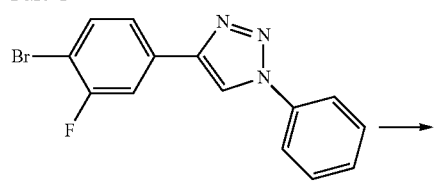

133

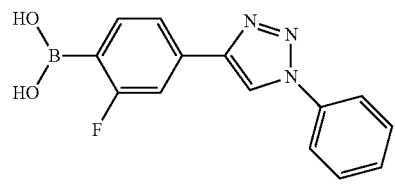

134

The aryl bromide 133 was converted to arylboronic acid 134 by Method 1. [M–H]⁻=282.1 m/z. Activity: B Example 124

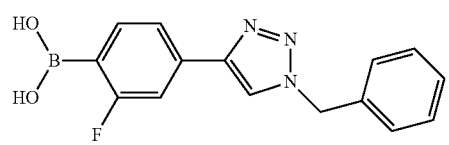

137

Part A

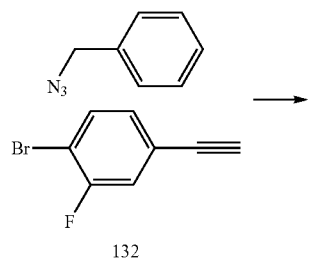

132

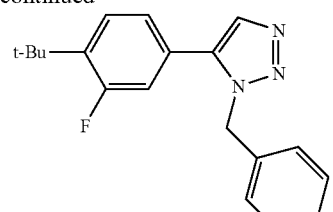

135

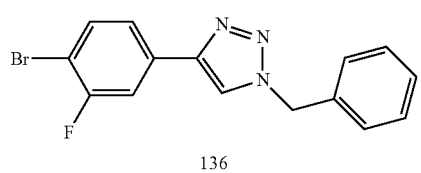

136

4-Bromo-3-fluorophenylacetylene (900 mg, 4.5 mmol, 1.0 equiv) and benzyl azide (600 mg, 4.5 mmol, 1.0 equiv) were suspended in water (15 ml) and heated in a sealed tube at 120° C. for 24 h. The mixture was cooled and extracted with ethyl acetate (50 ml), and the organic layer was washed with brine and dried over sodium sulfate. The 1,5-triazole 135 (10% yield) was precipitated from 40% ethyl acetate/hexanes, and the 1,4-triazole 136 (25% yield) was isolated after purification of the mother liquor by flash silica gel chromatography (5→60% ethyl acetate/hexanes).

Part B

The 1,4 isomer 136 was converted to boronic acid 137 by Method 4 and Method 5. [M–H]⁻=296.1 m/z. Activity: B Example 125

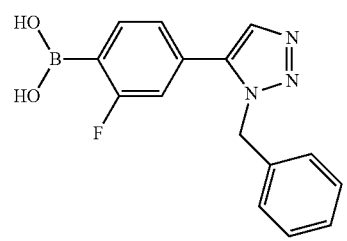

138

The 1,5-triazole-arylbromide 135 was converted to the arylboronic acid 138 by Method 1. [M—H]⁻=296.1 m/z. Activity: C Example 126

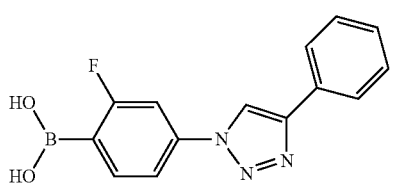

141

Part A

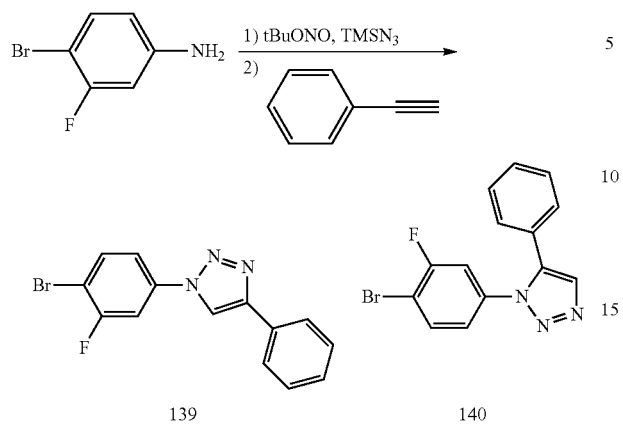

4-Bromo-3-fluoroaniline (1.0 g, 5.26 mmol, 1.0 equiv) was dissolved in 25 ml of CH3-CN and cooled to 0° C. With stirring, tert-BuONO (1.04 ml, 7.9 mmol, 1.5 equiv) was added portionwise over 5 minutes, followed by dropwise addition of trimethylsilylazide (0.67 g, 5.8 mmol, 1.2 equiv). The resulting pale-yellow solution was stirred at 23° C. for 1.5 h. The mixture was then diluted with water (50 ml) and extracted with ethyl acetate (50 ml). The organic layer was washed with water (50 ml), then brine (30 ml) and then dried over sodium sulfate. Concentration in vacuo gave a yellow oil used without purification.

Crude azide (490 mg, 2.25 mmol, 1.0 equiv) and phenylacetylene (231 mg, 2.25 mmol, 1.0 equiv) were suspended in water (15 ml) and heated in a sealed tube at 120° C. for 24 h. The mixture was cooled and extracted with ethyl acetate (50 ml), and the organic layer was washed with brine and dried over sodium sulfate. The 1,5-triazole 140 (25% yield) was precipitated from 40% ethyl acetate/hexanes, and the 1,4-triazole 139 (45% yield) was isolated after purification of the mother liquor by flash silica gel chromatography (5→60% ethyl acetate/hexanes).

Part B

The 1,4-regioisomer 141 was converted to the arylboronic acid by Method 4. [M−H]⁻=282.1 m/z. Activity: B Example 127

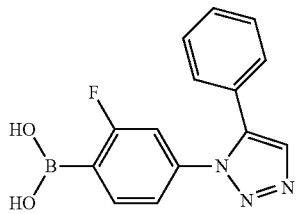

The 1,5-triazole-arylbromide 142 was converted to the arylboronic acid by Method 1. [M−H]=282.1 m/z. Activity: C Example 128

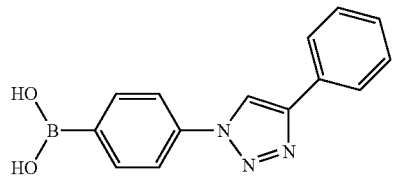

1,4-Triazole 143 was prepared according to the procedure described in example 126. [M−H]⁻=264.1 m/z. Activity: A Example 129

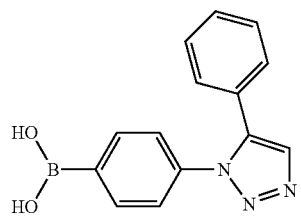

1,5-Triazole 144 was prepared according to the procedure described in example 127. [M−H]⁻=264.1 m/z. Activity: B Example 130

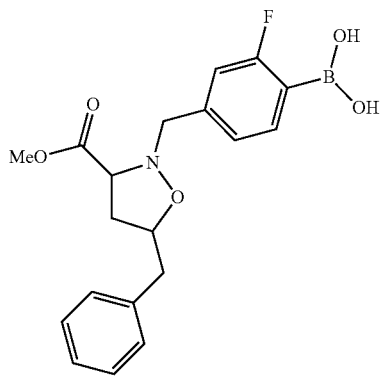

Part A

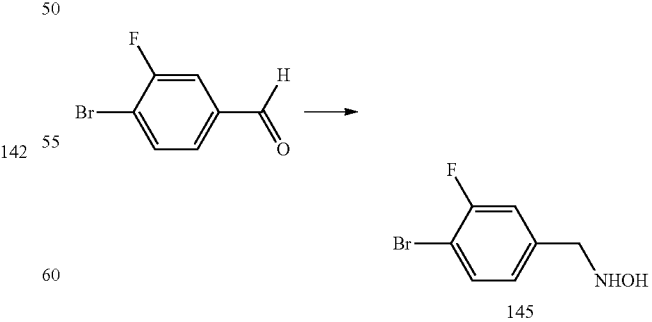

A flask is charged with 4-bromo-3-fluorobenzylaldehyde (1.5 g, 7.5 mmol, 1.0 equiv) in MeOH-THF (3:1, 20 mL) was added an aqueous solution of hydroxylamine (0.67 g, 1.3 equiv. in 2 mL water) in one portion. The ph was adjusted to 9 with 6N KOH, and stirred at rt for 2 h. After the disappearance of the aldehyde by TLC analysis, sodium cyanoborohydride (0.93 g, 2 equiv.) was added and the solution was acidified to pH 2-3 using concentrated HCl. The solution was allowed to stir over night. The solution was basified with 2N KOH to a pH of 11, extracted with DCM (3×50 mL), dried, concentrated in vacuo to afford a off white solid hydroxylamine 145 (1.4 g).

Part B

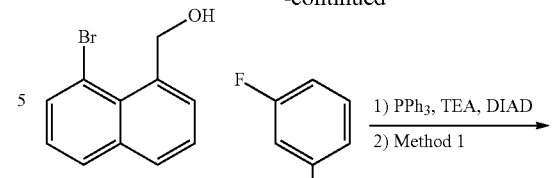

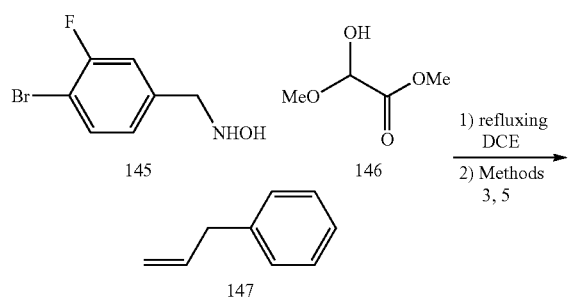

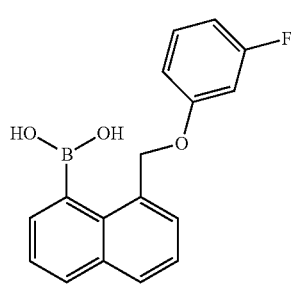

The mixture of 145 (500 mg, 1.0 equiv.), 146 (820 mg, 3 equiv.), 147 (400 mg, 1.5 equiv.) and 1 g of 4 Å molecular sieves in 5 mL of 1,2-dichloroethane was heated at reflux for 14 h. TLC analysis showed no more starting material remaining. The mixture was cooled to rt and filtered to remove sieves and wash solid with ethyl acetate. The organic mixtures were washed with brine, dried and concentrated. Purification on silica gel (0-30% ethyl acetate in hexanes) gave isoxazolidine as a yellow oil (470 mg). Conversion to the boronic acid 148 was achieved by Methods 3 and 5. [M−H]⁻=372.1 m/z. Activity: B Example 131

(8-Bromo-1-naphthyl)methanol 149 (210 mg, 1.0 equiv.), phenol 150 (130 mg, 1.3 equiv.), triphenylphosphine (465 mg, 2.0 equiv.), triethylamine (0.25 mL, 2.0 equiv.) were dissolved in 2 mL THF and cooled to 0° C. under nitrogen. Diisopropyl azodicarboxylate (0.34 mL, 2.0 equiv.) was added dropwise and the mixture was warmed to rt and stirred overnight. The mixture was concentrated and purified using flash silica gel chromatography (12 g, 0-10% EtOAc in hexanes) to provide coupled product 100 mg. Conversion to boronic acid 151 was achieved by Method 1. [M−H]⁻=295.1 m/z. Activity: D Example 132

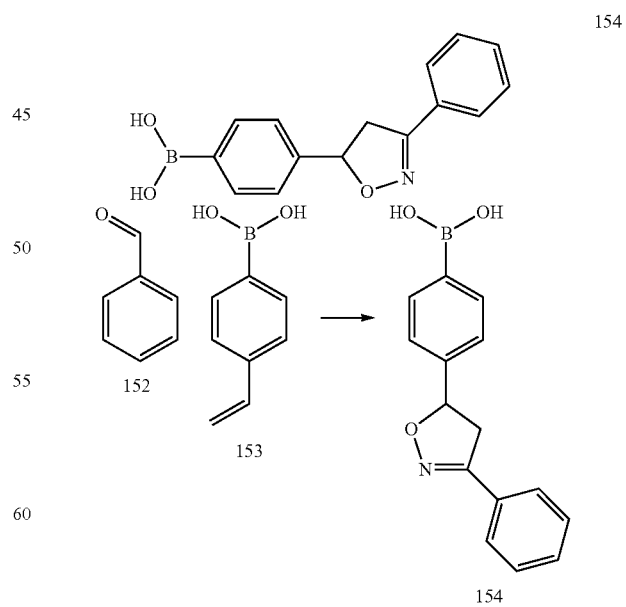

Compound 152 was synthesized via Method 12 from 152 and 153. [M−H]⁻=266.1 m/z. Activity: A

Example 133
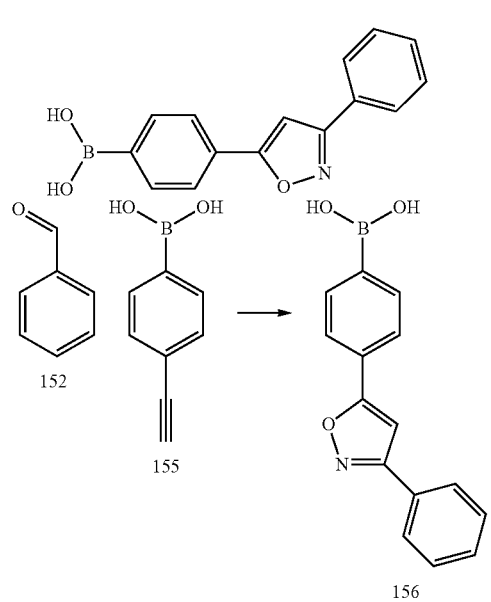
Compound 156 was synthesized via Method 12 from 152 and 155. [M−H]⁻=264.1 m/z. Activity: A
Example 134
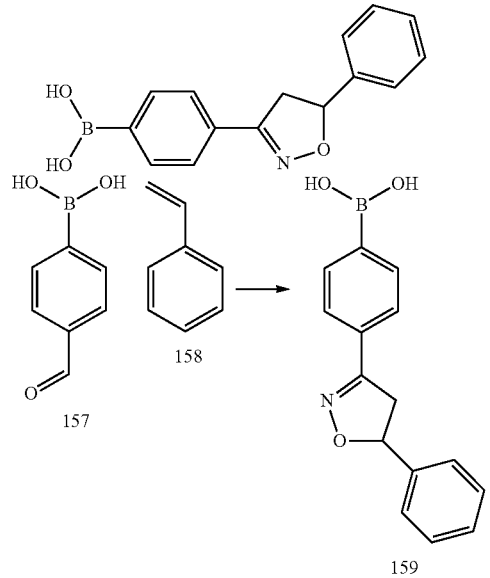
Compound 159 was synthesized via Method 12 from 157 and 158. [M−H]⁻=266.1 m/z. Activity: A
Example 135
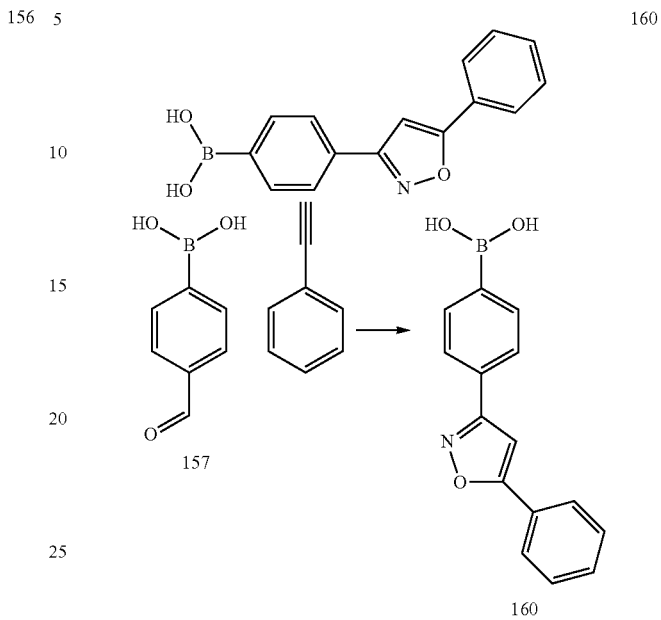
Compound 160 was synthesized via Method 12 from phenylacetylene and 157. [M−H]⁻=264.1 m/z. Activity: A
Example 136
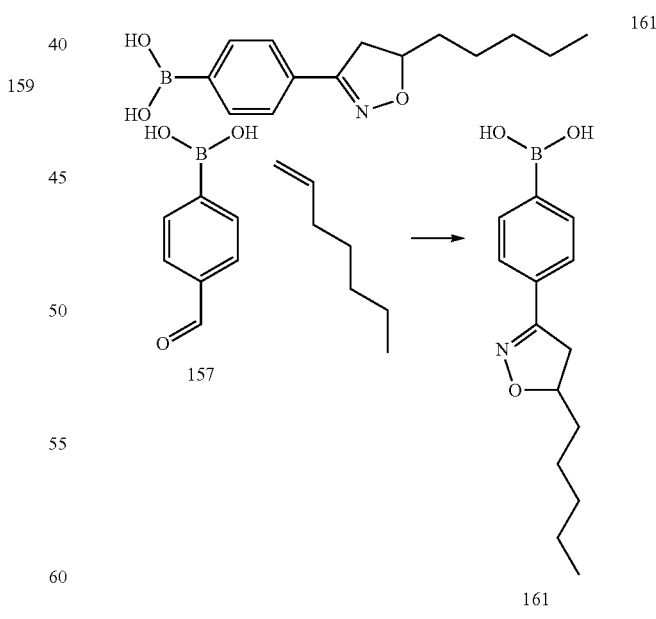
Compound 161 was synthesized via Method 12 from 1-heptene and 157. [M−H]⁻=260.2 m/z. Activity: A

Example 137
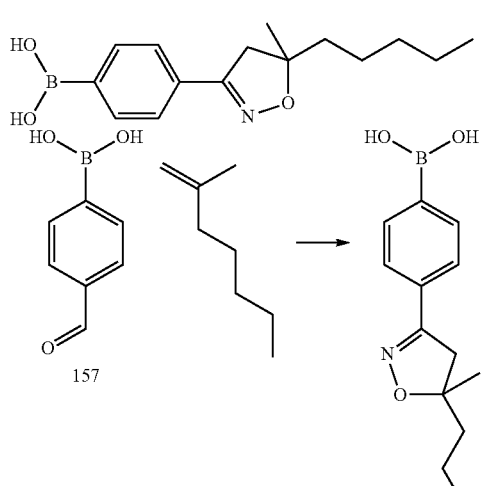
Compound 162 was synthesized via Method 12 from 2-methyl-1-heptene and 157. [M−H]⁻=274.2 m/z. Activity: A
Example 138
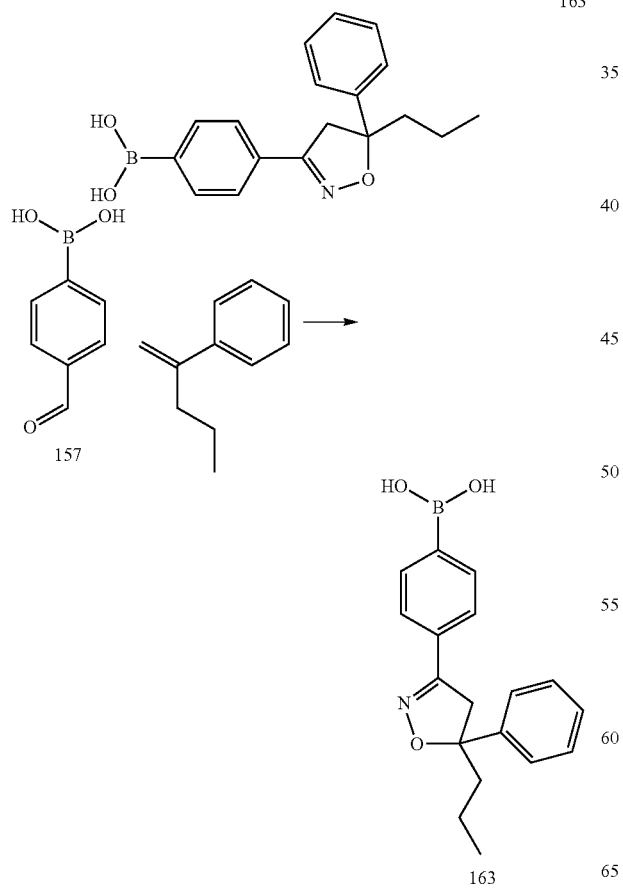
Compound 163 was synthesized via Method 12 from β-propylstyrene and 157. [M−H]⁻=308.2 m/z. Activity: C
Example 139
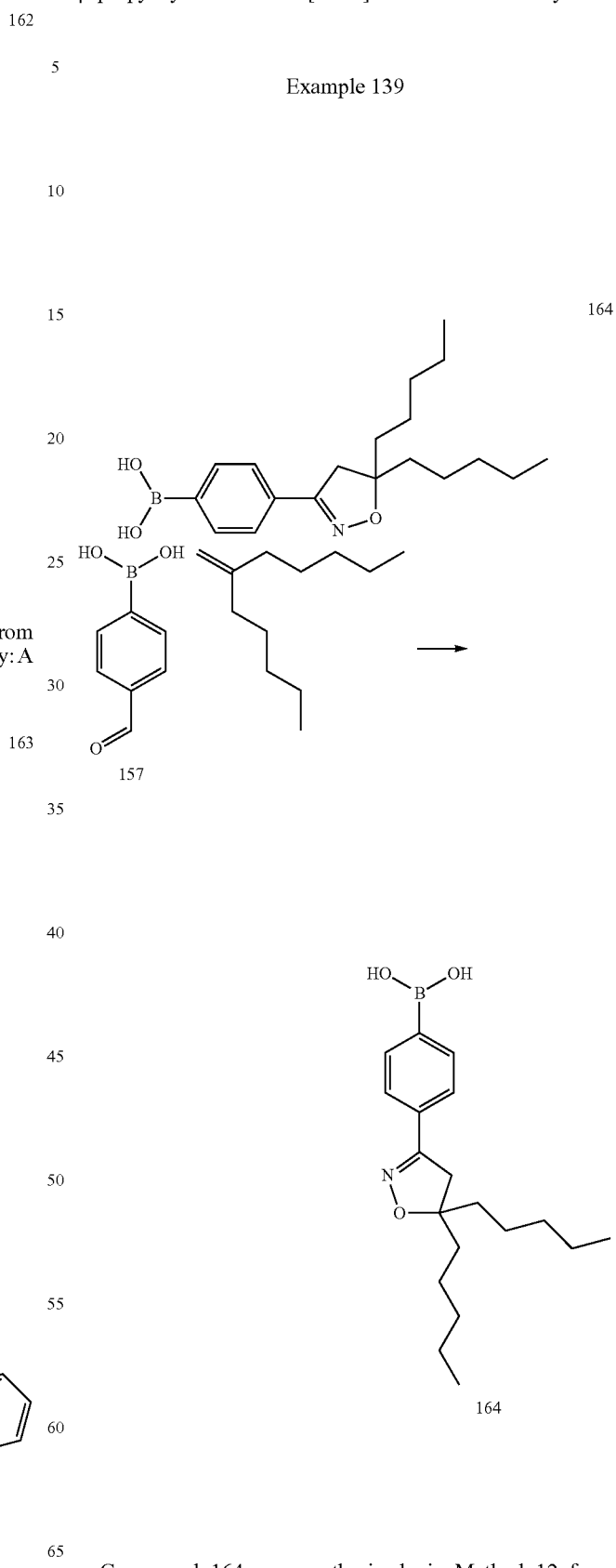
Compound 164 was synthesized via Method 12 from 2-pentyl-1-hexene and 157. [M−H]⁻=330.2 m/z. Activity: C

Example 140

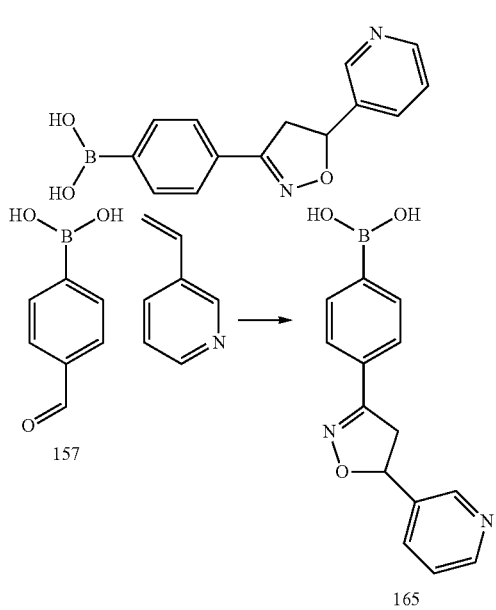

Compound 165 was synthesized via Method 12 from 3-vinylpyridine and 157. [M−H]⁻=267.1 m/z. Activity: B

Example 142

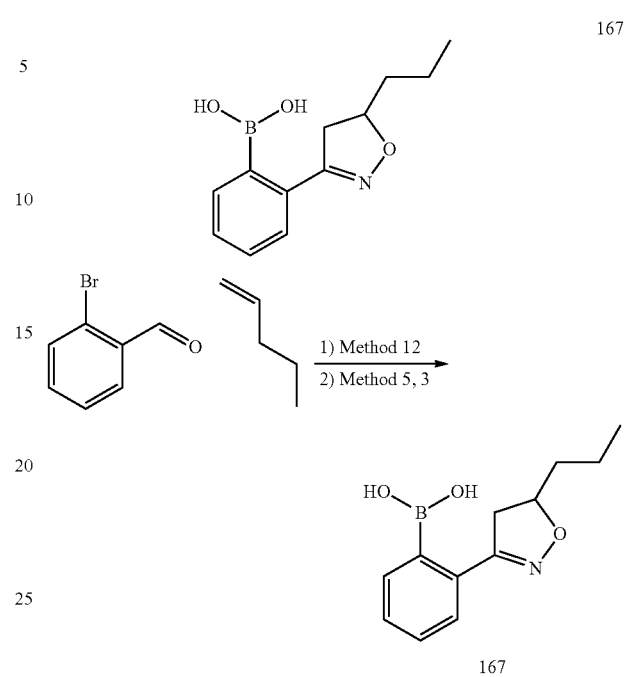

Compound 167 was synthesized via Method 12 from 2-bromobenzaldehdye and 1-pentene, followed by methods 5 and 3. [M−H]⁻=232.1 m/z. Activity: B

Example 141

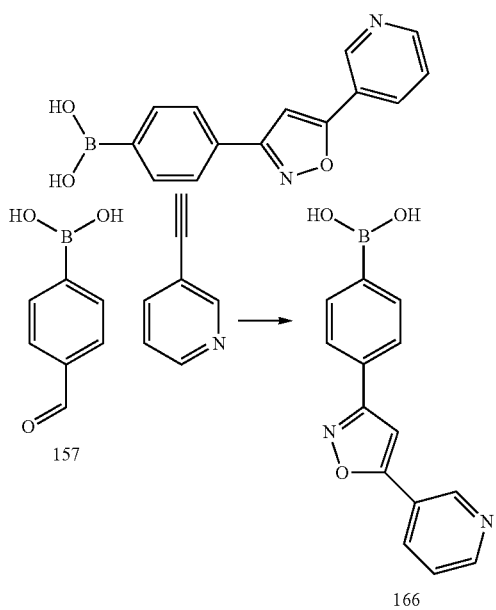

Compound 166 was synthesized via Method 12 from 3-pyridylacetylene and 157. [M−H]⁻=265.1 m/z. Activity: A

Example 143

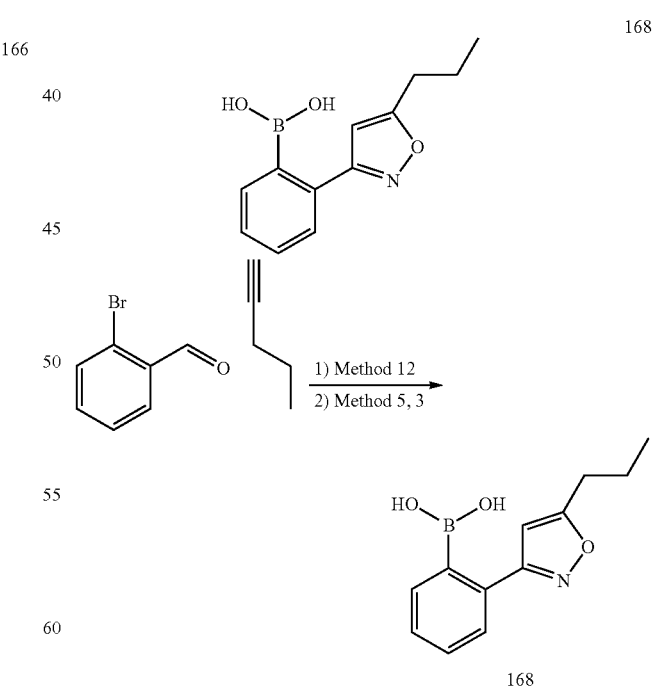

Compound 168 was synthesized via Method 12 from 2-bromobenzaldehdye and 1-pentyne, followed by methods 5 and 3. [M−H]⁻=230.1 m/z. Activity: D

Example 144

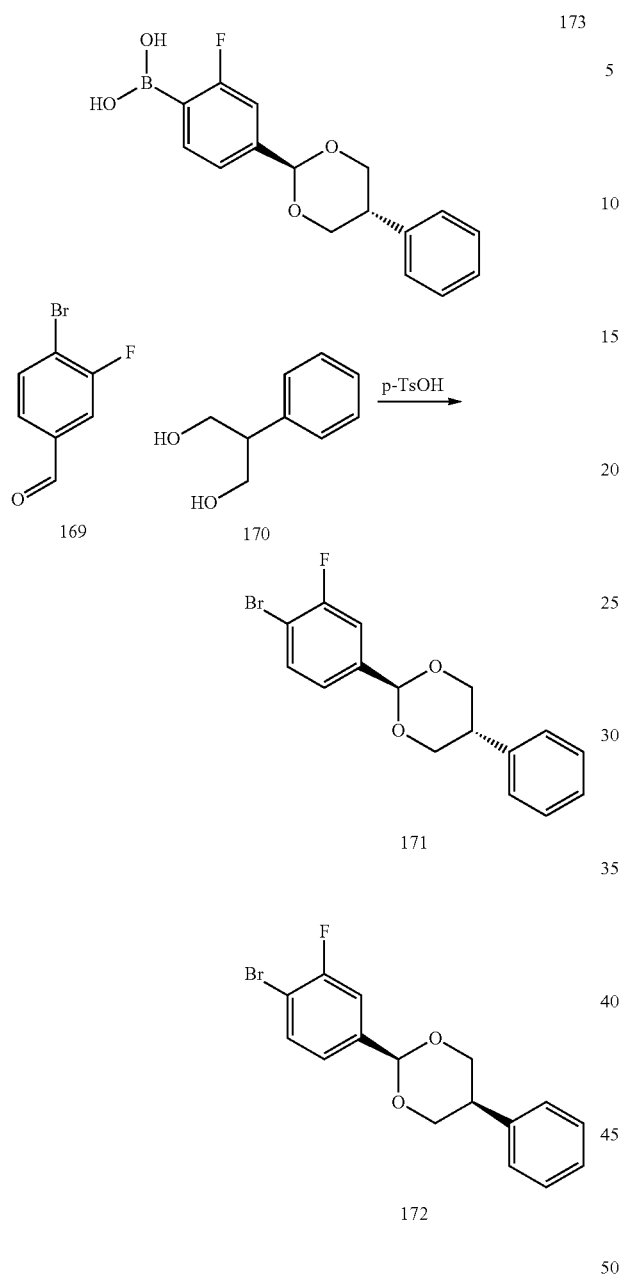

A mixture of 1,3-dihydroxypropane 170 (340 mg, 2 mmol, 1.0 equiv.), 4-bromo-3-fluorobenzaldehyde 169 (450 mg, 2 mmol, 1.0 equiv.), and p-toluenesulfonic acid (0.1 g, 0.25 equiv.) in toluene (30 mL) was refluxed for 24 h with a Dean-Stark trap attached for removal of water. The mixture was diluted with EtOAc, washed with sat. sodium bicarbonate and brine, dried and concentrated. The crude mixture was purified on a silica gel column (5-20% EtOAc in hexane) to give major isomer 171 (210 mg) and minor isomer 172 (70 mg). Compound 173 was synthesized from 171 according to Method 1. [M–H]⁻=301.1 m/z. Activity: A

Example 145

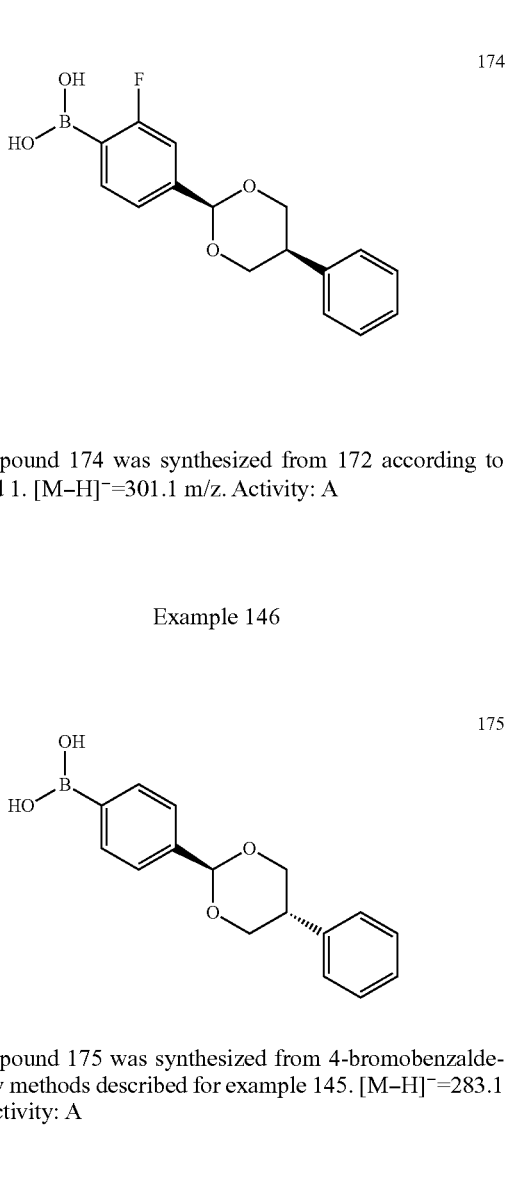

Compound 174 was synthesized from 172 according to Method 1. [M–H]⁻=301.1 m/z. Activity: A

Example 146

175

Compound 175 was synthesized from 4-bromobenzaldehyde by methods described for example 145. [M–H]⁻=283.1 m/z. Activity: A

Example 147

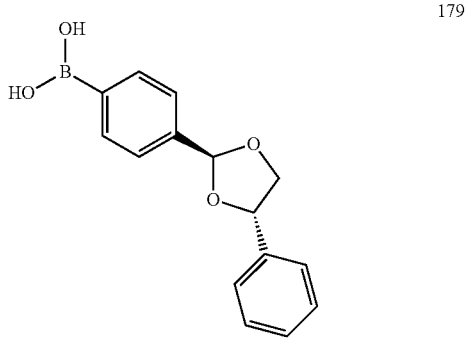 [SMILES: OB(O)c1ccc([C@H]2OC[C@H](c3ccccc3)O2)cc1]

Step A

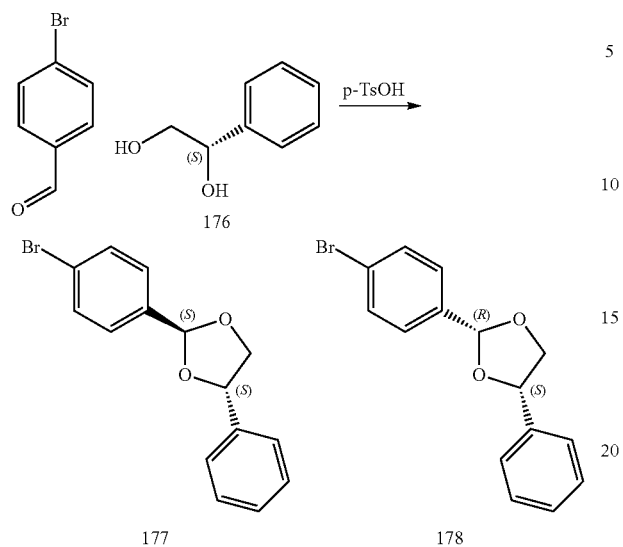

To a mixture of diol 176 (540 mg, 3.9 mmol, 1.0 equiv.), 4-bromobenzaldehyde (795 mg, 4.3 mmol, 1.1 equiv.), and p-toluenesulfonic acid (1 g, 5.3 mmol, 1.3 equiv) in toluene (6 mL) was added crushed molecular sieves 1.2 g. The mixture was stirred at rt for 3.5 h, then 10 ml of sat. NaHCO₃ was added. The mixture was filtered through celite, washed with EtOAc. The combined organic layers were washed with water, brine, dried and concentrated. The crude was purified on a silica gel column (hexane to 5-20% EtOAc in hexane) to give trans product 177 590 mg and cis product 178 540 mg.

Step B

Compound 179 was synthesized from 177 by Method 1. [M–H]⁻=269.1 m/z. Activity: A Example 148

Compound 180 was synthesized from 178 by Method 1. [M–H]⁻=269.1 m/z. Activity: A Example 149

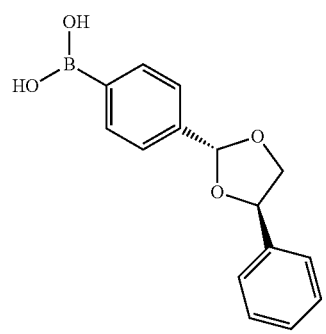

Boronic acid 181 was prepared by methods described for example 147. [M–H]⁻=269.1 m/z. Activity: A Example 150

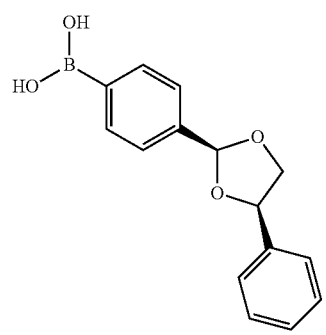

Boronic acid 182 was prepared by methods described for example 148. [M–H]⁻=269.1 m/z. Activity: A Example 151

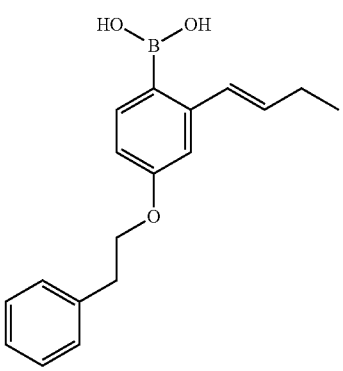

201

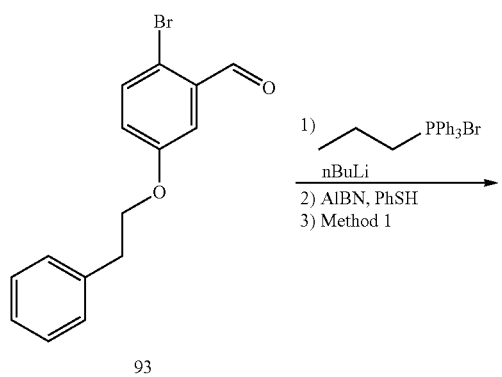

93

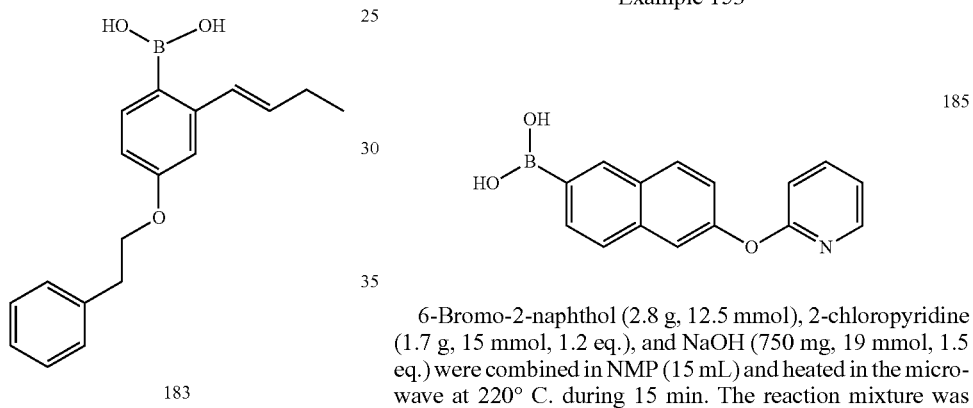

183

To the suspension of propyltriphenylphosphonium bromide (140 mg, 1.1 equiv.) in 3 mL of THF is added drop wise 0.16 mL of a 2.5 M solution of BuLi in hexanes under nitrogen at 0 C. After 15 min, the red solution is cooled at −78° C. and treated with benzaldehyde 93 (100 mg, 1 equiv.) in 1 mL THF. After an additional 15 min, the solution was slowly warmed to rt for 1 h, then water (2 ml) and brine (10 ml) are added followed by an extractive workup using ethyl acetate (100 ml). The organic extract is dried (MgSO$_4$), filtered, concentrated, and purified to give desired product olefin as 1:3 trans to cis mixture. The mixture was dissolved in 2 ml toluene, AIBN (5 mg) and PhSH (5 µl) were added. The solution was heated to 80° C. for 2 h, cooled to rt and filtered through short silica gel column. Hexanes was used to wash the product out and the combined solution was concentrated to give the aryl bromide as a single trans isomer. The aryl bromide was converted by Method 1 to boronic acid 183. [M−H]$^-$=295.1 m/z. Activity: B

202

Example 152

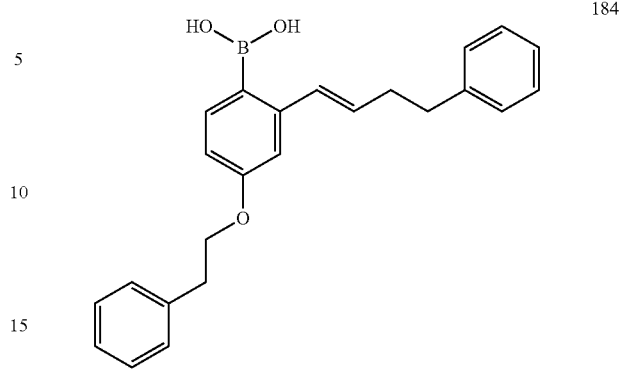

184

Compound 184 was by methods described for example 151, using 3-phenylpropyl triphenylphosphonium bromide in place of propyltriphenylphosphonium bromide. [M−H]= 371.2 m/z. Activity: C Example 153

185

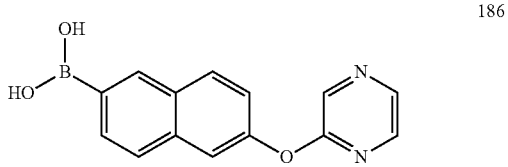 [SMILES: OB(O)c1ccc2cc(Oc3cnccn3)ccc2c1]

6-Bromo-2-naphthol (2.8 g, 12.5 mmol), 2-chloropyridine (1.7 g, 15 mmol, 1.2 eq.), and NaOH (750 mg, 19 mmol, 1.5 eq.) were combined in NMP (15 mL) and heated in the microwave at 220° C. during 15 min. The reaction mixture was diluted with water and extracted into MTBE; the organic phase was dried on Na$_2$SO$_4$ and concentrated. Chromatography on silica (1→10% EtOAe/hexanes) gave 6-bromonaphthalene-2-(2-pyridyl)ether as a white solid, 3.31 g. This material was converted to the 6-pinacolboronate via Method 3 and the free boronate via Method 5, giving compound 185 as a white solid (1.11 g, 38%). [M−H]$^-$=264.1 m/z. Activity: A Example 154

186

6-Hydroxynaphthalene-2-boronic acid (1.5 g, 8 mmol) was dissolved in MTBE (75 mL) and stirred with pinacol (943 mg, 8 mmol) for 1 h, then dried on Na$_2$SO$_4$ and concentrated to crude pinacol ester which was used without further purification.

This crude ester (220 mg, 0.81 mmol), NaOH (150 mg, 3.7 mmol, 4.5 eq.), and chloropyrazine (215 uL, 2.4 mmol, 3 eq.)

were dissolved in DMF (3 mL) and heated via microwave at 160° C. for 15 min. Dilution with water and extraction into EtOAc, followed by purification via chromatography on silica gel (4→20% EtOAc/hexanes) gave the pinacol ester as a yellow oil. This was deprotected to the free boronic acid via Method 5 to give 186 as a yellowish solid (172 mg, 79%), approx. 90% pure by rp-hplc. [M−H]⁻=265.1 m/z. Activity: A Example 155

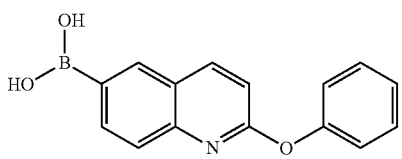

187

6-Bromo-2-chloroquinoline (2.5 g, 10.3 mmol) was converted, via Methods 11, 3, and 5, to compound 187 (1.31 g, 47%) as a white solid. [M−H]⁻=264.1 m/z. Activity: A Example 156

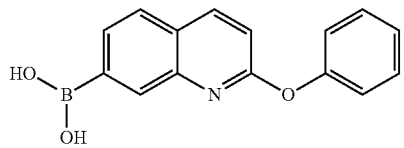

188

7-Bromo-2-chloroquinoline (250 mg, 1.0 mmol) was converted, via Methods 11, 3, and 5, to compound 188 (113 g, 41%) as a white solid. [M−H]⁻=264.1 m/z. Activity: A Example 157

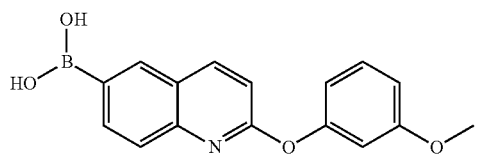

189

6-Bromo-2-chloroquinoline (250 mg, 1.0 mmol) and 3-methoxyphenol (330 uL, 3. eq.) were converted, via Methods 11, 3, and 5, to compound 189 (141 mg, 46%) as a white solid. [M−H]⁻=294.1 m/z. Activity: A Example 158

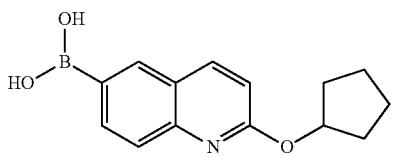

190

6-Bromo-2-chloroquinoline (250 mg, 1.0 mmol) and potassium tert-butoxide (230 mg, 2.0 eq.) were dissolved in cyclopentanol (3 mL) and heated by microwave at 150° C. for 30 min. Extraction from water into MTBE and drying on Na₂SO₄ gave the crude ether. This was converted, via Methods 3 and 5, to compound 190 (66 mg, 25%) as a yellow waxy solid. [M−H]⁻=256.1 m/z. Activity: A Example 159

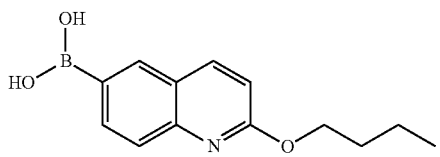

191

6-Bromo-2-chloroquinoline (250 mg, 1.0 mmol) and potassium tert-butoxide (230 mg, 2.0 eq.) were dissolved in n-butanol (3 mL) and heated by microwave at 150° C. for 30 min. Extraction from water into MTBE and drying on Na₂SO₄ gave the crude ether. This was converted, via Methods 3 and 5, to compound 191 (74 mg, 29%). [M−H]⁻=244.1 m/z. Activity: A Example 160

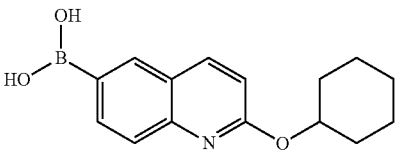

192

6-Bromo-2-chloroquinoline (250 mg, 1.0 mmol) and potassium tert-butoxide (230 mg, 2.0 eq.) were dissolved in cyclohexanol (3 mL) and heated at 120° C. for 16 hours. Extraction from water into MTBE and drying on Na₂SO₄ gave the crude ether. This was converted, via Methods 3 and 5, to compound 192 (156 mg, 57%). [M−H]⁻=270.1 m/z. Activity: B

Example 161

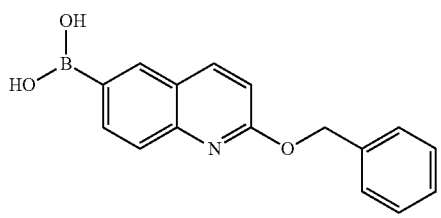

193

6-Bromo-2-chloroquinoline (200 mg, 0.8 mmol) and NaH (40 mg, 2.0 eq.) were dissolved in BnOH (2 mL) and heated at 120° C. for 16 hours. Extraction from water into MTBE and drying on $Na_2SO_4$ gave the crude ether. This was converted, via Methods 3 and 5, to compound 193 (40 mg, 18%). [M−H]⁻=278.1 m/z. Activity: A

Example 162

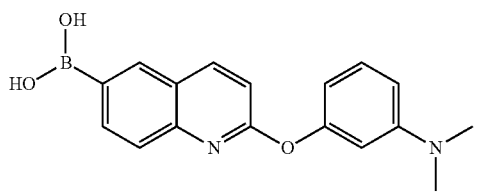

194

6-Bromo-2-chloroquinoline (250 mg, 1.0 mmol) and 3-(dimethylamino)phenol (3 mmol, 3.0 eq.) were converted, via Methods 11, 3, and 5, to compound 194 (140 mg, 44%). [M−H]⁻=307.1 m/z. Activity: A

Example 163

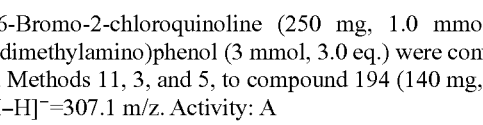

195

6-Bromo-2-chloroquinoline (250 mg, 1.0 mmol) and 3-nitrophenol (3 mmol, 3.0 eq.) were converted, via Methods 11, 3, and 5, to compound 195 (83 mg, 26%). [M−H]⁻=309.1 m/z. Activity: A

Example 164

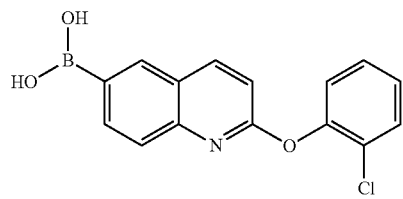

196

6-Bromo-2-chloroquinoline (250 mg, 1.0 mmol) and 2-chlorophenol (3 mmol, 3.0 eq.) were converted, via Methods 11, 3, and 5, to compound 196 (132 mg, 43%). [M−H]⁻=298.1 m/z. Activity: A

Example 165

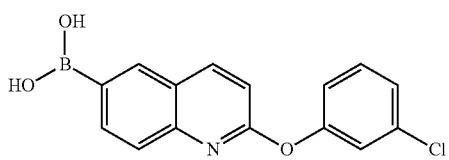

197

6-Bromo-2-chloroquinoline (250 mg, 1.0 mmol) and 3-chlorophenol (3 mmol, 3.0 eq.) were converted, via Methods 11, 3, and 5, to compound 197 (93 mg, 30%). [M−H]⁻=298.1 m/z. Activity: A

Example 166

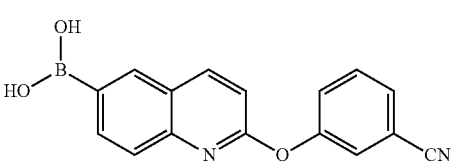

198

6-Bromo-2-chloroquinoline (250 mg, 1.0 mmol) and 3-cyanophenol (3 mmol, 3.0 eq.) were converted, via Methods 11, 3, and 5, to compound 198 (46 mg, 15%). [M−H]⁻=289.1 m/z. Activity: A

Example 167

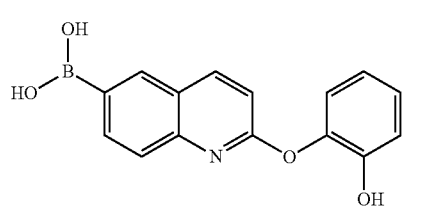

199

6-Bromo-2-chloroquinoline (250 mg, 1.0 mmol) and catechol (3 mmol, 3.0 eq.) were converted, via Methods 11, 3, and 5, to compound 199 (78 mg, 28%). [M–H]⁻=280.2 m/z. Activity: A Example 168

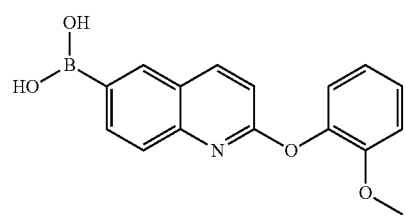
200

6-Bromo-2-chloroquinoline (250 mg, 1.0 mmol) and guaiacol (3 mmol, 3.0 eq.) were converted, via Methods 11, 3, and 5, to compound 200 (159 mg, 61%). [M–H]⁻=294.1 m/z. Activity: A Example 169

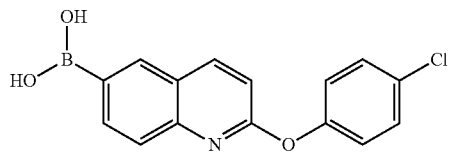
201

6-Bromo-2-chloroquinoline (250 mg, 1.0 mmol) and 4-chlorophenol (3 mmol, 3.0 eq.) were converted, via Methods 11, 3, and 5, to compound 201 (63 mg, 21%). [M–H]⁻=298.1 m/z. Activity: A Example 170

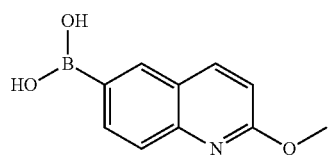
202

6-Bromo-2-chloroquinoline (200 mg, 0.8 mmol) and 25% methanolic NaOMe (2 mL) were heated at 50° C. for 16 hours. Extraction from water into EtOAc and drying on Na₂SO₄ gave the crude ether. This was converted, via Methods 3 and 5, to compound 202 (110 mg, 66%). [M–H]⁻=202.1 m/z. Activity: B Example 171

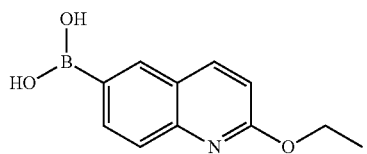
203

Ethoxyquinoline 203 was prepared by methods used for example 170. (110 mg, 66%). [M–H]⁻=215.1 m/z. Activity: B Example 172

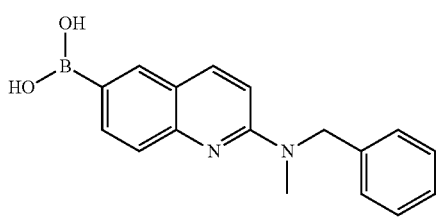
204

6-Bromo-2-chloroquinoline (200 mg, 0.8 mmol) and N-methylbenzylamine (2 mL) were heated at 120° C. for 16 hours. Extraction from 2M NaOH into DCM and drying on Na₂SO₄ gave the crude 2-aminoquinoline. This was converted, via Methods 3 and 5, to compound 204 (110 mg, 46%). [M–H]⁻=291.1 m/z. Activity: A Example 173

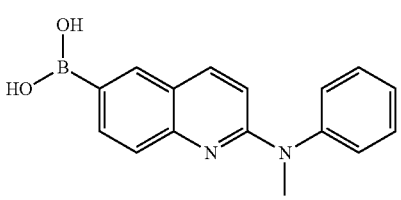
205

6-Bromo-2-chloroquinoline (250 mg, 1.0 mmol) and N-methylaniline (2 mL) were heated at 120° C. for 16 hours. Extraction from 2M NaOH into DCM and drying on Na₂SO₄ gave the crude 2-aminoquinoline. This was converted, via Methods 3 and 5, to compound 205 (88 mg, 31%). [M–H]⁻=277.0 m/z. Activity: B

Example 174

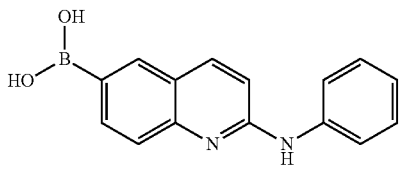

206

6-Bromo-2-chloroquinoline (1 g, 4.1 mmol) and aniline (8 mL) were heated at 100° C. for 16 hours. Some dark color was removed by pushing through a plug of silica gel with MTBE. The eluent was taken up in hexanes, washed with water, and concentrated; the residue was shaken with water (100 mL) and hexanes (20 mL), giving a beige solid which was collected by filtration and washed with water. This material was converted, via Methods 3 and 5, to compound 206 (647 mg, 60%). [M−H]⁻=263.1 m/z. Activity: A

Example 175

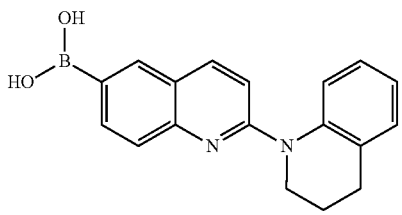

207

6-Bromo-2-chloroquinoline (250 mg, 1.0 mmol) and tetrahydroquinoline (2 mL) were heated at 120° C. for 16 hours. The material was taken up in DCM (20 mL) and treated with NEt₃ (6 mL) and Ac₂O (3 mL) for 2 h, then extracted from 0.1 M NaOH into DCM. Drying on Na₂SO₄ and concentration gave a crude residue which was converted, via Methods 3 and 5, to compound 207 (151 mg, 48%). [M−H]⁻=303.1 m/z. Activity: B

Example 176

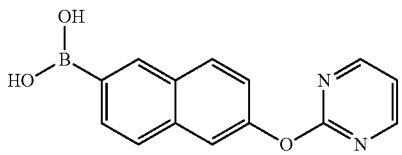

208

6-hydroxynaphthalene-2-boronic acid (1.5 g, 8 mmol) was dissolved in MTBE (75 mL) and stirred with pinacol (943 mg, 8 mmol) for 1 h, then dried on Na₂SO₄ and concentrated to crude pinacol ester which was used without further purification.

This crude ester (220 mg, 0.81 mmol), NaOH (150 mg, 3.7 mmol, 4.5 eq.), and 2-bromo-pyrimidine (390 mg, 2.4 mmol, 3.0 eq.) were dissolved in DMF (3 mL) and heated via microwave at 160° C. for 15 min. Dilution with water and extraction into EtOAc, followed by purification via chromatography on silica gel (4→20% EtOAc/hexanes) gave the pinacol ester as a yellow oil. This was deprotected to the free boronic acid via Method 5 to give 208 (54 mg, 25%). [M−H]⁻=265.1 m/z. Activity: A

Example 177

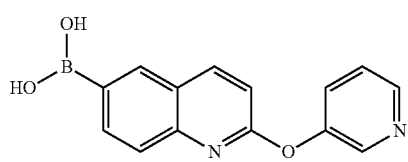

209

6-Bromo-2-chloroquinoline (250 mg, 1.0 mmol) and 3-hydroxypyridine (3 mmol, 3. eq.) were converted, via Methods 11, 3, and 5, to compound 209 (69 mg, 26%). [M−H]⁻=265.1 m/z. Activity: A

Example 178

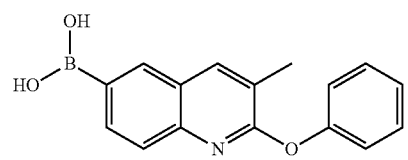

210

A solution of 4-bromoaniline (9.0 g, 52.3 mmol) in PhMe (100 mL) and pyridine (8.5 mL, 110 mmol, 2.0 eq.) was cooled in an ice bath and slowly treated with propionyl chloride (5.5 mL, 63 mmol, 1.2 eq.). After 2 h, the reaction mixture was added to 0.1 M HCl and extracted into EtOAc. Concentration followed by recrystallization of the residue from EtOH/water gave N-propionyl-4-bromoaniline (10.64 g, 89%). [M−H]⁻=278.1 m/z.

Phosphorous oxychloride (3 mL, excess) was treated with DMF (650 uL, 8.7 mmol, 1.5 eq.) and the solution allowed to return to ambient temperature. N-propionyl-4-bromoaniline (1.32 g, 5.8 mmol, 1 eq.) was added and the mixture heated at 85° C. for 4 h. The hot mixture was poured onto ice (100 g), stirred until melted, and the solids were collected by filtration. Washing with water and drying in vacuo gave clean 6-bromo-2-chloro-3-methylquinoline (914 mg, 61%).

This intermediate (250 mg, 1.0 mmol) and phenol (3 mmol, 3. eq.) were converted, via Methods 11, 3, and 5, to compound 210 (118 mg, 42%). [M−H]⁻=278.1 m/z. Activity: A

Example 179

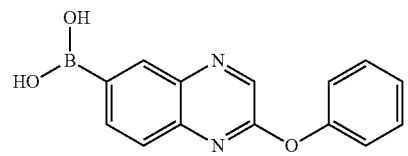

211

2-Quinoxalinol (2.9 g, 20 mmol) and silver sulfate (3.1 g, 10 mmol, 0.5 eq.) in sulfuric acid (20 mL) were treated with bromine (1.03 mL, 20 mmol, 1.0 eq.). After stirring at ambient temperature for 18 h, the reaction mixture was diluted with carbon tetrachloride (50 mL), heated to 50° C., and filtered. The filtrate was poured onto ice and the solids collected by filtration and recrystallized from HOAc, giving 6-bromo-2-quinoxalinol (1.8 g, 40%).

6-Bromo-2-quinoxalinol (631 mg) in POCl$_3$ (6.3 mL) was refluxed for 2 h, then poured onto ice. The solution was neutralized to pH 7 by addition of NH$_4$OH, and the resulting solid collected by filtration. Washing with water and drying in vacuo gave 6-bromo-2-chloroquinoxaline (627 mg, 92%).

This intermediate (250 mg, 1.0 mmol) and phenol (3 mmol, 3.0 eq.) were converted, via Methods 11, 3, and 5, to compound 211 (4.4 mg, 2%). [M−H]$^-$=265.1 m/z. Activity: B Example 180

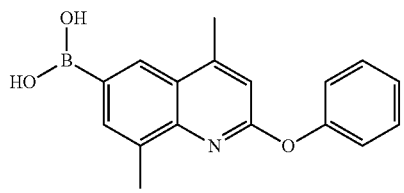

212

4-Bromo-2-methylaniline (1.8 g, 10 mmol) in PhMe (25 mL) was treated with ethyl acetoacetate (1.3 mL, 11 mmol, 1.1 eq.) and refluxed during 18 h. Upon cooling a precipitate of N-acetoacetyl-4-bromo-2-methylaniline (1.59 g, 60%) formed, which was collected by filtration and used without further purification.

This acetoacetamide (1 g, 3.7 mmol) was dissolved in sulfuric acid (5 mL) and heated at 120° C. during 2 h. The hot solution was poured onto ice (100 g), giving a white solid which was collected by filtration, washed with water, and dried in vacuo to give 6-bromo-4,8-dimethyl-2-quinolone (418 mg, 45%).

This quinolone (410 mg, 1.6 mmol) in POCl$_3$ (5 mL) was refluxed for 2 h, then poured onto ice. The solution was neutralized to pH 7 by addition of NH$_4$OH, and the resulting solid collected by filtration. Washing with water and drying in vacuo gave 6-bromo-2-chloro-4,8-dimethyl-quinoline (407 mg, 93%).

This intermediate (200 mg, 0.74 mmol) and phenol (3 mmol, 3.0 eq.) were converted, via Methods 11, 3, and 5, to compound 212 (141 mg, 65%). [M−H]$^-$=292.1 m/z. Activity: B Example 181

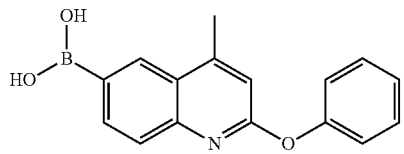

213

Compound 213 was produced in a manner analogous to compound 212, using 4-bromoaniline in place of 4-bromo-2-methylaniline. Yield 131 mg. [M−H]$^-$=278.1 m/z. Activity: A Example 182

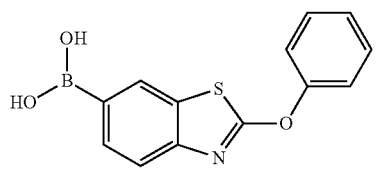

214

A solution of 6-bromobenzothiazolin-2-one (500 mg, 2.2 mmol) in POCl$_3$ (5 mL) was refluxed during 18 h, then poured onto ice. The solution was neutralized to pH 9 by addition of NH$_4$OH, and the resulting solid collected by filtration. Washing with water and drying in vacuo gave 6-bromo-2-chlorobenzothiazole (450 mg, 83%).

This intermediate (200 mg, 0.8 mmol) and phenol (3 mmol, 3.0 eq.) were converted, via Methods 11, 3, and 5, to compound 214 (25 mg, 12%). [M−H]$^-$=270.1 m/z. Activity: A Example 183

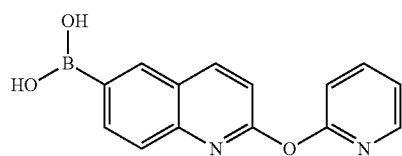

215

6-Bromo-2-chloroquinoline (500 mg, 2.0 mmol) and 2-hydroxypyridine (3 mmol, 3.0 eq.) were converted, via Methods 11, 3, and 5, to compound 215 (35 mg, 7%). [M−H]$^-$=265.1 m/z. Activity: A Example 184

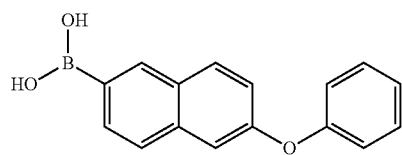

216

6-Hydroxynaphthalene-2-boronic acid (1.5 g, 8 mmol) was dissolved in MTBE (75 mL) and stirred with pinacol (943 mg, 8 mmol) for 1 h, then dried on Na$_2$SO$_4$ and concentrated to crude pinacol ester which was used without further purification.

Phenylboronic acid (140 mg, 1.1 mmol, 2.0 eq.) was coevaporated with PhMe twice to produce the anhydride. This was treated with crude 6-hydroxynaphthalene-2-boronic acid pinacol ester (150 mg, 0.56 mmol), DCM (5 mL), NEt$_3$ (400 uL, 3 mmol, 5 eq.), and cupric acetate (100 mg, 0.53 mmol, 0.95 eq.) and stirred at ambient temperature during 16 h. The mixture was extracted from 0.1M NaOH into DCM, dried on Na$_2$SO$_4$, concentrated, and chromatographed on silica gel (0→2% EtOAc/hexanes) to give 6-phenoxynaphthalene-2-boronic acid pinacol ester, which was deprotected via Method 5 to provide compound 216 (54 mg, 37%). [M−H]$^-$=263.1 m/z. Activity: A Example 185

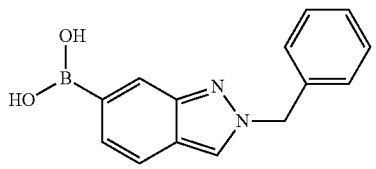

217

The corresponding pinacol ester (22 mg, 0.066 mmol) was cleaved according to Method 5 to give compound 217 (17 mg, quant.). [M−H]$^-$=251.1 m/z. Activity: A Example 186

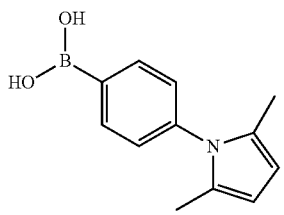

218

The corresponding bromide (256 mg, 1.0 mmol) was reacted according to Method 2 to give compound 218 (37 mg, 17%). [M−H]$^-$=214.1 m/z. Activity: D Example 187

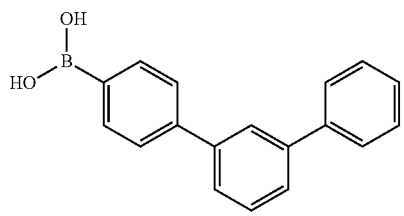

219

The corresponding bromide (336 mg, 1.1 mmol) was converted via Methods 3 and 5 to compound 219 (77 mg, 26%). [M−H]$^-$=273.1 m/z. Activity: B Example 188

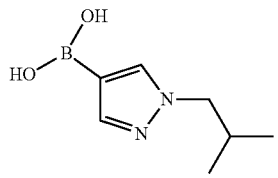

220

The corresponding pinacol ester (200 mg, 0.8 mmol) was cleaved according to Method 5 to give compound 220 (89 mg, 66%). [M−H]=181.1 m/z. Activity: C Example 189

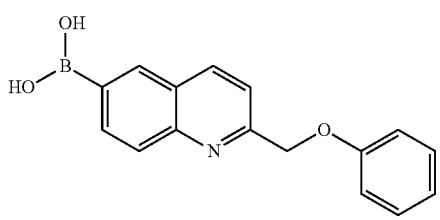

221

6-Bromoquinaldine (1 g, 4.5 mmol) in CCl$_4$ (6 mL) was treated with NBS (750 mg, 4.2 mmol, 0.95 eq.) and a few crystals of benzoyl peroxide and refluxed during 2 h. The hot solution was filtered, the filtrated cooled, and the resulting crystals collected by filtration and used without further purification.

A solution of phenol (60 mg, 0.63 mmol, 2.0 eq.) in NMP was treated with 60% NaH dispersion (25 mg, 0.63 mmol, 2.0 eq.) and the dibromoquinaldine produced in the previous step (150 mg, 0.31 mmol). After stirring at ambient temperature for 18 h, the reaction was extracted from 0.1M NaOH into MTBE, dried on Na$_2$SO$_4$, concentrated, and chromatographed on silica gel (0→10% EtOAc/hexanes) to give a-phenoxy-6-bromoquinaldine (93 mg, 94%).

This bromide was converted via Methods 3 and 5 to compound 221 (48 mg, 58%). [M−H]$^-$=278.1 m/z. Activity: B Example 190

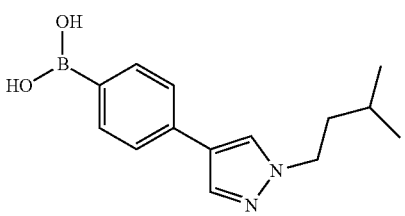

222

4-Bromoiodobenzene (460 mg, 1.6 mmol, 1.5 eq.), 1-isoamylpyrazole-4-boronic acid (200 mg, 1.1 mmol), potassium acetate (100 mg, 1.0 eq.), Pd(dppf)Cl$_2$ (100 mg, 0.1 eq.), and Cs$_2$CO$_3$ (1 g, 3.0 eq.) in DMSO (5 mL) were heated under argon at 80° C. during 1 h. The reaction mixture was extracted from water into ether, dried Na$_2$SO$_4$, concentrated, and chromatographed on silica gel (0→10% EtOAc/hexanes) to give 1-isoamyl-4-(4-bromophenyl)pyrazole (263 mg, 82%).

This bromide was converted via Methods 3 and 5 to compound 222 (147 mg, 64%). [M−H]=257.2 m/z. Activity: A Example 191

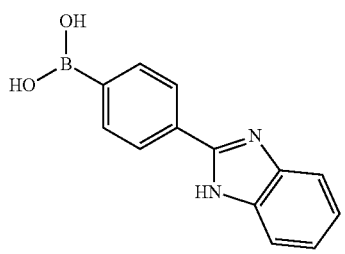

223

The corresponding iodide (125 mg, 0.4 mmol) was converted via Methods 3 and 5 to compound 223 (9 mg, 10%). [M−H]$^-$=237.1 m/z. Activity: D Example 192

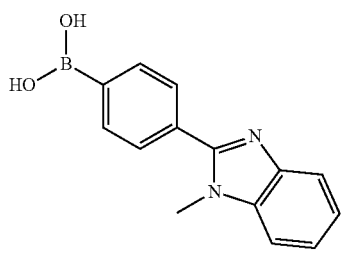

224

2-(4-Iodophenyl)benzimidazole (200 mg, 0.6 mmol) was methylated with iodomethane (180 mg, 1.2 mmol, 2.0 eq.) and NaH (45 mg, 1.8 mmol, 3 eq.) in DMF (3 mL) for 18 h. Dilution with diethyl ether, washing with water, drying over Na$_2$SO$_4$, and chromatography (10→25% EtOAc/hexanes) gave 1-methyl-2-(4-iodophenyl)benzimidazole (124 mg, 59%).

This iodide was converted via Method 2 to compound 224 (9 mg, 10%). Activity: D

Example 193

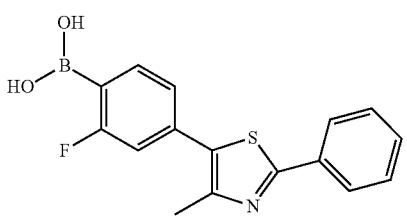

225

4-Bromo-3-fluoroiodobenzene (250 mg, 0.7 mmol, 1.2 eq.), 4-methyl-2-phenylthiazole-5-boronic acid pinacol ester (170 mg, 0.6 mmol), potassium acetate (70 mg, 1.0 eq.), Pd(dppf)Cl$_2$ (70 mg, 0.1 eq.), and Cs$_2$CO$_3$ (700 mg, 3.0 eq.) in DMSO (5 mL) were heated under argon at 80° C. during 1 h. The reaction mixture was extracted from water into diethyl ether, dried over Na$_2$SO$_4$, concentrated, and chromatographed on silica gel (5→10% EtOAc/hexanes) to give the corresponding bromide to 225 (169 mg, 85%).

This bromide was converted via Methods 3 and 5 to compound 225 (15 mg, 10%). Activity: B Example 194

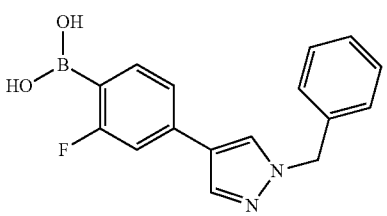

226

4-Bromo-3-fluoroiodobenzene (250 mg, 0.8 mmol, 1.2 eq.), 1-benzylpyrazole-4-boronic acid pinacol ester (200 mg, 0.7 mmol), potassium acetate (70 mg, 1 eq.), Pd(dppf)Cl$_2$ (70 mg, 0.1 eq.), and Cs$_2$CO$_3$ (700 mg, 3.0 eq.) in DMSO (5 mL) were heated under argon at 80° C. during 1 h. The reaction mixture was extracted from water into diethyl ether, dried over Na$_2$SO$_4$, concentrated, and chromatographed on silica gel (5→10% EtOAc/hexanes) to give the corresponding bromide to 226 (193 mg, 83%).

This bromide was converted via Methods 3 and 5 to compound 226 (13 mg, 8%). [M−H]$^-$=295.1 m/z. Activity: A Example 195

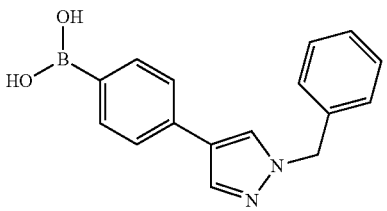

227

4-Bromo-iodobenzene (240 mg, 0.8 mmol, 1.2 eq.), 1-benzylpyrazole-4-boronic acid pinacol ester (200 mg, 0.7 mmol), potassium acetate (70 mg, 1 eq.), Pd(dppf)Cl$_2$ (70 mg, 0.1 eq.), and Cs$_2$CO$_3$ (700 mg, 3.0 eq.) in DMSO (5 mL) were heated under argon at 80° C. during 1 h. The reaction mixture was extracted from water into diethyl ether, dried over Na$_2$SO$_4$, concentrated, and chromatographed on silica gel (5→10% EtOAc/hexanes) to give 1-benzyl-4-(4-bromophenyl)pyrazole (218 mg, 99%).

This bromide was converted via Methods 3 and 5 to compound 227 (142 mg, 73%). [M−H]$^-$=277.1 m/z. Activity: A

Example 196

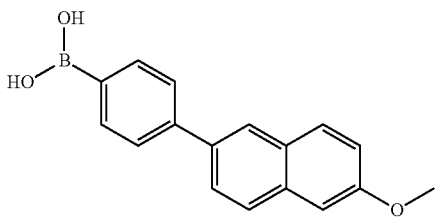

228

4-Bromo-iodobenzene (250 mg, 0.9 mmol, 1.2 eq.), 2-methoxynaphthalene-6-boronic acid (150 mg, 0.7 mmol), potassium acetate (70 mg, 1.0 eq.), Pd(dppf)Cl$_2$ (70 mg, 0.1 eq.), and Cs$_2$CO$_3$ (700 mg, 3.0 eq.) in DMSO (5 mL) were heated under argon at 80° C. during 1 h. The reaction mixture was extracted from water into diethyl ether, dried over Na$_2$SO$_4$, concentrated, and chromatographed on silica gel (5→20% EtOAc/hexanes) to 2-methoxy-6-(4-bromophenyl)naphthalene (131 mg, 56%).

This bromide was converted via Methods 3 and 5 to compound 228 (47 mg, 41%). [M–H]$^-$=277.1 m/z. Activity: B

Example 197

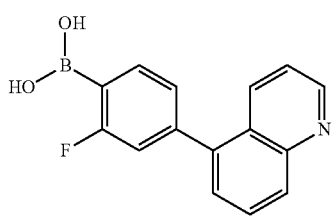

229

4-Bromo-3-fluoroiodobenzene (250 mg, 0.8 mmol, 1.2 eq.), quinoline-5-boronic acid (120 mg, 0.7 mmol), potassium acetate (70 mg, 1 eq.), Pd(dppf)Cl$_2$ (70 mg, 0.1 eq.), and Cs$_2$CO$_3$ (700 mg, 3.0 eq.) in DMSO (5 mL) were heated under argon at 80° C. during 1 h. The reaction mixture was extracted from water into ether, dried over Na$_2$SO$_4$, concentrated, and chromatographed on silica gel (5→20% EtOAc/hexanes) to give 5-(4-bromo-3-fluorophenyl)quinoline (220 mg, quant.).

This bromide was converted via Methods 3 and 5 to compound 229 (39 mg, 20%). [M–H]$^-$=266.1 m/z. Activity: B

Example 198

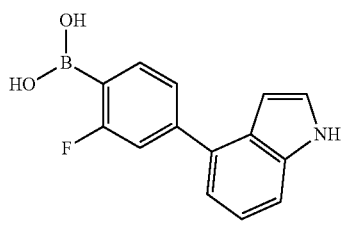

230

4-Bromo-3-fluoroiodobenzene (250 mg, 0.8 mmol, 1.2 eq.), indole-4-boronic acid (110 mg, 0.7 mmol), potassium acetate (70 mg, 1 eq.), Pd(dppf)Cl$_2$ (70 mg, 0.1 eq.), and Cs$_2$CO$_3$ (700 mg, 3 eq.) in DMSO (5 mL) were heated under argon at 80° C. during 1 h. The reaction mixture was extracted from water into ether, dried Na$_2$SO$_4$, concentrated, and chromatographed on silica gel (5→15% EtOAc/hexanes) to give 4-(4-bromo-3-fluorophenyl)indole (164 mg, 83%).

This bromide was converted via Methods 3 and 5 to compound 230 (77 mg, 53%). [M–H]$^-$=254.1 m/z. Activity: B

Example 199

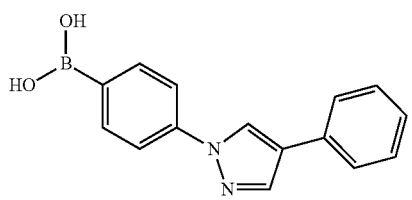

231

2-Phelylmalondialdehyde (200 mg, 1.4 mmol) in EtOH (10 mL) was treated with 4-bromophenylhydrazine HCl (300 mg, 1.4 mmol) and NEt$_3$ (200 uL, 1.4 mmol) and refluxed for 1 h. The solution was diluted slightly with water, chilled, and the resulting precipitate of 1-(4-bromophenyl)-4-phenylpyrazole collected by filtration (179 mg, 44%).

This bromide was converted via Methods 3 and 5 to compound 231 (35 mg, 23%). [M–H]$^-$=263.1 m/z. Activity: A

Example 200

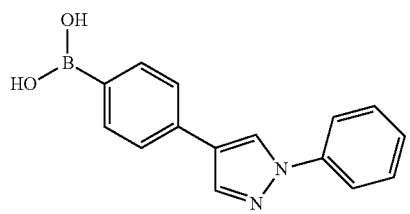

232

2-(4-Bromophenyl)malondialdehyde (250 mg, 1.1 mmol) in EtOH (10 mL) was treated with phenylhydrazine (110 uL, 1.1 mmol) and refluxed for 1 h. The solution was diluted slightly with water, chilled, and the resulting precipitate of 4-(4-bromophenyl)-1-phenylpyrazole collected by filtration (270 mg, 82%).

This bromide was converted via Methods 3 and 5 to compound 232 (155 mg, 68%). [M–H]$^-$=263.0 m/z. Activity: A

Example 201

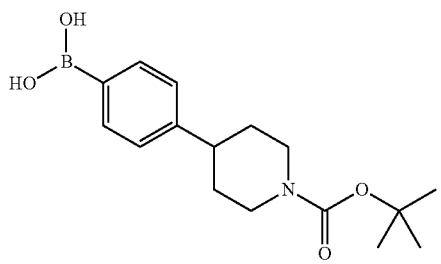

233

4-(4-Bromophenyl)piperidine HCl (1 g, 3.7 mmol) in DCM (6 mL) was treated with K$_2$CO$_3$ (1.3 g, 9 mmol, 2.5 eq.) and Boc2O (1.35 g, 6 mmol, 1.6 eq). The mixture was diluted with water, extracted with MTBE, washed with brine, dried on Na$_2$SO$_4$, and concentrated. Chromatography on silica gel (2>8% EtOAc/hexanes) gave 1 Boc 4 (4-bromophenyl)piperidine (944 mg, 76%). This bromide was converted via Method 3 to 1-Boc-4-(4-boronophenyl)piperidine pinacol ester (1.16 g, quant.).

A portion of this ester (270 mg) was deprotected via Method 5 to give compound 233 (144 mg, 68%). [M–H]$^-$=304.2 m/z. Activity: A

Example 202

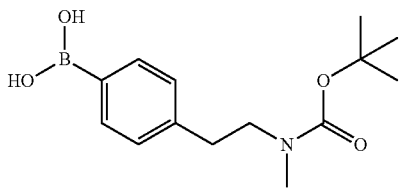

234

4-Bromophenethylamine (2 mL, 13 mmol) in DCM (12 mL) was treated with K$_2$CO$_3$ (2.7 g, 20 mmol, 1.5 eq.) and Boc2O (3.1 g, 14 mmol, 1.1 eq.). The mixture was diluted with water, extracted with MTBE, washed with brine, dried on Na$_2$SO$_4$, and concentrated to give clean N-Boc-4-bromophenethylamine (4 g, quant.).

This carbamate was dissolved in DMF (40 mL) and treated with 60% NaH dispersion (1.7 g, 42 mmol, 3.0 eq.) and MeI (1.7 mL, 28 mmol, 2.0 eq.). After stirring at ambient temperature 18 h, the reaction mixture is extracted from 0.1M NaOH into MTBE, dried on Na$_2$SO$_4$, and concentrated to clean N-Boc-N-methyl-bromophenethylamine (4.67 g, quant.). 1 g of this bromide (3.2 mmol) was converted via Method 3 to N-Boc-N-methyl-4-boronophenethylamine pinacol ester (981 mg, 85%).

A portion of this ester (150 mg) was deprotected via Method 5 to give compound 234 (95 mg, 82%). [M–H]$^-$=278.1 m/z. Activity: A

Example 203

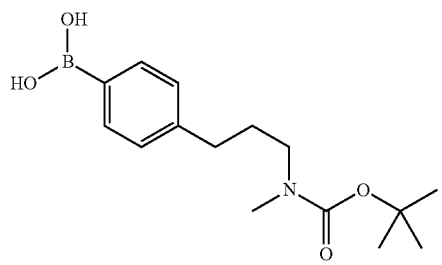

235

A solution of 4-bromodihydrocinnamic acid (1.5 g, 6.6 mmol) in THF (10 mL) and DMF (10 mL) was treated with 2.0M methylamine in THF (10 mL, 3.0 eq.) and HBTU (2.75 g, 7.2 mmol, 1.1 eq.) The mixture was diluted with water, extracted with MTBE, washed with brine, dried on Na$_2$SO$_4$, and pushed through a pad of silica gel using 50% EtOAc/hexanes, giving N-methyl-4-bromodihydrocinnamide.

This amide was dissolved in THF (20 mL) and treated with borane-dimethylsulfide complex (1.25 mL, 13 mmol, 2.0 eq.) and refluxed for 3 h. The reaction was quenched with MeOH, then treated with 6M HCl to a pH of 1 and concentrated in vacuo. The residue was extracted from 1M NaOH into DCM, dried Na$_2$SO$_4$, and concentrated to N-methyl-3-(4-bromophenyl)propylamine (562 mg, 38%) which is used without further purification.

This amine in DCM (5 mL) was treated with K$_2$CO$_3$ (500 mg, 3.7 mmol, 1.5 eq.) and Boc2O (900 mg, 4 mmol, 1.6 eq.). The mixture was diluted with water, extracted with MTBE, washed with brine, dried on Na$_2$SO$_4$, concentrated, and chromatographed to give clean N-Boc-N-methyl-3-(4-bromophenyl)propylamine (546 mg, 68%). This bromide was converted via Method 3 to N-Boc-N-methyl-3-(4-boronophenyl)propylamine pinacol ester (594 mg, 95%).

A portion of this ester (100 mg) was deprotected via Method 5 to give compound 235 (59 mg, 76%). [M–H]$^-$=292.2 m/z. Activity: A

Example 204

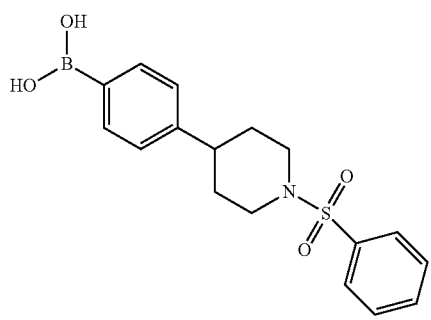

236

1-Boc-4-(4-boronophenyl)piperidine pinacol ester (887 mg, 2.3 mmol), prepared in the synthesis of compound 233, was dissolved in TFA (10 mL), stirred for 1 h, and coevaporated with twice with PhMe to give deprotected salt with pinacol ester intact (by NMR and LC). 190 mg of this salt (0.47 mmol) in DCM (5 mL) was treated with NEt$_3$ (250 uL, 1.8 mmol, 3.8 eq.) and benzenesulfonyl chloride (75 uL, 0.57 mmol, 1.2 eq.). After stirring at ambient temperature 16 h, the reaction mixture was diluted with DCM and concentrated onto silica gel. Chromatography (3→45% EtOAc/hexanes) gave 1-benzenesulfonyl-4-(4-boronophenyl)piperidine pinacol ester. Deprotection of this ester via Method 5 gave compound 236 (80 mg, 49%). [M−H]⁻−344.1 m/z. Activity: B Example 205

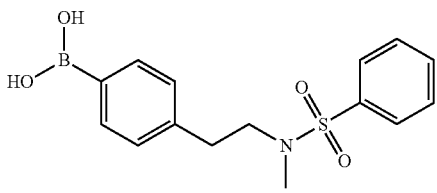

237

N-Boc-N-methyl-4-boronophenethylamine pinacol ester (430 mg), prepared in the synthesis of compound 234, was dissolved in TFA (5 mL), stirred for 1 h, and coevaporated with twice with PhMe to give deprotected salt with pinacol ester intact (by NMR and LC). 208 mg of this salt (0.55 mmol) in DCM (5 mL) was treated with NEt₃ (250 uL, 1.8 mmol, 3.3 eq.) and benzenesulfonyl chloride (85 uL, 0.67 mmol, 1.2 eq.). After stirring at ambient temperature 16 h, the reaction mixture was diluted with DCM and concentrated onto silica gel. Chromatography (2→15% EtOAc/hexanes) gave N-benzenesulfonyl-N-methyl-4-boronophenethylamine pinacol ester. Deprotection of this ester via Method 5 gave compound 237 (117 mg, 66%). [M−H]⁻=318.1 m/z. Activity: A Example 206

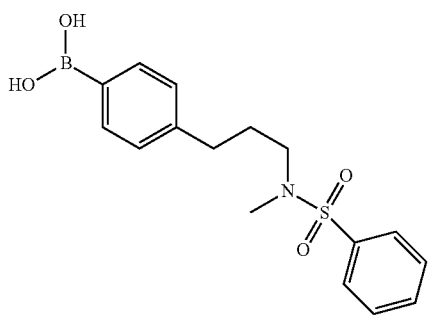

238

N-Boc-N-methyl-3-(4-boronophenyl)propylamine pinacol ester (494 mg), prepared in the synthesis of compound 235, was dissolved in TFA (5 mL), stirred for 1 h, and coevaporated with twice with PhMe to give deprotected salt with pinacol ester intact (by NMR and LC). 256 mg of this salt (0.66 mmol) in DCM (5 mL) was treated with NEt₃ (300 uL, 2.2 mmol, 3.3 eq.) and benzenesulfonyl chloride (100 uL, 0.79 mmol, 1.2 eq.). After stirring at ambient temperature 16 h, the reaction mixture was diluted with DCM and concentrated onto silica gel. Chromatography (2→15% EtOAc/hexanes) gave N-benzenesulfonyl-N-methyl-3-(4-boronophenyl)propylamine pinacol ester. Deprotection of this ester via Method 5 gave compound 238 (135 mg, 62%). [M−H]⁻= 332.1 m/z. Activity: A Example 207

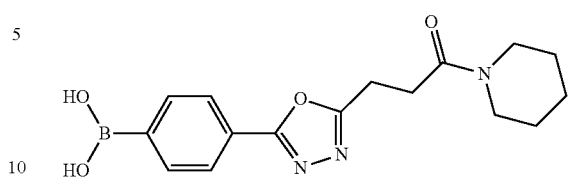

239

Oxadiazole 239 was prepared in 2 steps by first forming the oxadiazole from 4-(4,4,5,5-tetramethyl-1,3,2-dioxaborolan-2-yl)benzohydrazide and 4-oxo-4-(1-piperidinyl)butanoic acid using Method 7 followed by Method 5 and was isolated after precipitation from the reaction mixture. [M−H]⁻=328.1 m/z. Activity: B Example 208

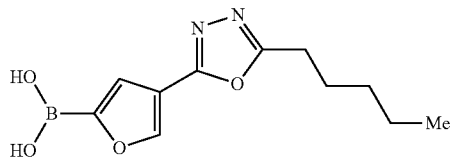

240

Oxadiazole 60 was prepared in 2 steps by first forming the oxadiazole from 5-(4,4,5,5-tetra-methyl-1,3,2-dioxaborolan-2-yl)furan-3-carboxylic acid and hexanoic hydrazide using Method 8 followed by Method 5 and was isolated after precipitation from the reaction mixture. [2M−H₂O]⁻=481.0 m/z. Activity: B Example 209

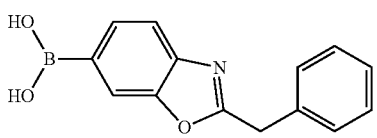

241

Benzoxazole 241 was prepared in 3 steps by first forming the benzoxazole from 2-amino-5-chlorophenol and phenyl acetic acid using Method 13 followed by conversion to the boronate ester using Method 15 followed by Method 5. [M−H]⁻=252.0 m/z. Activity: A Example 210

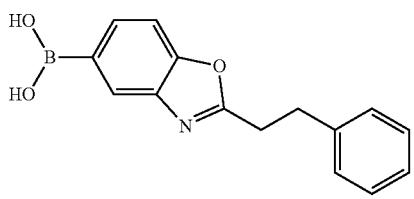

242

Benzoxazole 242 was prepared in 3 steps by first forming the benzoxazole from 2-amino-4-bromophenol and 3-phenylpropionic acid using Method 13 followed by conversion to the boronate ester using Method 3 followed by Method 5. [M−H]⁻=266.1 m/z. Activity: A

Example 211

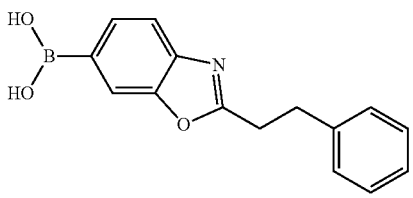
243

Benzoxazole 243 was prepared in 3 steps by first forming the benzoxazole from 2-amino-5-chlorophenol and 3-phenylpropionic acid using Method 13 followed by conversion to the boronate ester using Method 15 followed by Method 5. [M−H]⁻=266.1 m/z. Activity: A

Example 212

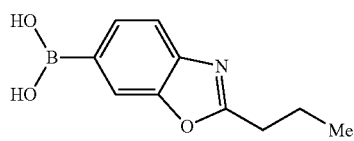
244

Benzoxazole 244 was prepared in 3 steps by first forming the benzoxazole from 2 amino-5-chlorophenol and butyric acid using Method 13 followed by conversion to the boronate ester using Method 15 followed by Method 5. [M−H]⁻=204.1 m/z. Activity: A

Example 213

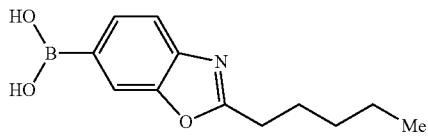
245

Benzoxazole 245 was prepared in 3 steps by first forming the benzoxazole from 2-amino-5-chlorophenol and hexanoic acid using Method 13 followed by conversion to the boronate ester using Method 15 followed by Method 5. [M−H]⁻=233.9 m/z. Activity: A

Example 214

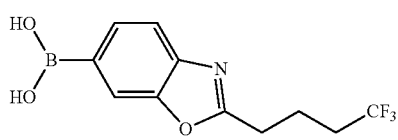
246

Benzoxazole 246 was prepared in 3 steps by first forming the benzoxazole from 2-amino-5-chlorophenol and 5,5,5-trifluoropentanoic acid using Method 13 followed by conversion to the boronate ester using Method 15 followed by Method 5. [M−H]⁻=272.1 m/z. Activity: A

Example 215

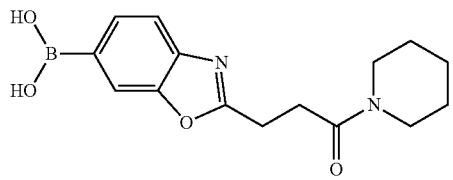
247

Benzoxazole 247 was prepared in 3 steps by first forming the benzoxazole from 2-amino-5-chlorophenol and 4-oxo-4-(1-piperidinyl)butanoic acid using Method 13 followed by conversion to the boronate ester using Method 15 followed by Method 5. [M−H]⁻=301.1 m/z. Activity: B

Example 216

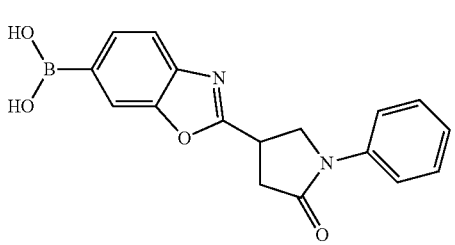
248

Benzoxazole 248 was prepared in 3 steps by first forming the benzoxazole from 2-amino-5-chlorophenol and 5-oxo-1-phenyl-pyrrolidine-3-carboxylic acid using Method 13 followed by conversion to the boronate ester using Method 15 followed by Method 5. [M−H]⁻=321.1 m/z. Activity: B

Example 217

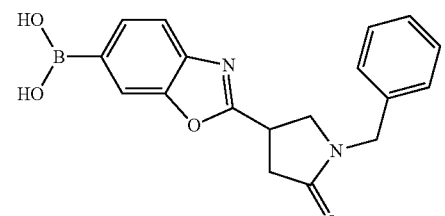
249

Benzoxazole 249 was prepared in 3 steps by first forming the benzoxazole from 2-amino-5-chlorophenol and 5-oxo-1-phenyl-pyrrolidine-3-carboxylic acid using Method 13 followed by conversion to the boronate ester using Method 15 followed by Method 5. [M−H]=335.1 m/z. Activity: B

Example 218

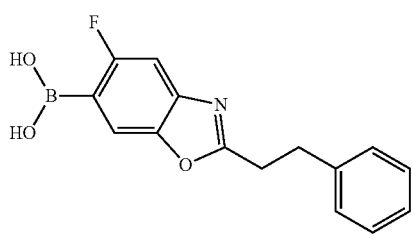

253

Part A

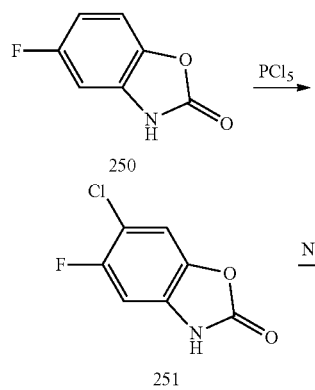

5-Fluoro-2(3H)-benzoxazolone 250 (0.50 g, 1.0 equiv) and phosphorus pentachloride (1.36 g, 2.0 equiv) were placed in a microwave reactor vial. The reaction was sealed and heated to 175° C. in a microwave reactor for 45 min. The reaction was then quenched with excess saturated sodium bicarbonate (100 mL) which resulted in significant fuming. The reaction mixture was then transferred to a separatory funnel with excess water and ethyl acetate at which point the water layer was washed with ethyl acetate (2×50 mL). The organic layers were combined, dried over MgSO$_4$ and concentrated under vacuum to provide 500 mg of the desired product 251 that was taken on directly to the next step.

Compound 251 (0.50 g, 1.0 equiv) was suspended in 10 mL of water in a microwave reactor vial. Sodium hydroxide (1.60 g, 15.0 equiv) was added and the mixture was stirred at room temperature until all the sodium hydroxide dissolved. The reaction was then heated to 150° C. in a microwave reactor for 20 min after which 1N HCl was added until a solid crashes out (pH ~7). The solid is isolated via vacuum filtration, washed with excess water and dried on the high vac to provide 300 mg of the desired aminophenol 252 (70% yield).

Part B

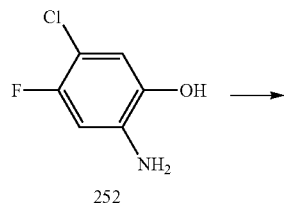

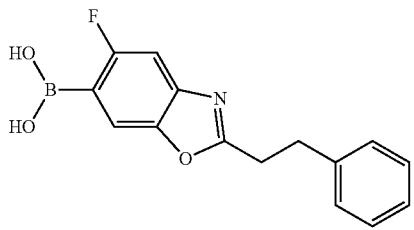

253

Benzoxazole 253 was prepared in 3 steps by first forming the benzoxazole from 2-amino-5-chloro-4-fluorophenol 252 and 3-phenylpropionic acid using Method 13 followed by conversion to the boronate ester using Method 15 followed by Method 5. [M–H]$^-$=284.1 m/z. Activity: A

Example 219

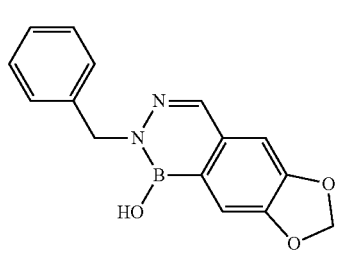

254

Benzodiazoborine 254 was prepared using the analogous procedure as example 98 except that N-benzylhydrazine was used in place of 2-hydroxyethyl hydrazine and (2-formyl-4,5-methylenedioxy)phenylboronic acid was used in place of benzene boronic acid 98. [M–H]$^-$=279.1 m/z. Activity: D

Example 220

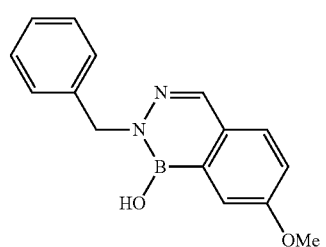

255

Benzodiazoborine 255 was prepared using the analogous procedure as example 98 except that N-benzylhydrazine was used in place of 2-hydroxyethyl hydrazine and 5-methoxy-2-formylphenylboronic acid was used in place of benzene boronic acid 98. [M–H]$^-$=265.1 m/z. Activity: D

Example 221

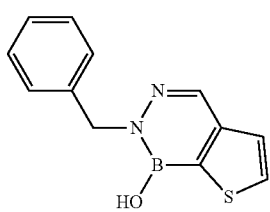
256

Benzodiazoborine 256 was prepared using the analogous procedure as example 98 except that N-benzylhydrazine was used in place of 2-hydroxyethyl hydrazine and 3-formylthiophene-2-boronic acid was used in place of benzene boronic acid 98. [M−H]⁻=241.1 m/z. Activity: D

Example 222

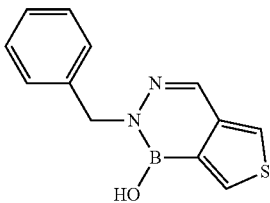
257

Benzodiazoborine 257 was prepared using the analogous procedure as example 98 except that N-benzylhydrazine was used in place of 2-hydroxyethyl hydrazine and 4-formylthiophene-3-boronic acid was used in place of benzene boronic acid 98. [M−H]⁻=241.1 m/z. Activity: D

Example 223

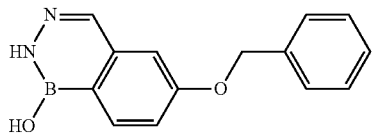
258

Benzodiazoborine 258 was prepared using the analogous procedure as example 98 except that hydrazine was used in place of 2-hydroxyethyl hydrazine and 4-(benzyloxy)-2-formylphenylboronic acid was used in place of benzene boronic acid 98. [M−H]⁻=251.1 m/z. Activity: D

Example 224

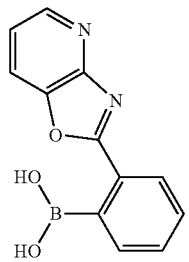
259

Benzoxazole 259 was prepared in 2 steps by first forming the benzoxazole from 2-amino-3-hydroxypyridine and 2-bromo benzoic acid using Method 13 followed by conversion to the boronic acid using Method 1. [M−H]⁻=239.0 m/z. Activity: D

Example 225

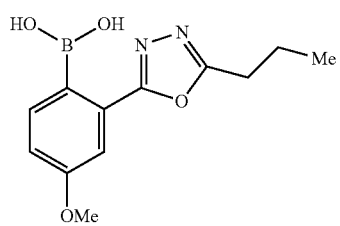
260

Oxadiazole 260 was prepared in 2 steps starting with oxadiazole formation between 2-bromo-5-methoxybenzoic acid and butyric hydrazide using Method 8 followed by lithiation using Method 1. [M−H]⁻=261.1 m/z. Activity: D

Example 226

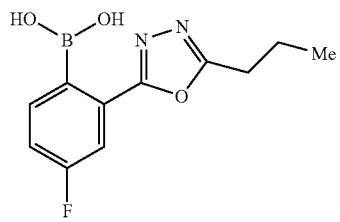
261

Oxadiazole 261 was prepared in 2 steps starting with oxadiazole formation between 2-bromo-5-fluorobenzoic acid and butyric hydrazide using Method 8 followed by lithiation using Method 1. [M−H]⁻=249.0 m/z. Activity: D

Example 227

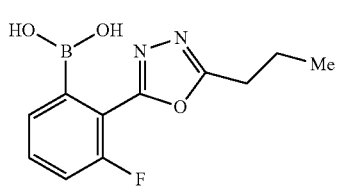
262

Oxadiazole 262 was prepared in 2 steps starting with oxadiazole formation between 2-bromo-6-fluorobenzoic acid and butyric hydrazide using Method 8 followed by lithiation using Method 1. [M–H]⁻=249.2 m/z. Activity: D

Example 228

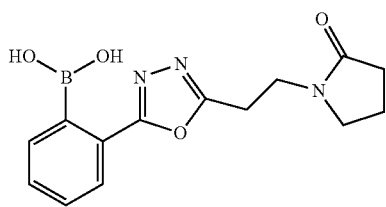
263

Oxadiazole 263 was prepared in 2 steps by first forming the oxadiazole from 2-(4,4,5,5-tetramethyl-1,3,2-dioxaborolan-2-yl)benzohydrazide and 3-(2-oxo-pyrrolidin-1-yl)-propionic acid using Method 7 followed by Method 5 and was isolated after precipitation from the reaction mixture. [M–H]⁻=300.1 m/z. Activity: D

Example 229

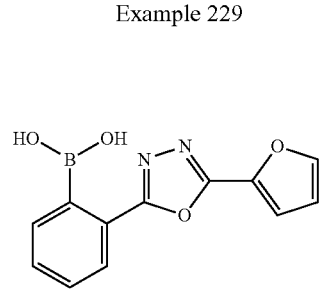
264

Oxadiazole 264 was prepared in 2 steps by first forming the oxadiazole from 2-(4,4,5,5-tetramethyl-1,3,2-dioxaborolan-2-yl)benzoic acid and furoic hydrazide using Method 8 followed by Method 5 and was isolated after precipitation from the reaction mixture. [M–H]=455.1 m/z. Activity: D.

Example 230

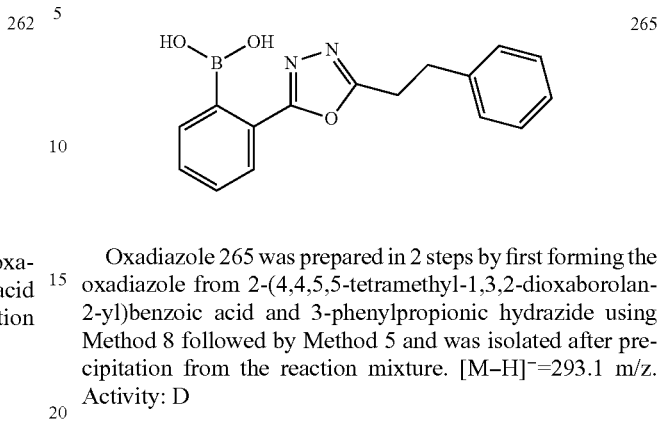
265

Oxadiazole 265 was prepared in 2 steps by first forming the oxadiazole from 2-(4,4,5,5-tetramethyl-1,3,2-dioxaborolan-2-yl)benzoic acid and 3-phenylpropionic hydrazide using Method 8 followed by Method 5 and was isolated after precipitation from the reaction mixture. [M–H]⁻=293.1 m/z. Activity: D

Example 231

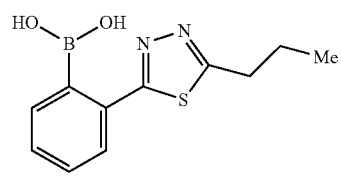
266

Thiadiazole 266 was prepared in 2 steps by first forming the thiadiazole from 2-bromobenzoic acid and butyric hydrazide using Method 9 followed by lithiation using Method 1. [M–H]⁻=247.1 m/z. Activity: D.

Example 232

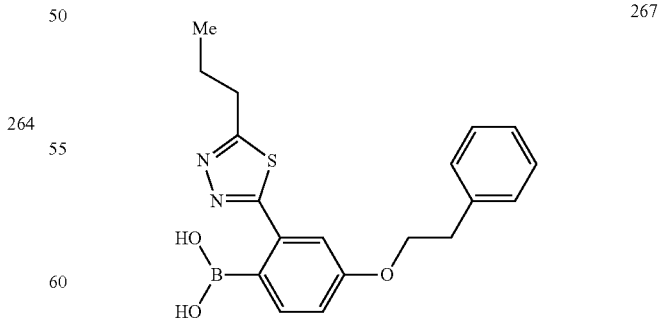
267

Thiadiazole 267 was prepared in 2 steps starting with thiadiazole formation between 2-bromo-5-phenethoxybenzoic acid 16 and propionic hydrazide using Method 9 followed by lithiation using Method 1. [M–H]⁻=267.1 m/z. Activity: A

Example 233

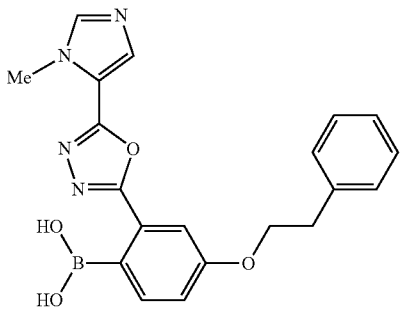

268

Oxadiazole 268 was prepared in 2 steps starting with oxadiazole formation between 2-bromo-5-phenethoxybenzoic acid 16 and 1-methyl-1H-imidazole-5-carbohydrazide using Method 7 followed by lithiation using Method 1. [M−H]⁻= 389.0 m/z. Activity: B.

Example 234

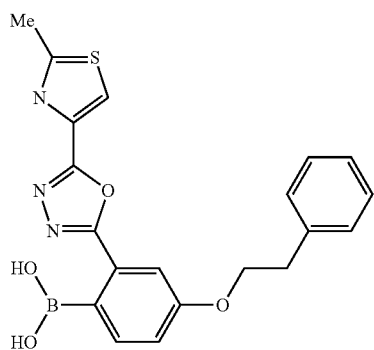

269

Oxadiazole 269 was prepared in 2 steps starting with oxadiazole formation between 2-bromo-5-phenethoxybenzoic acid 16 and 2-methyl-1,3-thiazole-4-carbohydrazide using Method 7 followed by lithiation using Method 1. [M+H]⁺= 408.3 m/z. Activity: C.

Example 235

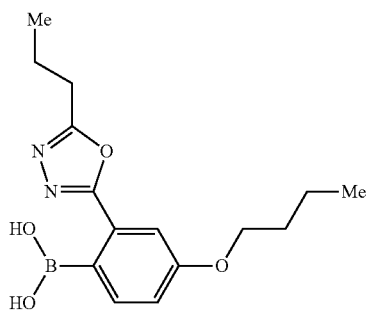

271

-continued

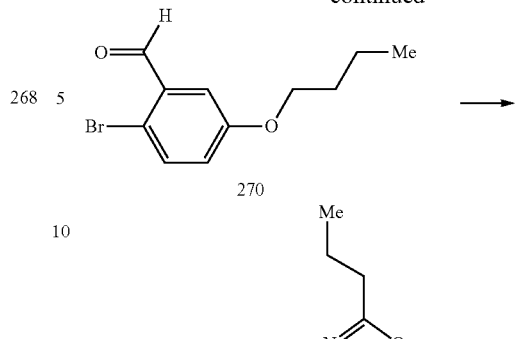

270

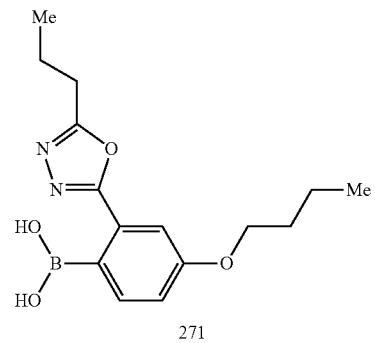

271

Oxadiazole 271 was prepared in analogous fashion to the oxadiazole 17 in example 12 except that 1-bromobutane was used in the place of phenethylbromide in part A to synthesize 2-bromo-5-butoxybenzaldehyde 270. Aldehyde 270 was then converted to the desired oxadiazole using the oxidation, cyclization and lithiation steps in part B. [M−H]⁻=303.2 m/z. Activity: B

Example 236

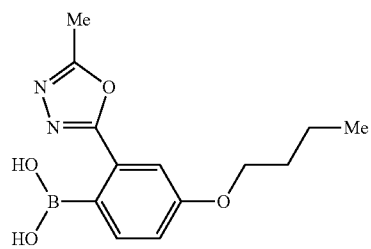

272

Oxadiazole 272 was prepared in analogous fashion to the oxadiazole 17 in example 12 except that 1-bromobutane was used in the place of phenethylbromide in part A to synthesize 2-bromo-5-butoxybenzaldehyde 270 and that acetic hydrazide was used in place of butyric hydrazide during the cyclization step in part B. [M−H]⁻=275.1 m/z. Activity: B

Example 237

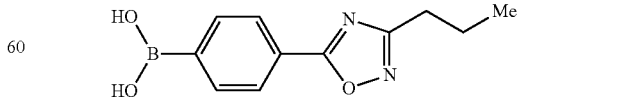

272

In a microwave reactor tube, 4-(4,4,5,5-tetramethyl-1,3,2-dioxaborolan-2-yl)benzoic acid (300 mg, 1.0 equiv), polystyrene—supported triphenylphosphine (3.0 equiv) and trichloroacetonitrile (0.18 mL, 2.0 equiv) were added, and the mixture was sealed and heated in a microwave reactor at 100° C. for 30 min. N-Hydroxy-butyramidine (0.14 mL, 1.1 equiv) was then added followed by N,N-diisopropyl ethylamine (0.43 mL, 2.0 equiv) and the reaction was reheated in a microwave reactor to 150° C. for 1 h. The concentrated reaction mixture was purified by flash silica gel chromatography (hexanes/ethyl acetate) to provide oxadiazole-aryl boronic acid pinacol ester in 32% yield. The boronate was then converted the boronic acid 272 using Method 5. [M−H]=231.1 m/z. Activity: A.

Example 238

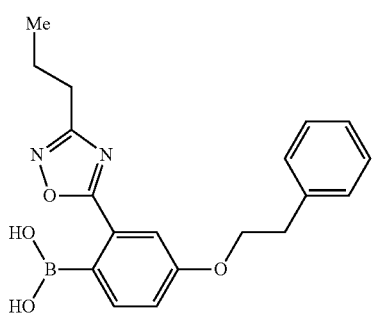

273

Oxadiazole 273 was prepared in two steps first using the analogous procedure as example 238 except that 2-bromo-5-phenethoxybenzoic acid 16 was used in place of 4-(4,4,5,5-tetramethyl-1,3,2-dioxaborolan-2-yl)benzoic acid. The resultant oxadiazole was then converted to the corresponding boronic acid using the lithiation conditions in Method 1. [M−H]⁻=351.2 m/z. Activity: B Example 239

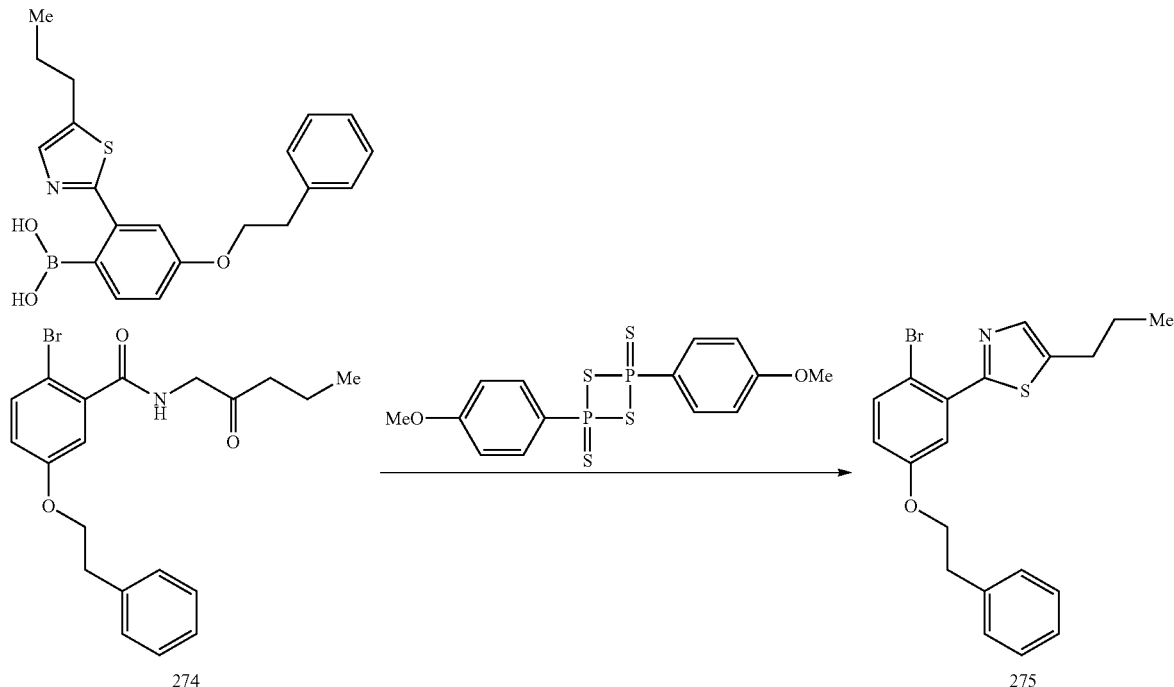

276

Thiazole 276 was prepared in 3 steps from 2-bromo-5-phenethoxybenzoic acid 16. Acid 16 (700 mg, 1.0 equiv) and 1-aminopentan-2-one hydrochloride (390 mg, 1.3 equiv) were dissolved in 20 mL anhydrous dichloromethane. HOBt (353 mg, 1.2 equiv) and EDC (501 mg, 1.2 equiv) were added followed by triethylamine (940 uL, 3.0 equiv). The reaction was allowed to stir for 12 h at room temperature after which point it was transferred to a separatory funnel with excess dichloromethane and washed with 0.5 M citric acid (2×75 mL) and saturated NaHCO₃ (2×75 mL). The organic layer was then dried over MgSO₄, filtered and concentrated to provide the desired ketoamide 274 as a yellow solid in quantitative yield (880 mg) which was used directly to form the thiazole the in the following step.

Ketoamide 274 (308 mg, 1.0 equiv) was added to a microwave reactor vial and dissolved in 5 mL anhydrous tetrahydrofuran after which Lawesson's reagent (462 mg, 1.5 equiv) was then added. The reaction was heated to 115° C. for 90 min in a microwave reactor after which point it was loaded directly onto silica gel and purified using flash silica gel chromatography using a gradient of 20-70% ethyl acetate/hexanes to provide 230 mg of the desired thiazole 275 in 50% yield.

The resultant thiazole 275 was then converted to the corresponding boronic acid using the lithiation conditions in Method 1. [M+H]⁺=368.2 m/z. Activity: B

Example 240

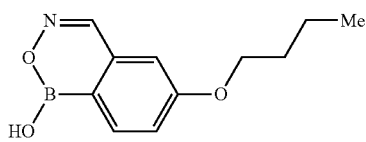

277

Benzodiazoborine 277 was prepared in 3 steps by first preparing the corresponding boronic acid aldehyde in analogous fashion to example 90 except that aldehyde 270 used in place of aldehyde 93. Benzodiazoborine 277 was then prepared using the analogous procedure as example 96 except that 4-butoxy-2-formylphenylboronic acid was used in the place of 98. $[M-H]^-=218.1$ m/z. Activity: C.

Example 241

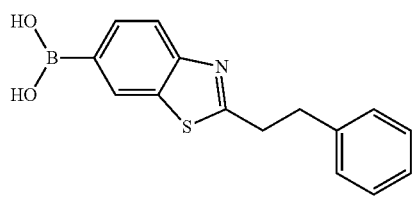

278

Benzothiazole 278 was prepared in 3 steps by first forming the benzothiazole from 2-amino-5-chlorothiophenol and 3-phenylpropionic acid using Method 13 followed by conversion to the boronate ester using Method 15 followed by Method 5. $[M-H]^-=282.2$ m/z. Activity: A.

Example 242

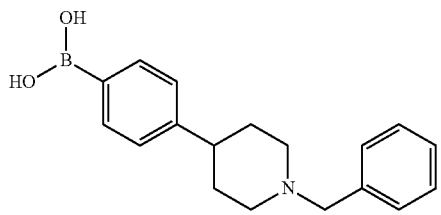

279

Piperidine 279 was prepared in 3 steps starting from 1-Boc-4(4-boronophenyl)piperidine pinacol ester 233 which was first deprotected as described in Example 204. This salt (150 mg, 0.374 mmol) was dissolved in tetrahydrofuran (5 mL) and treated with triethylamine (41.6 mg, 0.411 mmol, 1.1 eq.) and benzaldehyde (43.6 mg, 0.411 mmol, 1.1 eq.) and stirred for 30 minutes while being cooled in an ice bath. To this solution sodium triacetoxyborohydride (87 mg, 0.411 mmol, 1.1 eq.) was added in portions and the reaction was allowed to warm to ambient temperature and stir for 16 h. The reaction was diluted with ethyl acetate (50 mL) and washed with water (2×15 mL). The organic layer was dried over magnesium sulfate, filtered and evaporated onto silica gel. Purification using silica gel chromatography (gradient of 0 to 20% ethyl acetate/hexanes) gave 1-benzyl-4-(4-boronophenyl)piperidine pinacol ester. Deprotection of this ester via Method 5 gave compound 279 (30 mg, 30%). $[M-H]^-=294.2$ m/z. Activity: C.

Example 243

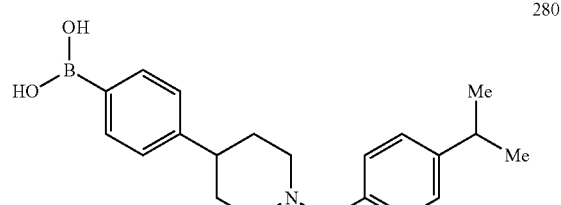

280

Piperidine 280 was prepared using the analogous procedure as example 242 except that 4-isopropylbenzaldehyde was used in place of benzaldehyde. $[M-H]^-=336.3$ m/z. Activity: B.

Example 244

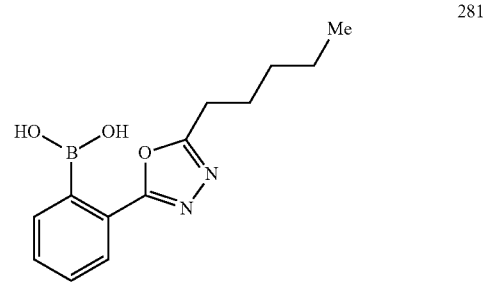 [SMILES: CCCCCc1nnc(-c2ccccc2B(O)O)o1]

281

Oxadiazole 281 was prepared in 2 steps by first forming the oxadiazole from 2-(4,4,5,5-tetramethyl-1,3,2-dioxaborolan-2-yl)benzoic acid and hexanoic hydrazide using Method 8 followed by Method 5 and was isolated and purified by using flash silica gel chromatography. $[M-H]^-=259.1$ m/z. Activity: D

Example 245

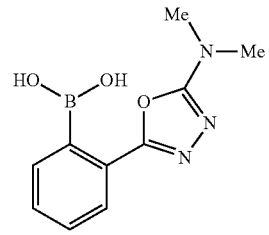

282

2-Bromobenzhydrazide (1.03 g, 4.8 mmol, 1.0 equiv) and 1,1'-carbonyldiimidazole (1.01 g, 6.23 mmol, 1.3 equiv) were heated in 1,4-dioxane (20 mL) for 4 h at 80° C. The mixture was concentrated in vacuo, and the resulting residue split between ethyl acetate and water (100 mL each). The organic layer was washed with brine, dried over sodium sulfate, and concentrated in vacuo to afford a white solid (1.1 g, 95% yield). A portion of this intermediate oxadiazolidinone (820 mg, 3.4 mmol, 1.0 equiv) was suspended in a solution of dimethylamine (2.0 M in THF, 20 mL) and stirred at 23° C. overnight. The resulting solution was concentrated in vacuo; the residue was re-suspended in dry dichloromethane (30 mL) and concentrated in vacuo. This residue was again re-suspended in dry dichloromethane (5 mL) and treated with p-toluenesulfonyl chloride (681 mg, 3.57 mmol, 1.05 equiv) and triethylamine (1.2 ml, 8.5 mmol, 2.5 equiv). After stirring at 23° C. for 16 h, the mixture was split between ethyl acetate and water (50 mL each), and the organic layer was washed with brined and dried over sodium sulfate. Concentration in vacuo gave a residue which, upon purification by silica gel chromatography (30→100% ethyl acetate/hexanes) gave dimethylamino-oxadiazole as a white solid. This bromide was converted to the boronic acid by Method 1, and was isolated and purified by using flash silica gel chromatography to provide 282 as a white solid. [2M–H$_2$O]$^-$=447.1 m/z. Activity: D Example 246

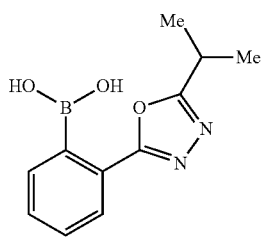

283

2-Bromobenzhydrazide (500 mg, 2.32 mmol, 1.0 equiv) and isobutyryl chloride (372 mg, 3.49 mmol, 1.5 equiv) were stirred with sodium bicarbonate (590 mg, 7.0 mmol, 3.0 equiv) in water and 1,4-dioxane (10 mL each), at 0° C. for 1 h. The mixture was split between ethyl acetate and water (50 mL each), and the organic layer was washed with brine, dried over sodium sulfate, and concentrated in vacuo to a white solid. This solid was dissolved in dry dichloromethane (5 mL), and the solution was concentrated to 2.5 mL in vacuo. This solution was treated with p-toluenesulfonyl chloride (465 mg, 2.44 mmol, 1.05 equiv) and triethylamine (0.8 ml, 5.8 mmol, 2.5 equiv) and stirred at 23° C. for 16 h. The mixture was split between ethyl acetate and water (50 mL each), and the organic layer was washed with brine, dried over sodium sulfate, and concentrated in vacuo to give oxadiazole as a clear oil. This bromide was converted to the boronic acid by Method 1, and was isolated and purified by using flash silica gel chromatography to provide 283 as a white solid. [M–H]$^-$=231.1 m/z. Activity: D Example 247

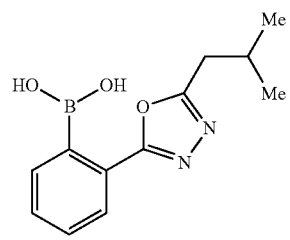

284

Oxadiazole 284 was prepared using the analogous procedure as example 246 except that isovaleryl chloride was used in place of isobutyryl chloride. [M–H]$^-$=245.1 m/z. Activity: D.

Example 248

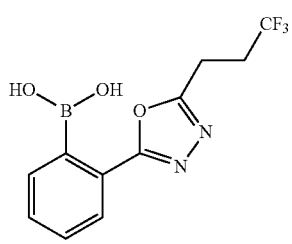

285

Oxadiazole 285 was prepared in 2 steps by first forming the oxadiazole from 2-(4,4,5,5-tetramethyl-1,3,2-dioxaborolan-2-yl)benzhydrazide and 3,3,3-trifluorobutanoic acid using Method 7 followed by Method 5 and was isolated and purified by using flash silica gel chromatography. [M–H]$^-$=285.0 m/z. Activity: D Example 249

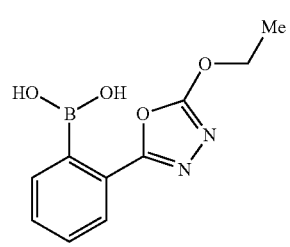

286

2-Bromobenzhydrazide (500 mg, 2.32 mmol, 1.0 equiv) and ethyl chloroformate (359 mg, 2.88 mmol, 1.2 equiv) were stirred with sodium bicarbonate (605 mg, 7.2 mmol, 3.0 equiv) in water and 1,4-dioxane (10 mL each), at 0° C. for 1 h. The mixture was split between ethyl acetate and water (50 mL each), and the organic layer was washed with brine, dried over sodium sulfate, and concentrated in vacuo to a white solid. This solid was dissolved in dry dichloromethane (5 mL), and the solution was concentrated to 2.5 mL in vacuo. This solution was treated with p-toluenesulfonyl chloride (480 mg, 2.52 mmol, 1.05 equiv) and triethylamine (0.84 ml, 6.0 mmol, 2.5 equiv) and stirred at 23° C. for 16 h. The mixture was split between ethyl acetate and water (50 mL each), and the organic layer was washed with brine, dried over sodium sulfate, and concentrated in vacuo to give oxadiazole as a clear oil. This bromide was converted to the boronic acid by Method 3 followed by method 5, and purification using silica gel chromatography gave the 286 as a white solid. [2M−H$_2$O]$^−$=488.8 m/z. Activity: D Example 250

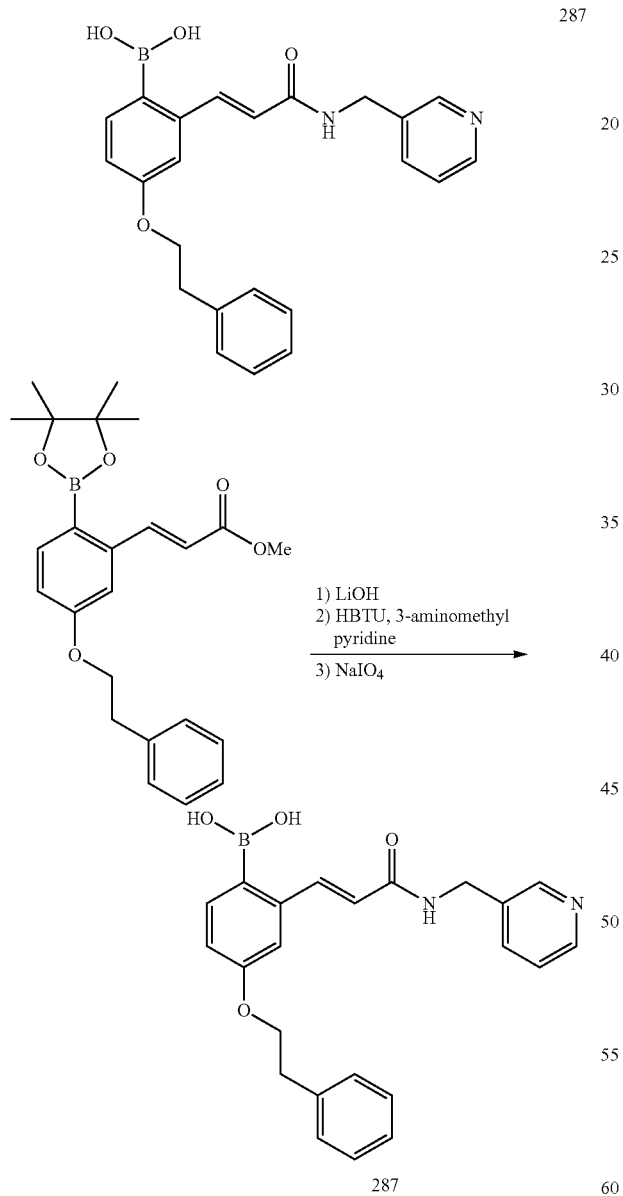

The pinacol ester of compound 100 (18 mg, 0.04 mmol, 1.0 equiv) was dissolved in 3:1 tetrahydrofuran/water (1.2 mL) and stirred with lithium hydroxide (6 mg, 0.26 mmol, 6.0 equiv) at 50° C. for 2 h. The mixture was diluted with ethyl acetate (50 mL), washed with 1N aqueous HCl (100 mL) and then brine (15 mL) and concentrated in vacuo to yield 17 mg of crude carboxylic acid, which was used in the next step without purification.

Carboxylic acid (8 mg, 0.02 mmol, 1.0 equiv) was dissolved in dry dichloromethane (1 mL) and treated with 3-aminomethyl pyridine (4 mg, 0.04 mmol, 2.0 equiv), HBTU (8 mg, 0.03 mmol, 1.5 equiv) and iPr$_2$EtN (8 mg, 0.06 mmol, 3.0 equiv). The mixture was stirred at 23° C. for 16 h and then split between 5% aqueous sodium bicarbonate and ethyl acetate (20 mL each). The organic layer was concentrated in vacuo to yield 10 mg crude product. The crude product was cleaved by Method 5 to produce the arylboronic acid 287 after HPLC purification. [M−H]$^−$=401.2 m/z. Activity: D Example 251

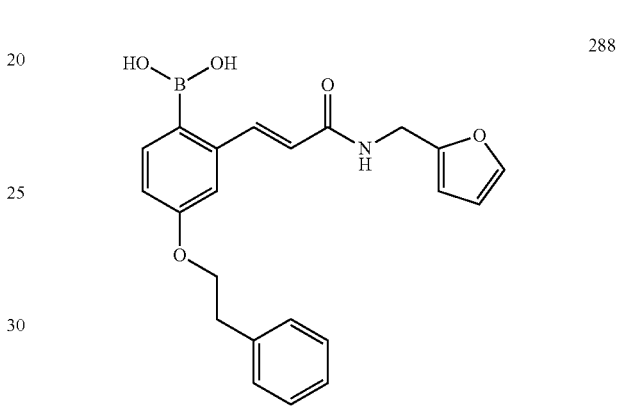

Boronic acid 288 was prepared using the analogous procedure as example 250 except 2-furylmethylamine was used in place of isobutyryl chloride. [M−H]$^−$=390.2 m/z. Activity: D.

Example 252

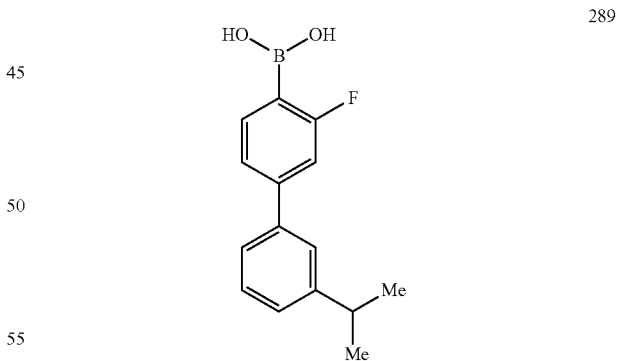

A mixture of 1-bromo-2-fluoro-4-iodobenzene (460 mg, 1.5 mmol, 1.0 equiv), 3-isopropylphenyl-boronic acid (250 mg, 1.5 mmol, 1.0 equiv), Pd(PPh$_3$)$_2$Cl$_2$ (35 mg, 0.05 mmol, 0.03 equiv) and NaHCO$_3$ (640 mg, in 4 mL water) were added to a flask and dioxane (4 mL) was added. The mixture was purged with argon for 5 min, and then stirred at 80° C. under an argon atmosphere for 6 h. The reaction was diluted with ethyl acetate (200 mL), washed with 60 mL water, then 40 mL brine, dried and concentrated. Purification via silica gel column chromatography with (gradient of 0-2.5% ethyl acetate/ hexanes) gave desired the biphenyl bromide as yellow oil 340 mg. The biphenyl bromide was converted to 289 by Method 1. [M−H⁻]⁻=357.1 m/z. Activity: A Example 253

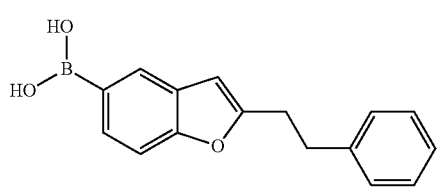

Part A

To a solution of 2-amino-4-bromophenol (2 g, 8.9 mmol, 1.0 equiv) in HCl (5 M, 12.5 mL, 7.0 equiv) was added drop-wise a solution of sodium nitrite (0.62 g, 8.9 mmol, 1.0 equiv) in water (5 mL) at 0° C. The mixture was stirred at this temperature for 30 min after which a cooled solution of KI (1.5 g, 8.9 mmol, 1.0 equiv) in H₂O (14 mL) was slowly added at 0° C. The mixture was then allowed to warm to room temperature and stirred overnight. The reaction mixture was diluted with ethyl acetate (200 mL) and the separated aqueous phase was extracted with ethyl acetate (100 mL×3). The combined organic fraction was washed with Na₂S₂O₃ (10%, 40 mL), water (100 mL×2) and brine (40 mL), dried over Na₂SO₄ and concentrated to dryness. The residue was purified by flash silica gel chromatography (ethyl acetate/hexanes) to afford 1.1 g 4-bromo-2-iodo-pheno as a yellow solid.

Part B

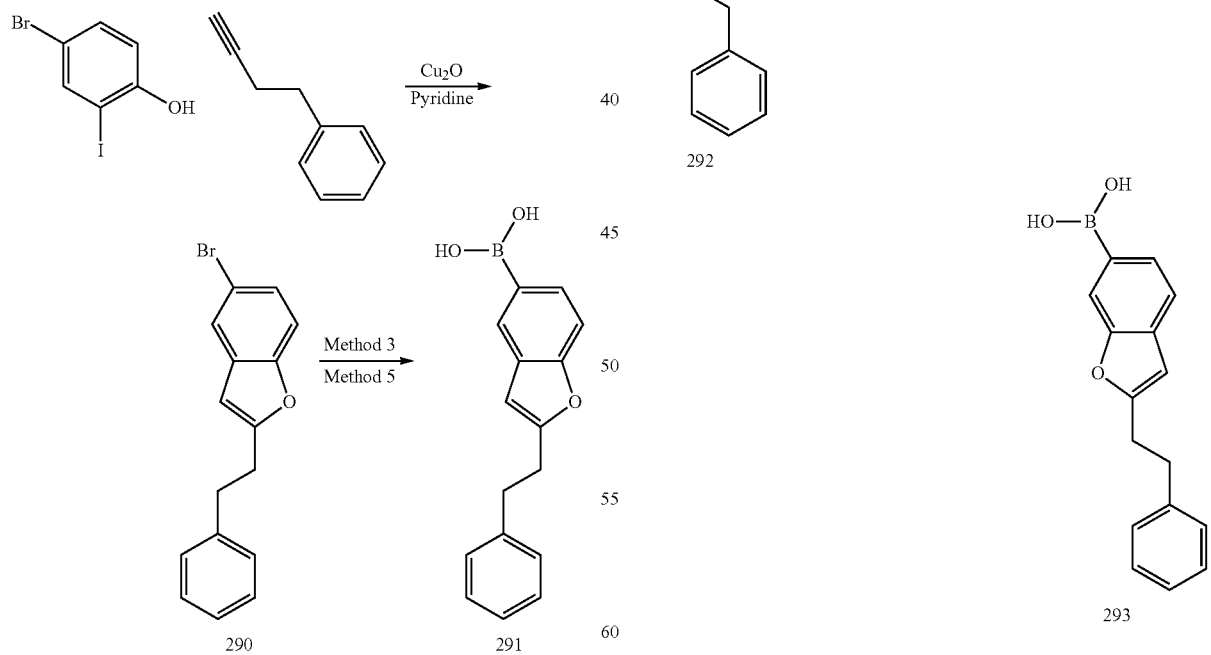

4-Phenyl-1-pentyne (131 mg, 1.0 mmol, 1.0 equiv) was added to a suspension of 4-bromo-2-iodophenol (300 mg, 1.0 mmol, 1.0 equiv) and Cu₂O (85 mg, 0.6 mmol) in dry pyridine (4 mL). The mixture was refluxed under nitrogen for 4 h. The mixture was filtered through celite and washed with ethyl acetate. The pyridine was evaporated under reduced pressure, and the residue was purified by chromatography (combiflash, hexane) gave partially pure desired product 290 (276 mg). The benzofuran bromide 290 was converted to desired boronic acid 291 by Method 3 followed by Method 5. [M−H]⁻=265.0 m/z. Activity: A.

Example 254

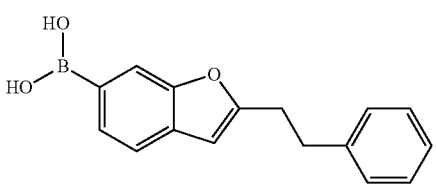

Part A

6-Chloro-2-phenethylbenzofuran 292 was prepared using the analogous procedure as example 253 except 2-amino-5-chlorophenol hydrochloride was used in place of 2-amino-4-bromophenol.

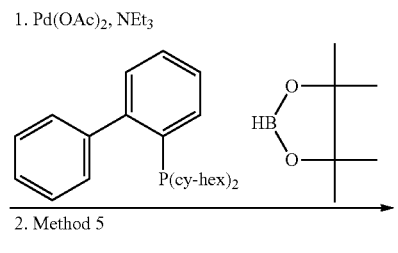

Part B

Benzofuran 293 was synthesized from 292 according to the following procedure: 292 (160 mg, 0.6 mmol, 1.0 equiv), tetramethyl dioxaborolane (160 mg, 1.2 mmol, 2.0 equiv), phospine ligand and palladium diacetate were added together in to 8 mL toluene. The mixture was purged with Ar for 5 min, and then was heated to 80° C. for 5 h. The reaction was cooled to room temperature and water (20 mL) was added after which diethyl ether (3×50 mL) was used to extract the product. The organic layer was washed with brine, dried (Na$_2$SO$_4$), and concentrated. Purification on combiflash (10-15-20% ethyl acetate in hexanes) gave 50 mg of the desired pinacol ester. This was converted to compound 293 by Method 5. [M−H]$^-$=265.2 m/z. Activity: A.

Example 255

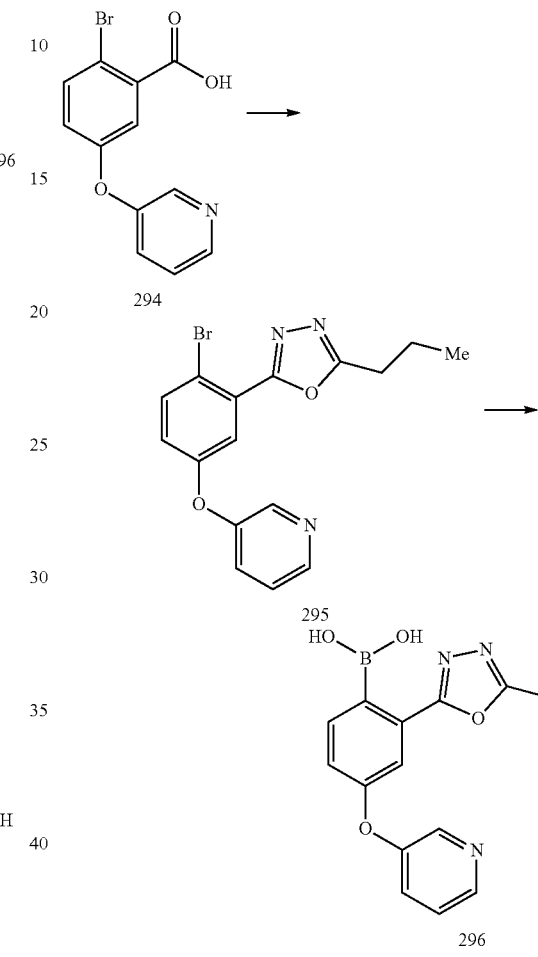

Part A

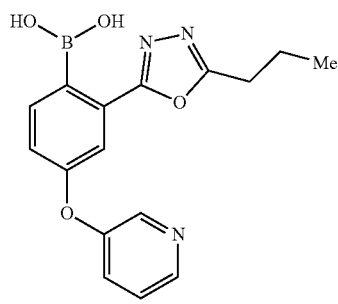

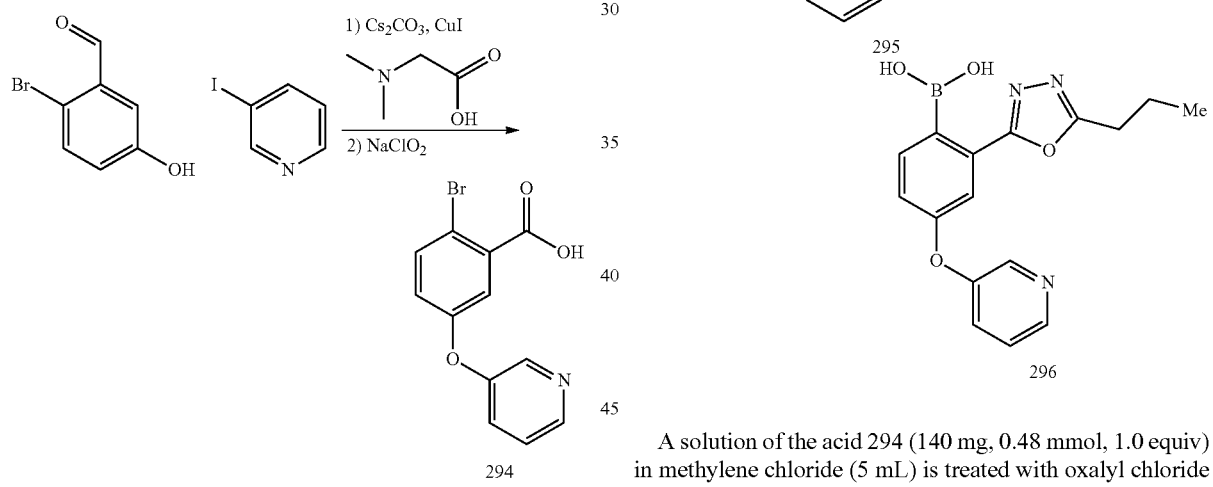

A mixture of 3-iodopyridine (980 mg, 4.8 mmol, 1.0 equiv), 2-bromo-5-hydroxybenzaldehyde (960 mg, 4.8 mmol, 1.0 equiv), cesium carbonate (3.11 g, 9.6 mmol, 2.0 equiv), copper iodide (182 mg, 0.96 mmol, 0.2 equiv), and N,N-dimethylglycine HCl salt (533 mg, 3.8 mmol, 0.8 equiv) are suspended in 10 mL of dioxane in a sealed tube and heated to 90° C. under a nitrogen atmosphere. After 16 h, the cooled mixture was filtered through a bed of celite with small amount of silica gel on top of it. Ethyl acetate (3×20 mL) was used to wash the celite. The filtrate was concentrated in vacuo. The residual oil was loaded on a silica gel column and eluted with ethyl acetate/hexanes (15-20%) to afford 0.4 g of the corresponding aldehyde.

A solution of the aldehyde (160 mg, 0.58 mmol, 1.0 equiv) in tetrahydrofuran (10 mL) is placed in a flask with stir bar and isoprene (404 mg, 5.8 mmol, 10 equiv), 2.7M phosphate buffer (1.7 mL, 4.6 mmol, 8.0 equiv), and NaClO$_2$ (208 mg, 2.3 mmol, 4.0 equiv) are added. The reaction is stirred at room temperature for 2 h and stopped by the addition of water (30 mL), acidification to pH 1 with 6M HCl, and extraction (3×50 mL methylene chloride). The organic layers are dried on Na$_2$SO$_4$ and concentrated to give 294 as a white foam (182 mg), which is used without further purification.

Part B

A solution of the acid 294 (140 mg, 0.48 mmol, 1.0 equiv) in methylene chloride (5 mL) is treated with oxalyl chloride (91 mg, 0.71 mmol, 1.5 equiv) followed by a drop of N,N-dimethylforamide and stirred 23° C. for 3 h. The mixture was concentrated in vacuo and resuspended in methylene chloride (6 mL). To this mixture were treated with triethylamine (96 mg, 0.96 mmol, 2.0 equiv) followed by butyric hydrazide (73 mg, 0.71 mmol, 1.5 equiv) and catalytic DMAP. After 20 min at 23° C., the reaction mixture was split between water and methylene chloride. The aqueous layer was back extracted again with methylene chloride. The combined organics were washed with 5% NaHCO$_3$ and then brine, dried over sodium sulfate and concentrated in vacuo to yield 150 mg crude material. The crude material was suspended in POCl$_3$ (6 mL) and heated at 90° C. for 2 h after which point the mixture was poured into ice water. Methylene chloride was used to extract the aqueous layer and the organic layer was washed with brine, dried over sodium sulfate, and concentrated in vacuo. HPLC purification (FA 10-80) gave oxadiazole 295 (8 mg), which was converted to compound 296 by Method 1. [M+H]$^+$=326.0 m/z. Activity: B.

Example 256

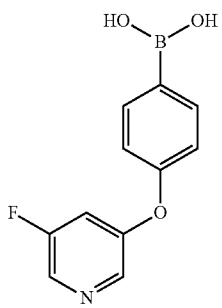

4-Bromo-3-fluorophenol (200 mg, 1.0 mmol, 1.0 equiv), 5-fluoropyridin-3-ylboronic acid (221 mg, 1.5 mmol, 1.5 equiv), copper (II) acetate (190 mg, 0.481 mmol, 1.0 equiv) and 4A MS were suspended in 10 mL methylene chloride. Triethylamine (530 mg, 5.0 mmol, 5.0 equiv) was then added after which point the reaction turned from blue to brown and was stirred at room temperature for 16 h under ambient atmosphere after which point the reaction turned back blue. The slurry was filtered through a small pad of celite and washed with 30% ethyl acetate in hexanes. The combined filtrate was concentrated in vacuo. Purification using flash silica gel chromatography gave the desired biaryl bromide (45 mg) which was converted to boronic acid 297 by Method 1. [M–H]⁻= 250.1 m/z. Activity: A.

Example 257

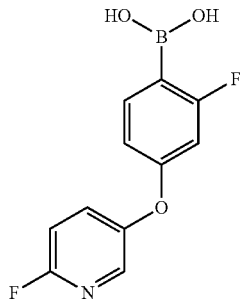

Biaryl boronic acid 298 was prepared using the analogous procedure as example 256 except that 4-fluoropyridin-3-ylboronic acid was used in place of 5-fluoropyridin-3-ylboronic acid. [M–H]⁻=250.1 m/z. Activity: A.

Example 258

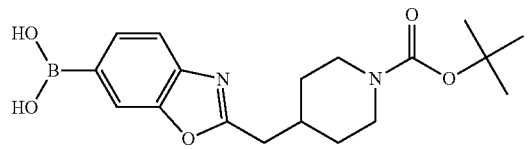

1-Boc-piperidin-4-ylacetic acid (1.7 g, 7.0 mmol, 1.0 equiv) and 4-chloro aminophenol (1.0 g, 7.0 mmol, 1.0 equiv) were added to a sealed flask. Acetonitrile (20 mL) was added followed by triphenylphosphine resin (11.1 g, 1.88 mmol/g, 4.0 equiv) and trichloroacetonitrile (2.0 g, 14 mmol, 2.0 equiv). The flask was sealed and heated at 100° C. for 20 h and cooled to room temperature. The resin was rinsed with excess tetrahydrofuran/methylene chloride (1:1). The resulting filtrate was then concentrated to yield the corresponding Boc-deprotected benzoxazole chloride. The solid was washed with 30% ethyl acetate in hexanes to get rid of the non polar impurities and used directly in next step.

To a solution of the amine (1.2 g, 4.8 mmol, 1.0 equiv) and triethylamine (1.5 g, 14.4 mmol, 4.0 equiv) in 70 mL of methanol was added di-tert-butyl dicarbonate (1.3 g, 5.7 mmol, 1.2 equiv) and the mixture stirred at room temperature for 24 h. The solvent was evaporated and the residue was suspended in 100 mL of ethyl acetate. The mixture was washed with a saturated sodium bicarbonate solution (50 mL) and subsequently with water (2×100 mL). The organic layer was dried with anhydrous sodium sulfate and concentrated. The Boc-protected benzoxazole chloride 1.2 g was obtained as yellow oil and was used directly in the conversion to the boronate ester using Method 15 to provide pinacol ester 300 followed by Method 5 to provide 299. [M–H]⁻=359.1 m/z. Activity: A.

Example 259

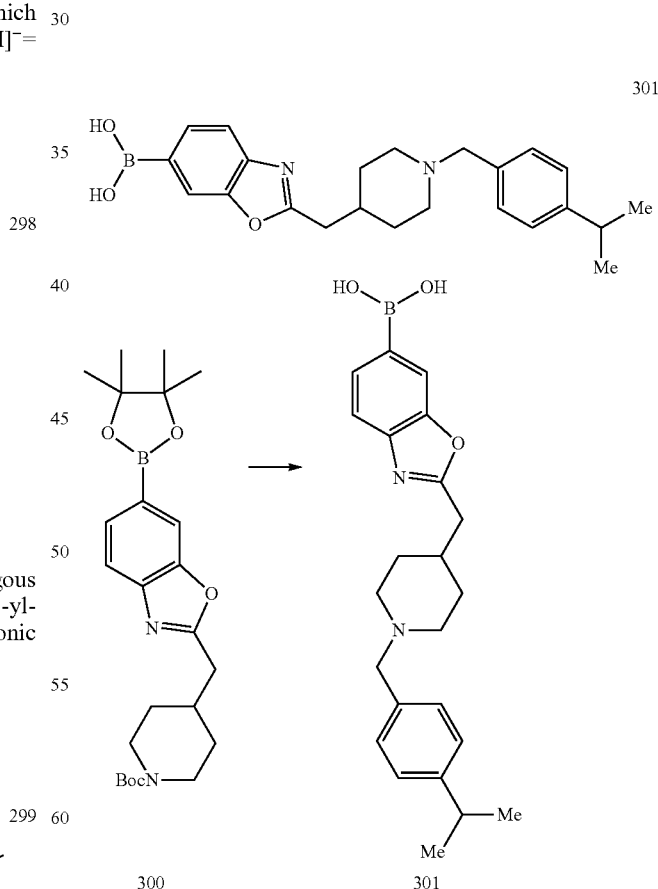

Boc protected benzoxazole pinacol ester 300 (600 mg, 1.4 mmol, 1.0 equiv) is stirred in trifluoroacetic acid (6 mL) for 1 h, after which point the solution was evaporated under reduced pressure. The crude material was azeotroped twice with toluene (75 mL) after which point the piperidine salt was used directly in the next step.

The crude amine TFA salt (200 mg, 0.45 mmol, 1.0 equiv) is dissolved in 4 mL dry methylene chloride. Triethylamine (181 mg, 1.82 mmol, 4.0 equiv) and 4-isopropylbenzaldehyde (135 mg, 0.9 mmol, 2.0 equiv) were added followed by the addition of sodium triacetoxyborohydride (386 mg, 1.82 mmol, 4.0 equiv). The reaction was stirred at room temperature for 20 h then concentrated. Methanol was added to the residue to quench the unreacted borohydride after which point the crude material was directly purified with HPLC (FA 10-80) to give 50 mg of pure pinacol ester, which was converted to compound 301 by Method 5. [M–H]⁻=391.2 m/z. Activity: B Example 260

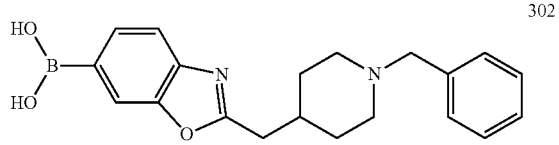 [SMILES: OB(O)c1ccc2nc(CC3CCN(Cc4ccccc4)CC3)oc2c1]

302

Benzoxazole 302 was prepared using the analogous procedure as example 259 except that benzaldehyde was used in place of 4-isopropylbenzaldehyde. [M–H]⁻=349.2 m/z. Activity: B.

Example 261

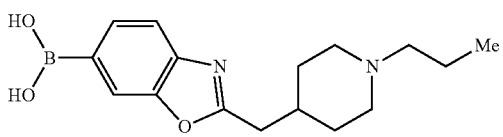

303

Benzoxazole 303 was prepared using the analogous procedure as example 259 except that propionaldehyde was used in place of 4-isopropylbenzaldehyde. [M–H]⁻=301.2 m/z. Activity: C.

Example 262

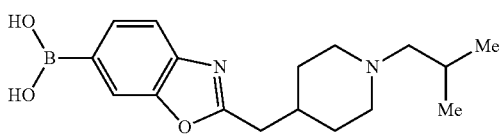

304

Benzoxazole 304 was prepared using the analogous procedure as example 259 except that isobutyraldehyde was used in place of 4-isopropylbenzaldehyde. [M–H]⁻=315.2 m/z. Activity: D.

Example 263

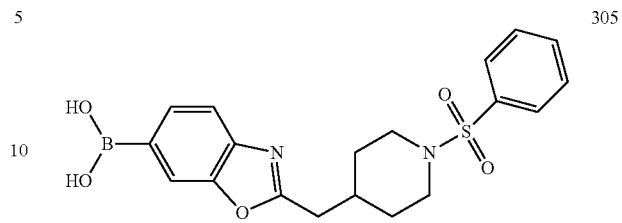

305

Boc-protected benzoxazole pinacol ester 300 is deprotected as in example 259 and the crude amine TFA salt (190 mg, 0.43 mmol, 1.0 equiv) is dissolved in 5 mL dry methylene chloride. Triethylamine (175 mg, 1.73 mmol, 4.0 equiv) followed by benzenesulfonyl chloride (153 mg, 0.86 mmol, 2.0 equiv) were added. The reaction was stirred at room temperature for 20 h and then concentrated under reduced pressure. Methanol was added to the residue and the crude material was directly purified with HPLC (FA 10-80) to give 70 mg pure sulfonamide pinacol ester product, which was converted to compound 305 by Method 5. [M–H]⁻=399.0 m/z. Activity: B.

Example 264

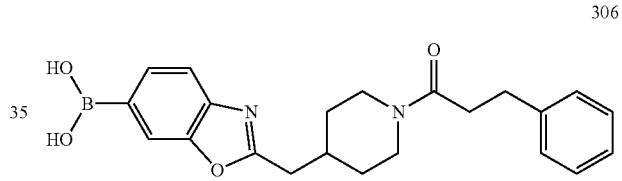

306

Boc-protected benzoxazole pinacol ester 300 is deprotected as in example 259 and the crude amine TFA salt (200 mg, 0.45 mmol, 1.0 equiv) is dissolved in 5 mL dry methylene chloride. Triethylamine (181 mg, 1.8 mmol, 4.0 equiv) and hydrocinnamoyl chloride (154 mg, 0.9 mmol, 2.0 equiv) were added. The reaction was stirred at room temperature for 20 h and then concentrated. Methanol was added to the residue and the crude material was directly purified with HPLC (FA 10-80) to give 60 mg pure amide pinacol ester product, which was converted to compound 306 by Method 5. [M–H]⁻=391.1 m/z. Activity: A.

Example 265

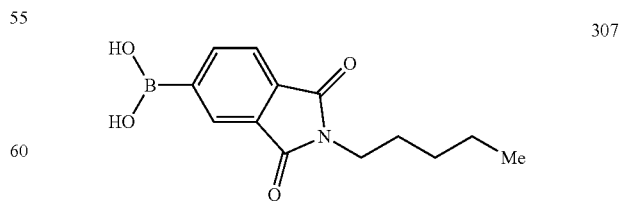

307

5-Bromophthalic anhydride (1.0 g, 4.4 mmol) in ethanol (10 mL) was treated with n-amylamine (562 uL, 4.9 mmol, 1.1 eq.) and heated at reflux overnight. The mixture was diluted into 0.1M HCl (100 mL) and the resulting white solid collected by filtration, washed with water, and dried in vacuo to give 136 mg of the corresponding phthalimide as a white solid. The filtrate was diluted with brine and chilled at −20° C. for 2d. A second crop of precipitate was collected, washed with water, and dried in vacuo to give another 116 mg phthalimide as a white solid. The crops are identical by NMR and combined to give a total yield of 252 mg (0.85 mmol, 19%). This material was used without further purification.

This precipitated phthalimide (250 mg, 0.84 mmol) was converted using methods 3 followed by method 5, to form boronic acid 307 (22 mg, 10%) as a white solid. [M−H]⁻=260.1 m/z. Activity: A.

Example 266

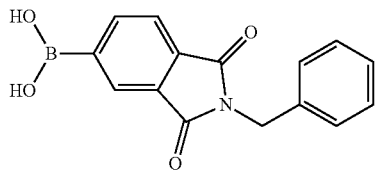

308

5-Bromo-2-benzylphthalimide was produced from 5-bromophthalic anhydride (1.0 g, 4.4 mmol) using the analogous procedure as example 265 except that benzylamine was used in the place of n-amylamine, to provide 421 mg (30%) of product as a white crystals.

This precipitated phthalimide (200 mg, 0.63 mmol) was converted using methods 3 followed by method 5, to form boronic acid 308 (67 mg, 38%) as an off-white solid. Activity: A.

Example 267

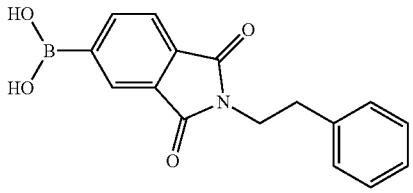

309

5-Bromo-2-phenethylphthalimide was produced from 5-bromophthalic anhydride (1.0 g, 4.4 mmol) using the analogous procedure as example 265 except that phenethylamine was used in the place of n-amylamine, to provide 521 mg (36%) of product as a white crystals.

This precipitated phthalimide (270 mg, 0.82 mmol) was converted using methods 3 followed by method 5, to form boronic acid 309 (106 mg, 44%) as a brownish powder. [M−H]⁻=294.0 m/z. Activity: A.

Example 269

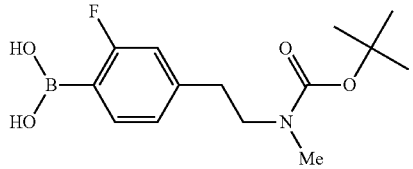

311

3-Fluoro-4-bromotoluene (5.0 g, 27 mmol) in carbon tetrachloride (50 mL) was treated with N-bromosuccinimide (7.0 g, 40 mmol, 1.5 eq) and heated to 80° C. Benzoyl peroxide (65 mg, 0.27 mmol, 0.01 eq.) was added and heating was continued for 1 h. The reaction was then cooled to ambient temperature and filtered, and the filtercake was washed sparingly with chloroform. The filtrate was washed with water and brine, dried over $Na_2SO_4$, and concentrated to give crude 3-fluoro-4-bromobenzyl bromide as a clear oil which was used without further purification.

This crude benzyl bromide (27 mmol) and sodium cyanide (2.38 g, 54 mmol, 2.0 eq.) were combined in ethanol (100 mL) and heated at 80° C. for 2 h. The reaction mixture was concentrated to dryness in vacuo, suspended in water, and extracted with ethyl acetate. Washing with brine and drying over $Na_2SO_4$ gave, after removal of the solvent, a red oil which was purified using silica gel chromatography (gradient of 2→12% ethyl acetate/hexanes) to provide 3-fluoro-4-bromophenylacetonitrile as white needles (1.96 g, 35% over 2 steps).

A solution of lithium aluminum hydride (1M in THF, 14 mL, 14 mmol, 3.0 eq.) was chilled in an ice bath and slowly treated with sulfuric acid (390 uL, 7.0 mmol, 1.5 eq.). After the visible reaction was complete, a solution of the nitrile produced above (1.0 g, 4.7 mmol) in tetrahydrofuran (10 mL) was dripped in to the mixture slowly. The mixture was stirred at 0° C. for 20 min, then refluxed for 30 min. After cooling to room temperature, the excess reagents were quenched with 2-propanol, followed by 4M NaOH. After stirring to assure complete reaction, the resulting suspension was filtered through celite and the filtercake was washed well with 2-propanol. The filtrate was concentrated to give crude 3-fluoro-4-bromophenethylamine as a clear oil which was used without further purification.

This crude material (4.7 mmol) was dissolved in methylene chloride (10 mL) and treated with potassium carbonate (1.0 g, 7.0 mmol, 1.5 eq.) and di-tert-butyldicarbonate (1.15 g, 5.2 mmol, 1.1 eq). The mixture was stirred at ambient temperature for 2 days, then diluted with water, extracted into MTBE, washed with brine, dried over $Na_2SO_4$, and concentrated to a white solid which contains excess dicarbonate reagent. The material was taken up in ethanol (20 mL) and treated with imidazole (200 mg). After stirring for a few minutes, the solvent was removed under vacuum and the residue dissolved in methylene chloride, washed several times with 1% HCl, and concentrated to give crude N-Boc-3-fluoro-4-bromophenethylamine as a yellow solid which was used without further purification.

This crude material (4.7 mmol) was dissolved in N,N-dimethylforamide (10 mL) and chilled in an ice bath. Sodium hydride dispersion (60% in mineral oil, 560 mg, 14 mmol, 3.0 eq.) was added and stirring continued until gas evolution ceased, then iodomethane (580 uL, 9.4 mmol, 2.0 eq,) was added and the mixture allowed to warm to room temperature.

After stirring overnight, the mixture is diluted with MTBE, washed with water and brine, dried over Na$_2$SO$_4$, and concentrated to give crude N-methyl-N-Boc-3-fluoro-4-bromophenethylamine (916 mg, 59% over 3 steps).

This material (916 mg, 2.76 mmol) was converted to the pinacolatoboronate (351 mg, 34%) using Method 3. This boronate ester (70 mg) was converted, via Method 5, to provide boronic acid 311 (52 mg) as a colorless oil. [M−H]$^−$=296.2 m/z. Activity: A.

Example 270

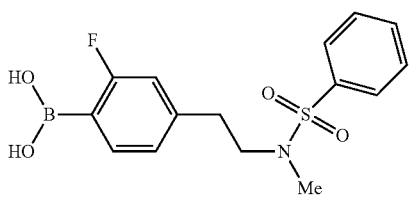

N-Methyl-N-Boc-3-fluoro-4-bromophenethylamine from Example 269 was converted to the corresponding boronate ester using method 3. This compound (280 mg, 0.74 mmol) was dissolved in trifluoroacetic acid (4 mL) and stirred for 1 h. The acid was removed under vacuum, and was then azeotroped twice with toluene, to give the crude trifluoroacetate salt of N-methyl-3-fluoro-4-pinacolboronato-phenethylamine as a clear viscous oil.

This crude salt (100 mg, 0.25 mmol) was taken up in methylene chloride (5 mL) and treated with triethylamine (150 uL, 1.0 mmol, 4.0 eq.). Benzenesulfonyl chloride (40 uL, 0.31 mmol, 1.2 eq.) was added and the solution stirred at ambient temperature overnight. The mixture was diluted with methylene chloride and treated with silica gel. Concentration and purification using silica gel chromatography (gradient of 2→18% ethyl acetate/hexanes) provided the benzenesulfonamide derivative as a clear oil.

This material was converted, via Method 5, to provide boronic acid 312 (29 mg, 34%) as a white solid. [M−H]$^−$=336.3 m/z. Activity: A.

Example 271

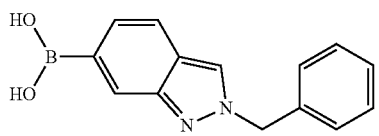

A solution of 2-fluoro-4-bromobenzaldehyde (5.09 g, 25 mmol) was dissolved in glyme (25 mL) and slowly treated over 10 minutes with anhydrous hydrazine (25 mL, 0.8 mol, 32 eq.). The resulting biphasic mixture was then held at reflux overnight. The reflux condenser was replaced with a short-path distillation head and about half the solvent distilled, at which time the reaction flask showed one phase and two phases were evident in the distillate. The undistilled residue was cooled and treated with water (25 mL), forming a white precipitate. This solid was collected by filtration, washed thoroughly with water, and dried in vacuo to give 6-bromoindazole (4.21 g, 85%) as white crystals.

6-Bromoindazole (3.63 g, 18 mmol) was suspended in dioxane (15 mL) and benzyl bromide (2.65 mL, 22 mmol, 1.2 eq.) was added. The reaction was heated to reflux overnight, then allowed to cool to 80° C. after which point ethyl acetate (50 mL) added. The cake was broken up with a spatula and after stirring for 20 min, the solids were filtered off and washed with ethyl acetate, giving glossy white crystals of the hydrobromide salt of 2-benzyl-6-bromoindazole. These were suspended in ethyl acetate (100 mL) and shaken with saturated NaHCO$_3$ (150 mL) until dissolution. The layers were separated and the aqueous layer was extracted with ethyl acetate (50 mL). The combined organic layers were concentrated to an off-white powder which was recrystallized from 66% ethanol (40 mL). Washing with water and drying in vacuo gave 2-benzyl-6-bromoindazole (3.30 g, 62%) as shiny white plates.

This material (3.0 g, 10.3 mmol) was converted to boronic acid 313 (1.8 g, 69%) as a white powder using method 3 followed by method 5. [M−H]$^−$=251.1 m/z. Activity: A.

Example 272

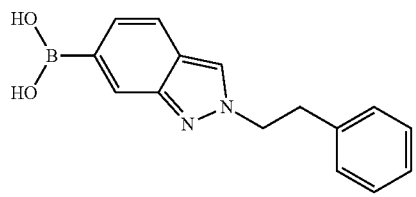

6-Bromoindazole, produced in example 271 (300 mg, 1.5 mmol) and sodium hydroxide (90 mg, 2.3 mmol, 1.5 eq.) were suspended in dioxane (3 mL) and phenethyl bromide (500 uL, 3.6 mmol, 2.4 eq). was added. The reaction was heated to 80° C. for 4 h. The product was extracted from water into MTBE, washed with brine, and dried with Na$_2$SO$_4$. Silica gel was added and the solvent removed after which purification using silica gel chromatography (gradient of 0→12% ethyl acetate/hexanes) separated two products, 1-phenethyl-6-bromoindazole (122 mg) and 2-phenethyl-6-bromoindazole (273 mg, 60%).

2-Phenethyl-6-bromoindazole (273 mg, 0.9 mmol) was converted to boronic acid 314 (152 mg, 63%) as an off-white foam using method 3 followed by method 5. [2M−H$_2$O]$^−$=513.0 m/z. Activity: A.

Example 273

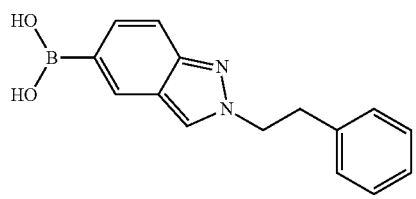

5-Bromoindazole, (300 mg, 1.5 mmol) and sodium hydroxide (90 mg, 2.3 mmol, 1.5 eq.) were suspended in dioxane (2 mL) and phenethyl bromide (500 uL, 3.6 mmol, 2.4 eq). was added. The reaction was heated to 80° C. for 4 h. The product was extracted from water into MTBE, washed with brine, and dried with Na$_2$SO$_4$. Silica gel was added and the solvent removed after which purification using silica gel chromatography (gradient of 0→15% ethyl acetate/hexanes) separated two products, 1-phenethyl-5-bromoindazole (134 mg) and 2-phenethyl-5-bromoindazole (228 mg, 50%).

2-Phenethyl-5-bromoindazole (228 mg, 0.76 mmol) was converted to boronic acid 315 (131 mg, 65%) as a tan foam using method 3 followed by method 5. [2M–H$_2$O]$^-$=513.1 m/z. Activity: A.

Example 274

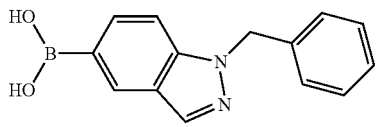

316

5-Bromoindazole, (500 mg, 2.5 mmol), tetrabutylammonium iodide (100 mg, 0.25 mmol, 0.1 eq.) and sodium hydroxide (150 mg, 3.8 mmol, 1.5 eq.) were suspended in para-xylene (10 mL) and benzyl bromide (360 uL, 3 mmol, 1.2 eq) was added. The reaction was heated to 130° C. overnight. The mixture was diluted with MTBE, washed with water and brine, and dried with Na$_2$SO$_4$. After partial concentration in vacuo to a xylene solution purification using silica gel chromatography (gradient of 0→10% ethyl acetate/hexanes) separated two products, 1-benzyl-5-bromoindazole (364 mg) and 2-benzyl-5-bromoindazole (302 mg).

1-Benzyl-5-bromoindazole (364 mg, 1.3 mmol) was converted to boronic acid 316 (126 mg, 40%) as a white solid using method 3 followed by method 5. [M–H]$^-$=251.1 m/z. Activity: A.

Example 275

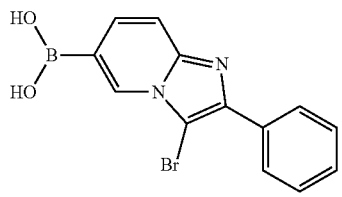

317

5-Borono-2-aminopyridine pinacol ester (250 mg, 1.1 mmol) and 94%-pure 2-bromoacetophenone containing 2,2,-dibromoacetophenone (250 mg, 1.25 mmol, 1.1 eq.) were combined in ethanol (2.5 mL) and subjected to microwave heating at a temperature of 130° C. for 30 min. The solvent was removed in vacuo and the pinacol ester cleaved using method 5. Purification using silica gel chromatography of the product (gradient of 0→30% methanol/methylene chloride) afforded only one compound, brominated imidazopyridine boronic acid 317 (84 mg) as a yellow crystalline solid. [M–H]$^-$=317.0 m/z. Activity: A.

Example 276

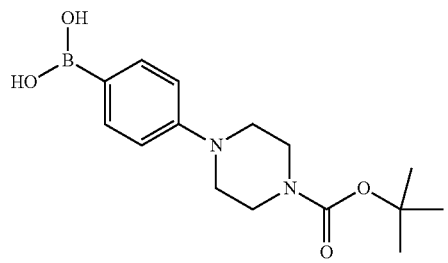

318

1-Boc-4-(4-boronophenyl)piperazine pinacol ester (200 mg, 0.52 mmol) was converted, via method 5, to boronic acid 318 (121 mg, 77%) as a white solid. [M–H]$^-$=305.1 m/z. Activity: B.

Example 277

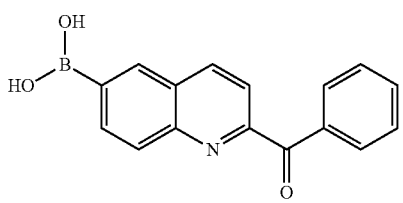

319

A solution of 2-chloro-6-bromoquinoline (250 mg, 1.0 mmol) and benzylnitrile (148 mg, 1.2 mmol, 1.2 eq.) in tetrahydrofuran (20 mL) was treated with 1.0M NaHMDS in THF (2.6 mL, 2.6 mmol, 2.5 eq.) and stirred at ambient temperature overnight. LC/MS showed complete conversion to the diarylacetonitrile intermediate. Saturated aqueous ammonium acetate (5 mL) and sodium peroxide (320 mg, 4.1 mmol, 4.0 eq.) were added and the solution stirred at room temperature for 24 h. LC/MS indicated incomplete conversion, about 40%. The reaction mixture was diluted with MTBE, washed with water and brine, dried over Na$_2$SO$_4$, treated with silica gel, concentrated, and purified using silica gel chromatography (gradient of 0→8% ethyl acetate/hexanes), giving two products, 2-(6-bromoquinoline-2-yl)-2-phenylacetonitrile (185 mg) and 2-benzoyl-6-bromoquinoline (97 mg, 30%).

2-Benzoyl-6-bromoquinoline (97 mg, 0.31 mmol) was converted to boronic acid 319 (42 mg, 50%) as a brownish solid using method 3 followed by method 5. [M–H]$^-$=276.1 m/z. Activity: A.

Example 278

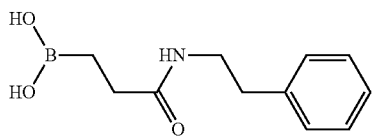

321

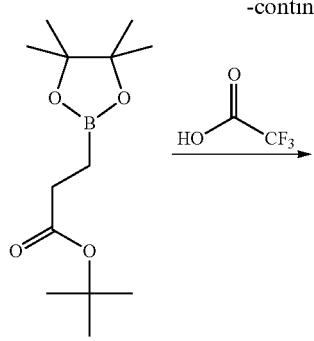

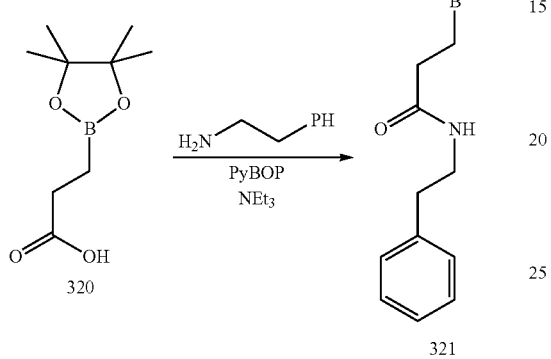

Tert-butyl 3-(4,4,5,5-tetramethyl-[1,3,2]dioxaborolan-2-yl) propionate (0.313 g) was dissolved in 5 mL of methylene chloride. Trifluoroacetic acid was added (0.5 mL) and the reaction was allowed to stir overnight at room temperature. The solvent and acid were then removed under vacuum and the crude mixture was azeotroped using toluene (2×50 mL) to provide crude deprotected acid 320 which was used directly.

A portion of acid 320 (72 mg, 1.0 equiv) was dissolved in 1 mL N,N-dimethyl foramide, followed by the addition of PyBOP (190 mg, 1.0 equiv) and phenethylamine (50 µL, 1.11 equiv). Triethylamine (150 µL, 3.0 equiv) was then slowly added and the reaction was allowed to stir at room temperature for 30 min. After this point the reaction was transferred to a separatory funnel with excess water and ethyl acetate. The water layer was extracted with ethyl acetate (3×50 mL) and dried over Na$_2$SO$_4$ and concentrated. This residue was used directly to form the desired boronic acid 321 using method 5 and was purified using semi-preparatory reverse phase liquid chromatography. [M–H]$^-$=220.1 m/z. Activity: C.

Example 279

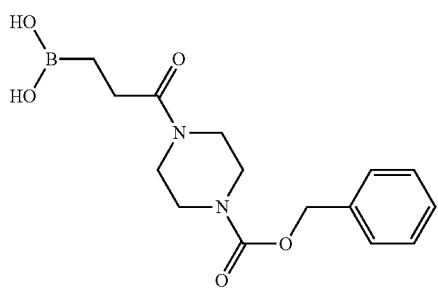

Boronic acid 322 was prepared using the analogous procedure as example 278 except that 1-(benzyloxycarbonyl)piperazine was used in place of phenethylamine. [M–H]$^-$=319.2 m/z. Activity: B.

Example 280

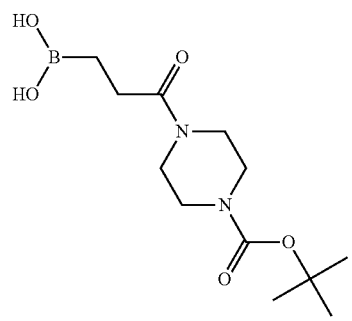

Boronic acid 323 was prepared using the analogous procedure as example 278 except that 1-Boc-piperazine was used in place of phenethylamine [M–H]$^-$=285.2 m/z. Activity: C.

Example 281

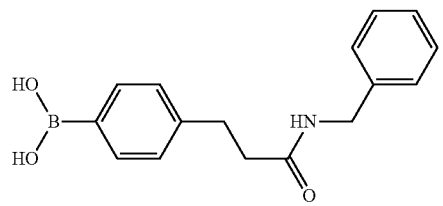

3-(4-Boronophenyl)propanoic acid (102 mg, 1.0 equiv) was dissolved in 2 mL N,N-dimethylformamide after which BOP (293 mg, 1.0 equiv), DIPEA (300 µL, 3.2 equiv) and benzylamine (100 uL, 1.78 equiv) were added and the reaction was allowed to stir for 16 h at room temperature. After this point, 25 mL of water was added and the mixture was transferred to a separatory funnel. The water layer was extracted with ethyl acetate (2×50 mL). The organics were combined, dried over MgSO$_4$, and concentrated to provide crude material that was purified by silica gel chromatography (gradient 50% ethyl acetate/hexanes to 1% methanol/ethyl acetate to provide 88 mg of boronic acid 324. [M–H]$^-$=282.2 m/z. Activity: C Example 282

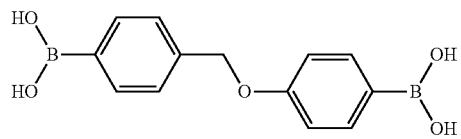

4-Hydroxyphenylboronic acid (63 mg, 1.0 equiv) was suspended in 2 mL 5% sodium bicarbonate solution and a 12 mL of tetrahydrofuran/water solution is added (1:1 v/v). 4-(Bromomethyl)phenylboronic acid (116 mg, 1.2 equiv) was then added and the reaction was allowed to stir for 16 h at room temperature. After this point, the tetrahydrofuran was removed under vacuum and the reaction was acidified to pH <2 with 1N HCl. The mixture was transferred to a separatory funnel and the water layer was extracted with methylene chloride (2×75 mL). The organics were combined, dried over MgSO$_4$ and concentrated to provide crude material that was purified by silica gel chromatography (gradient 50% ethyl acetate/hexanes to 5% methanol/ethyl acetate to provide boronic acid 325. [M–H]$^-$=271.1 m/z. Activity: C Example 283

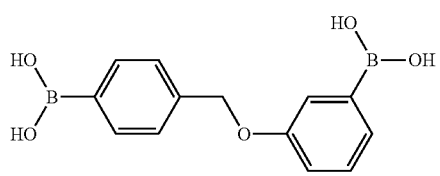

326

3-Hydroxyphenylboronic acid (40 mg, 1.05 equiv) and 4-(bromomethyl)phenylboronic acid (65 mg, 1.0 equiv) were dissolved in 6 mL solution of tetrahydrofuran/N,N-dimethylforamide (1:1 v/v). Sodium hydride (36 mg, 5.0 equiv) is added and the reaction is allowed to stir at room temperature overnight. Water (25 mL) is then added and the reaction is acidified to pH <2 with 1N HCl and transferred to a separatory funnel. The water layer is washed with ethyl acetate (1×75 mL) and diethyl ether (1×75 mL). The water layer is then concentrated under vacuum to provide crude oil which is triturated with tetrahydrofuran and methanol to provide the desired boronic acid 326. [2M–3H$_2$O]$^-$=488.0 m/z. Activity: A Example 284

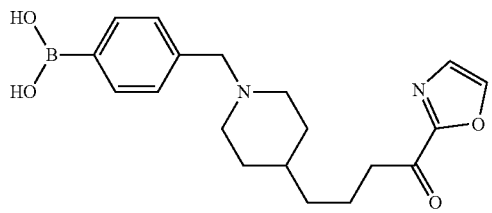

329

Part A

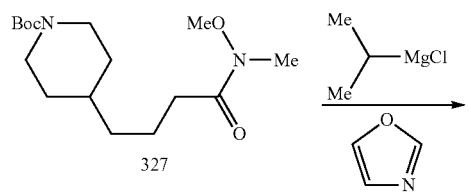

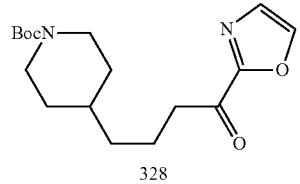

328

4-(1-Boc-piperidin-4-yl)-butanoic acid (6.45 g, 1.0 equiv) was dissolved in 40 mL methylene chloride and cooled to 0° C. in an ice bath. Ethyl chloroformate (2.9 mL, 1.28 equiv) was added followed, by N,N'-dimethylhydroxylamine hydrochloride (2.6 g, 1.1 equiv) and triethylamine (10 mL, 3.0 equiv). The reaction was allowed to warm to room temperature overnight during which time the was the formation of significant amounts of white precipitate. The reaction was then diluted with water (50 mL) and extracted with methylene chloride (2×75 mL). The combined organics were combined, dried over MgSO$_4$, and concentrated to provide crude 327 which was used directly in the next step.

Oxazole (710 mg, 1.3 equiv) was dissolved in 5 mL of tetrahydrofuran and cooled to −78° C. in a dry ice/acetone bath. Isopropyl magnesium chloride (5.0 mL, 2.0 M in diethyl ether, 1.23 equiv) was added over 5 minutes and the reaction was allowed to stir for 20 min at −20° C. during which time the solution turned orange. Weinreb amide 327 (2.56 g, 1.0 equiv) dissolved in 5 mL tetrahydrofuran was then added and the reaction was allowed to warm to room temp overnight. After this point, 40 nil, of saturated ammonium chloride was added after which the reaction was transferred to a reparatory funnel. The water layer was washed with diethyl ether (2×100 mL). The organic layers were dried over MgSO$_4$, filtered and concentrated to provide crude material which was purified using silica gel chromatography (gradient of 20-70% ethyl acetate/hexanes) to provide 500 mg of ketooxazole 328.

Part B

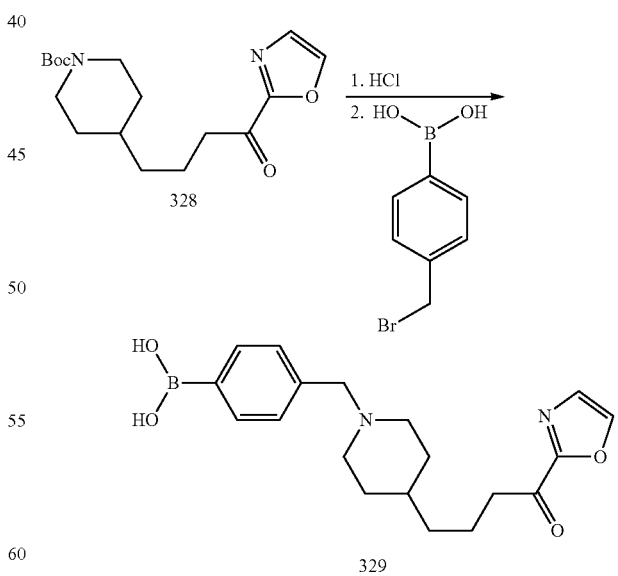

Ketooxazole 328 was dissolved in 15 mL diethyl ether. Anhydrous HCl was bubbled through the solution for a few seconds and allowed to stir for 20 min after which point TLC analysis indicated that there was no more starting material. The rxn was then concentrated and used directly.

4-(Bromomethyl)phenylboronic acid (125 mg, 1.03 equiv) and the HCl salt of 328 (146 mg, 1.0 equiv) were dissolved in 4 mL of methylene chloride. Hunig's base (300 µL) was added and the reaction was allowed to stir overnight with the formation of a significant amount of solid in the flask. The reaction is quenched with water and acidified to pH <2 with 1N HCl. However in this case the product stayed in the water layer. The organic layer was removed and a 5% solution of sodium carbonate was added which caused the desired product to crash out the water layer to provide boronic acid 329. [M−H]⁻=355.1 m/z. Activity: C.

Example 285

TABLE A

| Other boronic acids tested | |
|---|---|
| 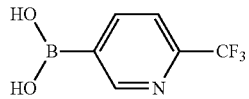 | C |
| 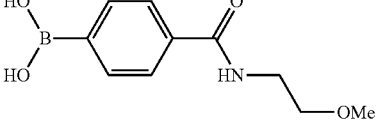 | D |
| 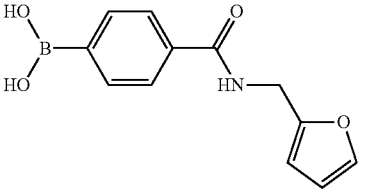 [SMILES: O=C(NCc1ccco1)c1ccc(B(O)O)cc1] | C |
| 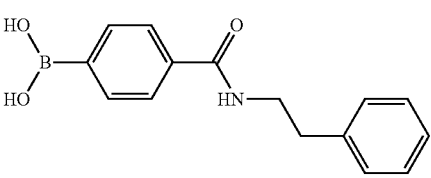 [SMILES: O=C(NCCc1ccccc1)c1ccc(B(O)O)cc1] | B |
| 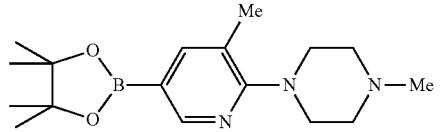 [SMILES: Cc1cc(B2OC(C)(C)C(C)(C)O2)cnc1N1CCN(C)CC1] | D |
| 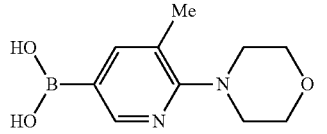 | D |
| 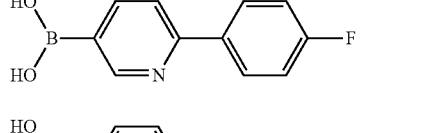 | D |
| 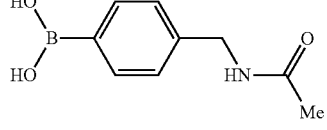 | B |

TABLE A-continued

| Other boronic acids tested | |
|---|---|
| 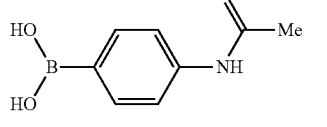 | C |
| 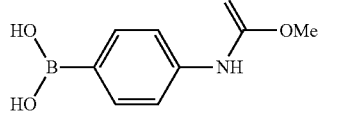 | B |
| 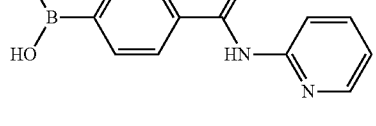 | A |
| 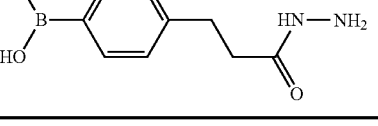 | B |
| 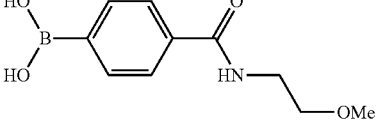 | D |
| 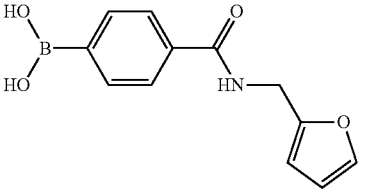 [SMILES: O=C(NCc1ccco1)c1ccc(B(O)O)cc1] | C |
| 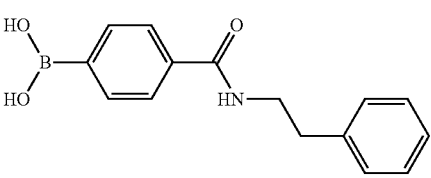 [SMILES: O=C(NCCc1ccccc1)c1ccc(B(O)O)cc1] | C |
| 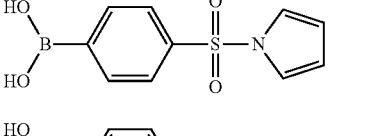 | C |
| 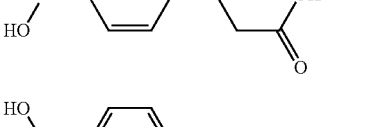 | D |
| 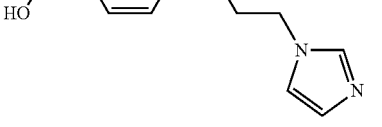 | C |

Biological Protocols

Example 286

Inhibition of Rat and Human FAAH

The following assays may be used to determine the inhibition of FAAH by the compounds of the present invention: (1) a fluorescence-based assay for fatty acid amide hydrolase compatible with high-throughput screening as described in Manjunath et al., *Analytical Biochemistry* (2005) 343:143-151; and (2) a high-throughput screening for the discovery of inhibitors of fatty acid amide hydrolase using a microsome-based fluorescent assay. Wang et al., *Biomolecular Screening* (2006) 1-9.

Rat FAAH Preparation:

Five rat livers were homogenized in five fold volume with ice cold Tris (20 mM pH 8.0) and 0.32 M Sucrose solution via an Ultra Turrax T25 homogenizer. All subsequent preparation steps were carried out at 4° C. The homogenate was centrifuged at 6000 g, for 20 minutes and the pellet, containing nuclear debris and mitochondria was discarded. The supernatant was centrifuged at 40,000 g for 30 minutes. The supernatant was discarded and the pellet solubilized via a dounce homogenizer in resuspension buffer (20 mM Hepes pH 7.8, 10% v/v glycerol, 1 mM EDTA, 1% triton X-100) overnight at 4° C. to resolubilize membrane bound FAAH. The solution was centrifuged at 40,000 g for 30 minutes and the pellet discarded. The supernatant containing rat FAAH was aliquoted and flash frozen with liquid nitrogen and stored for long term usage at −80° C.

Human FAAH Preparation:

COS-7 cells were split the day before, 1:5 into 150 mm×25 mm cell culture dishes (Corning Inc., Cat. No. 430599). Transient transfection took place at 30-40% confluency according to FuGENE 6 Transfection Reagent (Roche, Cat. No. 11814 443 001).

Transfection Procedure:

The FuGENE transfection 6 reagent (45 uL) was added to 1410 µL of media (DMEM, serum free without pen/strep) in a 15 mL conical tube and incubated at room temp for 5 minutes, followed by the addition of FAAH plasmid DNA (15 µg) (OriGene Cat. No. TC119221, Genbank Accession No. NM_001441.1, 0.67 ug/uL) and a further incubation of 15 minutes at room temperature. The resulting solution was added into one dish of 30-40% confluent COS-7 cells in a drop-wise manner. The COS-7 cell dish was subsequently incubated for 48 hours. The cells are then harvested.

Harvest Procedure:

Media was aspirated from the dishes and the cells rinsed with 10 mL PBS. The PBS was removed and 3 mL of PBS added to the dish. The dish was scraped to resuspend the cells, and the subsequent cell suspension collected into a 15 mL conical tube. The cells were pelleted by centrifugation at 1200 rpm for 5 minutes in a bench top centrifuge. PBS was removed and the cell pellet snap frozen in liquid nitrogen and stored at −80° C.

COS-7 Cells—FAAH Purification:

(1) Fractionation: Frozen cell pellets from transient transfections were thawed on ice and resuspended in 12.5 mM Hepes pH 8.0, 100 mM NaCl, 1 mM EDTA (10 mL/0.2 g cell pellet). The pellets were dounce homogenized and then sonicated to produce cell extract. The cell extract was subsequently centrifuged at 1000 g to remove cellular debris. The pellet was discarded and the supernatant centrifuged at 13,000 g for 20 minutes. The pellet contained membrane bound FAAH. The supernatant was discarded and the pellet resolubilized.

(2) Re-solubilization: The fraction of interest, (13,000 g, membrane fraction) was re-suspended in 2.3 mL re-suspension buffer (20 mM Hepes pH 7.8, 10% v/v Glycerol, 1 mM EDTA, 1% Triton X-100) and the sample incubated on ice for 1 hour and then centrifuged to remove any particulate matter. The supernatant containing solubilized human FAAH was aliquoted and snap frozen in liquid nitrogen and stored at −80° C. until use.

(3) Characterization: Protein Concentration determined by Bradford assay.
SDS gel and Western blot to confirm presence of FAAH
FAAH activity assay
Km determination—96-well assay
Linear dependence—96-well assay
Standard compound Ki determination—384-well assay Rat FAAH Biochemical Inhibition Assay; Materials and Methods:

Rat FAAH biochemical assays were carried out in a 96 well flat bottom black non-treated polystyrene plates (Corning Costar Catalogue #3915). FAAH reaction buffer: 50 mM Hepes (pH 7.5), 1 mM EDTA, 0.2% Triton X-100. FAAH substrate—AMC Arachidonoyl Amide (Cayman Chemicals Company, Catalog #10005098). The reaction was read in an Envision microtiter plate reader [Excitation filter 355 nm (40 nm bandpass); Emmision filter 460 nm (25 nm bandpass)]. The raw fluorescence was plotted on the y axis and the inhibitor concentration on the x axis to give a dose response inhibition curve. The data was fitted to a single site competitive inhibition equation, fixing the Km for the rat and human enzyme to 12 µM and 9 µM respectively.

Rat FAAH Biochemical Inhibition Assay; Experimental Protocol:

The principle of this assay was the hydrolysis of AMC-Arichodonoyl, a fluorescent analogue of Anandamide, which results in the formation of Arachidonic acid and AMC. The formation of AMC results in an increase in fluorescence (see, for example, Manjunath et al., *Analytical Biochemistry* (2005) 343:143-151; and Wang et al., *Biomolecular Screening* (2006) 1-9). The inhibition of product formation and hence fluorescence as a function of inhibitor concentration enables the determination of Ki for the compounds.

A 0.49 mg/ml Rat liver FAAH solution was made up in FAAH reaction buffer, and 78 ul pipetted into a 96 well plate. To this was added 2 uL of a 3 fold serially diluted inhibitor from a DMSO stock solution. The FAAH solution and inhibitor were incubated for 30 minutes at room temperature. The FAAH reaction was initiated by the addition of 80 µL of 40 µM AMC Arachidonoyl Amide in FAAH reaction buffer, yielding a final reaction FAAH rat liver preparation concentration of 0.25 mg/mL and AMC-Arachidonoyl substrate concentration of 20 µM, reaction volume 160 µL. The reaction was allowed to proceed for 4 hours at room temperature. The reaction was stopped by the addition of 80 µL 12 uM a-ketoheterocycle (Cayman Chemicals, catalogue #10435). The microtiter plate was read in the envision plate reader.

Human FAAH assay; Experimental Protocol:

A 0.1 mg/mL Human FAAH solution was made up in FAAH reaction buffer, and 24 ul pipeted into a 384 well plate. To this was added 1 µL of a 3 fold serially diluted inhibitor from a DMSO stock solution. The FAAH solution and inhibitor were incubated for 30 minutes at room temperature. The FAAH reaction was initiated by the addition of 25 µL of 40 µM AMC Arachidonoyl Amide in FAAH reaction buffer, yielding a final reaction human FAAH preparation concentration of 0.05 mg/ml and AMC-Arachidonoyl substrate concentration of 20 µM, reaction volume 50 µL. The reaction was allowed to proceed for 4 hours at room temperature. The reaction was stopped by the addition of 25 µL 12 µM a-keto-heterocycle (Cayman Chemicals, catalogue #10435). The microtiter plate was read in the envision plate reader.

The raw fluorescence was plotted on the y axis and the inhibitor concentration on the x axis to give a dose response inhibition curve. The data was fitted to a single site competitive inhibition equation, fixing the Km for the rat and human enzyme to 12 µM and 9 µM respectively.

Example 287

Inhibition of FAAH in its Native Cellular Environment

Cellular FAAH Inhibition Assay:

This assay measures the activity of FAAH in its native cellular environment. Radiolabelled anandamide, tritiated on its ethanolamine component was added to a cell suspension. Anadamide diffuses into the cell, whereby the native cellular FAAH hydrolyses anandamide into arachdonic acid and ethanolamine. The cellular reaction was quenched in a methanol/chloroform mixture. Ethanolamine partitions into the aqueous phase and was counted via a scintillation counter giving a measure of cellular FAAH activity Inhibition studies were performed by pre-incubating the cells with serially diluted inhibitor, followed by the addition of radiolabeled anandamide.

Cell Preparation:

RBL-2H3 and T-47D adherent cells were cultured via the standard protocols. Cells were trypsinized and washed 3 times in RPMI buffer plus 0.1% BSA. The cells were resuspended, counted and diluted to a final cell density of $1 \times 10^6$ cells/mL. Human PBMC were isolated from whole blood and used at a final cell density of $4.5 \times 10^6$ cells/mL in RPMI plus 0.1% BSA buffer.

Anandamide Substrate Solution:

A 10 nM $^3$H anandamide substrate solution was prepared by diluting from a 16.7 µM (1 µCi/µL) stock in RPMI buffer plus 0.1% BSA, and incubated at room temperature for 90 minutes. A substrate-inhibitor solution was made by adding serially diluted inhibitor from a DMSO stock solution to the desired concentration into the substrate solution.

Assay:

A 350 µL cell suspensions was incubated with serially diluted inhibitor added from a DMSO stock and incubated for 30 minutes with constant agitation. Cells were pelleted and the supernatant removed. The cells were resuspended in 300 µL of 10 nM substrate+serially diluted inhibitor, to maintain a constant free inhibitor concentration during the time-course of the reaction. The RBL-2H3 and T-47D cells were incubated with the substrate—inhibitor for 5 minutes and PBMC for 15 minutes. The reaction was quenched by the addition of 700 µL of methanol:chloroform (1:1 v/v), which lyses the cells and inactivates FAAH. Sampled were vortexed and centrifuged to separate the aqueous and organic solutions. $^3$H ethanolamine, the polar product of anandamide hydrolysis partitions into the aqueous phase and was counted via a scintillation counter.

Data Analysis:

The radioactivity in the aqueous phase was plotted with respect to inhibitor concentration to generate dose response inhibition curves, and the data fitted to determine the IC$_{50}$.

Example 288

FAAH Cell-Based Assay Protocol for Human and Rat Whole Blood

This assay measures the cellular activity of FAAH in whole blood via the hydrolysis of radiolabeled anandamide by the same methodology and principle used in the cell based assay described in Example 172. FAAH is found to be expressed in the cells of the immune system.

Substrate Solution:

$^3$H Anandamide (1 µC/µL, 16.7 µM stock) was added to a final concentration of 40 nM (4×) for the human whole blood assays and 20 nM (2×) for rat whole blood assays to the RMPI buffer plus 0.1% BSA. The $^3$H anandamide stock solutions were incubated for 90 minutes at room temperature prior to use in the whole blood assay.

Human Whole Blood Cellular FAAH Assay:

Human blood (262.5 µL) was pre-incubated with serially diluted inhibitor added from DMSO stock solution for 30 minutes. The assay was initiated by the addition of 40 nM $^3$H anandamide (87.5 µL) yielding a final assay volume of 350 µL and $^3$H anandamide substrate concentration of 10 nM. The reaction mixture was incubated for 30 minutes at room temperature, and the reaction stopped by the addition of 700 µL of methanol: chloroform (1:1 v/v). This lyses the cells and inactivates the FAAH. The solution was vortexed and $^3$H ethanolamine, the radiolabeled product of $^3$H anandamide hydrolysis partitioning into the aqueous phase, and was counted via a scintillation counter.

Rat whole Blood Cellular FAAH Assay:

Rat blood (175 µL) was pre-incubated with serially diluted inhibitor added from DMSO stock solution for 30 minutes. The assay was initiated by the addition of 20 nM $^3$H anandamide (175 µL) yielding a final assay volume of 350 ul and $^3$H anandamide substrate concentration of 10 nM. The reaction mixture was incubated for 30 minutes at room temperature, and the reaction stopped by the addition of 700 µL of methanol: chloroform (1:1 v/v). This lyses the cells and inactivates the FAAH. The solution was vortexed and $^3$H ethanolamine, the radiolabeled product of $^3$H anandamide hydrolysis partitioning into the aqueous phase, and was counted via a scintillation counter.

Data Analysis:

The radioactivity in the aqueous phase was plotted with respect to inhibitor concentration to generate dose response inhibition curves, and the data fitted to determine the IC$_{50}$.

Example 289

In Vivo Analysis of Boronic Acid and Boronic Ester Derivatives in a Pain Model

This assay may be used to evaluate the effect of the compounds of the present invention on the reflexive withdrawal of the rat from an acute noxious stimulus (hot surface).

(1) Heat plate to testing temperature (Hot plate analgesia meter; Harvard Apparatus)—takes about 10-15 min (the actual surface temperature is not reflected in the LED read out. The actual surface temperature is 10° C. less than the read out indicates).

| Read-out | Surface temp |
|---|---|
| 57° C. | 47° C. |
| 62° C. | 52° C. |
| 65° C. | 55° C. |

(2) Place plexi-glass cylinder on hot plate. Place rat within cylinder and start timer. When the rat either licks its hind paw or jumps, stop the timer and remove from hot plate. Record the response latency (in sec), usually 6-7 sec at 52° C. Measure baseline latencies for all rats.

(3) Inject drug or vehicle.

(4) Measure response 5, 15, 30, 60, 90, 120 min, etc. after drug injection. Cut-off time for 52° C. is 30 sec. A rat that does not respond by 30 sec. is assigned a latency of 30 sec.

(5) Clean hot plate surface in between time points with water, dry with kimwipe and wait until temperature read out has returned to 57° C.

Data may be expressed as either latency or percent maximum possible effect [% MPE=(drug latency−baseline latency)/(cut-off−baseline latency)×100].

Other temperatures may be used (e.g., 47° C., 55° C.). Cut-off time should be adjusted accordingly (e.g., 40 sec at 47° C.; 20 sec at 55° C.). Increased temperatures recruit myelinated afferents (Aδ-fibers) whereas lower temperatures involve unmyelinated afferents (c-fibers). Sensitivity to drug effects may be altered with different plate temperatures.

Example 290

Evidence for Covalent Complex Formation Between Serine-241 of FAAH and Boronic Acid Inhibitors Treatment of rat FAAH protein with the active site-directed irreversible inhibitor methoxy arachidonyl fluorophosphonate results in a crystal structure wherein methoxy arachidonyl phosphonate is covalently bound to the side chain of Ser-241 (Bracey et al., Science (2002) 298:1793-1796).

Based on this data, it is hypothesized that the boronic acid compounds provided by the present invention form reversible covalent complexes with the nucleophilic side chain of Ser-241. This hypothesis is consistent with the kinetic data. Molecular modeling studies of aryl boronic acid compounds provided herein indicates that the aryl ring can be directed to bind either in the narrow hydrophobic channel of the enzyme near Ser241, which is confluent with the membrane portion and the acyl chain binding pocket, or alternatively bind toward the cytosolic portion.

To distinguish between these two binding modes, a mutant protein was cloned and expressed which was identical to the rat FAAH protein sequence, except at four positions in the sequence: I491V, V495M, L192F, and F194Y. These four residues line the narrow hydrophobic channel near Ser-241 in the rat x-ray structure. Starting from the published X-ray crystal structure of rat FAAH, a 3-D homology model was built of human FAAH using the program DeepView (Nicolas Guex, Manuel Peitsch, Torsten Schwede Alexandre Diemand "DeepView/Swiss-Pdbviewer" (1995-2001)). Based on this 3-D homology model of the human protein, mutation of these four residues to the corresponding amino acids in the human sequence was predicted to significantly influence the binding of the aryl boronic acid compounds if the aryl ring is in close proximity to these residues.

The inhibition constant ($K_i$) was measured for a panel of eleven boronic acid-containing compounds differing in their ability to inhibit rat and human FAAH. Table B below summarizes the statistical analysis for the panel of eleven compounds, comparing the ratio of inhibition constants for the wild-type rat and human enzymes (R/H) to ratio of inhibition constants for the mutant rat and human enzymes (M/H). The data indicates that the compounds bind at Serine-241 with the aryl ring directed toward the narrow hydrophobic channel.

TABLE B

| R/H | M/H | |
|---|---|---|
| 11 | 11 | nObs |
| 2.99 | 1.08 | Mean |
| 3.45 | 0.48 | StDev |
| 0.02 | 0.49 | Min |
| 11.86 | 1.8 | Max |

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound of the following formula:

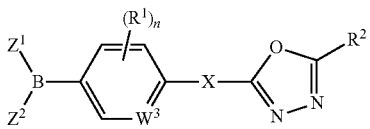

or a pharmaceutically acceptable salt or prodrug thereof;
wherein:
(i) $Z^1$ is —OH or —OR$^3$ and $Z^2$ is —OH, or —OR$^4$, an optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{2-6}$ heteroalkenyl, optionally substituted $C_{2-6}$ heteroalkynyl, optionally substituted $C_{6-10}$ aryl, or optionally substituted 5-10 membered heteroaryl; or

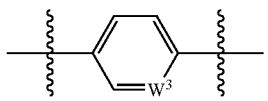

(ii) $Z^1$ is —OH or —OR$^3$, and $Z^2$ and wherein the ring is comprised of carbon atoms and optionally one or more additional heteroatoms independently selected from the group consisting of N, S and O taken together form an optionally substituted 5- to 7-membered ring;
$W^3$ is $CR^{15}$;
X is a covalent bond, —O—, —N=N—, —C=N—, —NR$^6$—, —C(NR$^6$)—, —S—, —C(O)—, —S(O)—, —S(O)$_2$, or optionally substituted $C_{1-6}$ alkylene, wherein one, two or three methylene units of the $C_{1-6}$ alkylene are optionally and independently replaced with one or more groups selected from —O—, —N=N—, —C=N—, —NR$^6$—, C(NR$^6$)—, —S—, —C(O)—, —S(O)—, and —S(O)$_2$—;
each instance of R$^1$ is, independently, halogen, —OR$^8$, —CF$_3$, —CN, —NO$_2$, —SO$_2$R$^8$, —SOR$^8$, —C(O)R$^8$, —CO$_2$R$^8$, —C(O)N(R$^8$)$_2$, —CHO, —N$_3$, —N$_2$R$^8$, —N(R$^8$)$_2$, —B(OH)$_2$, optionally substituted $C_{1-6}$ alkyl, optionally substituted $C_{2-6}$ alkenyl, optionally substituted $C_{2-6}$ alkynyl;

each instance of R$^2$ is, independently, —OR$^9$, —N(R$^9$)$_2$, optionally substituted $C_{1-6}$ alkyl, optionally substituted $C_{2-6}$ alkenyl, or unsubstituted $C_{6-10}$ aryl;
each instance of R$^3$ and R$^4$ is, independently, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{2-6}$ heteroalkenyl, optionally substituted $C_{2-6}$ heteroalkynyl, optionally substituted $C_{6-10}$ aryl, or optionally substituted 5-10 membered heteroaryl;
each instance of R$^6$, R$^8$ and R$^9$ is, independently, hydrogen, —SO$_2$R$^{11}$, —SOR$^{11}$, —C(O)R$^{11}$, —CO$_2$R$^{11}$, —C(O)N(R$^{11}$)$_2$, —C(O)NH(R$^{11}$), —C(O)NH$_2$, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{2-6}$ heteroalkenyl, optionally substituted $C_{2-6}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;
each instance of R$^{11H}$ is, independently, optionally substituted $C_{1-6}$alkyl, optionally substituted $C_{2-6}$ alkenyl, optionally substituted $C_{2-6}$alkynyl, optionally substituted $C_{1-6}$ heteroalkyl, optionally substituted $C_{2-6}$ heteroalkenyl, optionally substituted $C_{2-6}$ heteroalkynyl, optionally substituted $C_{3-10}$ carbocyclyl, optionally substituted 3-10 membered heterocyclyl, optionally substituted $C_{6-10}$ aryl, or optionally substituted 5-10 membered heteroaryl;
R$^{15}$ is hydrogen, halogen, —CF$_3$, optionally substituted $C_{1-6}$ alkyl, optionally substituted $C_{2-6}$ alkenyl, or optionally substituted $C_{2-6}$ alkynyl;
n is 0, 1, 2 or 3; and
with the proviso that the following compound is excluded:

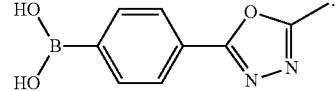

2. The compound of claim 1, wherein X is a covalent bond, —O—, or —(CH$_2$)—.

3. The compound of claim 1, wherein $Z^1$ and $Z^2$ are both OH.

4. The compound of claim 3, wherein n is 0.

5. The compound of claim 4, wherein $R^2$ is optionally substituted $C_{1-6}$ alkyl.

6. The compound of claim 5, wherein $R^2$ is $C_{1-6}$ alkyl substituted with optionally substituted phenyl.

7. The compound of claim 5, wherein $R^2$ is $C_{1-6}$ alkyl substituted with —$CF_3$ or —$CF_2CF_3$.

8. The compound of claim 5, wherein the $C_{1-6}$ alkyl is substituted with an optionally substituted 5- or 6-membered ring having 0-4 heteroatoms selected from N, O or S.

9. The compound of claim 5, wherein the $C_{1-6}$ alkyl is substituted with)-$N(R^0C(O)OR^0$, wherein each $R^0$ is independently hydrogen or $C_{1-6}$ alkyl.

10. The compound of claim 4, wherein $R^2$ is unsubstituted $C_{6-10}$ aryl or optionally substituted 5 to 10 membered heteroaryl.

11. The compound of claim 1, wherein n is 1.

12. The compound of claim 11, wherein $R^1$ is a halogen or —$CF_3$.

13. The compound of claim 11, wherein $R^2$ is unsubstituted $C_{6-10}$ aryl.

14. The compound of claim 1, which is:

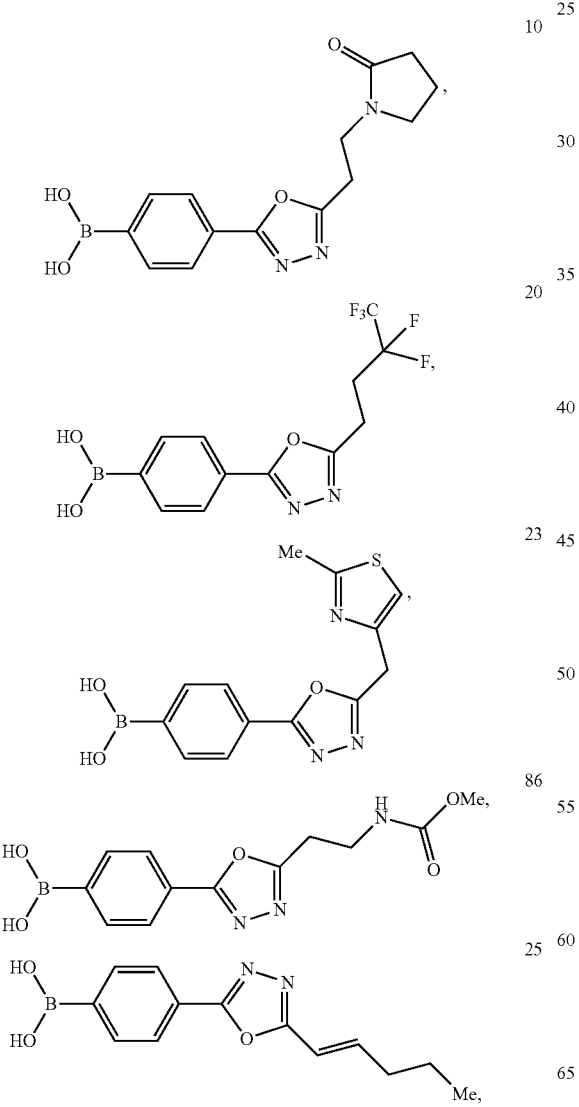

-continued

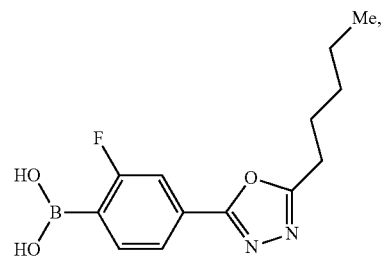

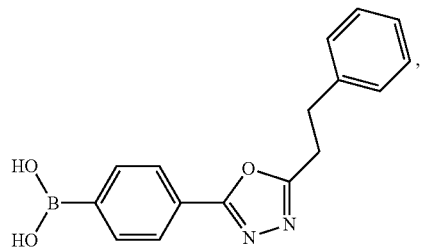

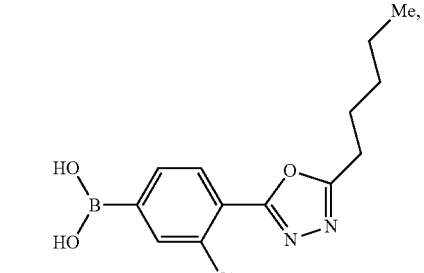

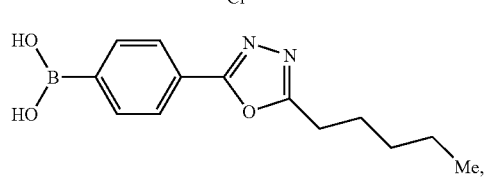

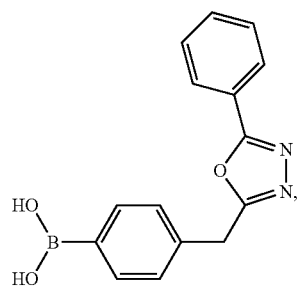

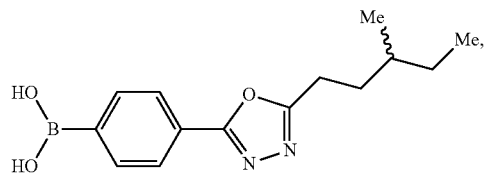

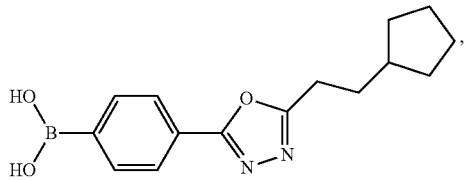

-continued
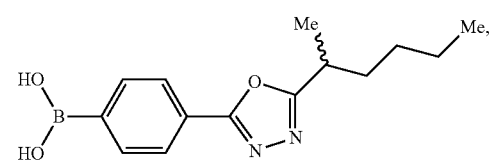
34
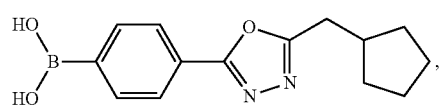
35
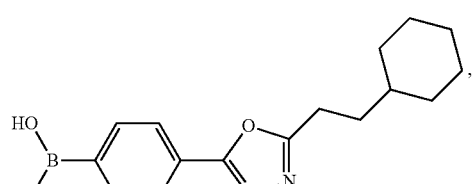
36
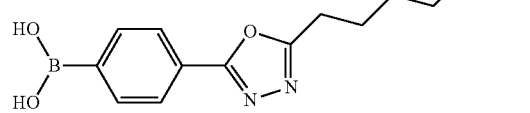
37
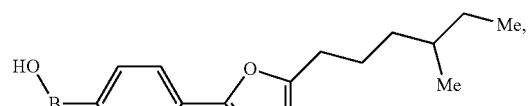
38
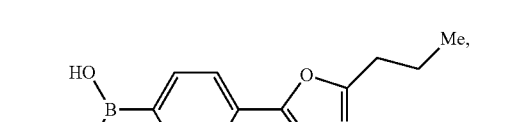
39
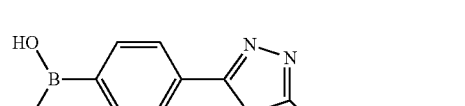
40
42
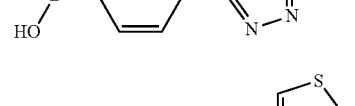
59
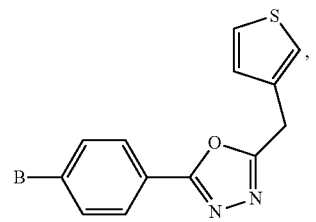
-continued
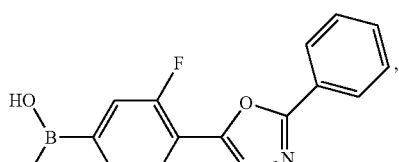
67
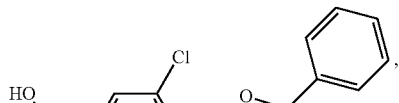
68
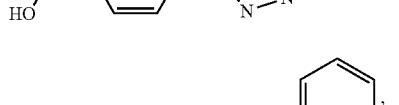
69
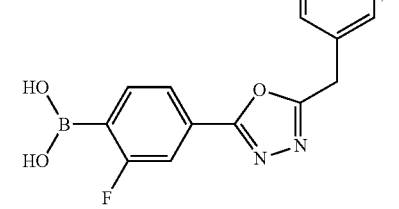
70
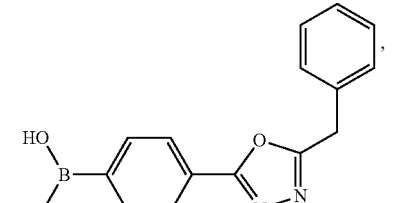
71
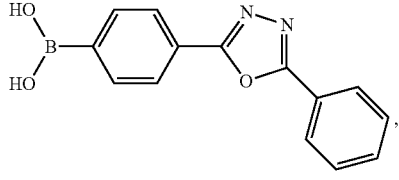
239
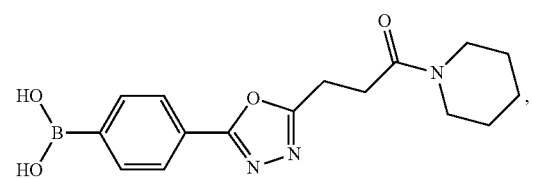
73
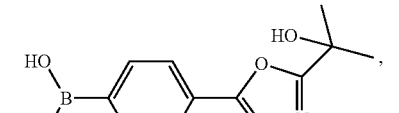
74
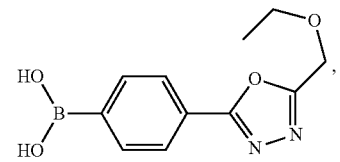

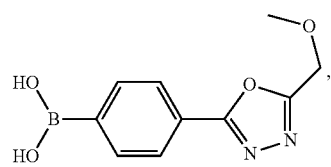
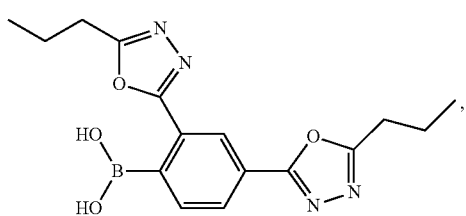
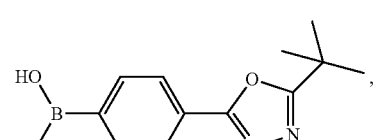
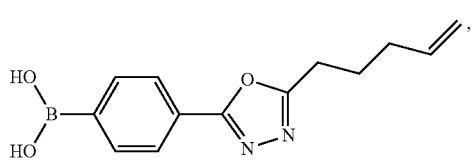
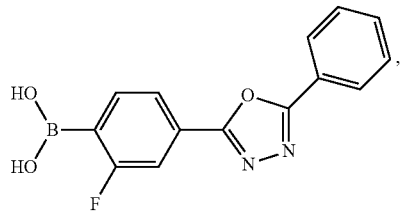
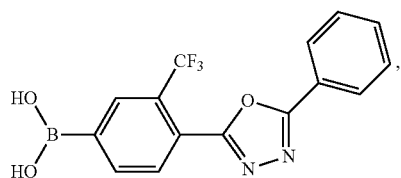
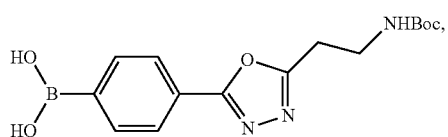
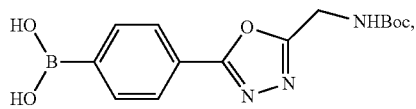
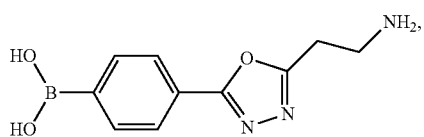
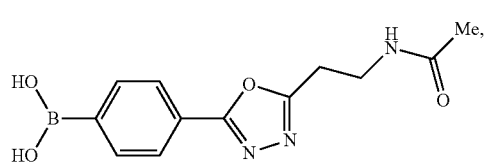
or a pharmaceutically acceptable salt or prodrug thereof.
15. The compound of claim 1, wherein the compound is:
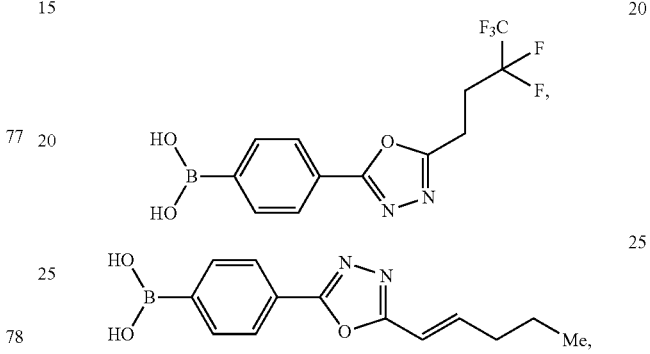
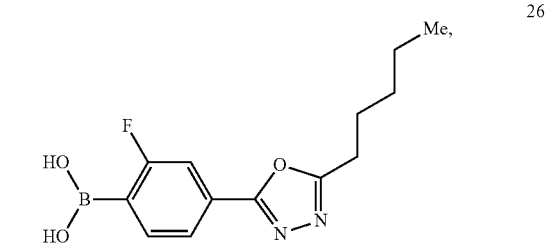
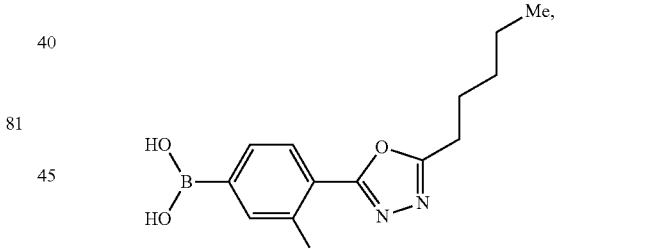
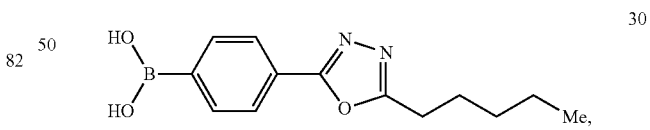
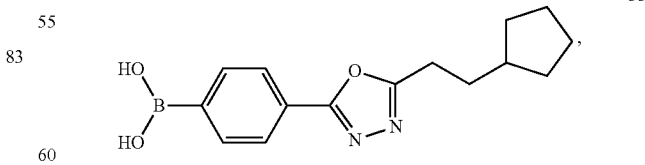
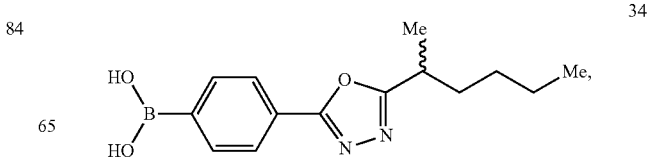

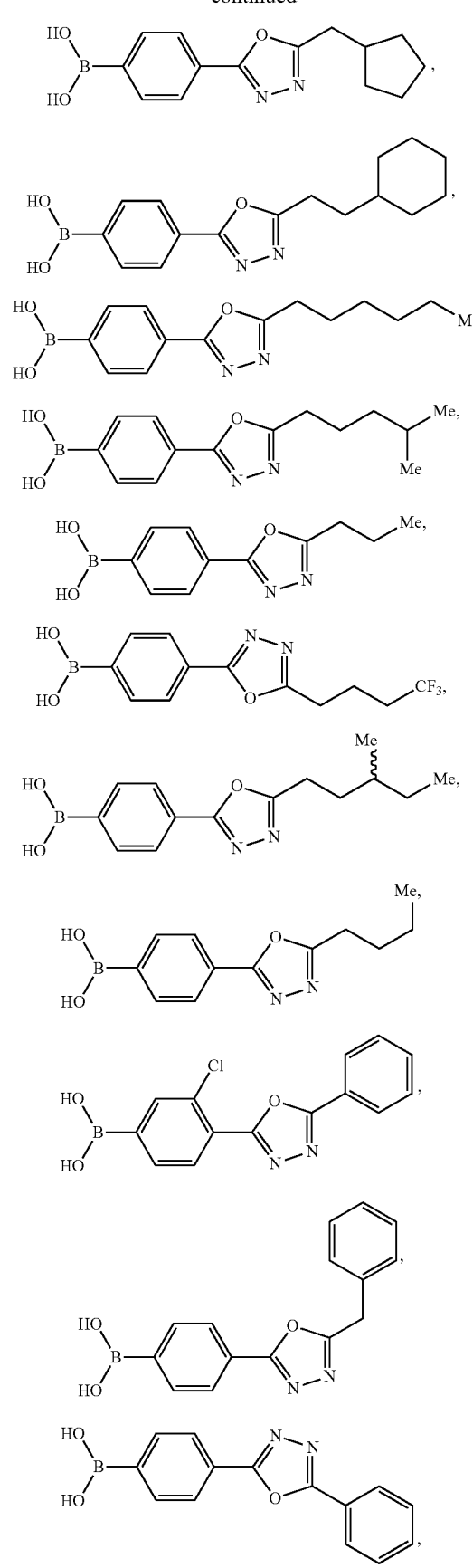
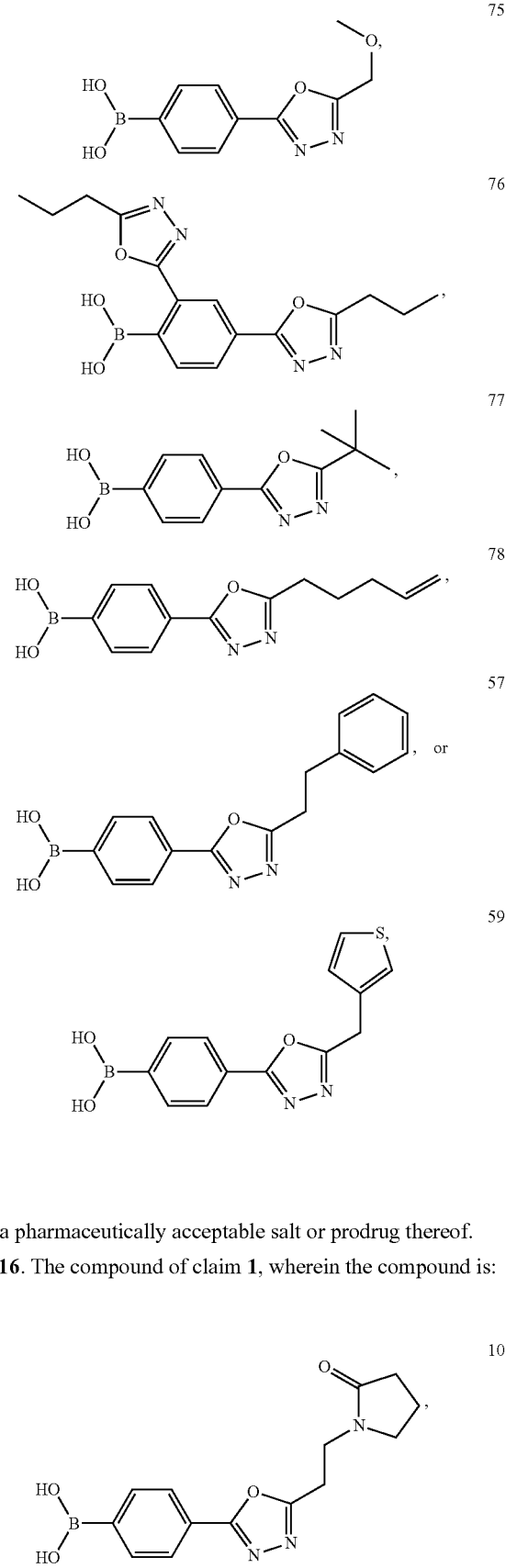
or a pharmaceutically acceptable salt or prodrug thereof.
16. The compound of claim 1, wherein the compound is:

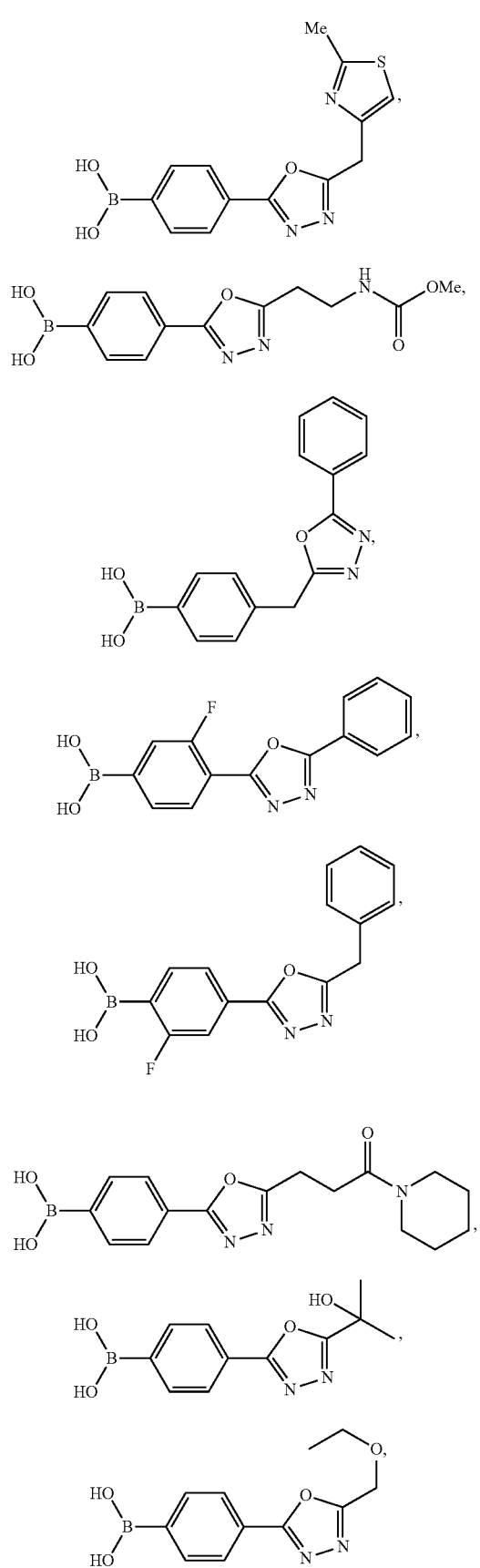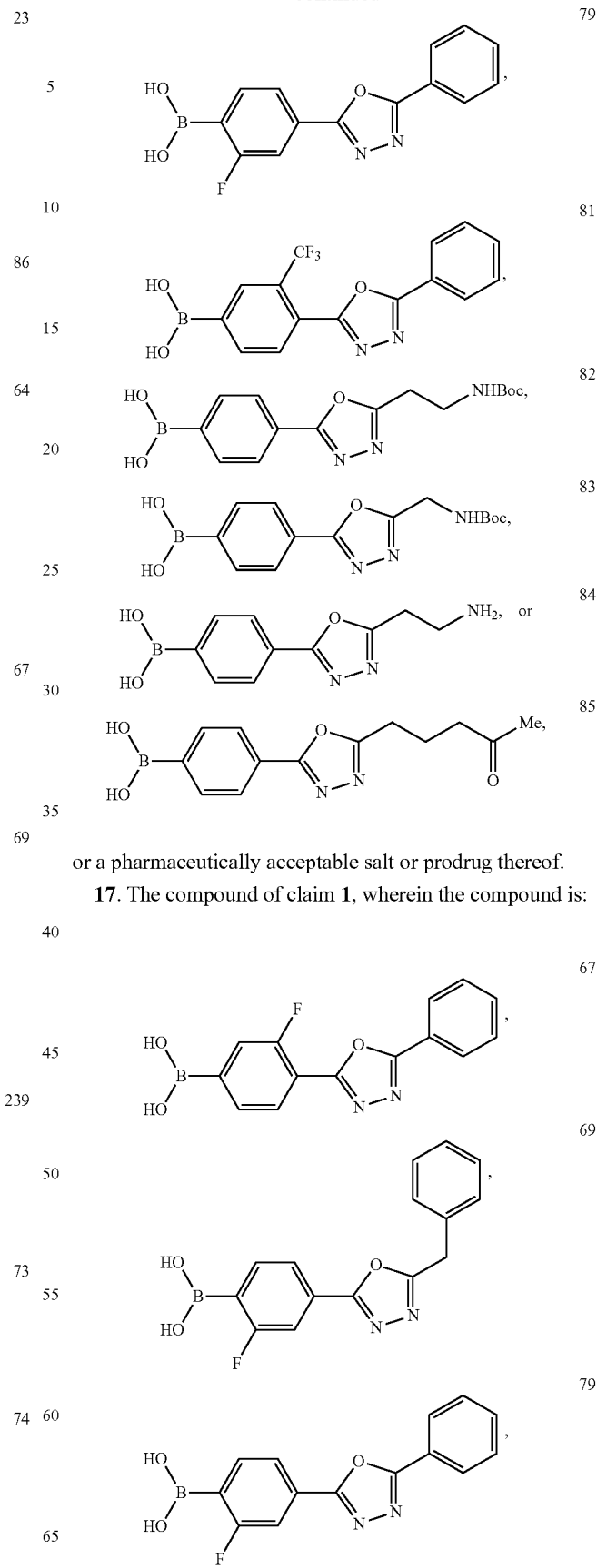
or a pharmaceutically acceptable salt or prodrug thereof.
17. The compound of claim 1, wherein the compound is:

-continued

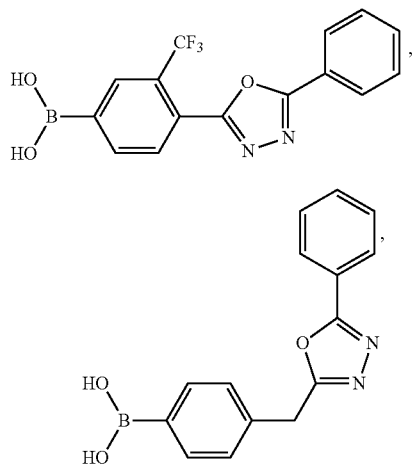

or a pharmaceutically acceptable salt or prodrug thereof.

18. The compound of claim 1, wherein the compound is:

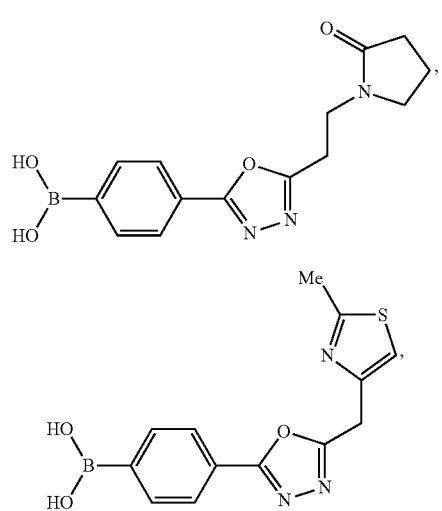

or a pharmaceutically acceptable salt or prodrug thereof.

19. The compound of claim 1, wherein the compound is:

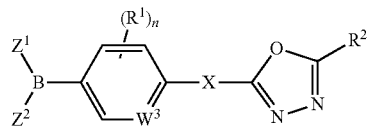

or a pharmaceutically acceptable salt or prodrug thereof.

20. A compound of the following formula:

$$\begin{array}{c}\text{structure}\end{array}$$

or a pharmaceutically acceptable salt or prodrug thereof;

wherein:

X is a covalent bond, —O—, or —(CH$_2$)—;

W$^3$ is CH;

Z$^1$ and Z$^2$ are both OH;

n is 0; and

R$^2$ is optionally substituted C$_{1-6}$ alkyl.

21. A pharmaceutical composition comprising a compound, or a pharmaceutically acceptable salt or prodrug thereof, of claim 1, and a pharmaceutically acceptable excipient, medium, or carrier.

* * * * *

UNITED STATES PATENT AND TRADEMARK OFFICE
CERTIFICATE OF CORRECTION

| | |
|---|---|
| PATENT NO. | : 8,957,049 B2 |
| APPLICATION NO. | : 12/901421 |
| DATED | : February 17, 2015 |
| INVENTOR(S) | : Mark L. Behnke et al. |

It is certified that error appears in the above-identified patent and that said Letters Patent is hereby corrected as shown below:

In the Claims

In claim 1:

column 269, please replace lines 40-52 with the following:

(ii) $Z^1$ is –OH or –$OR^3$, and $Z^2$ and 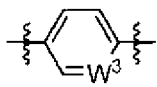 taken together form an optionally substituted 5– to 7–membered ring;

column 270, line 42, please replace "$R^{11H}$" with – $R^{11}$ –;

In claim 9, column 271, line 13, please replace ")-N($R^0$C(O)$OR^0$" with – N($R^0$)C(O)$OR^0$ –; and In claim 16, column 280, please replace " 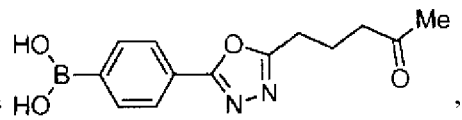 " with 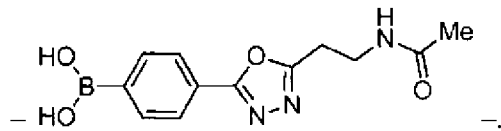 –.

Signed and Sealed this
Fifteenth Day of September, 2015

Michelle K. Lee
*Director of the United States Patent and Trademark Office*